(12) United States Patent
Alitalo et al.

(10) Patent No.: US 8,029,984 B2
(45) Date of Patent: Oct. 4, 2011

(54) MATERIALS AND METHODS FOR COLORECTAL CANCER SCREENING, DIAGNOSIS AND THERAPY

(75) Inventors: Kari Alitalo, Helsinki (FI); Tatiana Petrova, Helsinki (FI); Antti Nykanen, Helsinki (FI)

(73) Assignee: Licentia, Ltd., Helsinki (FI)

( * ) Notice: Subject to any disclaimer, the term of this patent is extended or adjusted under 35 U.S.C. 154(b) by 711 days.

(21) Appl. No.: 10/567,630

(22) PCT Filed: Aug. 6, 2004

(86) PCT No.: PCT/EP2004/008819
§ 371 (c)(1),
(2), (4) Date: May 30, 2006

(87) PCT Pub. No.: WO2005/014854
PCT Pub. Date: Feb. 17, 2005

(65) Prior Publication Data
US 2007/0026405 A1 Feb. 1, 2007

Related U.S. Application Data

(60) Provisional application No. 60/494,221, filed on Aug. 8, 2003.

(51) Int. Cl.
*C12Q 1/68* (2006.01)
*C12P 19/34* (2006.01)
*C07K 16/00* (2006.01)
*C07H 21/02* (2006.01)

(52) U.S. Cl. ............ 435/6; 435/91.2; 435/7.1; 536/23.1

(58) Field of Classification Search ........................ None
See application file for complete search history.

(56) References Cited

U.S. PATENT DOCUMENTS

| | | | |
|---|---|---|---|
| 4,946,778 | A | 8/1990 | Ladner et al. |
| 5,093,246 | A | 3/1992 | Cech et al. |
| 5,116,742 | A | 5/1992 | Cech et al. |
| 5,225,337 | A | 7/1993 | Robertson et al. |
| 5,254,678 | A | 10/1993 | Haseloff et al. |
| 5,750,652 | A | 5/1998 | Artavanis-Tsakonas et al. |
| 5,780,300 | A | 7/1998 | Artavanis-Tsakonas et al. |
| 5,939,598 | A | 8/1999 | Kucherlapati et al. |
| 6,004,924 | A | 12/1999 | Ish-Horowicz et al. |
| 6,083,904 | A | 7/2000 | Artavanis-Tsakonas |
| 6,121,045 | A | 9/2000 | McCarthy et al. |
| 6,262,025 | B1 | 7/2001 | Ish-Horowicz et al. |
| 6,291,210 | B1 | 9/2001 | Sakano et al. |
| 6,380,362 | B1 | 4/2002 | Watson et al. |
| 6,433,138 | B1 | 8/2002 | Zimrin et al. |
| 6,436,650 | B1 | 8/2002 | Artavanis-Tsakonas et al. |
| 2001/0051344 | A1* | 12/2001 | Shalon et al. ............... 435/6 |
| 2003/0087807 | A1 | 5/2003 | Greenspan |
| 2003/0224516 | A1 | 12/2003 | Dobie |
| 2005/0271636 | A1 | 12/2005 | Oliver et al. |
| 2006/0088532 | A1 | 4/2006 | Alitalo et al. |
| 2007/0110744 | A1 | 5/2007 | Alitalo et al. |

FOREIGN PATENT DOCUMENTS

| | | |
|---|---|---|
| WO | WO 96/34096 | 10/1906 |
| WO | WO 90/07641 | 7/1990 |
| WO | WO 93/23569 | 11/1993 |
| WO | WO 94/02602 | 2/1994 |
| WO | WO 96/33735 | 10/1996 |
| WO | WO 96/34096 | 10/1996 |
| WO | WO-00/06726 | 2/2000 |
| WO | WO-02/24221 | 3/2000 |
| WO | WO 00/32765 | 6/2000 |
| WO | WO-01/12664 | 2/2001 |
| WO | WO 03/027285 | 4/2003 |
| WO | WO-03/027285 | 4/2003 |
| WO | WO-03/047532 | 6/2003 |
| WO | WO-03/080640 | 10/2003 |
| WO | WO-2005/026362 | 3/2005 |

OTHER PUBLICATIONS

Cheung V.G. et al. Nature Genetics (Mar. 2003) vol. 33, p. 422-425.*
Hoshikawa Y. et al. Physiol Genomcs (2003) vol. 12, p. 209-219.*
Chen G. et al. Molecular and Cellular Proteomics Apr. 2002;1(4):304-13.*
Parr C. Int J Oncol. Aug. 2003;23(2):533-9.*
Rockman S.P. et al. Journal of Biological Chemistry (2001) vol. 276, No. 48, Issue of Nov. 30, pp. 45113-45119.*
Kinzler et al., "Lessons from Hereditary Colorectal Cancer," *Cell*, 87, 159-170 (1996).
Lohela et al., "Lymphangiogenic Growth Factors, Receptors and Therapies," *Thrombosis and Haemostasis*, 90(2):167-184 (2003).
Maillard et al., "Notch and Cancer: Best to Avoid the Ups and Downs," *Cancer Cell*, 203-205 (2003).
Petrova et al., "Effects of Lymphatic Transcription Factor Prox-1 on Cell Cycle Progression," *J. Submicro. Cyt. Path.*, 32(3):406 (2000).
Wigle et al., "An Essential Role for *Prox1* in the Induction of the Lymphatic Endothelial Cell Phenotype," *EMBO J.*, 21(7):1505-1513 (2002).
Xia et al., "siRNA-mediated Gene Silencing in Vitro and in Vivo," *Nat. Biotech.*, 20(10):1006-1010 (2002).
International Search Report for International Application No. PCT/EP2004/008819, mailed Dec. 29, 2004.
Written Opinion for International Application No. PCT/EP2004/008819, mailed Dec. 29, 2004.
Artavanis-Tsakonas, Notch Signaling: Cell fate control and signal integration in development. *Science*, vol. 284, pp. 770-776 (1999).
Bach et al., Stem cells: The intestinal stem cell as paradigm. *Carcinogenesis*, vol. 21, pp. 469-476 (2000).
Bange et al., Cancer progression and tumor cell motility are associated with the FGFR4 Arg388 allele. *Cancer Res.*, vol. 62, pp. 840-847 (2002).
Brummelkamp et al., A system for stable expression of short interfering RNAs in mammalian cells. *Science*, vol. 296, pp. 550-553 (2002).
Cavallaro et al., N-CAM modulates tumour-cell adhesion to matrix by inducing FGF-receptor signaling. *Nat. Cell Biol.*, vol. 3, pp. 650-657 (2001).
Chowrira et al., Extensive phosphorothioate substitution yields highly active and nuclease-resistant hairpin ribosymes. *Nucleic Acids Res.*, vol. 20, pp. 2835-2840 (1992).

(Continued)

*Primary Examiner* — Stephen Kapushoc
(74) *Attorney, Agent, or Firm* — Marshall, Gerstein & Borun LLP

(57) ABSTRACT

The invention provides materials and methods for colorectal cancer screening, diagnosis, and therapy.

22 Claims, 3 Drawing Sheets

OTHER PUBLICATIONS

Cole et al., Generation of human monoclonal antibodies reactive with cellular antigens. *Proc. Natl. Acad. Sci. (USA)*, vol. 80, pp. 2026-2030 (1983).

Daubendiek et al., Generation of catalytic RNAs by rolling transcription of synthetic DNA nanocircles. *Nat. Biotechnol.*, vol. 15, No. 3, pp. 273-277 1997.

Elbashir et al., RNA interference is mediated by 21- and 22-nucleotide RNAs. *Genes Dev.*, vol. 15, pp. 188-200 2001.

Elbashir et al., Duplexes of 21-nucleotide RNAs mediate RNA interference in cultured mammalian cells. *Nature*, vol. 411, pp. 494-498 2001.

Fawell et al., Tat-mediated delivery of heterologous proteins into cells. *Proc. Natl. Acad. Sci. (USA)*, vol. 91, pp. 664-668 (1994).

Ferkol et al., Regulation of the phosphoenolpyruvate carboxykinase/human factor IX gene introduced into the livers of adult rats by receptor-mediated gene transfer. *FASEB J.*, vol. 7, pp. 1081-1091 (1993).

Fingl et al., Chapter 1: General Principles. "The Pharmacological Basis of Therapeutics," pp. 1 (1975).

Fire et al., Potent and specific genetic interference by double-stranded RNA in *Caenorhabditis elegans*. *Nature*, vol. 391, pp. 806-811 (1998).

Fujimori et al., Regulation of lipocalin-type prostaglandin D synthase gene expression by Hes-1 through E-box and interleukin-1β via two NF-κB elements in rat leptomeningeal cells. *J. Biol. Chem.*, vol. 278, pp. 6018-6026 (2003).

Giles et al., Caught up in a WNT storm: Wnt signaling in cancer. *Biochem. Biophys. Acta.*, vol. 1653, pp. 1-24 2003.

Gupta et al., Colorectal cancer prevention and treatment by inhibition of cyclooxygenase-2. *Nat. Rev. Cancer*, vol. 1, pp. 11-21 (2001).

Hong et al., Prox1 is a master control gene in the program specifying lymphatic endothelial cell fate. *Dev. Dyn.*, vol. 225, pp. 351-357 (2002).

Hutvagner et al., A microRNA in a multiple-turnover RNAi enzyme complex. *Science*, vol. 297, pp. 2056-2060 (2002).

Jensen et al., Control of endodermal endocrine development by Hes-1. *Nat. Genet.*, vol. 24, pp. 36-44 (2000).

Jordan et al., Expression of functional CXCR4 chemokine receptors on human colonic epithelial cells. *J. Clin. Invest.*, vol. 104, pp. 1061-1069 (1999).

Joutel et al., Notch3 mutations in CADASIL, a hereditary adult-onset condition causing stroke and dementia. *Nature*, vol, 383, pp. 707-710 (1996).

Kaneda et al., Increased expression of DNA cointroduced with nuclear protein in adult rat liver. *Science*, vol. 243, pp. 375-378 (1989).

Kato et al., Expression of hepatitis B virus surface antigen in adult rat liver. *J. Biol. Chem.*, vol. 266, pp. 3361-3364 (1991).

Kawasaki et al., Hes1 is a target of microRNA-23 during retinoic-acid-induced neuronal differentiation of NT2 cells. *Nature*, vol. 423, pp. 838-842 (2003).

Koizumi et al., Design of RNA enzyme distinguishing a single base mutation in RNA. *Nucleic Acid Res.*, vol. 17, pp. 7059-7071 (1989).

Kurreck et al., Design of antisense oligonucleotides stabilized by locked nucleic acids. *Nucleic Acids Res.*, vol. 30, pp. 1911-1918 (2002).

Ladner et al., dUTP nucleotidohydrolase isoform expression in normal and neoplastic tissues: association with survival and response to 5-fluorouracil in colorectal cancer. *Cancer Research*, vol. 60, pp. 3493-3503 (2000).

Lee et al., Expression of small interfering RNAs targeted against HIV-1 rev transcripts in human cells. *Nat. Biotechnol.*, vol. 20, pp. 500-505 (2002).

Li et al., Alagille syndrome is caused by mutations in human Jagged1, which encodes a ligand for Notch1. *Nature Genet.*, vol. 16, pp. 243-251 (1997).

Lima et al., Combinatorial screening and rational optimization for hybridization to folded hepatitis C virus RNA of oligonucleotides with biological antisense activity. *J. Biol. Chem.*, vol. 272, pp. 626-638 (1997).

Long et al., Self-cleaving catalytic RNA. *FASEB J.*, vol. 7, pp. 25-30 (1993).

Martinez et al., Single-stranded antisense siRNAs guide target RNA cleavage in RNAi. *Cell*, vol. 110, pp. 563-574 (2002).

Morrison et al., Chimeric human antibody molecules: mouse antigen-binding domains with human constant region domains. *Proc. Natl. Acad. Sci. (USA)*, vol. 81, pp. 6851-6855 (1984).

Nagahara et al., Transduction of full-length TAT fusion proteins into mammalian cells: TAT-p27Kip1 induces cell migration. *Nature Medicine*, vol. 4, pp. 1449-1452 (1998).

Nicolau et al., Liposomes as carriers for in vivo gene transfer and expression. *Methods Enzymol.*, vol. 149, pp. 157-176 (1987).

Ojwang et al., Inhibition of human immunodeficiency virus type 1 expression by a hairpin ribozyme. *Proc. Natl. Acad. Sci. (USA)*, vol. 89, pp. 10802-10806 (1992).

Palmer et al., Vitamin D(3) promotes the differentiation of colon carcinoma cells by the induction of E-cadherin and the inhibition of beta-catenin signaling. *J. Cell Biol.*, vol. 154, pp. 369-387 (2001).

Perales et al., Gene transfer in vivo: sustained expression and regulation of genes introduced into the liver by receptor-targeted uptake. *Proc. Natl. Acad. Sci. (USA)*, vol. 91, pp. 4086-4090 (1994).

Perrotta et al., Cleavage of oligoribonucleotides by a ribozyme derived from the hepatitis delta virus RNA sequence. *Biochem*, vol. 31, pp. 16-17 (1992).

Petrova et al., Lymphatic endothelial reprogramming of vascular endothelial cells by the Prox-1 homeobox transcription factor. *EMBO J.*, vol. 21, pp. 4593-4599 (2002).

Quaroni et al., p27(Kip1) is an inducer of intestinal epithelial cell differentiation. *Am. J. Physiol. Cell. Physiol.*, vol. 279, pp. C1045-C1057 (2000).

Schwarze et al., In vivo protein transduction: delivery of a biologically active protein into the mouse. *Science*, vol. 285, pp. 1569-1572 (1999).

Sosa-Pineda et al., Hepatocyte migration during liver development requires Prox1. *Nat. Genet.*, vol. 25, pp. 254-255 (2000).

Symons, Small catalytic RNAs. *Ann. Rev. Biochem.*, vol. 61. pp. 641 (1992).

Takeda et al., Construction of chimaeric processed immunoglobulin genes containing mouse variable and human constant region sequences. *Nature*, vol. 314, pp. 452-454 (1985).

Tomita et al., Isolation and characterization of a highly malignant variant of the SVV480 human colon cancer cell line. *Cancer Res.*, vol. 52, pp. 6840-6847 (1992).

Tuschl, Expanding small RNA interference. *Nat. Biotechnol.*, vol. 20, pp. 446-448 (2002).

Usman et al., Hammerhead ribozyme engineering. *Current Opin. Struct. Biol.*, vol. 6, pp. 527-533 (1996).

van de Wetering et al., The beta-catenin/TCF-4 complex imposes a crypt progenitor phenotype on colorectal cancer cells. *Cell*, vol. 111, pp. 241-250 (2002).

White et al., Vascular endothelial growth factor-D expression is an independent prognostic marker for survival in colorectal carcinoma. *Cancer Res.*, vol. 62, pp. 1669-1675 (2002).

Wigle et al., Prox1 function is required for the development of the murine lymphatic system. *Cell*, vol. 98, pp. 769-778 (1999).

Wigle et al., Prox1 function is crucial for mouse lens-fibre elongation. *Nat. Genet.*, vol. 21, pp. 318-333 (1999).

Wigle et al. An essential role for Prox1 in the induction of the lymphatic endothelial cell phenotype. *EMBO J.* 21:1505-1513 (2002).

Yamada et al., Fibroblast growth factor receptor (FGFR) 4 correlated with the malignancy of human astrocytomas. *Neurol Res.*, vol. 24, pp. 244-248 (2002).

Yang et al., Targeted inactivation of the p21(WAF1/cip1) gene enhances Apc-initiated tumor formation and the tumor-promoting activity of a Western-style high-risk diet by altering cell maturation in the intestinal mucosal. *Cancer Res.*, vol. 61, pp. 565-569 (2001).

Yang et al., Requirement of Math1 for secretory cell lineage commitment in the mouse intestine. *Science*, vol. 294, pp. 2155-2158 (2001).

Yu et al., RNA interference by expression of short-interfering RNAs and hairpin RNAs in mammalian cells. *Proc. Natl. Acad. Sci. (USA)*, vol. 99, pp. 6047-6052 (2002).

Zeng et al., Both natural and designed micro RNAs can inhibit the expression of cognate mRNAs when expressed in human cells. *Mol. Cell*, vol. 9, pp. 1327-1333 (2002).
International Preliminary Report on Patentability. PCT/EP2004/008819, dated Feb. 13, 2006.
Artavanis-Tsakonas, *Science*, vol. 284, pp. 770-776 (1999).
Bach et al., *Carcinogenesis*, vol. 21, pp. 469-476 (2000).
Bange et al., *Cancer Res.*, vol. 62, pp. 840-847 (2002).
Brummelkamp et al., *Science*, vol. 296, pp. 550-553 (2002).
Cavallaro et al., *Nat. Cell Biol.*, vol. 3, pp. 650-657 (2001).
Chowrira et al., *Nucleic Acids Res.*, vol. 20, pp. 2835-2840 (1992).
Cote et al., *Proc. Natl. Acad. Sci. (USA)*, vol. 80, pp. 2026-2030 (1983).
Daubendiek et al., *Nat. Biotechnol.*, vol. 15, No. 3, pp. 273-277 (1997).
Elbashir et al., *Genes Dev.*, vol. 15, pp. 188-200 (2001).
Elbashir et al., *Nature*, vol. 411, pp. 494-498 (2001).
Fawell et al., *Proc. Natl. Acad. Sci. (USA)*, vol. 91, pp. 664-668 (1994).
Ferkol et al., *FASEB J.*, vol. 7, pp. 1081-1091 (1993).
Fingel et al., "The Pharmacological Basis of Therapeutics," Ch. 1, pp. 1 (1975).
Fire et al., *Nature*, vol. 391, pp. 806-811 (1998).
Fujimori et al., *J. Biol. Chem.*, vol. 278, pp. 6018-6026 (2003).
Giles et al., *Biochem. Biophys. Acta.*, vol. 1653, pp. 1-24 (2003).
Gupta et al., *Nat. Rev. Cancer*, vol. 1, pp. 11-21 (2001).
Hong et al., *Dev. Dyn.*, vol. 225, pp. 351-357 (2002).
Hutvagner et al., *Science*, vol. 297, pp. 2056-2060 (2002).
Jensen et al., *Nat. Genet.*, vol. 24, pp. 36-44 (2000).
Jordan et al., *J. Clin. Invest.*, vol. 104, pp. 1061-1069 (1999).
Joutel et al., *Nature*, vol. 383, pp. 707-710 (1996).
Kaneda et al., *Science*, vol. 243, pp. 375-378 (1989).
Kato et al., *J. Biol. Chem.*, vol. 266, pp. 3361-3364 (1991).
Kawasaki et al., *Nature*, vol. 423, pp. 838-842 (2003).
Koizumi et al., *Nucleic Acid Res.*, vol. 17, pp. 7059-7071 (1989).
Kurreck et al., *Nucleic Acids Res.*, vol. 30, pp. 1911-1918 (2002).
Ladner et al., *Cancer Research*, vol. 60, pp. 3493-3503 (2000).
Lee et al., *Natl. Biotechnol.*, vol. 20, pp. 500-505 (2002).
Li et al., *Nature Genet.*, vol. 16, pp. 243-251 (1997).
Lima et al., *J. Biol. Chem.*, vol. 272, pp. 626-638 (1997).
Long et al., *FASEB J.*, vol. 7, pp. 25-30 (1993).
Martinez et al., *Cell*, vol. 110, pp. 563-574 (2002).
Morrison et al., *Proc. Natl. Acad. Sci. (USA)*, vol. 81, pp. 6851-6855 (1984).
Nagahara et al., *Nature Medicine*, vol. 4, pp. 1449-1452 (1998).
Nicolau et al., *Methods Enzymol.*, vol. 149, pp. 157-176 (1987).
Ojwang et al., *Proc. Natl. Acad. Sci. (USA)*, vol. 89, pp. 10802-10806 (1992).
Palmer et al., *J. Cell Biol.*, vol. 154, pp. 369-387 (2001).
Perales et al., *Proc. Natl. Acad. Sci. (USA)*, vol. 91, pp. 4086-4090 (1994).
Perrotta et al., *Biochem*, vol. 31, pp. 16-17 (1992).
Petrova et al., *EMBO J.*, vol. 21, pp. 4593-4599 (2002).
Quaroni et al., *Am. J. Physiol. Cell. Physiol.*, vol. 279, pp. C1045-C1057 (2000).
Schwarze et al., *Science*, vol. 285, pp. 1569-1572 (1999).
Sosa-Pineda et al., *Nat. Genet.*, vol. 25, pp. 254-255 (2000).
Symons, *Ann. Rev. Biochem.*, vol. 61, pp. 641 (1992).
Takeda et al., *Nature*, vol. 314, pp. 452-454 (1985).
Tomita et al., *Cancer Res.*, vol. 52, pp. 6840-6847 (1992).
Tuschl, *Nat. Biotechnol.*, vol. 20, pp. 446-448 (2002).
Usman et al., *Current Opin. Struct. Biol.*, vol. 6, pp. 527-533 (1996).
van de Wetering et al., *Cell*, vol. 111, pp. 241-250 (2002).
White et al., *Cancer Res.*, vol. 62, pp. 1669-1675 (2002).
Wigle et al., *Cell*, vol. 98, pp. 769-778 (1999).
Wigle et al., *Nat. Genet.*, vol. 21, pp. 318-333 (1999).
Yamada et al., *Neurol Res.*, vol. 24, pp. 244-248 (2002).
Yang et al., *Cancer Res.*, vol. 61, pp. 565-569 (2001).
Yang et al., *Science*, vol. 294, pp. 2155-2158 (2001).
Yu et al., *Proc. Natl. Acad. Sci. (USA)*, vol. 99, pp. 6047-6052 (2002).
Zeng et al., *Mol. Cell*, vol. 9, pp. 1327-1333 (2002).

\* cited by examiner

8,029,984 B2

SEQUENCE LISTING

```
<160> NUMBER OF SEQ ID NOS: 50

<210> SEQ ID NO 1
<211> LENGTH: 49275
<212> TYPE: DNA
<213> ORGANISM: Homo sapiens
<220> FEATURE:
<221> NAME/KEY: misc_feature
<223> OTHER INFORMATION: Prox-1 Genomic

<400> SEQUENCE: 1
ggaaatgaaa aagaaaaag aaaaaaaaaa aaaagacct gcgtcctgga agagctagtg      60
tgagccgggc gccgctcgcg ccgtctcccg ctttgcatag tgcccgcaga tggctcgctc     120
cggcccaggc gcggcgatcc agtcgtcccg aagctgtggc agggtggggg tgggggtggg     180
ggccggggat ggaggccggg gaggggggagc gcagggcccc tctcccctcc tctcttccca     240 gccctcacc cccaccccctt ttatattttt ttttcctccc aagttctctt gccttgctat     300
ccccccttga atccgaaggc gcctcgcgat tgggtgctgg ggccgggtac gtcagataga     360
ctgtgacgtg cagtcttcct gtttccttca gctgtgtctt aaagtaaatc ttgttgtgga     420
gcggagccct cagctgaggg agcgctctga aataatacac cattgcagcc ggggaaagca     480
gagcggcgca aaagagctct cgccgggtcc gcctgctccc tctccgcttc gctcctcttc     540
tcttctttac ccttctcctc tctcctcctc tgctgctctc tcctctcctc ccgctcttct     600
ctctcctcct ctcctgctct ctcctcttcc cttagctcct cttcttttct tctcctcttc     660
ttccctctcc tcgcctctcc cctgctcctc ttctctcgtc tcccctcccc tcccgcctct     720 ctctccccctc tccctctccc actcgccccg ctcgctcgct cgctgtcgca cagactcacc     780
```

```
gtcccttgtc caattatcat attcatcacc cgcaagatat caccgtgtgt gcactcgcgt    840
gttttcctct ctctgccggg ggaaaaaaaa gagagagaga gagatagaga gagagagaga    900
gagagagaga gagaggctcg gtcccactgc tccctgcacc gcgtaagtat cttcttcttc    960
ccctcgtgag tccctcccct tttccagaat cacttgcact gtcttgttct tgaatgagaa   1020
aggaagaaaa gagcctccca ttactcgagac ccgtgtaaac attattcccc ccaggagaaa   1080
atggtgttat tcaaatgaat cataataaaa tagcctctaa acagtttcta agcgggagcc   1140
tccgtggaac tcagcgctcc gctcctccca gttcctaaga gtaagtgatc ctcttggctt   1200
ttatttcttt ctctttcctg ctggtggctg ggggtggcgg tggcgatggg ggggaggctg   1260
atgttgctgg acttgtcgct gatcttgtca ccttttgtgt actgtttctg gggtgtgagg   1320
aggcgtttgc tcccttttcct tctttctcct gctctctctt ctcaggagag aggaccgcga   1380
gagggaccgg gtcgcttttt tgttcgtgga gatccccgct ttccgccaaa ccccatcctt   1440
ccgatctccc caggctaaaa ctccggggcc ggtcccccttg tcctttctct ttgtcttgtt   1500
tattatagct gcctttcttc ccggctcttc caatttgctt gtcatttgca tacctttcac   1560
ttctcctttt ttaaccccag cagaggaccg ggaactggga ggaggagaga gggaggtggg   1620
ggggcgctct gttactttcg tctcaaaacg ctgtcgaagc cgaattgtgg aaatccggct   1680
tggaggggag cggtgatggg tcccgggaaa cgcgcgcggc gcccctcttc cgagctcctg   1740
gacccagggc tgggtcaagt tgagtagggt aaggcggcac cgggaggctc ggggggtcgc   1800
gtggcggtgg gattgggaca ccagcacgag gaggaccgga ggatcgcggg ccgggtaaga   1860
gtagggggtt cttgggcagc agaaatggga ggcgatgaat ctcccagcca tcgctggcag   1920
actatggtgt tgggcagctt cggtctggtc tcgtctgggt ggtacctacc gttttgcccc   1980
agttaggagg actggggagg gaggacagga gaggtgagag taattgttac tgggaagact   2040
agtgaggagg gcgggaagag ggagggaaga gctgctatct tgcctgagca gatcaggagg   2100
gggacgcagt gggcggggggg agacatcacc caaagtccag tttagcaagt tgttgattct   2160
tctggtgtgc cagcccgtta ctcccctgc tgaagctgaa ggttggtgga gtgatggagc   2220
gtggggatgg taaaggagga gtaagtagct ttccacagac tcccaggtct ctggccccctt   2280 cccagcttct tgggaaattg agagcccctcc aggcagacag agaacagaac tagaaggagg   2340
ggtggtgctt agtcttaaat agctcaagga ggcaggttgg agtgtgaaac tgctgttctt   2400
ggcaacccag aaggctactc tgcctggggg aaggctggaa actcacctgc ttgttttttat   2460 ttttccgaga agatctgtgc tgtctccttg agcttataaa aacagaggaa gcacagggtg   2520
gcctcctcgc aaagtcaagg ctagaagact cccttctcct gttctctttt ccactcatgc   2580
cctcccttat ttaaaaaaaa aaaaaaaaag aaagaaaaga aaaaaaaaag aactcatttc   2640
ctttcctaac ctaggtaggc agaaatctat tagcagagtg cgcatgggca gggcctgaca   2700
ggtgtgttgt gtcaagaaag acaggtgcaa atttcctctg tgtctgtgtg tgtctgtaca   2760
gctctagacc acaatgcttg ctcgagggtt ggagaggttt atgaatttat ggttgtcctg   2820
gttaatagga ttgtctgggc taatgggaat tgggctgttg ttcttttgag ccctgccatg   2880
tgagttcttg gggtgggggg tggggcaagt ttggtatgtg tttgtttatt tttcttaagg   2940
atattggcag tctactgctg aggctgtgtc ccaggcttct gtctgccagt cagcccaaag   3000
cacccccact ttaggcagca ggtggaggga gactgacttt tcctttgctt cctaccagtt   3060
tatgcctatc tcccaggtct gtgcttggca gagagagaga gagagagaga gaactgtcgt   3120
gtgtgtgtgt gtgtgtgtgt gtgtgtgtgt gtgtgtgtgt ttgtgtgtgt gtggtgtatg   3180
```

```
ctttggatag caatgagtgg tgtgtaactg ccaagaattc caaagtcagt ttgaaagtgt    3240
tactgttgtt aaagcttatc tttttaagca tgctttctcc ttgcccagaa agaataggta    3300
tgtacataaa ctcttttcaag tcatatgtta aataatctca taaagtagaa tgagcctgtc    3360
attgtcccag acatgtgcca aatgtcctag atatgaattt gatggagaaa gaaaatctca    3420
agtacatgag aaggtaactg tgcttttcta ttctgatgca agatgtgaga agtcagttct    3480
acagggaatt tcttgcaaga acttctgagt atttccaaaa tgaaatttt tgtgtgtgtt    3540 gagggaggaa aacgagagta ttcacattaa cttgtccatg ggttaaaaca tggacatgta    3600
tatgtaatag taaaataggt gaagctaagg actgtggctt gatgtgtgag gaaagttgtt    3660
gggaattcaa tgtaagcact atatctggct tcttaaaact tgacctttta aaattatctt    3720
taaacagact acttctgtag actgagttgc acaggaatag gttggttggc aaatggtttt    3780
tgctcattgg ctttgtgttt gggtagttat tgtttccatg aaaatgagat cgtatgtgtc    3840
atttattctg tagacttcaa cattaacgtc cccccacctc ccaaacacac acacacacac    3900
ccaatacttt ccttggatgc ttttgaagtt ctttggtaat taaatgtca tctatgccta    3960 tgttcatttg ctttattttt aataggggtt atctgtgctt ggcacttatt gatattttat    4020
gtgtccatta tgcagaattc tatttagttt aatcaccacc ttgtgggaaa aaaagtcat    4080 gcatacataa catgcatctt tgttctcact ttattcattt cctagcatca ttcctctata    4140
agcagcacat gctatcttaa aacctaagct ggcttattct gtaagttgcc agacttcctc    4200
tttatttgtt taaaactcaa acaggcctct tttcatgaat gtcttatatc attttaggga    4260
ttgtcttgaa tttgcagtgt aatataaga agttttaggt ttcagattaa caaaagaaat    4320
tataaaatgt gactgatgtt ataatatgaa aatagattgt gcatgatgta tcattatagg    4380
attttaatta agtacctgtg taacttggaa aggaaccata tacataagga atttctcaga    4440
cttattgcct gtgcattctc aaaggacatt tagagagttc aattttctgc aaaaagaaaa    4500
aagtgtattt tcttaagatt atttcacact ctgtcttatt tacctatctg ataagttgtt    4560 acttttaaa caagtagaaa ttaatatttt aggcatgtct cagaaaatgt tctgtgttca    4620
ttttgcaggt gaaaagtgtg tggaattttt gatgggatgg gagaatctta aatgaaatct    4680
taaatgattt gagaagtata ttatgacagg aaatttaaaa acctgataac gcaatcttag    4740
ttaatttagg tattaactta tgtcaagtga gttcttcaaa ataaatatca aaggttttct    4800
taacctgata gggagcagaa atatctccaa tatctctgaa gaaaaagttg ctaattagca    4860
gaaacaaatt cttgaatgta gtgaagggga caatttaatg attcagggc tacttaaatc    4920 agaccatctg atttttcccc tttgaatcac taatttccag attgatttga atattctttt    4980
gttaatgata tcctatttga aatttcataa ccaggttgac ccaagtagat tagaggccca    5040
tacaaagatg attttctaaa agaagtcaag tgtaggcttg cacaatttct tcaaataatt    5100
ttatcaacaa agacagatca tctaaataat ccaagcagga aaccatgcca accttacact    5160
ctccctgcct cataaaagat ttgtctgaac tatctggata attaccgtaa tgaaacactt    5220
ctttgtccag aatctggact ccagatagat gcagtaaaag ttgaatcctc ctccccgaaa    5280
taacttcttt attaaagtag agcacttaac cactttatac ttcacgctgc agtgttcctt    5340
tgaaattctt tactgaaaat tctttcctcc taaccttaag tcatcagttt ccttagaatt    5400
ttgcatgtta aagagaatgt cagataattc agatattaaa ggagactctt tggagtagt    5460 taaacctgt tttgattata cctggatgtt tattcttcta atatctttt ctgggaggaa    5520 tctgctatgt taagatatgc attgtataag aattactaaa gcatttgtgt aggttatata    5580
```

```
cgaagtgatg caacaaaata tttaatgatg aaaaactcta tatagacttt cacattaatt    5640 aaagagggt ttacaggaat agagtaagtg tatccgatca ataatacatt tgggttcaaa    5700
ttctcatcag tattttttctg catccttgct gatttggaca tccaccagtg ttgatcaaaa    5760
gcttcatatt gcctagtgaa actgaaaatt aatgttaaaa tgcaaatatg atatgcatca    5820
ataataattg caggtgaaac atgatagctt aatacatatc ttgagaaata aaggagttta    5880
aaaaatatca atgataaagt cattccatgg cttcctttaa attctgaact ggaatatcat    5940
ggaagcactt gggaaatgtt tttaagagat ttaatttata ttatggtaac gtaacagtac    6000
attttcttat gtggtaaata tattcatata gatatcttgt ttatgaaatg tgatgctaat    6060
aaagtgctgt gtcaaccggt tattattatt aatcatgcc tatagcttcc atgggttatg    6120
gttccagtgt gtgctaccac tatacttta tttctaaatt aaatctaagc tatatggaga    6180
gatatattta tttgtgccta ttaatataat gccttgtcct ggattatata atttatctta    6240
tttttcccat ttgttttgtc ttatttgtta tgttccagct ggacatttta caacaagacc    6300
taaaagtatt taaattcttt tagcccaaga cagatacaaa tcgttattta atctaaaaat    6360
gttgactgaa atagaattac aaaattagtt tagtttggtg aatatcaagg gagttatatc    6420
ttgttcttaa cagactccac aagcatttct ttccaccta ggaagagcac agccctcctc    6480
ttggctccag catggggcag ggatgcagct gttgatacct aggctagatg agaggaagtg    6540
cagttgacgc agaggtaaat ggcagttgga aaggaagga tgcctgggga tgaccttgtg    6600
ctcatcagcg acaccagtct gtcctttcca agcctgtgtg gcagagctgc tcttcccaca    6660
gcaaggatgg caggaggaaa gtccagtttg ggtgttaggg tgaacaggga gagaaaaaat    6720
actgcaaaaa gtttgtttga cattttgatt ggagatccat gtgctttgca ggtgatagtc    6780
aagagaaaag gatttgcata caaatagaaa agatgtaaaa tttaaaaata agggcaataa    6840
gctctatttt ggggaaggtg atatacacac agaaaaaagt cttccttgta accgcccccc    6900
atgcaagtgt ttctttgatt aacagagctt tgaaatgatt catccttttt cttgtctcag    6960
cctctccttg ttcttttctgt catctgacag ctaacctgat ttatcagatc taatgtgttt    7020
gtgtagtatt tgtcactgca ttttttgtatt cctgaaacca attttattat tagtgtttga    7080
aagggtctca atcattctga attcaatttt gaacccaatg ttgtagttct tgagaactcc    7140
atctccattc taagttcagg aaattttatc ctgaagcatg caaaaagtat ttcattctca    7200
agcatgcaaa tatatatata tatatatata tatatatata tatatatata tatatatata    7260
taaagaggta tcattttgct ttcatgatac cctaaagcag gctcttttaa aatgttttat    7320
ctttctatag aaaccaggag caaagatttc atgaggaaat cactgtcact taaaaaaata    7380
tacatattgt tgccatctaa gcattgagca ttttcttgat ttttacaggt tatttcatgc    7440
tgaaattatg cctatttgca tggatagtca ttcttttaaag ctagccacag atgcagtcct    7500
agggagcacg tagatgtttt tacaggtgaa ccgaaagaga tgggagccgt tccagacact    7560
ctgcatgctg cctttggcaa tggacccgt tattgtgaag atgtgctctg ttaagcaaac    7620
gtgaagttta atattagata aacccaacgt gaaaaaaatt ttcattttct tcataaaatg    7680
ttaattataa acaaaaagat gtgacatctt atatgtctac aaaatttggg attagcatca    7740
ctagttaata agttacacaa tgtcaagtgc cttttatgaa attcaaagaa ggatgttctc    7800 ttttttatact gtgtttccaa gaaacaatgg aagttcatat acaaagaaat atttcccttt    7860
ctcacacatt tgatggacat tattttcttt cttcttata tatcttctttt cagttttttc    7920 tgtttttttt tttcctttaa tttggcacag gaaataaggt tcacaaatcc tgtatgttaa    7980
```

```
agagtttctt tgggcattgg acatattatt ttggcagatt taaacagaag gaaactagtc    8040
ctgaagatat atttatcttt atctcggtca ataacttatt attcctcata ttgatttcta    8100
aaatgtggta acatccttgt tttgcagtga atccaacttt gtaataattt gtcattaaaa    8160
ggacattatg aaaatgtata aatattctta tagttacatt aagatatatc aacagatatc    8220
atcttcacct atgattttac aagtaaaaaa tgcatagcta agctaaataa gcagacttat    8280
aaaatgacta ttgtgcattt atttcaatgc taaactgacc atttatgttt gaaagatgct    8340
gctgctaagg gtgttctcct tcccatttta catatgacaa aaatattgta aaattcaaga    8400
ataaaagctc tctattatat atttgcattt attttagagt cctttccctt taatagcgtt    8460
aaaaccacac taattgtaat gcagaaatgc aattttttcat gtgaatttct catagtctca    8520
aaatttaacc ttatttctta agtatagagc agtttcatct tccttataat atgaatctca    8580
atgcccaaaa tttaatcaat tggttgtcag aggctgtgtt cttataatct actgtttctt    8640
ctgaagataa acagtatcat tttaggcatt tgtgagagag aatcatatta ctggtgctta    8700
agcagttttt gcttaatttt tttttaatct taatccatct taaaccagtg gagcagaaat    8760
atttaaaaat gtttcatttc aagcagagtg cataataaat tgcaataatt gtaatgtgcc    8820
ataaatccca gagcctatgc attttgcatt tgattcagga ttgaggtcag gaaatttgga    8880
gaaatttaaa gaaaatgatt catcagtcct tttgttctgt tggccagggt cccgggattc    8940
ttgagctgtg cccagctgac gagcttttga agatggcaca ataaccgtcc agtgatgcct    9000
gaccatgaca gcacagccct cttaagccgg caaaccaaga ggagaagagt tgacattgga    9060
gtgaaaagga cggtagggac agcatctgca tttttgcta aggcaagagc aacgtttttt    9120
agtgccatga atccccaagg ttctgagcag gatgttgagt attcagtggt gcagcatgca    9180
gatggggaaa agtcaaatgt actccgcaag ctgctgaaga gggcgaactc gtatgaagat    9240
gccatgatgc cttttccagg agcaaccata atttcccagc tgttgaaaaa taacatgaac    9300
aaaaatggtg gcacggagcc cagtttccaa gccagcggtc tctctagtac aggctccgaa    9360
gtacatcagg aggatatatg cagcaactct tcaagagaca gccccccaga gtgtctttcc    9420
ccttttggca ggcctactat gagccagttt gatatggatc gcttatgtga tgagcacctg    9480
agagcaaagc gcgcccgggt tgagaatata attcggggta tgagccattc ccccagtgtg    9540
gcattaaggg gcaatgaaaa tgaaagagag atggccccgc agtctgtgag tccccgagaa    9600
agttacagag aaaacaaacg caagcaaaag cttccccagc agcagcaaca gagtttccag    9660
cagctggttt cagcccgaaa agaacagaag cgagaggagc gccgacagct gaaacagcag    9720
ctggaggaca tgcagaaaca gctgcgccag ctgcaggaaa agttctacca aatctatgac    9780
agcactgatt cggaaaatga tgaagatggt aacctgtctg aagacagcat gcgctcggag    9840
atcctggatg ccagggccca ggactctgtc ggaaggtcag ataatgagat gtgcgagcta    9900
gacccaggac agtttattga ccgagctcga gccctgatca gagagcagga aatggctgaa    9960
aacaagccga gcgagaagg caacaacaaa gaaagagacc atgggccaaa ctccttacaa    10020
ccggaaggca aacatttggc tgagaccttg aaacaggaac tgaacactgc catgtcgcaa    10080
gttgtggaca ctgtggtcaa agtcttttcg gccaagccct cccgccaggt tcctcaggtc    10140
ttcccacctc tccagatccc ccaggccaga tttcagtca atggggaaaa ccacaatttc    10200
cacaccgcca accagcgcct gcagtgcttt ggcgacgtca tcattccgaa ccccctggac    10260
acctttggca atgtgcagat ggccagttcc actgaccaga cagaagcact gccccctggtt    10320 gtccgcaaaa actcctctga ccagtctgcc tccggccctg ccgctggcgg ccaccaccag    10380
```

```
ccctgcacc agtcgcctct ctctgccacc acgggcttca ccacgtccac cttccgccac   10440
cccttccccc ttcccttgat ggcctatcca tttcagagcc cattaggtgc tccctccggc   10500
tccttctctg gaaagacag agcctctcct gaatccttag acttaactag ggataccacg   10560
agtctgagga ccaagatgtc atctcaccac ctgagccacc acccttgttc accagcacac   10620
ccgcccagca ccgccgaagg gctctccttg tcgctcataa agtccgagtg cggcgatctt   10680
caagatatgt ctgaaatatc accttattcg ggaagtgcaa tatcctttta ttttcccctc   10740
gaggaaaaaa caaaccaaaa aaggtttccc aaaaggttgg gtttacacaa tatctagagt   10800
aatgtagatt agtatcttct taagaaggca acctttccca ttattcaaag gataggctt    10860 ttatcagcat gcgtgtgcca ttcctgattg cagaaaagct taaaactaag ccaacatctt   10920
tgcagcttcc acaagttgtt cactgccttg aggagctcct atttaatatg tgctttctca   10980
gcagtgtttt ttttctgctg ttcttcctgc attatcttct tatccctatc tcttaaaaaa   11040
aataaagaag tagatttaga gatgagaaaa cagtctcatt gtaaatactg attgaattct   11100
ctcagatatt ttttaaagat ggtaagttta atagaataag gagaaaagtc agttttcaga   11160
tccctaagat cccataagaa gaattctcag tgtaaaccat ctgcaaggct tctggtccgt   11220
ttaaagacag cccgatgaaa tcttaggaag agcgctttac aagtgggagg ttgaggagga   11280
agaaaaatgg atgtgggtgg ggagttagtc tctctttcat cttttaagtga gacttttttt   11340 tttaaggaaa tatacaggta ctgatttatt cagacagcat cggtctctct cccgttcacc   11400
caaggtctgt tctttgggtc tggtgcagct gcctctatgc atgattaacc tctgttcagc   11460
catacacaga aatcttttgt cccaacatac acaaagcaaa ttattttgga aagcgagaga   11520
gcacaattaa atataaaact cagctgtatt cgacttaaaa atggctcttt ttatgattct   11580
tttaaattct gaaactgacg tttatgtaga gataacagtt atatttttt attaggccta    11640 tcccgaactc cagctatttt taactgaaga tttttttttc tctctgtata tcggttcttt   11700
ctgtaaattt tttaaaaatc ttgtggtcgt tggtcttttg ggagtagtaa aatagtagca   11760
tttgggggca ggtggaggca tgtttcttat ataataaaca gatggatata aaatttagca   11820
attaagttgg ctgtgactaa atttaggatt ttgagcaatt gtcttgatga ctagagattg   11880
acattttcat atctaagccc actccagagg ctgccacgta agtgcaaagt cccagctatt   11940
ggtggaaata tgttttcctg gttagtggag gtcgtacttc aagccacctc tcaggataat   12000
agtgtagatt tctgataggg tgaactacta gggccctaat catgagtcct gcttgggcag   12060
ttaaacatgg agtctctctt atactgagca agagaagaac attgtaacag aaagggaaga   12120
gaaagatgtg ggagatttct acatatacgt agaaatggag ttttagcttg gttgttgatt   12180
tcacttggac cttttgaaga tctaaaattc aatccaccag ccatgaatca aagctgcacc   12240
aagcaccatg ccttacatat tataagcagg cagtaaatat tgatcaaatg attggaatat   12300
cgctgttggt gatgagaaag gcaaagtaag aagacacaat ggcttgaatg gttttgtgc    12360 cctttgcaaa aagagcatct tcagaggttc atgtaaggct aatgtctagg gctaagaccc   12420
cattgcaccc cagagatctc ttaacttcat tttgaaccag gtagttgtga tagtgggttc   12480
tttctgtctc tctctctctc ttacacacac acacacacac acacagacac acacacacag   12540
agtaaagtga catgcgtgcc aattttggtg aatatttaaa gatttaatgc caggtttcaa   12600
aactcctgta agtccacact aagctcttta gttcaagatg ccagtttatg gttttctttt   12660
aaattagact tttcattata accagatcat tataattatg gctgtgcttt ttgttttag    12720 tcttctagga aaaaaatctt ttagattgct ttaagtgttg gctatgttca ttgtctcaac   12780
```

```
ctctccaaat ccccggagga attttgagga tttgaattga aataagttcc ttttattttg   12840
atacatatca aaggctttaa agaaaatata gttgcttctt cttcagaggc atgacttctc   12900
ctttcttcta tcaacataac tttctgtcga gcggtgattc tgttgggaaa cacccgtgtt   12960
catgtgaaat gttagttgct cacactcaga attgtttctt tcatatagct aaataatgtc   13020
ggcctctcgt ggcaattagt gattacattt tccacctttt ggccttctat gctcctattc   13080 ttttccccccc tctactatta atacattgca cttttaacca tttatctcat tggtatatta   13140
tttctcagga agagtaagat aggcaaacaa ccttttctat agttcccaca attctgaaac   13200
cagtgaggat ctgttggttt gtagagagat tgggcccact tttctcctgt ctctacctct   13260
gtatggcagt gtgttcttcc cttgatttaa ctgttagtgt gtaggcaaaa ttctcaagct   13320
tttactttga agaaatatct gggaatcaca gtgagtgatg tcttacttca attttaggga   13380
tacggggcca tatatgatcc ggttgtacag ttattcctcg aaaagatcaa tagaaatggg   13440
cagaaatgta atgaaatggt acaactgtga ttgctattat tatgttttaa ttttcgttc   13500 atggctttcc aaactgttat atataattta attttcagg aaaaattatc tcccactcca   13560
aaaggtacca tctgtttttt gaacaaagta gctaagataa aactattaa gaacaccagc   13620 ttatcaggtc aacccattct acattcacca cattaaacat atatgttctg taggatagaa   13680
cacactacct cattatccca tctagtagaa gggaaatagt gaatgtgtat gcaagttaaa   13740
ctgaatttca gtgcacctgc tccaagggct catgtcttgg attttaaaaa tatgttcagt   13800
atctttgcaa atgaatctgt ttaatcaaat attaagtttt attcaaattc caaagaaac   13860 agtcagccaa ttgctttttct tcatgatgtt ccttgtcatt catcctcttt gcatctcaag   13920
aaaaatagcc tagtttaggc cccaaacatt tgcatgcacc cagttaaagc acaagaggag   13980
tagtataagc cgttaagacg tgcaggtgaa gaaattgagc ctgttctctg aaacagccgg   14040 cttttttctac tcaacttta gggagaatgt tagaaagact tgaagtttag aaaggaaaat   14100
ggtttagtaa tttgaaatta aaatccaacc aggaaccata gattagaaat gaatttctga   14160
aatttgaaac catccacaga aattgatctt atacatttt agaagtcttg tggaggctat   14220
agtacttata ttagctagag caaaacatgt agattaaaga ctaaaagact tgggctcct   14280 acactacccc cctcccctga aaaaattat aaagtaagta aattaaaaaa aaaaaatccc   14340
tacactacac agccctccga ttatggtgaa cttcctagtg ggagttacga cttgctctat   14400
cactgtcatt atgtgagaga gtttagatct tttctcccca ttttagtttc taggggggaaa   14460 acctcttaga aacttagcaa attagggaat aaggcagaac taaaattctt taggttcaa   14520 atgttttgga aaatgtaagt agtctcaacc catttgctgg gaactgcagc acgtacaatc   14580
tctagctaca atccagagtt tagctggaaa aaaagaattt tcttcctccg ctttcacagc   14640
ttattattct cccatttgcc ttttttgctgc ctccgctgct cctcccgtgg ctgctgttta   14700
ggtaaggtta tattgtactt ggtaaacaga caacacttag gttctcaggt tgtttgaaca   14760
ctgctttacg ttcagctgca gtaccctgct tctctgatct tttatattcc cgagcagatg   14820
tctttcatta atttatggat ttatcatctt ttcttttttt tttctttttt cttttttttt   14880 ttttttttaca cctggcagct gtctcaagtt tcaacagtta ttgtctattt tgcattacac   14940
atagaattga atgtcatctg tcttcacaaa gctatggcta agagaattga ggcacagcca   15000
catgagctgc tgggacagat cttgtttgcg ttccatcccc cctcaccca ctcccctta   15060 cctccttaat atttatttgt gctcattttc tttcctggcc ttgaatggag cttagctcgt   15120
gttcagtaca gctgtatgtt tactgaatct attccatcat gagtcattgt gcgtgtgtaa   15180
```

```
gtatcctgga acagctagt gcttctttgg aagaacagtt gcttttcagc acaagcactt    15240
aaaagggaaa ttaaccaatt ggtcagttca gatttatttt gaggagaaaa aaaggattat    15300
ctaactgttg cctttaaat gtttcattag ttatttttaa tagtttatta gaaacatata    15360
ttttatggga atttttatctt aattacacaa taagcaagag ataaagatta attctgtgtt    15420
ccatttcaac tgatcagttc caagtattac caacaggaaa cattttaaag caaaaatgaa    15480
cttgagaaat ccaaatcaga ataattttt gttagataaa aagcctctaa atactgatca     15540
aaataaaatg gatattttac tttttttaga taaaaagaac aaaaacatct tagcataaat    15600
tagatgtatt aaaagcttca ggaagttttg gtagctcagt gcccatctaa gaaacacaga    15660
aaaacacttt gtattttgta tgacaccaaa ttttaaaaga tttgtgactt ccaattaaat    15720
gcatgacgtt gtcttaatgt agccatctga aagaaaagat tagaacccag atctgagagt    15780
gtctgtcaaa gtttggactt gcctaaaact cttatcacaa ggcagtcgca gacagcttgc    15840
aactattatt tcacttatcc atttggacag atggtcctga agtgtgctgg gctccttag     15900
tcttctgtat cagtctaatg gaggttactg gagggccttt cagccctctc cttggcacaa    15960
gaagtatgtc agtcataaat tatcgtcttt gtaatcatta aggatctcaa acaaaaacac    16020
aagttcagtt aagctgcttt ggcttacaga tataaaatca aatttctttt ctttagtgtt    16080
tattttcagt ttaacaaaaa ataaaaaaat aaaaaacctg cactacttaa cttttctatt    16140
tacagaccaa ggtgatcttt ttaaaattgc atgggatatt aaagggaatg ttaattgaac    16200
aaattctcag cagaatattt ggttaaacac cctgttataa gtagtcaaga gcttatccat    16260
attaatttga ttatgcttct ctagtaactt tctggtttcc ctccattctt aagattagtc    16320
acgctagact tgatgaaggt catttggaaa attttacctt tcctaaatat ctgtgtttat    16380
ttgacatttc tgcctaaggg gtgaaatttt tgttgggtag ttgtgtgagt gtgtttgtgt    16440
gtgtgtttgc acacacaagc acactttctt ttctttttt tcttattttt cttagacact     16500
cttctaaaag aaaatcctta gagaagcttc taggaagggc ccttaattga ccttgtgggg    16560
gaccacattg atttttctcca cgtgcatctt catttctgat aaattataaa gccattaatt    16620
tgctgaggaa atggcagggc caggctgcgg cacagatgtg accagagcca tcccagctct    16680
gagtctgctg aggagtgcca agaatctggg ggagaatcag gaagcctgga ttgttatggt    16740
tagcctcaca ttctcttggg aactgtttta gttgctgctg tttacagatc taaaaggtaa    16800
tgatgttttcc agataaatag gccttcttat ttgggtaag tggccattta ttgatctgct     16860
aacccacatg tattgatttg ttagccccaa ctactgcgtc actctcaaag gagttaacta    16920
taaatccaag acaggcaaat tgtatttggt tttggaccat tgctttcaca aaagcaacag    16980
ccccctccct gtcctctcca tgccaaaact actcttccca agttttagct attatttaaa    17040
aggaaaaaca attaaaagga tataataaga taaaaagcaa gtgagtcaag atgctccatt    17100
agattaacac taaaaggtaa aatgtgaaac ttgcatagca gtgttcaaaa taatgcattt    17160
tatattttca tgtacattag tagaataatt tgctttaaac tgcagagtgt ggagagaaga    17220
acaaacagaa ctgtaattgc aaggaagaaa aaaaaacctc ttatgacaag agttgtgtag    17280
tacatgttgg gtgcatttgt ctccttagca acaagtgaat gtatagatag cctaccgacc    17340
taaagcaagg aaaatatttt gccatcctca ccctaaagta gccaagattc tgcaactcaa    17400
ttgtgcatcc tcaccattgc atgtggcaac ctctgacagg cgacggtcac tgagcaaatg    17460
gcagcaagtt agcaatggat gccatagcca gtgtcatata ccttccagca ctcccaccgc    17520
agcttgatgg acccccagac tctatggagg tggggactgg agggagggag gtgggagtcc    17580
```

```
ttgtgcttac agaattgctt ttccttaacc aattgcatcc tacatgcagg aaggattgtc   17640
acccaatcac ttgaaaaaag caaagctcat gttttttttat acccgttatc ccagctccaa  17700
tatgctgaag acctacttct ccgacgtaaa ggtagggact tttttttattc ttaattttttt 17760 cattttctat gcatgtggca gtaatttgaa ctcccggaag ttaatggaga tgaatgtgga   17820
attggtttat tcctacacct gtgttataat tgatttaatg cacttgtctt tttgtctaaa   17880
ggtgtgttaa gcaaagatgc cacttgtgta ttaagattgg aagactggtg ttaataagtt   17940
gcatgggttt ccaatgtagt ctgaaaaact tagcctctgt ctttatatgt ttgagtagct   18000
tctttgaaga aatttcagct ggtaatggat gggtgtgctt tagagaatgt ttttcccctc   18060
ccctcagcaa cagtaaactg tttctgtttt tgtttctgtt ggtttcccca tatttgtgct   18120
tatgaaagca aactctagca cctctttttc cccctgtcga aaaggagcgt acattgaaat   18180
tctctatgca gtagctgctt aaaaacaaaa gtgatgattg tctcttattt acaacttaat   18240
ttgttgttga tgtagagtac actgagcata aggagaatga ataaagtgac agattcagga   18300
cacattattc aaatgaggat atgaaagctg tcggcctaca gctgcagcct ccctcattct   18360
acagaatatt gggacctcct ggttctctct gtgtgtgtat gcgtgtgtgt gtgtgtgtgt   18420
gtatgtgtct gtgtctgtgt gtgggtttta agtaattgtt tgcatcaact tgatgttgtg   18480
ttaatcatct gtaactttt aaaacataga ttgggttttg atgatgataa tgacacacat    18540
ggtatcatta tcccaggaac ttgataaaca ctacattagc tgagattagt ttattagggg   18600
tgggtgtttt ttccccactc ctccccctgcc cacccccata tgtacaagtt cttctttctg  18660
ccatggagaa ctcacaagct gccaaaacac actcgctctt ccactgctcc ccgcacgcag   18720
cttgttttgt gcttgatgcc caagtggctt cattggcccc attttgcagg ccaactcatt   18780
tcagtttcct tcactggtgt tttatttggc cttataagaa aagttctgtt ttccctcctg   18840
tttgcttttg aattgtgtat caacttcagc cttttatctt tctccttccc tggctgtgct   18900
ccttaagtgg aaggcttgtt ttctccttgt tcagcaccag caaactgggc aagatgggga   18960
ggcagggaaa gtccatcacg taaatgtctg gataagacta agtgagcaca aacaaggctg   19020
agtgacacag aggccaggaa aagggtttgg gctttgtaga ggacaatcta gaatacacaa   19080
attgaaggca atttgtcacc tggttgagga ctgaccagct tctagagtct agtagaacct   19140
ggtaaagttt gtcttccagg gaatcctccc aacattttag ttctaggagg ggacatggag   19200
gacagggaga aaagggttat tgtgtgcaca tatgtgtgtg tgtgtgtctg tgtgtgcaga   19260
tgtccatgtt actcattcct tttagggcaa tgatcttcag tgttgtgaaa taataatgac   19320
aataacttat attctttgca tagcaatttt cacccagaag taggccaaag agctttacca   19380
actgcacaca taggtgtcac tcacccacca cggaaacaca gccacctgga gggtgggaaa   19440
cagcagccat tctgagccaa cactacccaa cagtagacgt caatattaga aacaatcatt   19500
ttttgtgaga gttcaagcat gcgtgcatgt gtgtggtgtg tggtggcaag tggggaagat   19560
tattgatctg tagctttata aataccatgc aatacaaacc aacaagaaac tgttcccatt   19620
cctctagaat gccctagca attcagcttt gcaaataacc actgactctg tgtagataac   19680
aatggaatac ctgggtgaat atttttatttt caaaagcact aatattcaga ttgttgattc   19740
tatccatacc ttaccatac tggaagagaa ggctgttaaa gtatatgtga gtctggttac   19800
taccaattat ccactgtaat ggagggggaaa cagtagaaca tatcaggcaa agcagaaaat  19860
cactgaaggt cacttctctt ttattttttgg aaggaattat acatttttaa cttttcctaat 19920 tatgttttttt ctttggttag taataaaatga atttgtatttt cttgagctta cactgatgag 19980
```

```
agtagaaagc catgcaaaga aagggaaagg tagtccaggc aatgtggtcc agagactttc   20040
cagaaaacaa tggcagagca ttctgggatt tcttcaatat taaggataat cacagatgtg   20100
aatattgaca atgtatacac acacatatgt gcatgtgcat gggttcacaa tacacatata   20160
catatataca catatctata gcttgacatt gacatacaga tagacaagtg tgtctattta   20220
tttgcaaggc tgaaagaaat agatatttct ttatatatga atatacaatc caaacttttta  20280 ttttggccag gattcaagaa atcactagag aaattgggga agagaactta gggtcttctc   20340
agaaatgaaa cctgcatcat ttatctggaa caagatatat gcatgtatct atggaccatg   20400
taatgcttgt tataatgaca tgaggctcta cttggtcatg gccacattca tctaggagaa   20460
aattcctaac tttagtaaaa tgtactcttt caaataataa agttatttta ttcaattttt   20520
tttttttgag acggaatttc actcttgtca cccaggctgg agtgcaatgg tgcaatctca   20580
gctcactgca acctccacct cctgggttca agagattctc ctgcctcagc ctcccaagaa   20640
gctgggatta caggaatgtg ccaccacgcc tggctaattt ttgtattttt ttagtagag   20700 acggggtttc accatgttgg cgaagcttgt cttgaactcc tgacctcaaa tgatctgcct   20760
gccttggcgt cccaaagtgc tgggattaca ggcatgagcc accgcgctca gccctcatat   20820
tttatttagt gatcataagt tcattttgca agcaaaaaca aaaacaaac aacaacaaca    20880 acaacaaaaa aaaccaggag aaaaaaatgt gagcagaaaa tatcttgttt cctgaatatg   20940
gtataacgta atggtccatc aaagccacac ttggaggata gagctagatg gggtaaatcc   21000
tctgacttgc tctagaaggt gagtcatgcc aaagtggtgc ccactccttt gtatttctcc   21060
ttaggaatgg acacagtgct taactctcca caaatgactt ccacctgggt aagaggtaaa   21120
tgcttttcaa ttaccttgga acgaaagagg tagagggaaa tcatacaatt cagagatgtt   21180
ggcatggcga gagttcttct tctacagggg tgatgtatat gaaggatgaa accagggccg   21240
acctagttta actcctagag caagaatcta aacaaagttc tatgttctca cagagagcca   21300
acttaattcc ctcataatga catttagcca aacaaaaagc tcagctcatc ggggctacaa   21360
atcctttgag aaggacaagt ggacaaatgt gagagagctg ccagggatcg atgggccgca   21420
ccagctccct gttcactact gggtgctgat tttaatgtac aaactaataa ctcttagacc   21480
actaagtaca gcagattcag tgtcatttta gctttgaaga acagacgctc acagcttttc   21540
aagccggcag tgttaaatga tgtatctcat tccctccacc ccttgagtca actgctgcct   21600
agccagatta aggtgtcaga ttgatttgtt ttatacatct tttgaccatg ctcattgaat   21660
atttaggaag tttcttcagc ccatattgag gctgagatgt cccgtgggaa gcattaatca   21720
aagtcacaga gactcgtaca ctgtggaaac acagcctctt tattgtagcg attagttttt   21780
gcagtaacac attaacacac tacagagctt tcctttatag aacaattgat ccttttcttg   21840
taagccacta cagaatgagg gaaattaact ctttaaagtt taatacttttt tctcccccag   21900 tgtgaatatc tagaaaagcg ggggcttgct tttgctttta gccggcgact aaaactgaac   21960
aaattttagt tcacttctcc tggagggaaa ccctgttcct taggctgttg ggctggtcat   22020
ttcgcttgcc tcatgtttgg ggagtctgtt gttttttgtcc attctttctc tctggtattt   22080
ccattctcca acaataagct ttaaatctcc ctttatgtcc cattcgtaaa taatggcaag   22140
tgcacttact tttttgtcct ccccattagg tcattcgtga ccattctaga aaaaaaatac   22200
ccttctattt ttttcctcta cagtactctt gtccatatga gacaatgtct tgtaacaatg   22260
cagaagccta atcccatgt caaagcaatt ttcattcccc agtgcacagc ctgctatcat    22320
tttgtaatgt tttgtttctt attctaaaag aattaaaaag gaacagtaag ccgtcacggg   22380
```

```
ggcctgtagt ccttatctca gtgtctggaa atttggacag tgtattttac tgctgagata   22440
aaatggaaag aactccaagt tcagcaaatc gtaatgggtt taagttctat tgaaatcggc   22500
aaccagaaga tcagataatg ggggtccttc agttgtcttt ttaatcgggt tccccgcgag   22560
gctgaataga gacagagcag acacacagag tgaaaatata attcttggat aggttaagta   22620
catgtttgaa ctcttgcaag cagaagcgat ttgctgatga cttaatcatt ttctggtcaa   22680
ttatctgtaa gggcccttgc aactccatgg caattatgat gcaagttggc cttttgggag   22740
aaacaccagt ctctctgctt ctgtttcctt gtgacttcca ttctctgcca taaattttca   22800
ttcatttatt atctttgcta gtatagaaac aactttctgt gtagtaatta gagccccaat   22860
acacacttta gctgtcatct tgttggagtc tggatgttct catggcctgt gtttgataag   22920
tgctctttgt tgattttga tgaatgtaca tcttttctg ggggcccagg gaaggggatg   22980
cctgtgatga caaaaggcag ggggttgtct gtcagcccgc tgatataga gctatggatt   23040 tattggtttt gacttggcaa gttgagactc atctgtcctt tacgtgagca gaggactgtc   23100
aataaggatg gtatcatttg cagtgcatcc agaaagacat cttcatttca aaggtcatca   23160
ggaaaccttg gtaaacaaag ttttaaggcc taaccatgtt atagtaactt ggcatttaaa   23220
aaaatgtaat aaagctcctg tctatgccat ctgtgtactg tgtcctaacc atgcctccca   23280
aatggcagag ataccaaggg aggggacat gggtcttatc caatgctggc ttcaggaagc   23340
aggtgaacag gcaccaggag ctgaccagac ctcaccagac atgaatgccg tgggcaaaca   23400
ttaagtggaa tcacagttgg atggacatgg gaatcactca ttgccaaaaa aataagcaaa   23460
tgccaactcc tcccatttg tgggaaggcc atttgtctgc attgaagggg gctgtaatgc   23520
ggtgatacaa atcctcactt aaaaaaaaaa agtatatcaa actagtggta gagtcatgtg   23580
gcacatcacc tctggtacat gggagtaaca acacttccag gattctatgg cttcaatgaa   23640
tgtccataag aagtatataa atgcaagttg ttctactgaa agatgaagaa caatggttaa   23700
aaataaagat gttcggctta aggaaagtct gatttagaat gtgacttttc cacttgaaag   23760
gtagagggtt gtgatatgat ttccattact gacaggtttt tataatttct tgtaagtata   23820
ttcttcctct tgcctctctt gccaccattt tggtggagtt aaatacgtat cttccaagt   23880 aaagaaggga cgggaacatt aaaaatgctt cagacactta aaaaaataaa tgaagaaaat   23940
ggcaatgttc ttatcctttt caacatttaa atttaacagt tcaacagatg cattacctct   24000
cagctcatca agtggtttag caatttccgt gagttttact acattcagat ggagaagtac   24060
gcacgtcaag ccatcaacga tggggtcacc agtactgaag agctgtctat aaccagagac   24120
tgtgagctgt acagggctct gaacatgcac tacaataaag caaatgactt tgaggtagga   24180
actaatcttt attttttggt catctccctt ttcctttttt aaaaaattta ttttctttag   24240
aaatgtaccc aaatctgttt ttgtgttggt ttcgcataca agcatccccc aatagagtaa   24300
caggtagagc tgtgatgagg agcttccata gtccccattg gaatcatgag gctctgaccc   24360
actgccattt tttccccatt ccctggcttt tcagcttgtg tggaagactc atttggccac   24420
agaaagggaa actgtagaat ccaaagaaaa atggcagcaa gcagcaaaga cagagtgatt   24480
cattttccaa ggaagaggtc cctactccaa tagaccttt tcatatttag gttctgagag   24540
gtcaatgagc tgatacatgc tatgtgcaat ggtagctacc aatgttattt tcttaaaaag   24600
tctagaaacg ttgatggggg agtgatcatg gtttctgact ttgacattta gtcccttttgt   24660 ggaggaaatg gtatgataat ttactaagta catagcataa gagatccatt gacatctttt   24720
tttgggattt tgtttctgtt tttgttctt ttggaggaga gactcgtgtg ttttgcctaa   24780
```

```
gtgtaccttc acaagcatgc tgctctttgt acaaacactc tcatacacac ttatatatat    24840
ctgtgacgtg tatattctag atccacacaa agcagcatag agaattccca gaaagcaata    24900
tccatgcaac aatgaaagat gtgtggctat gagtaaggca tttctttatg ggctaatgtg    24960
gtgcctcagc aaacagtttt catcacaacg tgatgactct ctgtgagaca acactagcaa    25020
atctcccagt actcacaaag gcattttgct gagccctgct ggctgaggca acagtagttg    25080
gaggtgggaa catggcaaga attctgcagg ctgaactccc tgatgatgag atcagacagg    25140
ctgtggcttg acaaagttgg tccatttctt gtattatctt ggctagatgc tgtgccatct    25200
tgagggtagg aattttttct ccaacgtctg tgtgcacttg gaccttatgt taatattctt    25260
gctttcttct tgtagatagg tatccaggaa tacccaggaa gttccaaatt tcaaaggaaa    25320
gaggacacct tggcctcgct ctgtcaatta aggggtctga cccctagtac tcttcctgct    25380 tgccccctc cttttttcg gctcttgtcc ctacagttct tggcaatgca gaccagttat    25440
agtggcttat aaagaattga atatggaagc tcagcaatgg ggaagtcata gttttctttt    25500
gaaagtttga gtagttatag tgtaagctac ctatttgtct ttgctctcta agactaatat    25560
attttttgcc aaatgtgtga taaatgaagt ttgggtggtg tgtgtgtgtg tgtgtgtgtg    25620
tgtgtgtttg ctaaatacat taaaagtgag aattcttcgt gtactgctcc actattttaa    25680
aatctgtttt taaagtctca gttgtaatag agcactggct cactataatg acagagcact    25740
agcaggcttc ttctaaagct gaagaatatg attatggcta accattttaa agaaatctca    25800
ttaagagcat cttttctccc ctgcctttct gctaagcctg ttgccctaaa ccttaagcta    25860
agagacttct gtgtgctagt gaattattta cattacatga tgacataagt atctgtttgg    25920
cagcatacat caagcttcat gaaagaattg cccaagattc atgagatgac ttctgcattt    25980
ttgctatata aaatacccaa gaggacaagt ccttaaagtg cgcacgaggg ttttcgggtt    26040
gcttaaacct tacctggttg gaatttaatc cgctacccac aggccagggg ccaaaatgac    26100
acaaacaggg gatggctggc atcaggaggt acccgacaag ctgctccatt tagcatcatc    26160
taaatcctct ttaatatgat taacatctaa tatttctctc tttgtgaatc atatccactt    26220
ccagccaggc cacctctcct ttatctgcag tgtctatttt aagactgctt cactgcaagg    26280 agtatgggc ccgggcagga attttgtcac ttctcatgtg acttcggaca gttattggac    26340
tattctggat ctgattcctc cttcagtgaa agaagggaa gaaagcagga ccatgcagtg    26400
tgtcctgccc cctctactca cacacttaca catccatatg cacacacgcg taccgaccac    26460
cacacataat cctaatatca cgaaatcgtt tttctttag cctctcggtc tggctcattt    26520
actgacaaaa gtttcagata aggtgagccc ttcttttccg tgcctttgtg catggaggtc    26580
actgcttaag tgagatgctt aaaaagccac cgttcttatc gtggtagctt tgctagtgtg    26640
ggccgtggct gagagccaaa agtagatccg gcaccttcag ctgaataccct ccactgatac    26700 tgtgtgcacg gctttacttt tgtatttaag tttctcctct taaggtcaag taaaatgaac    26760
ctatagttta agtattagca agtgaagagg atggcaaaat ggagaactgt gctacaaaca    26820
gagctaaacc atggtagagg gactttgaag ctacgtctac acggtgcccc aagatccagt    26880
cgattccaag gaatcgtgtc acccagctta gtaggagctg gtcaaacaat aaaatgtctt    26940
attgattgta ttcccagact tctcaatcaa ttgttgggaa caataataaa atagctaaca    27000
tttattgact gtttactaat gacctaggca ctcttctaag tgttttacca aaatagggct    27060
tatttaatgt gggtaataat aatgacagtg ataccaatat aataacaaga aaacttcag    27120 tttgcccaaa gctttactat tcttcaagtt attctaactg ggcagaggca gatcgagcca    27180
```

```
gggagagaga aggaggtttg acgtctcttc actactactt tattccttct ttctctcctc    27240
taccccttgt cttctctcag ccttctactc ccatctctgc ctctgtcaga agcttgctag    27300
tggcaccttt gtcactgctt agcaccacct ccgtccagcc cctgctgctg atggctctca    27360
aggctggaga ggctgctgac ccctggccta caggaaaata aagcagatgg ggaaagttta    27420
tcagcagcga agagggagtg gcttgcctgc tctcctctcc tagaccctgc atttcctggc    27480
ctttatgagt acaggacctt ctaagtggca gtagagcttg ttctgccttt tgtatcagtt    27540
tacacaattg ccagaattct tggcacggtg tgcagactta gggtggtgag cgtttgagaa    27600
gacccaaggg atgtggaaga agacacccaa ggggaaaaat acgaaataca cttttagttt    27660
gtgctaaagg gcagaagctt ggccatatca caccgggtgg ggtgtcttgc ttctgtgcgt    27720
gagtgtgtga ggcacgcagg agaggggtgt gtaattatgt gctgtatcct tcatttctgc    27780
tcctcacatt taatgagatt ggcaacaata aatttgtctt tccaggtgtg atggtatata    27840
tttctatgct tcattctcac ttcactttga agggcttcca aaaaaatttt tatgggcaga    27900
aagagcaagt ttgggattcc ttcccagttt ttaaatcata ctgatacttg tgactttagg    27960
ggcgtatgag ttgdatttta tcgcttttgt tgttttcctc acaactgtgg caggaaaaga    28020
agatgacgat ctctgtcagt ttctgaggct ggtttacctg ttttgcaaag agctccaccg    28080
agacaactaa cttgtgtaac tcacaaaggt taattgcaca acgtaaggag ccaaaagaca    28140
tagcagctat atgtgcagct gcgaaaggca gaatcatcca aaggttggag ggtttgttac    28200
cgcctgagtg taggttgaga aaagaatgtg ccagattcct tcatccagtc acattgagct    28260
ctctttctca ttccagggta ccgggaggta gtgtttccca cgccatggta agccacacat    28320
ccctcctggg cccctcagtg gctagtcatt cacctgtagg cagggtctaa gtttccagta    28380
agaatgacag atctccccta tcctcgctaa aggcccaggt ttggggatgg aaggcttcaa    28440
aataaattga atagggaact tgattcactc attagtggcc ttatgaatgc cattttctaa    28500
ggtactaata cctcactggg cagatgctcc atcttagaga ctgtgggttt gacattttc    28560 tgggtgacac atgacaggga agaagggtac ttccgcacac ctttgaatgt gttttcttac    28620
tttcctcttg gaaatagaaa ataaaaaaca cacccccacc ccaccccaa cacacacaca    28680 cactaataca tacacacttg ctgaatatgt tctctacccc ataccaccc ttttcttaac    28740 ctactcccac tttcaataga acccacattt cagaagattt aatatatttg gaagactttt    28800
attcgcattg tcatctcttt aaagaaaaat gaggacaggt ggatttagga agcgcttccc    28860
tctgctccaa atagatcctt aaatatgagt gatcgtttag aaaactggca catgagtgag    28920
agcctttcac tgctgttgca gtcttttggc ctcaaagctg ctgagccgtt taaataatcg    28980
cataacacac tcttggtggg tggcgaggag gaaaagaaac ccttaccatt tcttcccttg    29040
ccagtcccac cgttgacaag ccaaattgat cttttaagag atcaaatgaa tgttctctaa    29100
atatatgtac acacatggct gcctggaaac gtattccttc cacagaatga ttgcctgaaa    29160
tttgaaggag agcgcagtaa agacaccagg ttggaagtgg ggttgaaggg ctaggggtg    29220 gagtggaggt agaattctat gcgtgcatga ggcttcactt ttgtacactg tccttttggg    29280
attcaaggtg ttcatcagta taatgaagcg ggcccattga tttatcatct atttggtaat    29340
gtcattgcat ttttagctcc ctgtgtcttt tttgtcattg ggttacattc aagcacagta    29400
agatcaactt taaaacctcc ttactcaaca gctttattag ttatagcatt ccatgacctt    29460
tctcaacatt cttaaagaaa aagatacagt gtaatgtcgc tttactttgc ttattgtcct    29520
ttgttggggt gaacaaagca ttttctacag tggctatatc acataattat acagctttca    29580
```

```
atagcagtgt cttggcacat atcaaagttc agaggagcct ttagaaaaaa aaaaagatgt   29640
tttgtggcag cctagggagg gtctcatctt tccttcagaa aatagttcaa ggctcttctg   29700
tcaagcttcc ctacttagag cttttttctc tcctgcttca taaagtttaa aggggattca   29760
gtggagttct atgatctatt tcctttgaaa gattgttcct cggcacagag aggccctttg   29820
acttcaagag ttcacagatt catgtcttta ggtatcatat gtctgacctt atcagttact   29880
ccatttaatg taggagaaaa agtctcaact ctttgtgttt gtctgttttg cctctgtgaa   29940
atgatttggt gaaaagacca tccttttaa cacaccactg agaggccgtt tctgactgta   30000
acctaccctg tggcttttct ctctttaaaa aaaaaaaaaa tcgtccttgt gttttgtgta   30060
tggatgagtt cacagtgaga atagaattat acaagggcag gcgcacacac aaaaaaatct   30120
ttgctttcct ccctcacctc ccgcaccccc ccacaaatga tctattggct ctctcggcgg   30180
ctgtacccca acaggcgaag ccatttagca aacacagagg tagcggctgt ggtgctggga   30240
cagtggtggg ttttcccttg cttcgaccta cccctaaggc cttcataatt aattgtcctt   30300
cagcgatgag gaaagttcag aaacagtgtg tggagtgatg cctattgtct gatattcagt   30360
tctccttgcc ttggttcttt ttcttcatcc cacaaagggt tatcaatggg agaaagagag   30420
caagttctct tctgagagct gctggtggtg gctgtagctt tcagtgggat gttatcattg   30480
tgttcagccc atcctggatt aaatgtctga agaagttcta acaaccttt gaaagacagc   30540 ctgtttattt cgcctagatg aaacaaattc atttagcaaa ccaaagcttg ttcgaagttg   30600
gccacccctt ttcacatggc agataacatt atagatcaaa tttcttcatt tttccccccg   30660
caggatgtta tttaacttga actgtttggt tctttgtcag tcacagggca gaaattttaa   30720
tgactattca ctcactgctc ttaaatacat caatattaat ttacaataat acagtttttg   30780
ctaacatcct ttttgatgaa gcgtagacgt ttaatacttg aaagcagata attagtttaa   30840
aaatattgtt tctccttcaa tgactgcctt cagccaatct tcaattctat cttgtaagat   30900
gatgtgaaac aaacgcattt tgtcttcctg cacccccaa ttttggctg agatacaaaa   30960 taaagatgca gtgtggagag agctatttga gaagggtagg aaaagagaa ccgtctatta   31020 atgatcatta tactactgtt cctgttaaat agggtgaagc caagaaaaac aaatataatc   31080
gttcttccga ggagagcagt tgaactagta aatcacagag gtttaaaata actacattgt   31140
agtgttcatg acaacttcaa ggctgaaggg aaccatattt aaaggcaatc tctgtgtctc   31200
ttatagcagt ttcttttgga ggaagagacc gacaggatgg ccagaatcaa ttctgccccc   31260
tttgctcttt gaaacaatt tcacaacaga ccttttggta tttaaagaga acctgtatat   31320
ggaagttgac acaactaata tagtcatacc aaaaagggg tcataaaaaa ttaaagttct   31380
tcttatgaat ctttcatgag aagcaatgaa aagggacact agtgtagcca agttctttgt   31440
gctacaagct cttcttccgg gctctgagct attgttcttt cagctcctca aacagacttt   31500
cactttcaaa ctgacaaaag tcacttaaaa gccagacagc tgtactaaca cccacctt   31560 actgagcaag agccactggc aggtgacaag gcctgctgag agaccttgtt gaaaatgagc   31620 agggtgact ttctcgtgcc ttaacgttgc ttttgcactc actttgagat ggcccattga   31680
ctgctctttt tgcccccca ccccaaaaca ggctccccaa aatatgttgt gcattttctt   31740
tgcagtgtgc aacattgaca tccgtgatca tatttctgcc ttcacctgt gtggctaggc   31800 acgggttctg ggaaatttgt gcccttctag cagaagacag ggagtttgac tcacaaaact   31860
cctgctgcct cttttccttt tgcccctcca ttcgttcaa atctcactta aggttttcag   31920
atttctgttg cctcactagg gttggataga aaacacccac caaagatggg tgcaaacctc   31980
```

```
accttcggat ttaagatcta ggcagagatc gttaggtggg tagtcctgcc tgcatcccga    32040
ccctcagggc agcagccgtc gtgggccatg ggaggcctcc ctgtgtgcgc attacaggcc    32100
tcccctcccc tgtcaccttg tgtacagtct ggtctgtgac actgatggtg attatgtcat    32160
tattttgctc tgggggccct ggcacatctg cagagcccaa gcacatcttc tttgttgcgt    32220
tggcaaatgt cccacgccgc aaatgcttca ttagccctgc tgccggcctc cttgccagac    32280
gcctgtgccc aaatcccggc ttcttttttgc tccgttcttt tgtgtagctg atgatcatgt    32340
attcatcttc ctggttcttc cccattttcc tcgacttctg aactccagat gtcccagttt    32400
tcttgcccaa atcactccga agtctacaat gcgaaatgaa gtgactcttt acccttgaat    32460
ccttccccac tcctgaccac cttctcctact ttttttcccc caaatgaata gtgactttga    32520
atagctcgcc accatgaaga ctaacgtttt caaacttgca atctgaaaag acaccaagtg    32580
attgcttcca gtttatgatg agagacaggg ttagaatgag tttggcatta ttagatattg    32640
cttattatct gtgtgccttc ctcctccgtc cccactctgc cccctcact atttccttgg    32700 atcctttatt tgcacctgtg cattgccaca ttttaccaat tttctgaaag cactttgaaa    32760
tgtgagtaca gaaaatactc ttcatgcctc gctgtgcacg ttacagtctt ctgaaggttc    32820 cttttctctaa gtgaatcttc atctccactc taccctctcc caaaaccact gcccccctcct    32880 tctgccccag ccctcaacaa tgacctacta ttagatactt acagtgatta acacttggct    32940
gttttggaaa cagctaaaac atttctctct ctaaagtttt attctatata tctaacagag    33000
ccacagcttt tgtgaaggtg tactggtttc tacattagct gcagtaaatt ttagagctta    33060
atatcttggg ctgtgatgga tactacataa ttggtatgtt taattttccc ttaaatttga    33120
attaattgat ctgtgttagc atattatgag cagcttttcc aatagagttt aactagtttt    33180
taaattctct aactactgca acataaaatg atttaaatgt ctccatcttt gagcaaacca    33240
taagatttta gttttcaggt gtagttaaag gagttaagtg tatatttat ggaaatcatg    33300 gttagatcac tgccatgaat tgtaatttga aattcaagac aaagactctg ttaagggtta    33360
aagaaaactt cctcagagga atgagttgcc acattgtacc gggttgctga gattttcaaa    33420
tacctatcaa agaggggcac aagaatatgc atgttgcaaa tattaggacc aatgtagcca    33480
acaaggtgag aagagaggtg gtcagatcag gcgggtgggc tccccaaccc attgtcagcc    33540
ctgtgcaggg agcatattgg gagaggctgg tacctgtcat tgaatcattt ttcaaaaggc    33600
tcgagatata tccaaaatat tcctaacctc ccagttgccc accattatgg ttttatcacc    33660
catgagtttt acttaaacct ttttttaaact taatctcatt gtcagaatat accactcctt    33720
aagataataa ttctctaagt gtattacctg ctgggaaaat actatcttct ttttacggct    33780
ctaaacgtga ttcccctaga actccacagg gatagcccct gttataatat cctgggattg    33840
tgaagagggt tgtgtccata ttctccattt cctttctgat tttacagact ttgatcatta    33900
ctccctctta atcttcatct ctccagatta aggagctcta atccttttta aaagcctaat    33960
ctcatacagt aagtgggctg ccctggatca ttttagctgc cctgctgtaa tgcgcttcca    34020
gcctgactgt gttttttctga gggacagtta cagttactaa ctcacacagc agaactccag    34080
gtgtgggcag tcatgccacg gtttggtgat ggtgccttgt gcacacccaa tgggactttt    34140
ttgattaccc caaaagtttta tcctcagaag ctggaattct tgagttggat tcagtagtg    34200 cttattggtt aaaatgatcc tatgagacca gctgatcaga ctcttggcaa atactctggc    34260
aaatatgatt gtgtctatag gacataccca gccaaataga aaataggcag atccaccctg    34320
ccctccagat gttttcagtg ttcttgtaga tcaagcactg gggtatttga catcatgagg    34380
```

```
agatagcctt agtcttgaac ttgagtctat aataatgaca gctctggggg aaagctccag   34440 tttctgctttt atttgatgtt attctcaggc aggcaatgaa atgttcacct gcaagtagtc   34500 aatatttttat ataaaacatc cccttgaaat cttacaaaga aaatgctttg gggagtcttt   34560
ccactgtcag tggtcctgga tcaataccgt tgtaggactt acagcatgga ctctccagcc   34620
aggccctggg atcaaatccc agctctgctg cttttctagca gtgaaaccct ggcaagtgtc   34680
ttaccctgcc tgtacttcag tttccttatc tgtaaaatag gggatgtaat agtgactact   34740
tcacagagtg ttgtgagaat taaatgaatc tacacaattg tattagcaca agtaagtgc    34800 tgtataagca ttcacattta ttcatttgca gagccaagta aatgttacct tgttgctgtg   34860
acatctgtgg tccaattatt gcaccatttc ctgctgaccc taaataggaa agtaaacaaa   34920
cgggcaatga gggagctctc atcagaattg gaacatatat tcaacgtaaa actggttttc   34980
acaagagcaa gtgttcctgc tctgaatgtg gctgaaaagg cgacactagc ctggaacagc   35040
tccaggactc tggggtcatc cgttccagat gagaaggaca cgatgagatg ctgggggtgg   35100
tggaaggagc actggcctgg agggtctggc tctggccata cctgcctcat tgtggtctac   35160
tgtgctcacc ttttggaaag tgataagatt aaattcaaga gtttcattct agctctgaaa   35220
ttttgtgact ctagagtaga ggggcagttt cattctagct ctgaaatttt gtgactctag   35280
aatagagggg tattctgcat tctctaaata agtctctttt tgagtcttgg tcatgttgca   35340
aagctttaag cagtgagtat agaggccctg ggaatccaga tggcttccat gtgaggcccc   35400
ttctaccctg gtgactctgc tgcagcttaa ttatctcagt caaaatctcc agggtgccca   35460
ttttcgtttt ctcccaaggc cctatttgca gatctgaatc tcaacagtgc ccttggagac   35520
atggcaattc ccttactggg attatagaga ctaattttttc aaattcatac acaatttatt   35580
gactgaattg gcactatcat tagacttgct gctcacttta tttgttgcct tggccagggt   35640
ggccaaacaa tgaggaaatt tgtcagtgaa gccctcatgc cattgggttt tctcacacat   35700
tccatgcagg cctcaacaca gactatcagc atttataata tgcattaact tctatataat   35760
gtacgtctcc tctcttttcag agcagaattg gctatgtttt ttttttttatt cttttatttt   35820 tttattttttt tgagacacag agtgttgcac tgttgcctaa gctggagtac agtggcatga   35880
tttcagctca ccacaacctc cacctctcgg gctccagcga ttctcctgcc tcagcctccc   35940
aagtagctgg gattacaggt gtgcatcact atgcccagcc agaattggca gttttagatg   36000
atataactac cttccctact aagcctactt ggtagtgttt gcaaaagcaa caccacccctt   36060 ttctttaaat attccccaaa tgatagtaat atagatcatg aaagtctttt cccttgagat   36120
tgttttgtat gtgtgagagt ttgtggttgg gaggtattga gtcctcatac aagccatttg   36180
gatatgtatt cttcatattt cttatggcta ttgcacctaa gttctgtttt cttaaggcta   36240
cattaacatt ttaaattaga atatggtgct aaaagtgact ttcagtaaaa ggtaatgtat   36300
tccctgagaa caagtaaata cttgggcagg gagggatggt ttgagtagag gtgaaaacag   36360
agaaatgatg ggaagctgac catatgtaga agaagctgaa aggtcatggt ttcaaggcca   36420 ctgtgttttcc tttcatttag agcatccact tttaaagatt tatcattttc agtgacctga   36480
aggcgtacaa gataatctgt gtagatacct gaaactgcct ttcaacaagg ccagtcctag   36540
gtattgacag catcctaggt tgtcccaccc taaacattac ctcaagtccc attgggtagg   36600
agtctagtgg acttccaaaa gccccccgagt tcattctgca atctgcctgt ctttgcaatc   36660
tatttacctg tcttgaaaaa gggattccaa agcccttcac aagctcttaa gtagcatttg   36720
aaatacagcc catccttagt tttgcaaagg gtgattgcag agaaagacaa atagaattcc   36780
```

```
ctggaaatac agaatagaat ttctctgaca gaacaaagat cttgcagtca aaaccaaggg   36840
atgggattga ggccaataat ccccatcctt tcctaaagca actcggatat tatttggggt   36900
gtcataagct attgccagca gagtgccagc atcccccatg aacttgtgtt ctctgaagct   36960
ctgtctgatt tcctaccatc tgtatcacaa gcgctttctt tggtgtttac tatgagcaat   37020 cccttctca tcacaacctg cctgaacccc acttcctaac agcttctccc taggctcctt   37080
actcacattg ctccatcaat agcaatacag ggcacacaga ctagttttaa tattagccta   37140
ggcaaagctt aattatgaag gtaaagctgt ggcagaaaac aatcacgtaa tacattctcg   37200
aacgaaacag gagtaactgt ggattatctg tgccccagct tcccttcatg caatattgga   37260
gtgtttgtgc tatgttgttt ttggataatg tcccatccaa gaatggcacc aagcttggcc   37320
ctgcttcttt taccacctca cccagtaatt gtagcaaaag ttaaacttca agggctgtca   37380
gcttgtcttg aactcagaca ccaatggcac caaatttacg gggctgactt aaaggggaat   37440
ttgttaacac tacaaagtga ctggtatatg attgcagggc ttattttttcc acctaagtat   37500 tgagctgatt tgtcagatgt gtcatgaagc agggatacat tcctctgttt agcacattta   37560
aatatgtact ggcaggaaag ctcccaatta aacgttccta atcagagcag ggtaagactg   37620
aagtcttcct ggtccttgac caccacgtgt gtggtttatt aactctgttc ccgtagacat   37680
aggcagcctt aactccatcg ggggaatggt ctggccttac aggtcgaatt caagtgaatc   37740
aatcgaacta tcctccaaga tagagcagaa tgaaagaccc aggatcagtg cagaatgaaa   37800
gaccattagg cctctagaaa agctgttagc cctcaagttt ggctaaaagc aggggctggc   37860
aaagtatggc ctatgggcag agctgccct caatctgttt ttatggcttc aagctaagaa   37920
tgacttaaat ttttaaacag ttgtaaaaaa taaggagaat atccaaccta gaccaaatat   37980
ggcccacaga gcctatgtat ttattacctg gcccttact ggcaaatttt gctgaccacc   38040
ggctgaaggt tttttctctt ctgtgggaca tgaactctct gagattcctt ctagttctga   38100
agttccaaaa ttctgtgatt ccttttttt tttttttttg agatggagtc tcactctgtc   38160
acccaggctg gagtgcagtg gcatgatctc agctcactgc aacctccgcc tcttgggttc   38220
aagcaattct ctgcctcagc ctcctgaata gctgggattg cgggcgccag ccaccacgcc   38280
cggctaattt ttttgtattt ctagtagaga cggggtttca ccatcttggc caggttggta   38340
ttgaactcct gacctcatga ttcacccgcc tcagcctccc aaagtgctgg gattacaggc   38400
gtgagccacc gcaccggcc aattccatga gtctttgatg gaatagtctt ggtccagctc   38460
ttacctgaac agcctaccag atgagcaatt tctgcacagt gcttccagtt gtttttaaga   38520
tcttaacagt atctgtgtag tatctcaggg ggagagaatg aggtattagg ttttagtttt   38580
tgatgctttt tccttgattt tgcttgcata tttgtttgtt tgtttaaact tggaatcact   38640
ttttaagacc tatgcagagt ttgggagaga aggaaaattt gcttcatcgc gaccaataat   38700
gtgacaatta tgtttcctaa cacgtataat accaagacct ccatgtgtga gcaaataaac   38760
tagccactta aagcacgttc actgaccaaa tttcagcccc acgaaataat tttgacagtc   38820
tctcatagac atttgtcatt ctgctcctag caagctagta ctatcttcta ctggggctat   38880
ggaagagatg gttttactta ccttgatctc tacatgcaga attgccaatg gaatacttac   38940
ataatttaaa atgtatgcac aatttattaa acgtagaata gaagatgtta agacatcctt   39000
ttctattacc tgaaagtcac aattattcga aatgctcaaa tctagaacat tgttgataat   39060
tatataatat tttaacaaca catatgttat caacatcata atgctgtaga aatttattg    39120 tgaattttgt attttctaaa tactcttaaa agacaaagac tcaaattcag gtagaaaaac   39180
```

```
aaagaagata ctcagggtgt atctctgccc ttcattcatt gctgtggtca gagaagtctg   39240
tgtgaggggt ttggccggta gcagccccccc agatccgtac actgcagacc aaaattcagc   39300
tcctgtgatg cttttccatg gagtttccct gtcaattcaa ggtagatcct caacctccct   39360
ccttggcagt ttgcatgtga ctgttcattc tttttattac atttcctcca ggggccatt    39420 ttcaccatgt catatctgtt tgctatcagc atttataagg gctggtgtgg cattggagga   39480
tgtcaagtgg tctgacttgg aagtgtactg ccacaaactc catgtaggtg acaggaggag   39540
agacctgctt tcccgttgcc acttttggga ttatccctgc aactctttcc gtctggctga   39600
caaaaacctt ggggctattg ggtggctcat cacttctgct ccttctctag cctttccctg   39660
ggtttgcttc ccccaacccc cacacccccct cgcacattaa catgacattg cctggtgagc   39720
acagaagaga gcagcttcca ccagctgaaa cctctgatct caaactcact agagagtttg   39780
gcttcgggat tttggcaaga aggccgattg cccatcaggt cagcatgaat aaagatttct   39840
ttcttccctt ctttttttaaa gtcaagcatc aaccgaaact gctcccaaag ctctgtctct   39900
caagacaatt taacccccttt cacctaagta cattttctat tttgaatgca tggtactttg   39960
ttttattctt ttcctgtgag atgaccaaga aatctactat atgtaaaatt tgaaagccaa   40020
gtcaattcta aaccaggctt atcattttta aagtatgttt atccagcttt gtagtaggaa   40080
caagcagact gtttgaaggc cacatacttt tcaaaccctg gttgcaacac gtctgccccg   40140
ttttgaaact gtctttatct agccgagaaa acgaaaatct atttgacaaa gtggcactct   40200
ggccagttta tcttgcaata tggctttagc tcactgagtc tattgattc cttaaattaa    40260 tgtttacaga atgctactga attttgctca acagaacatt gttctttcga agctttatat   40320
atatatatat ataaaagaga tacagactgt tattgccatg tgttcctttg tttagaccaa   40380
ggaaacatag ttttttaggtt tttttttttc ttaagacagc cttgaactat agccacttcc   40440
tacaagcatt tacttttcac atatttaaac agcaaaacat gtaactagaa agtgggccca   40500
aactgcatgg gtattagacg aatctaatcc tcagtgttcc tgaaagctga atgccacctg   40560
gagcatcaga gggagaaagc ctttagtcct aagcccagat gttgctggag aaccttcctc   40620
tgcctcattt ggggtaactc ggcaggcacc cgaaagcaac ttcacagcca gtgctcctgg   40680
atcctgctag ttttttccaaa cacaagcatc ctaataaaat tcaaacacca tttagctgtt   40740
tgggaactct aaatataaca tcttgcccttt tgaccacggt gctcagtgtt caatacacaa   40800
aacctaatct ctaaagatga ttttaaaact gaccttccca gagaagtaca cgtatccatt   40860
cagctacgaa cagtgcagaa aacaggattt tgactcataa ttatgaaatg gccaaaataa   40920 aacttagggga acacaaagca acttttctca accggttgac tcagccaaca aactcaccca   40980
agcgaacctc ctcagagcac ctctcaaaac gatgctttgc agacatttat taatcacagt   41040
gaatgcttcc caggaattag ggctcctctt taaaatctca aacttgtaaa ccaccttata   41100
tttggatgat attttatgct tcccaaagtg cattcatgtt ttcttttcca tttgatcctc   41160
ccctggaatg agagggcact ggaatagaat ctcaggattc actgtgtata gcatcctgca   41220
ccattccttc tcttctggag ggcctgttag tcccccggctg tacacacagg ataaatgcat   41280
gcatgactgc aaagggagac ccttagtaac cacatcttgt gaccatattt tacagctcca   41340
tgattcctct tttcagcctc tggcaggaga gtttagtgtg agtgagacag tgaagaggag   41400
cagcaataac gtatctgttc ttggcttttc atctgataat ctctatgagg agttactaaa   41460
gcatctgagt ttatccattt aagtccactc tgtctgcagt gtaagtcccc agcttgtgcc   41520
actgctgtca ggagatgagt ctctccttga tcgatattta cttaacaaac agcagggatg   41580
```

```
ggagagtttg tttagaggaa tcatgtgcac tctagggtga atgaatgctc gggaaagtac   41640
ttcaactatt tgtctccttc cctaagattt ttgtgtacgt gtgtgtgcac acacgtgtgc   41700
agatgcccat tctcttttta acttctccaa agacacttcg aagtcatcta gaaaaatacc   41760
tcgctatgta tgattggtac atcattatac cgttaaggag ctaatgatgc agatgcagtt   41820
tttctaaccc agcaaagttt ggttcttctt ttgtgctctt atatagagca caaaagagac   41880
tcttaggata aactaaatgc acaagcatct acctttgacc cctttcagat gagtggaagg   41940
gaagaaaata cggatggaaa caataaaagc agtttgacaa ggcagctctt cactatgtat   42000
ttttgatggc attacctata tattttttaaa ggcccacagg gacaaaaagt aactttctcc   42060 aattttttcag agctgcttca gcattagata tatttaactc tactactgta tatgaattcc   42120
acggtgtgaa aattgagaga gcactgttct ttcgagttcc ctgaaacaat tgcttgaagg   42180
ctcaagtcag cctcttgaat gcagttgact tggaggcatc tggggctaga tcgagggtt    42240 ttgtttctgg gtgtggggag aggctggggg gtggctgggg agttatttat ttatttgatt   42300
ttgtgaatcg gagttgtaaa agccatctga atattcatg cagaatagtc tgagaagccc    42360
gtttctgttt tatttaccgc acagtagaac agccacagcg gattagttct acaatacccg   42420
taacaaaagc ccaacagctg atgcatgtga tgttaggagg tgacaaaaca gttaaagtat   42480
gctgctggct acaggcaagc agtcagcaga tgcagacaaa agggtttgtg acaagaataa   42540
ctctctctcc aaggcgagca gtgaagagta tccaaaatac cagtacccctt ttctccttga   42600 cattgtcttc ttacagtcag catttttattg ccctttttata gtataaaaaa aaatggagga   42660
ggaagaagaa ggaaaaccca cacacaaact aattcaccaa aatactaggc aggattgtac    42720
tttcccattc gctagccatg cctgccagta cacgtgtcct tttccatttc tccatcgaag   42780
caagtttgaa aaaaaaaatt agcttaaaag atcagctata aagatgattt cccttgaaaa   42840
gtttgtaatc tattgatagg cttgataggc cattggagcc tttggttacg ggttgggggg   42900
tgggtggcca gggaaagaag tcgatgcctg gtttgttttc tgtccatttc agtgaagatc   42960
atttcagtga tgaaatgagg ccagagggcc aattttttaaa ggggattgag gagggaggag   43020
tgtccatgga gaactgagca aggggcaagg tttaggtccc ccgcaagagg ctgatgaatg   43080
agcttacgga cggttcagag gtgtgaaaaa tgagcttctc tgtctccaga aaataggaga   43140
ggctgtcttc tttttaacct ttgtaattcc ccttctattc tctgtgacat tcattcagct   43200
gccaagagcg tttggcaagg tttgggccag cgagcacact tccagtgacc gctaaccttg   43260
gtatgtcctg acacttatga tgagtatctg caggacacag aaggcaggca gcctgctatg   43320
tcaggctttt attatgtact gcagaggcta gggacagtca gtttaataaa acaaatcatc   43380
cttgaaggta aagcaactgg gaagaggagg aagacaggag aaaaatgtgt ctttgccact   43440
cattccgatg gaaaaaaaaa agaacagcaa acaaccacc cacccaacac accgtgtgtg    43500
tgtgtgtgtg tgtgtgtgtg tgtgtgcgcg cgcgcgcatt cgcgcacgca cacacacgcg   43560
caacccagct gtggactggg cagacttgaa aacctcctct cattttctgc atttcatgga   43620
agcccagaag gctcttgttt gctctgagga gactcaagtc tgtgatgaaa ttggtagaag   43680
ctgatagcca accccttca aatttatgca tatcttcaag tacctcatta ctttatattc    43740
ttctccaaat atcaaggcaa gaccatctgg ggtgacgttc ctatattggg atgcttttt    43800 atcaaaacaa agtttccact ctcctctcct gaggaacgct gggcaaagca gctcccacaa   43860
tagcctcaga gttccagcca aagacttgg aagccttttg tttttttccct gtggcatgtc    43920 caaaggcagg gccttctccc ctcctccgcc cgccctcccc agccgcctgc attgtcttgc   43980
```

```
attccagtga cttgattgac tgttaccacc tgatgctgag gagatactct agggttcatt   44040
ctgcagattg ttgggttcta ttaaaagaaa cctagataag ggattacttg tcactaaggg   44100
attttctgca gatgtttatt ggtgatggga aagccattag gtgtgaagag gtgcagaaaa   44160
atatggacaa catcattctg ataagactgg tttctaagat gctcccacaa aacatcagaa   44220 agtacccct attattctgt taaatggagc tgggtgtttt caagcagagg taaaggtctc   44280 ttttccatg ggtgatgttt ctatgtgtgg atgaaattca ctggaaccct ctcagaagat   44340
cagttgctac ccaaaagtgt acctctggga gccaccaaac acatgagttg ctccagtagt   44400
tcagtatctc attacaactt tcttttgtcc agtccagtcc attgcatgag tatcacctca   44460
aagtaagcac tatattaact aatcatttta tttgttcaca aagaattcat ttcttcccaa   44520
atataaacca ataaccaaag tctcctccag ggcatctttt ataccatttc catttatttt   44580
gaagttacta gattctctgt ggttttcaa gattacagag gcacagcttt tcaaggtttt   44640
ggtgcctcat ataaatagta gaaattgctg aaaaagcatt aaaagggagc cagcatcgtt   44700
taatgcaaag acaccttacc tcacagtaat ctcttcatct catcatttct tcatctcata   44760
caatctcatg ctttcttcat ctataaagtg atgatttctg agatctattc gaactctttg   44820
aattctacct tactttacca ttattttaaa cttctttttt ttttttatt tttgagatgg   44880 ggtctcactg tcacccaggc tgtagtgcaa tggtgcaacc tcagctcact gcaacctccg   44940
ccacctgggc tcaagccatc ctctcacctc cacctcccag tagctgggac cacaggcatg   45000
tgccaccaca cccagctaat ttttttgcat ttttggtaga gacggggttt catcatgttg   45060
ctcaggctga agcttccctt tattaagtat tgttaaagta ttaagtaact gccactctag   45120
agcaatatgg agtaaagcag aaggcaagat ctcactatga gctatttacc aaataacttt   45180
gcaaaagata ctctgctgag gctccttatc tagagacacc ttatgatgag gtaattgaaa   45240
gtacataaaa gtagataaaa agttaaacag catcaagaca caaatgcaaa aggtgataaa   45300
ggataaccta tgattgccac cacaagaaag gaatatttaa aacagattaa acccactaa    45360 aaaccattaa caagcatgac gaactataaa aatgatgaag aggagactgc atacaaccc    45420 caaagaagtt gccttgttct catgcaaatc ctacaactac acttccctcc ctcccctgct   45480
gctgatgttc tagatgtacc tcttctctct cctctgacag tcttgaacaa tgcctgccct   45540
tcccctgtcc ctggttcccc agacctcctg tgcagttctt ggtgtgggca gggcttccgg   45600
ccttctctgg cttctctggg gcagctgccc acaccttcac ccctcaaagc tctctgccat   45660
gtcatgctgc atccctgagt gctcaaggaa catagaattt cactgaggct gtattgccgt   45720
tggctgatga aaccacccctt cttgaaacgt ttattttaat aaatgcctat aattggccag   45780
gtgcagtggc tcacacctgt aatctcagca ctttgggagg ccaagacggg cagatcacct   45840
gaggttggga gttggagacc agcctggcca acatggtgaa accccatctc tactgaaaat   45900
acaaaagtta gccaggcgtg atggcacttg cctgtaatct cagctactca ggaggctaag   45960
gcaggagagt ctcatgaacc caggaggcag aggttgcagt gagccaggat catgccactg   46020
cactccagcc tgggtgacag agcaaaactc catctcaaat aaataaatta ataaatgcct   46080
atgattatgt ttctgtagca tttggctaac agctcccaat ccaaggagtg agagtgggca   46140
gttgctccgc ttcactgttc tccagccaca ttccctccct cagtgatgct catttgatag   46200
aatgtggagg attatctttg ggggtggagg tgactgtgct agaaaagatt gcttcacgaa   46260 ttttatttg tataatgtga gtgggagggc taagctctcc tccaacaaat actcatgtat   46320
acaagacatt tgggaggaaa tcacccaaag gcctgtagaa aatccacatg aattctcagc   46380
```

```
agagaatggc ccttgaggtg tatgggtttg cacattcatg gcggacaagg cggcactttg   46440
aaggattttc caggcaacac tgggaattat gtcctaagaa atgggccagt gtgaaagtct   46500
ttaggagggt ctgataaaaa tgtaagctta agactgattg gccccaaaag gagtcccttt   46560
catttttttc tgcagagtta ttacatttct ttataaacaa caattaactt gccataggga   46620
acaatgaact tctttgtcca attttaaacg tgaaaaacag tgatgtcggg tgatgattct   46680
ggttttcttt accagttact actattgtta aaaagtacat tgcacccaag gtgggaagaa   46740
agagatgaaa catgttcaac attacactac ttccttttta ctttggtacg tggcatgtct   46800
gaacttagat gaaatgtctt tcatctcttg tatatgcgta gataaatatg gctacatgta   46860
cacctatgat acgtttatgt cctcatacgt ctgcacttaa tgtaaaaatg aaactttact   46920
ggtgtataag taccccacta aaagaaatct actaagtgtc aatgtgtact tggaaaatca   46980
tgagttcatg gattattctg tgattccatt atgttggtgt ggggatagat agaccatgct   47040
gtactataag taacttccaa agaacactaa ataagtacat cagtagctac tgcttttcctt   47100 agtcaagaga tcagattaat aagtaattaa gagaacacac acacacacac aacacacata   47160
catattaatt gctgtggaag aaaagcctta agaaattggg gttctaaaat gaatatttgg   47220
ggaatgttta ttttggatga taaggacctt gaggaatttc cttaccctct ctgagcctca   47280
gttttctatt gtgtaactgg gataataaca ccccttagag agattgggag aactgaatga   47340
cataattcac attcagtaca taaaacatag cctggcaagt agtaaatact cgaaaaaagt   47400
tagtttgtat tattattatt atcagctgaa taaatcactc tcttatggag caattctaat   47460
ctcaaggtta agtagtttct gatgtaatat tttaggatca gttttgtgac ttcatgttaa   47520
tattattatt ttactccttt atgtatatag aatactttat attgcagatt aatatacaac   47580
ttagcatctg agtcaacaat cctctgagac aaacagataa ctgagatttt agaagatttt   47640
cttcatttaa agcttgggtt taatttataa agaagcccaa ctatttgtta ttctatttg    47700 agaacgtatt ttgttttcat catggcaatc aaaagaaat aggattcaaa ttctgaaaaa    47760
ataattggag actttcttct ggatagcact tatttaataa agtgaggaat cccaaaagtc   47820
acatcccata ttcctatcct aatatccaca atgaaatccc agttttttcaa taggtctgcg   47880 ttggatcttt catacactct tcttaaaaca aagctgtcaa ccccacatca caatgcttct   47940
atatataatg actttacatt aaaagaatag aagccagcta tttttagaaa atgcaggtgc   48000
catgtaagcc cctttctgca agaatgatct tagctcagtt tccttggaat aactgtagac   48060
ttgaaactga aaactttatt aatgccattg tctccttgta tcagcaggtt ccagagagat   48120
tcctggaagt tgctcagatc acattacggg agttttttcaa tgccattatc gcaggcaaag   48180
atgttgatcc ttcctggaag aaggccatat acaaggtcat ctgcaagctg gatagtgaag   48240
tccctgagat tttcaaatcc ccgaactgcc tacaagagct gcttcatgag tagaaatttc   48300
aacaactctt tttgaatgta tgaagagtag cagtccccctt tggatgtcca agttatatgt   48360
gtctagattt tgatttcata tatatgtgta tgggaggcat ggatatgtta tgaaatcagc   48420
tggtaattcc tcctcatcac gtttctctca ttttctttttg ttttccattg caaggggatg   48480
gttgttttct ttctgccttt agtttgcttt tgcccaaggc ccttaacatt tggacactta   48540
aaatagggtt aattttcagg gaaaaagaat gttggcgtgt gtaaagtctc tattagcaat   48600
gaagggaatt tgttaacgat gcatccactt gattgatgac ttattgcaaa tggcggttgg   48660
ctgaggaaaa cccatgacac agcacaactc tacagacagt gatgtgtctc ttgtttctac   48720
tgctaagaag gtctgaaaat ttaatgaaac cacttcatac atttaagtat tttgtttggt   48780
```

-continued

| | |
|---|---|
| ttgaactcaa tcagtagctt ttccttacat gtttaaaaat aattccaatg acagatgagc | 48840 |
| agctcacttt tccaaagtac cccaaaaggc caaattaaaa aagaaaaata atcactctca | 48900 |
| agccttgtct aagaaaagag gcaaactctg aaagtcgtac cagtttcttc tggaggcaaa | 48960 |
| gcaattttgc acaaaaccag ctctctcaag atgagactag aaaattcatac ctggtcttgt | 49020 |
| agccacctct ctaaacttga aaataggttc ttcttcataa gtgagcttac atcattcttc | 49080 |
| ataaagaaaa atcctataac ttgttatcat ttttgcttca gatactaaaa ggcactaagt | 49140 |
| ttccaattta cgctgctcaa cttttgtttat atgcttaaaa ggattctgtt tacttaacaa | 49200 |
| tttttttcccc taaaatacta ttttctgaat acttccttcc agtaaggaat aaaggaaagc | 49260 |
| ccaacttggc cataa | 49275 |

<210> SEQ ID NO 2
<211> LENGTH: 3097
<212> TYPE: DNA
<213> ORGANISM: Homo sapiens
<220> FEATURE:
<221> NAME/KEY: misc_feature
<223> OTHER INFORMATION: Prox-1 DNA

<400> SEQUENCE: 2

| | |
|---|---|
| ggcacgaggc ccctttttcca gaatcacttg cactgtcttg ttcttgaatg agaaaggaag | 60 |
| aaaagagcct cccattactc agacccgtgt aaacattatt ccccccagga gaaaatggtg | 120 |
| ttattcaaat gaatcataat aaaatagcct ctaaacagtt tctaagcggg agcctccgtg | 180 |
| gaactcagcg ctccgctcct cccagttcct aagaggtccc gggattcttg agctgtgccc | 240 |
| agctgacgag cttttgaaga tggcacaata accgtccagt gatgcctgac catgacagca | 300 |
| cagccctctt aagccggcaa accaagagga gaagagttga cattggagtg aaaaggacgg | 360 |
| tagggacagc atctgcattt tttgctaagg caagagcaac gttttttagt gccatgaatc | 420 |
| cccaaggttc tgagcaggat gttgagtatt cagtggtgca gcatgcagat ggggaaaagt | 480 |
| caaatgtact ccgcaagctg ctgaagaggg cgaactcgta tgaagatgcc atgatgcctt | 540 |
| ttccaggagc aaccataatt tcccagctgt tgaaaaataa catgaacaaa aatggtggca | 600 |
| cggagcccag tttccaagcc agcggtctct ctagtacagg ctccgaagta catcaggagg | 660 |
| atatatgcag caactcttca agagacagcc ccccagagtg tctttcccct tttggcaggc | 720 |
| ctactatgag ccagtttgat atggatcgct tatgtgatga gcacctgaga gcaaagcgcg | 780 |
| cccgggttga gaatataatt cggggtatga gccattcccc cagtgtggca ttaaggggca | 840 |
| atgaaaatga agagagatg gccccgcagt ctgtgagtcc ccgagaaagt tacagagaaa | 900 |
| acaaacgcaa gcaaaagctt cccagcagc agcaacagag tttccagcag ctggtttcag | 960 |
| cccgaaaaga acagaagcga gaggagcgcc gacagctgaa acagcagctg gaggacatgc | 1020 |
| agaaacagct cgccagctg caggaaaagt tctaccaaat ctatgacagc actgattcgg | 1080 |
| aaaatgatga agatggtaac ctgtctgaag acagcatgcg ctcggagatc ctggatgcca | 1140 |
| gggcccagga ctctgtcgga aggtcagata tgagatgtg cgagctagac ccaggacagt | 1200 |
| ttattgaccg agctcgagcc ctgatcagag agcaggaaat ggctgaaaac aagccgaagc | 1260 |
| gagaaggcaa caacaaagaa agagaccatg ggccaaactc cttacaaccg gaaggcaaac | 1320 |
| atttggctga gaccttgaaa caggaactga acactgccat gtcgcaagtt gtggacactg | 1380 |
| tggtcaaagt cttttcggcc aagcctccc gccaggttcc tcaggtcttc ccacctctcc | 1440 |
| agatccccca ggccagattt gcagtcaatg gggaaaacca caatttccac accgccaacc | 1500 |

-continued

```
agcgcctgca gtgctttggc gacgtcatca ttccgaaccc cctggacacc tttggcaatg      1560
tgcagatggc cagttccact gaccagacag aagcactgcc cctggttgtc cgcaaaaact      1620
cctctgacca gtctgcctcc ggccctgccg ctggcggcca ccaccagccc ctgcaccagt      1680
cgcctctctc tgccaccacg ggcttcacca cgtccacctt ccgccacccc ttccccttc       1740 ccttgatggc ctatccattt cagagcccat aggtgctcc ctccggctcc ttctctggaa       1800
aagacagagc ctctcctgaa tccttagact taactaggga taccacgagt ctgaggacca      1860
agatgtcatc tcaccacctg agccaccacc cttgttcacc agcacacccg cccagcaccg      1920
ccgaagggct ctccttgtcg ctcataaagt ccgagtgcgg cgatcttcaa gatatgtctg      1980
aaatatcacc ttattcggga agtgcaatgc aggaaggatt gtcacccaat cacttgaaaa      2040
aagcaaagct catgtttttt tatacccgtt atcccagctc caatatgctg aagacctact      2100
tctccgacgt aaagttcaac agatgcatta cctctcagct catcaagtgg tttagcaatt      2160
tccgtgagtt ttactacatt cagatggaga agtacgcacg tcaagccatc aacgatgggg      2220
tcaccagtac tgaagagctg tctataacca gagactgtga gctgtacagg gctctgaaca      2280
tgcactacaa taaagcaaat gactttgagg ttccagagag attcctggaa gttgctcaga      2340
tcacattacg ggagttttc aatgccatta tcgcaggcaa agatgttgat ccttcctgga      2400
agaaggccat atacaaggtc atctgcaagc tggatagtga agtccctgag attttcaaat      2460
ccccgaactg cctacaagag ctgcttcatg agtagaaatt tcaacaactc tttttgaatg      2520
tatgaagagt agcagtcccc tttggatgtc caagttatat gtgtctagat tttgatttca      2580
tatatatgtg tatgggaggc atggatatgt tatgaaatca gctggtaatt cctcctcatc      2640
acgtttctct cattttcttt tgtttttccat tgcaagggga tggttgtttt ctttctgcct      2700
ttagtttgct tttgcccaag gcccttaaca tttggacact taaaataggg ttaattttca      2760
gggaaaaaga atgttggcgt gtgtaaagtc tctattagca atgaagggaa tttgttaacg      2820
atgcatccac ttgattgatg acttattgca aatggcggtt ggctgaggaa aacccatgac      2880
acagcacaac tctacagaca gtgatgtgtc tcttgtttct actgctaaga aggtctgaaa      2940
atttaatgaa accacttcat acatttaagt attttgtttg gtttgaactc aatcagtagc      3000
ttttccttac atgttaaaa ataattccaa tgacagatga gcagctcact tttccaaagt       3060
accccaaaag gccaaattaa aaaaaaaaaa aaaaaaa                                3097
```

<210> SEQ ID NO 3
<211> LENGTH: 737
<212> TYPE: PRT
<213> ORGANISM: Homo sapiens
<220> FEATURE:
<221> NAME/KEY: misc_feature
<223> OTHER INFORMATION: Prox-1 Protein

<400> SEQUENCE: 3

```
Met Pro Asp His Asp Ser Thr Ala Leu Leu Ser Arg Gln Thr Lys Arg
1               5                  10                  15

Arg Arg Val Asp Ile Gly Val Lys Arg Thr Val Gly Thr Ala Ser Ala
            20                  25                  30

Phe Phe Ala Lys Ala Arg Ala Thr Phe Phe Ser Ala Met Asn Pro Gln
        35                  40                  45

Gly Ser Glu Gln Asp Val Glu Tyr Ser Val Val Gln His Ala Asp Gly
    50                  55                  60

Glu Lys Ser Asn Val Leu Arg Lys Leu Leu Lys Arg Ala Asn Ser Tyr
65                  70                  75                  80
```

-continued

```
Glu Asp Ala Met Met Pro Phe Pro Gly Ala Thr Ile Ile Ser Gln Leu
                85                  90                  95

Leu Lys Asn Asn Met Asn Lys Asn Gly Gly Thr Glu Pro Ser Phe Gln
            100                 105                 110

Ala Ser Gly Leu Ser Ser Thr Gly Ser Glu Val His Gln Glu Asp Ile
        115                 120                 125

Cys Ser Asn Ser Ser Arg Asp Ser Pro Pro Glu Cys Leu Ser Pro Phe
    130                 135                 140

Gly Arg Pro Thr Met Ser Gln Phe Asp Met Asp Arg Leu Cys Asp Glu
145                 150                 155                 160

His Leu Arg Ala Lys Arg Ala Arg Val Glu Asn Ile Ile Arg Gly Met
                165                 170                 175

Ser His Ser Pro Ser Val Ala Leu Arg Gly Asn Glu Asn Glu Arg Glu
            180                 185                 190

Met Ala Pro Gln Ser Val Ser Pro Arg Glu Ser Tyr Arg Glu Asn Lys
        195                 200                 205

Arg Lys Gln Lys Leu Pro Gln Gln Gln Gln Ser Phe Gln Gln Leu
    210                 215                 220

Val Ser Ala Arg Lys Glu Gln Lys Arg Glu Glu Arg Arg Gln Leu Lys
225                 230                 235                 240

Gln Gln Leu Glu Asp Met Gln Lys Gln Leu Arg Gln Leu Gln Glu Lys
                245                 250                 255

Phe Tyr Gln Ile Tyr Asp Ser Thr Asp Ser Glu Asn Asp Glu Asp Gly
            260                 265                 270

Asn Leu Ser Glu Asp Ser Met Arg Ser Glu Ile Leu Asp Ala Arg Ala
        275                 280                 285

Gln Asp Ser Val Gly Arg Ser Asp Asn Glu Met Cys Glu Leu Asp Pro
    290                 295                 300

Gly Gln Phe Ile Asp Arg Ala Arg Ala Leu Ile Arg Glu Gln Glu Met
305                 310                 315                 320

Ala Glu Asn Lys Pro Lys Arg Glu Gly Asn Asn Lys Glu Arg Asp His
                325                 330                 335

Gly Pro Asn Ser Leu Gln Pro Gly Lys His Leu Ala Glu Thr Leu
            340                 345                 350

Lys Gln Glu Leu Asn Thr Ala Met Ser Gln Val Val Asp Thr Val Val
        355                 360                 365

Lys Val Phe Ser Ala Lys Pro Ser Arg Gln Val Pro Gln Val Phe Pro
    370                 375                 380

Pro Leu Gln Ile Pro Gln Ala Arg Phe Ala Val Asn Gly Glu Asn His
385                 390                 395                 400

Asn Phe His Thr Ala Asn Gln Arg Leu Gln Cys Phe Gly Asp Val Ile
                405                 410                 415

Ile Pro Asn Pro Leu Asp Thr Phe Gly Asn Val Gln Met Ala Ser Ser
            420                 425                 430

Thr Asp Gln Thr Glu Ala Leu Pro Leu Val Val Arg Lys Asn Ser Ser
        435                 440                 445

Asp Gln Ser Ala Ser Gly Pro Ala Ala Gly Gly His His Gln Pro Leu
    450                 455                 460

His Gln Ser Pro Leu Ser Ala Thr Thr Gly Phe Thr Thr Ser Thr Phe
465                 470                 475                 480

Arg His Pro Phe Pro Leu Pro Leu Met Ala Tyr Pro Phe Gln Ser Pro
                485                 490                 495

Leu Gly Ala Pro Ser Gly Ser Phe Ser Gly Lys Asp Arg Ala Ser Pro
            500                 505                 510
```

-continued

```
Glu Ser Leu Asp Leu Thr Arg Asp Thr Thr Ser Leu Arg Thr Lys Met
    515                 520                 525

Ser Ser His His Leu Ser His His Pro Cys Ser Pro Ala His Pro Pro
    530                 535                 540

Ser Thr Ala Glu Gly Leu Ser Leu Ser Leu Ile Lys Ser Glu Cys Gly
545                 550                 555                 560

Asp Leu Gln Asp Met Ser Glu Ile Ser Pro Tyr Ser Gly Ser Ala Met
                565                 570                 575

Gln Glu Gly Leu Ser Pro Asn His Leu Lys Lys Ala Lys Leu Met Phe
            580                 585                 590

Phe Tyr Thr Arg Tyr Pro Ser Ser Asn Met Leu Lys Thr Tyr Phe Ser
        595                 600                 605

Asp Val Lys Phe Asn Arg Cys Ile Thr Ser Gln Leu Ile Lys Trp Phe
    610                 615                 620

Ser Asn Phe Arg Glu Phe Tyr Tyr Ile Gln Met Glu Lys Tyr Ala Arg
625                 630                 635                 640

Gln Ala Ile Asn Asp Gly Val Thr Ser Thr Glu Glu Leu Ser Ile Thr
                645                 650                 655

Arg Asp Cys Glu Leu Tyr Arg Ala Leu Asn Met His Tyr Asn Lys Ala
            660                 665                 670

Asn Asp Phe Glu Val Pro Glu Arg Phe Leu Glu Val Ala Gln Ile Thr
        675                 680                 685

Leu Arg Glu Phe Phe Asn Ala Ile Ile Ala Gly Lys Asp Val Asp Pro
    690                 695                 700

Ser Trp Lys Lys Ala Ile Tyr Lys Val Ile Cys Lys Leu Asp Ser Glu
705                 710                 715                 720

Val Pro Glu Ile Phe Lys Ser Pro Asn Cys Leu Gln Glu Leu Leu His
                725                 730                 735

Glu

<210> SEQ ID NO 4
<211> LENGTH: 21
<212> TYPE: RNA
<213> ORGANISM: Homo sapiens
<220> FEATURE:
<221> NAME/KEY: misc_feature
<223> OTHER INFORMATION: Prox-1 A16 sense

<400> SEQUENCE: 4
cugcaagcug gauagugaag u                                              21

<210> SEQ ID NO 5
<211> LENGTH: 21
<212> TYPE: RNA
<213> ORGANISM: Homo sapiens
<220> FEATURE:
<221> NAME/KEY: misc_feature
<223> OTHER INFORMATION: Prox-1 A16 antisense

<400> SEQUENCE: 5
uucacuaucc agcuugcaga u                                              21

<210> SEQ ID NO 6
<211> LENGTH: 21
<212> TYPE: RNA
<213> ORGANISM: Homo sapiens
<220> FEATURE:
<221> NAME/KEY: misc_feature
<223> OTHER INFORMATION: Prox-1 A25 sense
```

-continued

```
<400> SEQUENCE: 6
cuaugagcca guuugauauu u                                              21

<210> SEQ ID NO 7
<211> LENGTH: 21
<212> TYPE: RNA
<213> ORGANISM: Homo sapiens
<220> FEATURE:
<221> NAME/KEY: misc_feature
<223> OTHER INFORMATION: Prox-1 A25 antisense

<400> SEQUENCE: 7
auaucaaacu ggcucauagu u                                              21

<210> SEQ ID NO 8
<211> LENGTH: 21
<212> TYPE: RNA
<213> ORGANISM: Homo sapiens
<220> FEATURE:
<221> NAME/KEY: misc_feature
<223> OTHER INFORMATION: EGFP A18 sense

<400> SEQUENCE: 8
gacguaaacg gccacaaguu u                                              21

<210> SEQ ID NO 9
<211> LENGTH: 21
<212> TYPE: RNA
<213> ORGANISM: Homo sapiens
<220> FEATURE:
<221> NAME/KEY: misc_feature
<223> OTHER INFORMATION: EGFP A18 antisense

<400> SEQUENCE: 9
acuuguggcc guuuacgucu u                                              21

<210> SEQ ID NO 10
<211> LENGTH: 3362
<212> TYPE: DNA
<213> ORGANISM: Homo sapiens
<220> FEATURE:
<221> NAME/KEY: misc_feature
<223> OTHER INFORMATION: Beta-catenin

<400> SEQUENCE: 10
aagcctctcg gtctgtggca gcagcgttgg cccggccccg ggagcggaga gcgaggggag      60
gcggagacgg aggaaggtct gaggagcagc ttcagtcccc gccgaccgc caccgcaggt     120 cgaggacggt cggactcccg cggcgggagg agcctgttcc cctgagggta tttgaagtat     180
accatacaac tgttttgaaa atccagcgtg gacaatggct actcaagctg atttgatgga     240
gttggacatg gccatggaac cagacagaaa agcggctgtt agtcactggc agcaacagtc     300
ttacctggac tctggaatcc attctggtgc cactaccaca gctccttctc tgagtggtaa     360
aggcaatcct gaggaagagg atgtggatac ctcccaagtc ctgtatgagt gggaacaggg     420
attttctcag tccttcactc aagaacaagt agctgatatt gatggacagt atgcaatgac     480
tcgagctcag agggtacgag ctgctatgtt ccctgagaca ttagatgagg gcatgcagat     540
cccatctaca cagtttgatg ctgctcatcc cactaatgtc cagcgtttgg ctgaaccatc     600
acagatgctg aaacatgcag ttgtaaactt gattaactat caagatgatg cagaacttgc     660
cacacgtgca atccctgaac tgacaaaact gctaaatgac gaggaccagg tggtggttaa     720
taaggctgca gttatggtcc atcagctttc taaaaaggaa gcttccagac acgctatcat     780
```

```
gcgttctcct cagatggtgt ctgctattgt acgtaccatg cagaatacaa atgatgtaga    840
aacagctcgt tgtaccgctg ggaccttgca taacctttcc catcatcgtg agggcttact    900
ggccatcttt aagtctggag gcattcctgc cctggtgaaa atgcttggtt caccagtgga    960
ttctgtgttg ttttatgcca ttacaactct ccacaacctt ttattacatc aagaaggagc   1020
taaaatggca gtgcgtttag ctggtgggct gcagaaaatg gttgccttgc tcaacaaaac   1080
aaatgttaaa ttcttggcta ttacgacaga ctgccttcaa attttagctt atggcaacca   1140
agaaagcaag ctcatcatac tggctagtgg tggaccccaa gctttagtaa atataatgag   1200
gacctatact tacgaaaaac tactgtggac acaagcaga gtgctgaagg tgctatctgt    1260
ctgctctagt aataagccgg ctattgtaga agctggtgga atgcaagctt taggacttca   1320
cctgacagat ccaagtcaac gtcttgttca gaactgtctt tggactctca ggaatctttc   1380
agatgctgca actaaacagg aagggatgga aggtctcctt gggactcttg ttcagcttct   1440
gggttcagat gatataaatg tggtcacctg tgcagctgga attctttcta acctcacttg   1500
caataattat aagaacaaga tgatggtctg ccaagtgggt ggtatagagg ctcttgtgcg   1560
tactgtcctt cgggctggtg acagggaaga catcactgag cctgccatct gtgctcttcg   1620
tcatctgacc agccgacacc aagaagcaga gatggcccag aatgcagttc gccttcacta   1680
tggactacca gttgtggtta agctcttaca cccaccatcc cactggcctc tgataaaggc   1740
tactgttgga ttgattcgaa atcttgccct tgtcccgca aatcatgcac ctttgcgtga    1800
gcagggtgcc attccacgac tagttcagtt gcttgttcgt gcacatcagg atacccagcg   1860
ccgtacgtcc atgggtggga cacagcagca atttgtggag ggggtccgca tggaagaaat   1920
agttgaaggt tgtaccggag cccttcacat cctagctcgg gatgttcaca accgaattgt   1980
tatcagagga ctaaatacca ttccattgtt tgtgcagctg ctttattctc ccattgaaaa   2040
catccaaaga gtagctgcag gggtcctctg tgaacttgct caggacaagg aagctgcaga   2100
agctattgaa gctgagggag ccacagctcc tctgacagag ttacttcact ctaggaatga   2160
aggtgtggcg acatatgcag ctgctgtttt gttccgaatg tctgaggaca gccacaaga    2220
ttacaagaaa cggctttcag ttgagctgac cagctctctc ttcagaacag agccaatggc   2280
ttggaatgag actgctgatc ttggacttga tattggtgcc cagggagaac cccttggata   2340
tcgccaggat gatcctagct atcgttcttt tcactctggt ggatatggcc aggatgcctt   2400
gggtatggac cccatgatgg aacatgagat gggtggccac caccctggtg ctgactatcc   2460
agttgatggg ctgccagatc tggggcatgc ccaggacctc atggatgggc tgcctccagg   2520
tgacagcaat cagctggcct ggtttgatac tgacctgtaa atcatccttt agctgtattg   2580
tctgaacttg cattgtgatt ggcctgtaga gttgctgaga gggctcgagg ggtgggctgg   2640
tatctcagaa agtgcctgac acactaacca agctgagttt cctatgggaa caattgaagt   2700
aaactttttg ttctggtcct ttttggtcga ggagtaacaa tacaaatgga ttttgggagt   2760
gactcaagaa gtgaagaatg cacaagaatg gatcacaaga tggaatttag caaaccctag   2820
ccttgcttgt taaaattttt ttttttttt tttaagaat atctgtaatg gtactgactt      2880
tgcttgcttt gaagtagctc ttttttttt tttttttttt ttttttgca gtaactgttt     2940
tttaagtctc tcgtagtgtt aagttatagt gaatactgct acagcaattt ctaatttta    3000
agaattgagt aatggtgtag aacactaatt aattcataat cactctaatt aattgtaatc   3060
tgaataaagt gtaacaattg tgtagccttt ttgtataaaa tagacaaata gaaaatggtc   3120
caattagttt cctttttaat atgcttaaaa taagcaggtg gatctatttc atgttttga    3180
```

-continued

```
tcaaaaacta tttgggatat gtatgggtag ggtaaatcag taagaggtgt tatttggaac    3240
cttgttttgg acagtttacc agttgccttt tatcccaaag ttgttgtaac ctgctgtgat    3300
acgatgcttc aagagaaaat gcggttataa aaaatggttc agaattaaac ttttaattca    3360
tt                                                                   3362
```

<210> SEQ ID NO 11
<211> LENGTH: 781
<212> TYPE: PRT
<213> ORGANISM: Homo sapiens
<220> FEATURE:
<221> NAME/KEY: misc_feature
<223> OTHER INFORMATION: Beta-catenin

<400> SEQUENCE: 11

```
Met Ala Thr Gln Ala Asp Leu Met Glu Leu Asp Met Ala Met Glu Pro
 1               5                  10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Asp Val Asp Thr Ser Gln Val Leu Tyr
 50                  55                  60

Glu Trp Glu Gln Gly Phe Ser Gln Ser Phe Thr Gln Glu Gln Val Ala
 65                  70                  75                  80

Asp Ile Asp Gly Gln Tyr Ala Met Thr Arg Ala Gln Arg Val Arg Ala
                 85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
```

```
                    325                 330                 335
Leu Trp Thr Thr Ser Arg Val Leu Lys Val Leu Ser Val Cys Ser Ser
                340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
        370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
        515                 520                 525

Glu Gln Gly Ala Ile Pro Arg Leu Val Gln Leu Leu Val Arg Ala His
    530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750
```

```
           Leu Pro Asp Leu Gly His Ala Gln Asp Leu Met Asp Gly Leu Pro Pro
                   755                 760                 765

Gly Asp Ser Asn Gln Leu Ala Trp Phe Asp Thr Asp Leu
                   770                 775                 780

<210> SEQ ID NO 12
<211> LENGTH: 2500
<212> TYPE: DNA
<213> ORGANISM: Homo sapiens
<220> FEATURE:
<221> NAME/KEY: misc_feature
<223> OTHER INFORMATION: TCF-4

<400> SEQUENCE: 12 cgggggatc ttggctgtgt gtctgcggat ctgtagtggc ggcggcggcg gcggcggcgg       60
ggaggcagca ggcgcgggag cgggcgcagg agcaggcggc ggcggtggcg gcggcggtta     120
gacatgaacg ccgcctcggc gccggcggtg cacggagagc cccttctcgc gcgcgggcgg     180
tttgtgtgat tttgctaaaa tgcatcacca acagcgaatg gctgccttag ggacggacaa     240
agagctgagt gatttactgg atttcagtgc gatgttttca cctcctgtga gcagtgggaa     300
aaatggacca acttctttgg caagtggaca ttttactggc tcaaatgtag aagacagaag     360
tagctcaggg tcctggggga atggaggaca tccaagcccg tccaggaact atggagatgg     420
gactccctat gaccacatga ccagcaggga ccttgggtca catgacaatc tctctccacc     480
ttttgtcaat tccagaatac aaagtaaaac agaaggggc tcatactcat cttatgggag      540
agaatcaaac ttcagggtt gccaccagca gagtctcctt ggaggtgaca tggatatggg      600
caacccagga acccttcgc ccaccaaacc tggttcccag tactatcagt attctagcaa       660
taatccccga aggaggcctc ttcacagtag tgccatggag gtacagacaa agaaagttcg     720
aaaagttcct ccaggtttgc catcttcagt ctatgctcca tcagcaagca ctgccgacta     780
caatagggac tcgccaggct atccttcctc caaaccagca accagcactt ccctagctc      840 cttcttcatg caagatggcc atcacagcag tgacccttgg agctcctcca gtgggatgaa     900
tcagcctggc tatgcaggaa tgttgggcaa ctcttctcat attccacagt ccagcagcta     960
ctgtagcctg catccacatg aacgtttgag ctatccatca cactcctcag cagacatcaa    1020
ttccagtctt cctccgatgt ccactttcca tcgtagtggt acaaaccatt acagcacctc    1080
ttcctgtacg cctcctgcca acgggacaga cagtataatg gcaaatagag gaagcggggc    1140
agccggcagc tcccagactg agatgctct ggggaaagca cttgcttcga tctattctcc     1200
agatcacact aacaacagct tttcatcaaa cccttcaact cctgttggct ctcctccatc    1260
tctctcagca ggcacagctg tttggtctag aaatggagga caggcctcat cgtctcctaa    1320
ttatgaagga cccttacact ctttgcaaag ccgaattgaa gatcgtttag aaagactgga    1380
tgatgctatt catgttctcc ggaaccatgc agtgggccca tccacagcta tgcctggtgg    1440 tcatgggac atgcatggaa tcattggacc ttctcataat ggagccatgg gtggtctggg     1500
ctcagggtat ggaaccggcc ttctttcagc aacagacat tcactcatgg tgggacccca    1560
tcgtgaagat ggcgtggccc tgagaggcag ccattctctt ctgccaaacc aggttccggt    1620
tccacagctt cctgtccagt ctgcgacttc ccctgacctg aacccacccc aggaccctta    1680
cagaggcatg ccaccaggac tacagggca gagtgtctcc tctggcagct ctgagatcaa    1740
atccgatgac gagggtgatg agaacctgca agacacgaaa tcttcggagg acaagaaatt    1800
agatgacgac aagaaggata tcaaatcaat tactagcaat aatgacgatg aggacctgac    1860
accagagcag aaggcagagc gtgagaagga gcggaggatg gccaacaatg cccgagagcg    1920
```

-continued

```
tctgcgggtc cgtgacatca acgaggcttt caaagagctc ggccgcatgg tgcagctcca    1980
cctcaagagt gacaagcccc agaccaagct cctgatcctc caccaggcgg tggccgtcat    2040
cctcagtctg gagcagcaag tccgagaaag gaatctgaat ccgaaagctg cgtgtctgaa    2100
aagaagggag gaagagaagg tgtcctcgga gcctcccct ctctccttgg ccggcccaca     2160
ccctggaatg ggagacgcat cgaatcacat gggacagatg taaaagggtc caagttgcca    2220
cattgcttca ttaaaacaag agaccacttc cttaacagct gtattatctt aaacccacat    2280
aaacacttct ccttaacccc cattttttgta atataagaca agtctgagta gttatgaatc   2340
gcagacgcaa gaggtttcag cattcccaat tatcaaaaaa cagaaaaaca aaaaaagaa     2400 agaaaaaagt gcaacttgag ggacgacttt ctttaacata tcattcagaa tgtgcaaagc    2460
agtatgtaca ggctgagaca cagcccagag actgaacggc                          2500
```

<210> SEQ ID NO 13
<211> LENGTH: 667
<212> TYPE: PRT
<213> ORGANISM: Homo sapiens
<220> FEATURE:
<221> NAME/KEY: misc_feature
<223> OTHER INFORMATION: TCF-4

<400> SEQUENCE: 13

```
Met His His Gln Gln Arg Met Ala Ala Leu Gly Thr Asp Lys Glu Leu
1               5                   10                  15

Ser Asp Leu Leu Asp Phe Ser Ala Met Phe Ser Pro Pro Val Ser Ser
            20                  25                  30

Gly Lys Asn Gly Pro Thr Ser Leu Ala Ser Gly His Phe Thr Gly Ser
        35                  40                  45

Asn Val Glu Asp Arg Ser Ser Ser Gly Ser Trp Gly Asn Gly Gly His
    50                  55                  60

Pro Ser Pro Ser Arg Asn Tyr Gly Asp Gly Thr Pro Tyr Asp His Met
65                  70                  75                  80

Thr Ser Arg Asp Leu Gly Ser His Asp Asn Leu Ser Pro Pro Phe Val
                85                  90                  95

Asn Ser Arg Ile Gln Ser Lys Thr Glu Arg Gly Ser Tyr Ser Ser Tyr
            100                 105                 110

Gly Arg Glu Ser Asn Leu Gln Gly Cys His Gln Gln Ser Leu Leu Gly
        115                 120                 125

Gly Asp Met Asp Met Gly Asn Pro Gly Thr Leu Ser Pro Thr Lys Pro
    130                 135                 140

Gly Ser Gln Tyr Tyr Gln Tyr Ser Ser Asn Asn Pro Arg Arg Arg Pro
145                 150                 155                 160

Leu His Ser Ser Ala Met Glu Val Gln Thr Lys Lys Val Arg Lys Val
                165                 170                 175

Pro Pro Gly Leu Pro Ser Ser Val Tyr Ala Pro Ser Ala Ser Thr Ala
            180                 185                 190

Asp Tyr Asn Arg Asp Ser Pro Gly Tyr Pro Ser Ser Lys Pro Ala Thr
        195                 200                 205

Ser Thr Phe Pro Ser Ser Phe Phe Met Gln Asp Gly His His Ser Ser
    210                 215                 220

Asp Pro Trp Ser Ser Ser Ser Gly Met Asn Gln Pro Gly Tyr Ala Gly
225                 230                 235                 240

Met Leu Gly Asn Ser Ser His Ile Pro Gln Ser Ser Ser Tyr Cys Ser
                245                 250                 255
```

```
Leu His Pro His Glu Arg Leu Ser Tyr Pro Ser His Ser Ser Ala Asp
            260                 265                 270

Ile Asn Ser Ser Leu Pro Pro Met Ser Thr Phe His Arg Ser Gly Thr
        275                 280                 285

Asn His Tyr Ser Thr Ser Ser Cys Thr Pro Pro Ala Asn Gly Thr Asp
        290                 295                 300

Ser Ile Met Ala Asn Arg Gly Ser Gly Ala Ala Gly Ser Ser Gln Thr
305                 310                 315                 320

Gly Asp Ala Leu Gly Lys Ala Leu Ala Ser Ile Tyr Ser Pro Asp His
                325                 330                 335

Thr Asn Asn Ser Phe Ser Ser Asn Pro Ser Thr Pro Val Gly Ser Pro
            340                 345                 350

Pro Ser Leu Ser Ala Gly Thr Ala Val Trp Ser Arg Asn Gly Gly Gln
        355                 360                 365

Ala Ser Ser Ser Pro Asn Tyr Glu Gly Pro Leu His Ser Leu Gln Ser
    370                 375                 380

Arg Ile Glu Asp Arg Leu Glu Arg Leu Asp Asp Ala Ile His Val Leu
385                 390                 395                 400

Arg Asn His Ala Val Gly Pro Ser Thr Ala Met Pro Gly Gly His Gly
                405                 410                 415

Asp Met His Gly Ile Ile Gly Pro Ser His Asn Gly Ala Met Gly Gly
            420                 425                 430

Leu Gly Ser Gly Tyr Gly Thr Gly Leu Leu Ser Ala Asn Arg His Ser
        435                 440                 445

Leu Met Val Gly Thr His Arg Glu Asp Gly Val Ala Leu Arg Gly Ser
    450                 455                 460

His Ser Leu Leu Pro Asn Gln Val Pro Val Pro Gln Leu Pro Val Gln
465                 470                 475                 480

Ser Ala Thr Ser Pro Asp Leu Asn Pro Pro Gln Asp Pro Tyr Arg Gly
                485                 490                 495

Met Pro Pro Gly Leu Gln Gly Gln Ser Val Ser Ser Gly Ser Ser Glu
            500                 505                 510

Ile Lys Ser Asp Asp Glu Gly Asp Glu Asn Leu Gln Asp Thr Lys Ser
        515                 520                 525

Ser Glu Asp Lys Lys Leu Asp Asp Asp Lys Lys Asp Ile Lys Ser Ile
    530                 535                 540

Thr Ser Asn Asn Asp Asp Glu Asp Leu Thr Pro Glu Gln Lys Ala Glu
545                 550                 555                 560

Arg Glu Lys Glu Arg Arg Met Ala Asn Asn Ala Arg Glu Arg Leu Arg
                565                 570                 575

Val Arg Asp Ile Asn Glu Ala Phe Lys Glu Leu Gly Arg Met Val Gln
            580                 585                 590

Leu His Leu Lys Ser Asp Lys Pro Gln Thr Lys Leu Leu Ile Leu His
        595                 600                 605

Gln Ala Val Ala Val Ile Leu Ser Leu Glu Gln Gln Val Arg Glu Arg
    610                 615                 620

Asn Leu Asn Pro Lys Ala Ala Cys Leu Lys Arg Arg Glu Glu Glu Lys
625                 630                 635                 640

Val Ser Ser Glu Pro Pro Pro Leu Ser Leu Ala Gly Pro His Pro Gly
                645                 650                 655

Met Gly Asp Ala Ser Asn His Met Gly Gln Met
            660                 665
```

<210> SEQ ID NO 14

<211> LENGTH: 9312
<212> TYPE: DNA
<213> ORGANISM: Homo sapiens
<220> FEATURE:
<221> NAME/KEY: misc_feature
<223> OTHER INFORMATION: Notch-1

<400> SEQUENCE: 14

| | | | | | |
|---|---|---|---|---|---|
| atgccgccgc | tcctggcgcc | cctgctctgc | ctggcgctgc | tgcccgcgct | cgccgcacga | 60 |
| ggcccgcgat | gctcccagcc | cggtgagacc | tgcctgaatg | gcgggaagtg | tgaagcggcc | 120 |
| aatggcacgg | aggcctgcgt | ctgtggcggg | gccttcgtgg | gccgcgatg | ccaggacccc | 180 |
| aacccgtgcc | tcagcacccc | ctgcaagaac | gccgggacat | gccacgtggt | ggaccgcaga | 240 |
| ggcgtggcag | actatgcctg | cagctgtgcc | ctgggcttct | ctgggcccct | ctgcctgaca | 300 |
| cccctggaca | atgcctgcct | caccaacccc | tgccgcaacg | ggggcacctg | cgacctgctc | 360 |
| acgctgacgg | agtacaagtg | ccgctgcccg | cccggctggt | cagggaaatc | gtgccagcag | 420 |
| gctgacccgt | gcgcctccaa | cccctgcgcc | aacggtggcc | agtgcctgcc | cttcgaggcc | 480 |
| tcctacatct | gccactgccc | acccagcttc | catggcccca | cctgccggca | ggatgtcaac | 540 |
| gagtgtggcc | agaagcccgg | gctttgccgc | cacggaggca | cctgccacaa | cgaggtcggc | 600 |
| tcctaccgct | gcgtctgccg | cgccaccac | actggcccca | actgcgagcg | ccctacgtg | 660 |
| ccctgcagcc | cctcgccctg | ccagaacggg | ggcacctgcc | gccccacggg | cgacgtcacc | 720 |
| cacgagtgtg | cctgcctgcc | aggcttcacc | ggccagaact | gtgaggaaaa | tatcgacgat | 780 |
| tgtccaggaa | acaactgcaa | gaacgggggt | gcctgtgtgg | acggcgtgaa | cacctacaac | 840 |
| tgccgctgcc | cgccagagtg | gacaggtcag | tactgtaccg | aggatgtgga | cgagtgccag | 900 |
| ctgatgccaa | atgcctgcca | gaacggcggg | acctgccaca | cacccacgg | tggctacaac | 960 |
| tgcgtgtgtg | tcaacggctg | gactggtgag | gactgcagcg | agaacattga | tgactgtgcc | 1020 |
| agcgccgcct | gcttccacgg | cgccacctgc | catgaccgtg | tggcctcctt | ctactgcgag | 1080 |
| tgtcccatg | gccgcacagg | tctgctgtgc | cacctcaacg | acgcatgcat | cagcaacccc | 1140 |
| tgtaacgagg | gctccaactg | cgacaccaac | cctgtcaatg | gcaaggccat | ctgcacctgc | 1200 |
| ccctcgggt | acacgggccc | ggcctgcagc | caggacgtgg | atgagtgctc | gctgggtgcc | 1260 |
| aaccctgcg | agcatgcggg | caagtgcatc | aacacgctgg | gctccttcga | gtgccagtgt | 1320 |
| ctgcagggct | acacgggccc | ccgatgcgag | atcgacgtca | acgagtgcgt | ctcgaacccg | 1380 |
| tgccagaacg | acgccacctg | cctggaccag | attggggagt | tccagtgcat | ctgcatgccc | 1440 |
| ggctacgagg | tgtgcactg | cgaggtcaac | acagacgagt | gtgccagcag | ccctgcctg | 1500 |
| cacaatggcc | gctgcctgga | caagatcaat | gagttccagt | gcgagtgccc | cacgggcttc | 1560 |
| actgggcatc | tgtgccagta | cgatgtggac | gagtgtgcca | gcacccctg | caagaatggt | 1620 |
| gccaagtgcc | tggacggacc | caacactta | acctgtgtgt | gcacggaagg | gtacacgggg | 1680 |
| acgcactgcg | aggtggacat | cgatgagtgc | gaccccgacc | cctgccacta | cggctcctgc | 1740 |
| aaggacggcg | tcgccacctt | cacctgcctc | tgccgcccag | gctacacggg | ccaccactgc | 1800 |
| gagaccaaca | tcaacgagtg | ctccagccag | ccctgccgcc | acgggggcac | ctgccaggac | 1860 |
| cgcgacaacg | cctacctctg | cttctgcctg | aaggggacca | caggacccaa | ctgcgagatc | 1920 |
| aacctggatg | actgtgccag | cagccctgc | gactcggca | cctgtctgga | caagatcgat | 1980 |
| ggctacgagt | gtgcctgtga | gccgggctac | acagggagca | tgtgtaacat | caacatcgat | 2040 |
| gagtgtgcgg | gcaaccctg | ccacaacggg | ggcacctgcg | aggacggcat | caatggcttc | 2100 |
| acctgccgct | gccccgaggg | ctaccacgac | cccacctgcc | tgtctgaggt | caatgagtgc | 2160 |

```
aacagcaacc cctgcgtcca cggggcctgc cgggacagcc tcaacgggta caagtgcgac    2220
tgtgaccctg ggtggagtgg gaccaactgt gacatcaaca acaatgagtg tgaatccaac    2280
ccttgtgtca acggcggcac ctgcaaagac atgaccagtg gctacgtgtg cacctgccgg    2340
gagggcttca gcggtcccaa ctgccagacc aacatcaacg agtgtgcgtc caacccatgt    2400
ctgaaccagg gcacgtgtat tgacgacgtt gccgggtaca agtgcaactg cctgctgccc    2460
tacacaggtg ccacgtgtga ggtggtgctg gccccgtgtg cccccagccc ctgcagaaac    2520
ggcggggagt gcaggcaatc cgaggactat gagagcttct cctgtgtctg ccccacgggc    2580
tggcaagcag ggcagacctg tgaggtcgac atcaacgagt gcgttctgag cccgtgccgg    2640
cacggcgcat cctgccagaa cacccacggc ggctaccgct gccactgcca ggccggctac    2700
agtgggcgca actgcgagac cgacatcgac gactgccggc ccaacccgtg tcacaacggg    2760
ggctcctgca cagacggcat caacacggcc ttctgcgact gcctgccctt cttccggggc    2820
actttctgtg aggaggacat caacgagtgt gccagtgacc cctgccgcaa cggggccaac    2880
tgcacggact gcgtggacag ctacacgtgc acctgccccg caggcttcag cgggatccac    2940
tgtgagaaca acacgcctga ctgcacagag agctcctgct tcaacggtgg cacctgcgtg    3000
gacggcatca actcgttcac ctgcctgtgt ccacccggct tcacgggcag ctactgccag    3060
cacgatgtca atgagtgcga ctcacagccc tgcctgcatg gcggcacctg tcaggacggc    3120
tgcggctcct acaggtgcac ctgcccccag ggctacactg gccccaactg ccagaacctt    3180
gtgcactggt gtgactcctc gccctgcaag aacggcggca aatgctggca gacccacacc    3240
cagtaccgct gcgagtgccc cagcggctgg accggccttt actgcgacgt gcccagcgtg    3300
tcctgtgagg tggctgcgca cgacaaggt gttgacgttg cccgcctgtg ccagcatgga    3360
gggctctgtg tggacgcggg caacacgcac cactgccgct gccaggcggg ctacacaggc    3420
agctactgtg aggacctggt ggacgagtgc tcacccagcc cctgccagaa cggggccacc    3480
tgcacggact acctgggcgg ctactcctgc aagtgcgtgg ccggctacca cggggtgaac    3540
tgctctgagg agatcgacga gtgcctctcc caccccctgcc agaacggggg cacctgcctc    3600
gacctcccca acacctacaa gtgctcctgc ccacggggca ctcagggtgt gcactgtgag    3660
atcaacgtgg acgactgcaa tccccccgtt gaccccgtgt cccggagccc caagtgcttt    3720
aacaacggca cctgcgtgga ccaggtgggc ggctacagct gcacctgccc gccgggcttc    3780
gtgggtgagc gctgtgaggg ggatgtcaac gagtgcctgt ccaatccctg cgacgcccgt    3840
ggcacccaga actgcgtgca gcgcgtcaat gacttccact gcgagtgccg tgctggtcac    3900
accgggcgcc gctgcgagtc cgtcatcaat ggctgcaaag gcaagccctg caagaatggg    3960
ggcacctgcg ccgtggcctc caacaccgcc cgcgggttca tctgcaagtg ccctgcgggc    4020
ttcgagggcg ccacgtgtga aatgacgct cgtacctgcg gcagcctgcg ctgcctcaac    4080
ggcggcacat gcatctccgg cccgcgcagc cccacctgcc tgtgcctggg cccttcacg    4140 gggccccgaat gccagttccc ggccagcagc ccctgcctgg gcggcaaccc ctgctacaac    4200 cagggggacct gtgagcccac atccgagagc cccttctacc gttgcctgtg cccgccaaa    4260 ttcaacgggc tcttgtgcca catcctggac tacagcttcg ggggtggggc cgggcgcgac    4320 atcccccgc cgctgatcga ggaggcgtgc gagctgccg agtgccagga ggacgcgggc    4380
aacaaggtct gcagcctgca gtgcaacaac cacgcgtgcg gctgggacgg cggtgactgc    4440
tccctcaact tcaatgaccc ctggaagaac tgcacgcagt ctctgcagtg ctggaagtac    4500
ttcagtgacg gccactgtga cagccagtgc aactcagccg gctgcctctt cgacggcttt    4560
```

```
gactgccagc gtgcggaagg ccagtgcaac ccctgtacg accagtactg caaggaccac   4620
ttcagcgacg ggcactgcga ccagggctgc aacagcgcgg agtgcgagtg ggacgggctg   4680
gactgtgcgg agcatgtacc cgagaggctg gcggccggca cgctggtggt ggtggtgctg   4740
atgccgccgg agcagctgcg caacagctcc ttccacttcc tgcgggagct cagccgcgtg   4800
ctgcacacca acgtggtctt caagcgtgac gcacacggcc agcagatgat cttcccctac   4860
tacggccgcg aggaggagct gcgcaagcac cccatcaagc gtgccgccga gggctgggcc   4920
gcacctgacg ccctgctggg ccaggtgaag gcctcgctgc tccctggtgg cagcgagggt   4980
gggcggcggc ggagggagct ggaccccatg gacgtccgcg gctccatcgt ctacctggag   5040
attgacaacc ggcagtgtgt gcaggcctcc tcgcagtgct tccagagtgc accgacgtg    5100 gccgcattcc tgggagcgct cgcctcgctg ggcagcctca acatccccta caagatcgag   5160
gccgtgcaga gtgagaccgt ggagccgccc ccgccggcgc agctgcactt catgtacgtg   5220
gcggcggccg cctttgtgct tctgttcttc gtgggctgcg gggtgctgct gtcccgcaag   5280
cgccggcggc agcatggcca gctctggttc cctgagggct tcaaagtgtc tgaggccagc   5340
aagaagaagc ggcgggagcc cctcggcgag gactccgtgg gcctcaagcc cctgaagaac   5400
gcttcagacg gtgccctcat ggacgacaac cagaatgagt gggggggacga ggacctggag   5460 accaagaagt tccggttcga ggagcccgtg gttctgcctg acctgacga ccagacagac    5520 caccggcagt ggactcagca gcacctggat gccgctgacc tgcgcatgtc tgccatggcc   5580
cccacaccgc cccagggtga ggttgacgcc gactgcatgg acgtcaatgt ccgcgggcct   5640
gatggcttca ccccgctcat gatcgcctcc tgcagcgggg gcggcctgga cgggcaac     5700 agcgaggaag aggaggacgc gccggccgtc atctccgact tcatctacca gggcgccagc   5760
ctgcacaacc agacagaccg cacgggcgag accgccttgc acctggccgc cgctactca    5820 cgctctgatg ccgccaagcg cctgctggag gccagcgcag atgccaacat ccaggacaac   5880
atgggccgca ccccgctgca tgcggctgtg tctgccgacg cacaaggtgt cttccagatc   5940
ctgatccgga accgagccac agacctggat gcccgcatgc atgatggcac gacgccactg   6000
atcctggctg cccgcctggc cgtggagggc atgctggagg acctcatcaa ctcacacgcc   6060
gacgtcaacg ccgtagatga cctgggcaag tccgccctgc actgggccgc cgccgtgaac   6120
aatgtggatg ccgcagttgt gctcctgaag aacggggcta caaagatat gcagaacaac   6180 agggaggaga cacccctgtt tctggccgcc cgggagggca gctacgagac cgccaaggtg   6240
ctgctggacc actttgccaa ccgggacatc acggatcata tggaccgcct gccgcgcgac   6300
atcgcacagg agcgcatgca tcacgacatc gtgaggctgc tggacgagta caacctggtg   6360
cgcagcccgc agctgcacgg agccccgctg ggggcacgc ccaccctgtc gccccgctc     6420 tgctcgccca acggctacct gggcagcctc aagcccggcg tgcagggcaa gaaggtccgc   6480
aagcccagca gcaaaggcct ggcctgtgga agcaaggagg ccaaggacct caaggcacgg   6540
aggaagaagt cccaggacgg caagggctgc ctgctggaca gctccggcat gctctcgccc   6600
gtggactccc tggagtcacc ccatggctac ctgtcagacg tggcctcgcc gccactgctg   6660
ccctccccgt tccagcagtc tccgtccgtg cccctcaacc acctgcctgg gatgccgac   6720 acccacctgg gcatcgggca cctgaacgtg gcggccaagc ccgagatggc ggcgctgggt   6780 ggggcggcc ggctggcctt tgagactggc ccacctcgtc tctcccacct gcctgtggcc   6840
tctggcacca gcaccgtcct gggctccagc agcgagggg ccctgaattt cactgtgggc   6900
gggtccacca gtttgaatgg tcaatgcgag tggctgtccc ggctgcagag cggcatggtg   6960
```

```
ccgaaccaat acaaccctct gcggggagt gtggcaccag gcccctgag cacacaggcc      7020
ccctccctgc agcatggcat ggtaggcccg ctgcacagta gccttgctgc cagcgccctg    7080
tcccagatga tgagctacca gggcctgccc agcaccggc tggccaccca gcctcacctg     7140
gtgcagaccc agcaggtgca gccacaaaac ttacagatgc agcagcagaa cctgcagcca    7200
gcaaacatcc agcagcagca aagcctgcag ccgccaccac caccaccaca gccgcacctt    7260
ggcgtgagct cagcagccag cggccacctg gccggagct tcctgagtgg agagccgagc     7320
caggcagacg tgcagccact gggcccagc agcctggcgg tgcacactat tctgccccag     7380
gagagccccg ccctgcccac gtcgctgcca tcctcgctgg tcccaccgt gaccgcagcc     7440
cagttcctga cgcccccctc gcagcacagc tactcctcgc ctgtggacaa cacccccagc    7500
caccagctac aggtgcctga gcacccctc ctcaccccgt ccctgagtc ccctgaccag      7560
tggtccagct cgtccccgca ttccaacgtc tccgactggt ccgagggcgt ctccagccct    7620
cccaccagca tgcagtccca gatcgcccgc attccggagg ccttcaagta acggcgcgc    7680
cccacgagac cccggcttcc tttcccaagc cttcgggcgt ctgtgtgcgc tctgtggatg    7740
ccagggccga ccagaggagc cttttaaaa cacatgtttt tatacaaaat aagaacgagg     7800
atttaatttt ttttagtat ttatttatgt acttttattt tacacagaaa cactgccttt     7860
ttatttatat gtactgtttt atctggcccc aggtagaaac ttttatctat tctgagaaaa    7920
caagcaagtt ctgagagcca gggttttcct acgtaggatg aaaagattct tctgtgttta    7980
taaaatataa acaagattc atgatttata aatgccattt atttattgat tcctttttc      8040
aaaatccaaa aagaaatgat gttggagaag ggaagttgaa cgagcatagt ccaaaaagct    8100
cctgggcgt ccaggccgcg cccttttccc gacgcccacc caaccccaag ccagcccggc     8160
cgctccacca gcatcacctg cctgttagga gaagctgcat ccagaggcaa acggaggcaa    8220
agctggctca ccttccgcac gcggattaat ttgcatctga aataggaaac aagtgaaagc    8280
atatgggtta gatgttgcca tgtgttttag atggtttctt gcaagcatgc ttgtgaaaat    8340
gtgttctcgg agtgtgtatg ccaagagtgc acccatggta ccaatcatga atctttgttt   8400
caggttcagt attatgtagt tgttcgttgg ttatacaagt tcttggtccc tccagaacca    8460
ccccggcccc ctgcccgttc ttgaaatgta ggcatcatgc atgtcaaaca tgagatgtgt    8520
ggactgtggc acttgcctgg gtcacacacg gaggcatcct acccttttct ggggaaagac    8580
actgcctggg ctgaccccgg tggcggcccc agcacctcag cctgcacagt gtccccagg     8640
ttccgaagaa gatgctccag caacacagcc tgggcccag ctcgcgggac ccgaccccc      8700
gtgggctccc gtgttttgta ggagacttgc cagagccggg cacattgagc tgtgcaacgc    8760
cgtgggctgc gtcctttggt cctgtccccg cagccctggc aggggggcatg cggtcgggca   8820
ggggctggag ggaggcgggg gctgcccttg ggccaccct cctagtttgg gaggagcaga     8880
ttttgcaat accaagtata gcctatggca gaaaaatgt ctgtaaatat gttttaaag       8940
gtggattttg tttaaaaaat cttaatgaat gagtctgttg tgtgtcatgc cagtgaggga    9000
cgtcagactt ggctcagctc ggggagcctt agccgcccat gcactgggga cgctccgctg    9060
ccgtgccgcc tgcactcctc agggcagcct ccccggctc tacgggggcc gcgtggtgcc     9120
atccccaggg ggcatgacca gatgcgtccc aagatgttga ttttactgt gttttataaa     9180
atagagtgta gtttacagaa aaagacttta aaagtgatct acatgaggaa ctgtagatga    9240
tgtatttttt tcatctttt tgttaactga tttgcaataa aaatgatact gatggtgaaa     9300
aaaaaaaaaa aa                                                        9312
```

<210> SEQ ID NO 15
<211> LENGTH: 2556
<212> TYPE: PRT
<213> ORGANISM: Homo sapiens
<220> FEATURE:
<221> NAME/KEY: misc_feature
<223> OTHER INFORMATION: Notch-1

<400> SEQUENCE: 15

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

-continued

```
Leu Cys His Leu Asn Asp Ala Cys Ile Ser Asn Pro Cys Asn Glu Gly
    370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
            405                 410                 415
Ser Leu Gly Ala Asn Pro Cys Glu His Ala Gly Lys Cys Ile Asn Thr
        420                 425                 430
Leu Gly Ser Phe Glu Cys Gln Cys Leu Gln Gly Tyr Thr Gly Pro Arg
    435                 440                 445
Cys Glu Ile Asp Val Asn Glu Cys Val Ser Asn Pro Cys Gln Asn Asp
450                 455                 460
Ala Thr Cys Leu Asp Gln Ile Gly Glu Phe Gln Cys Ile Cys Met Pro
465                 470                 475                 480
Gly Tyr Glu Gly Val His Cys Glu Val Asn Thr Asp Glu Cys Ala Ser
            485                 490                 495
Ser Pro Cys Leu His Asn Gly Arg Cys Leu Asp Lys Ile Asn Glu Phe
        500                 505                 510
Gln Cys Glu Cys Pro Thr Gly Phe Thr Gly His Leu Cys Gln Tyr Asp
    515                 520                 525
Val Asp Glu Cys Ala Ser Thr Pro Cys Lys Asn Gly Ala Lys Cys Leu
530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
            565                 570                 575
Tyr Gly Ser Cys Lys Asp Gly Val Ala Thr Phe Thr Cys Leu Cys Arg
        580                 585                 590
Pro Gly Tyr Thr Gly His His Cys Glu Thr Asn Ile Asn Glu Cys Ser
    595                 600                 605
Ser Gln Pro Cys Arg His Gly Gly Thr Cys Gln Asp Arg Asp Asn Ala
610                 615                 620
Tyr Leu Cys Phe Cys Leu Lys Gly Thr Thr Gly Pro Asn Cys Glu Ile
625                 630                 635                 640
Asn Leu Asp Asp Cys Ala Ser Ser Pro Cys Asp Ser Gly Thr Cys Leu
            645                 650                 655
Asp Lys Ile Asp Gly Tyr Glu Cys Ala Cys Glu Pro Gly Tyr Thr Gly
        660                 665                 670
Ser Met Cys Asn Ile Asn Ile Asp Glu Cys Ala Gly Asn Pro Cys His
    675                 680                 685
Asn Gly Gly Thr Cys Glu Asp Gly Ile Asn Gly Phe Thr Cys Arg Cys
690                 695                 700
Pro Glu Gly Tyr His Asp Pro Thr Cys Leu Ser Glu Val Asn Glu Cys
705                 710                 715                 720
Asn Ser Asn Pro Cys Val His Gly Ala Cys Arg Asp Ser Leu Asn Gly
            725                 730                 735
Tyr Lys Cys Asp Cys Asp Pro Gly Trp Ser Gly Thr Asn Cys Asp Ile
        740                 745                 750
Asn Asn Asn Glu Cys Glu Ser Asn Pro Cys Val Asn Gly Gly Thr Cys
    755                 760                 765
Lys Asp Met Thr Ser Gly Tyr Val Cys Thr Cys Arg Glu Gly Phe Ser
770                 775                 780
Gly Pro Asn Cys Gln Thr Asn Ile Asn Glu Cys Ala Ser Asn Pro Cys
```

```
                785                 790                 795                 800
Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
                820                 825                 830

Cys Ala Pro Ser Pro Cys Arg Asn Gly Gly Glu Cys Arg Gln Ser Glu
                835                 840                 845

Asp Tyr Glu Ser Phe Ser Cys Val Cys Pro Thr Gly Trp Gln Ala Gly
                850                 855                 860

Gln Thr Cys Glu Val Asp Ile Asn Glu Cys Val Leu Ser Pro Cys Arg
865                 870                 875                 880

His Gly Ala Ser Cys Gln Asn Thr His Gly Gly Tyr Arg Cys His Cys
                885                 890                 895

Gln Ala Gly Tyr Ser Gly Arg Asn Cys Glu Thr Asp Ile Asp Asp Cys
                900                 905                 910

Arg Pro Asn Pro Cys His Asn Gly Gly Ser Cys Thr Asp Gly Ile Asn
                915                 920                 925

Thr Ala Phe Cys Asp Cys Leu Pro Gly Phe Arg Gly Thr Phe Cys Glu
                930                 935                 940

Glu Asp Ile Asn Glu Cys Ala Ser Asp Pro Cys Arg Asn Gly Ala Asn
945                 950                 955                 960

Cys Thr Asp Cys Val Asp Ser Tyr Thr Cys Thr Cys Pro Ala Gly Phe
                965                 970                 975

Ser Gly Ile His Cys Glu Asn Asn Thr Pro Asp Cys Thr Glu Ser Ser
                980                 985                 990

Cys Phe Asn Gly Gly Thr Cys Val Asp Gly Ile Asn Ser Phe Thr Cys
                995                 1000                1005

Leu Cys Pro Pro Gly Phe Thr Gly Ser Tyr Cys Gln His Asp Val
                1010                1015                1020

Asn Glu Cys Asp Ser Gln Pro Cys Leu His Gly Gly Thr Cys Gln
                1025                1030                1035

Asp Gly Cys Gly Ser Tyr Arg Cys Thr Cys Pro Gln Gly Tyr Thr
                1040                1045                1050

Gly Pro Asn Cys Gln Asn Leu Val His Trp Cys Asp Ser Ser Pro
                1055                1060                1065

Cys Lys Asn Gly Gly Lys Cys Trp Gln Thr His Thr Gln Tyr Arg
                1070                1075                1080

Cys Glu Cys Pro Ser Gly Trp Thr Gly Leu Tyr Cys Asp Val Pro
                1085                1090                1095

Ser Val Ser Cys Glu Val Ala Ala Gln Arg Gln Gly Val Asp Val
                1100                1105                1110

Ala Arg Leu Cys Gln His Gly Gly Leu Cys Val Asp Ala Gly Asn
                1115                1120                1125

Thr His His Cys Arg Cys Gln Ala Gly Tyr Thr Gly Ser Tyr Cys
                1130                1135                1140

Glu Asp Leu Val Asp Glu Cys Ser Pro Ser Pro Cys Gln Asn Gly
                1145                1150                1155

Ala Thr Cys Thr Asp Tyr Leu Gly Gly Tyr Ser Cys Lys Cys Val
                1160                1165                1170

Ala Gly Tyr His Gly Val Asn Cys Ser Glu Glu Ile Asp Glu Cys
                1175                1180                1185

Leu Ser His Pro Cys Gln Asn Gly Gly Thr Cys Leu Asp Leu Pro
                1190                1195                1200
```

```
Asn Thr Tyr Lys Cys Ser Cys Pro Arg Gly Thr Gln Gly Val His
1205             1210                1215

Cys Glu Ile Asn Val Asp Asp Cys Asn Pro Pro Val Asp Pro Val
1220             1225                1230

Ser Arg Ser Pro Lys Cys Phe Asn Asn Gly Thr Cys Val Asp Gln
1235             1240                1245

Val Gly Gly Tyr Ser Cys Thr Cys Pro Pro Gly Phe Val Gly Glu
1250             1255                1260

Arg Cys Glu Gly Asp Val Asn Glu Cys Leu Ser Asn Pro Cys Asp
1265             1270                1275

Ala Arg Gly Thr Gln Asn Cys Val Gln Arg Val Asn Asp Phe His
1280             1285                1290

Cys Glu Cys Arg Ala Gly His Thr Gly Arg Arg Cys Glu Ser Val
1295             1300                1305

Ile Asn Gly Cys Lys Gly Lys Pro Cys Lys Asn Gly Gly Thr Cys
1310             1315                1320

Ala Val Ala Ser Asn Thr Ala Arg Gly Phe Ile Cys Lys Cys Pro
1325             1330                1335

Ala Gly Phe Glu Gly Ala Thr Cys Glu Asn Asp Ala Arg Thr Cys
1340             1345                1350

Gly Ser Leu Arg Cys Leu Asn Gly Gly Thr Cys Ile Ser Gly Pro
1355             1360                1365

Arg Ser Pro Thr Cys Leu Cys Leu Gly Pro Phe Thr Gly Pro Glu
1370             1375                1380

Cys Gln Phe Pro Ala Ser Ser Pro Cys Leu Gly Gly Asn Pro Cys
1385             1390                1395

Tyr Asn Gln Gly Thr Cys Glu Pro Thr Ser Glu Ser Pro Phe Tyr
1400             1405                1410

Arg Cys Leu Cys Pro Ala Lys Phe Asn Gly Leu Leu Cys His Ile
1415             1420                1425

Leu Asp Tyr Ser Phe Gly Gly Gly Ala Gly Arg Asp Ile Pro Pro
1430             1435                1440

Pro Leu Ile Glu Glu Ala Cys Glu Leu Pro Glu Cys Gln Glu Asp
1445             1450                1455

Ala Gly Asn Lys Val Cys Ser Leu Gln Cys Asn Asn His Ala Cys
1460             1465                1470

Gly Trp Asp Gly Gly Asp Cys Ser Leu Asn Phe Asn Asp Pro Trp
1475             1480                1485

Lys Asn Cys Thr Gln Ser Leu Gln Cys Trp Lys Tyr Phe Ser Asp
1490             1495                1500

Gly His Cys Asp Ser Gln Cys Asn Ser Ala Gly Cys Leu Phe Asp
1505             1510                1515

Gly Phe Asp Cys Gln Arg Ala Glu Gly Gln Cys Asn Pro Leu Tyr
1520             1525                1530

Asp Gln Tyr Cys Lys Asp His Phe Ser Asp Gly His Cys Asp Gln
1535             1540                1545

Gly Cys Asn Ser Ala Glu Cys Glu Trp Asp Gly Leu Asp Cys Ala
1550             1555                1560

Glu His Val Pro Glu Arg Leu Ala Ala Gly Thr Leu Val Val Val
1565             1570                1575

Val Leu Met Pro Pro Glu Gln Leu Arg Asn Ser Ser Phe His Phe
1580             1585                1590

Leu Arg Glu Leu Ser Arg Val Leu His Thr Asn Val Val Phe Lys
1595             1600                1605
```

```
Arg Asp Ala His Gly Gln Gln Met Ile Phe Pro Tyr Tyr Gly Arg
    1610            1615                1620

Glu Glu Glu Leu Arg Lys His Pro Ile Lys Arg Ala Ala Glu Gly
    1625            1630                1635

Trp Ala Ala Pro Asp Ala Leu Leu Gly Gln Val Lys Ala Ser Leu
    1640            1645                1650

Leu Pro Gly Gly Ser Glu Gly Gly Arg Arg Arg Glu Leu Asp
    1655            1660                1665

Pro Met Asp Val Arg Gly Ser Ile Val Tyr Leu Glu Ile Asp Asn
    1670            1675                1680

Arg Gln Cys Val Gln Ala Ser Ser Gln Cys Phe Gln Ser Ala Thr
    1685            1690                1695

Asp Val Ala Ala Phe Leu Gly Ala Leu Ala Ser Leu Gly Ser Leu
    1700            1705                1710

Asn Ile Pro Tyr Lys Ile Glu Ala Val Gln Ser Glu Thr Val Glu
    1715            1720                1725

Pro Pro Pro Pro Ala Gln Leu His Phe Met Tyr Val Ala Ala Ala
    1730            1735                1740

Ala Phe Val Leu Leu Phe Phe Val Gly Cys Gly Val Leu Leu Ser
    1745            1750                1755

Arg Lys Arg Arg Arg Gln His Gly Gln Leu Trp Phe Pro Glu Gly
    1760            1765                1770

Phe Lys Val Ser Glu Ala Ser Lys Lys Lys Arg Arg Glu Pro Leu
    1775            1780                1785

Gly Glu Asp Ser Val Gly Leu Lys Pro Leu Lys Asn Ala Ser Asp
    1790            1795                1800

Gly Ala Leu Met Asp Asp Asn Gln Asn Glu Trp Gly Asp Glu Asp
    1805            1810                1815

Leu Glu Thr Lys Lys Phe Arg Phe Glu Glu Pro Val Val Leu Pro
    1820            1825                1830

Asp Leu Asp Asp Gln Thr Asp His Arg Gln Trp Thr Gln Gln His
    1835            1840                1845

Leu Asp Ala Ala Asp Leu Arg Met Ser Ala Met Ala Pro Thr Pro
    1850            1855                1860

Pro Gln Gly Glu Val Asp Ala Asp Cys Met Asp Val Asn Val Arg
    1865            1870                1875

Gly Pro Asp Gly Phe Thr Pro Leu Met Ile Ala Ser Cys Ser Gly
    1880            1885                1890

Gly Gly Leu Glu Thr Gly Asn Ser Glu Glu Glu Asp Ala Pro
    1895            1900                1905

Ala Val Ile Ser Asp Phe Ile Tyr Gln Gly Ala Ser Leu His Asn
    1910            1915                1920

Gln Thr Asp Arg Thr Gly Glu Thr Ala Leu His Leu Ala Ala Arg
    1925            1930                1935

Tyr Ser Arg Ser Asp Ala Ala Lys Arg Leu Leu Glu Ala Ser Ala
    1940            1945                1950

Asp Ala Asn Ile Gln Asp Asn Met Gly Arg Thr Pro Leu His Ala
    1955            1960                1965

Ala Val Ser Ala Asp Ala Gln Gly Val Phe Gln Ile Leu Ile Arg
    1970            1975                1980

Asn Arg Ala Thr Asp Leu Asp Ala Arg Met His Asp Gly Thr Thr
    1985            1990                1995

Pro Leu Ile Leu Ala Ala Arg Leu Ala Val Glu Gly Met Leu Glu
```

```
              2000            2005            2010

Asp Leu Ile Asn Ser His Ala Asp Val Asn Ala Val Asp Asp Leu
    2015            2020            2025

Gly Lys Ser Ala Leu His Trp Ala Ala Ala Val Asn Asn Val Asp
    2030            2035            2040

Ala Ala Val Val Leu Leu Lys Asn Gly Ala Asn Lys Asp Met Gln
    2045            2050            2055

Asn Asn Arg Glu Glu Thr Pro Leu Phe Leu Ala Ala Arg Glu Gly
    2060            2065            2070

Ser Tyr Glu Thr Ala Lys Val Leu Leu Asp His Phe Ala Asn Arg
    2075            2080            2085

Asp Ile Thr Asp His Met Asp Arg Leu Pro Arg Asp Ile Ala Gln
    2090            2095            2100

Glu Arg Met His His Asp Ile Val Arg Leu Leu Asp Glu Tyr Asn
    2105            2110            2115

Leu Val Arg Ser Pro Gln Leu His Gly Ala Pro Leu Gly Gly Thr
    2120            2125            2130

Pro Thr Leu Ser Pro Pro Leu Cys Ser Pro Asn Gly Tyr Leu Gly
    2135            2140            2145

Ser Leu Lys Pro Gly Val Gln Gly Lys Lys Val Arg Lys Pro Ser
    2150            2155            2160

Ser Lys Gly Leu Ala Cys Gly Ser Lys Glu Ala Lys Asp Leu Lys
    2165            2170            2175

Ala Arg Arg Lys Lys Ser Gln Asp Gly Lys Gly Cys Leu Leu Asp
    2180            2185            2190

Ser Ser Gly Met Leu Ser Pro Val Asp Ser Leu Glu Ser Pro His
    2195            2200            2205

Gly Tyr Leu Ser Asp Val Ala Ser Pro Pro Leu Leu Pro Ser Pro
    2210            2215            2220

Phe Gln Gln Ser Pro Ser Val Pro Leu Asn His Leu Pro Gly Met
    2225            2230            2235

Pro Asp Thr His Leu Gly Ile Gly His Leu Asn Val Ala Ala Lys
    2240            2245            2250

Pro Glu Met Ala Ala Leu Gly Gly Gly Gly Arg Leu Ala Phe Glu
    2255            2260            2265

Thr Gly Pro Pro Arg Leu Ser His Leu Pro Val Ala Ser Gly Thr
    2270            2275            2280

Ser Thr Val Leu Gly Ser Ser Ser Gly Gly Ala Leu Asn Phe Thr
    2285            2290            2295

Val Gly Gly Ser Thr Ser Leu Asn Gly Gln Cys Glu Trp Leu Ser
    2300            2305            2310

Arg Leu Gln Ser Gly Met Val Pro Asn Gln Tyr Asn Pro Leu Arg
    2315            2320            2325

Gly Ser Val Ala Pro Gly Pro Leu Ser Thr Gln Ala Pro Ser Leu
    2330            2335            2340

Gln His Gly Met Val Gly Pro Leu His Ser Ser Leu Ala Ala Ser
    2345            2350            2355

Ala Leu Ser Gln Met Met Ser Tyr Gln Gly Leu Pro Ser Thr Arg
    2360            2365            2370

Leu Ala Thr Gln Pro His Leu Val Gln Thr Gln Gln Val Gln Pro
    2375            2380            2385

Gln Asn Leu Gln Met Gln Gln Gln Asn Leu Gln Pro Ala Asn Ile
    2390            2395            2400
```

| | | | | | | | | | | | |
|---|---|---|---|---|---|---|---|---|---|---|---|
| Gln | Gln | Gln | Gln | Ser | Leu | Gln | Pro | Pro | Pro | Pro | |
| | 2405 | | | | 2410 | | | | 2415 | | |
| Pro | Gln | Pro | His | Leu | Gly | Val | Ser | Ser | Ala | Ala | Ser |
| | | | 2420 | | | | 2425 | | | | |
| Gly | His | Leu | Gly | Arg | Ser | Phe | Leu | Ser | Gly | Glu | Pro |
| 2430 | | | | | | 2435 | | | | | 2440 |
| Ser | Gln | Ala | Asp | Val | Gln | Pro | Leu | Gly | Pro | Ser | Ser |
| | | | | 2445 | | | | | 2450 | | |
| Leu | Ala | Val | His | Thr | Ile | Leu | Pro | Gln | Glu | Ser | Pro |
| | | 2455 | | | | 2460 | | | | | |
| Ala | Leu | Pro | Thr | Ser | Leu | Pro | Ser | Ser | Leu | Val | Pro |
| 2465 | | | | | 2470 | | | | | 2475 | |
| Pro | Val | Thr | Ala | Ala | Gln | Phe | Leu | Thr | Pro | Pro | Ser |
| | | | 2480 | | | | | 2485 | | | |
| Gln | His | Ser | Tyr | Ser | Ser | Pro | Val | Asp | Asn | Thr | Pro |
| | | 2490 | | | | 2495 | | | | | 2500 |
| Ser | His | Gln | Leu | Gln | Val | Pro | Glu | His | Pro | Phe | Leu |
| | | | 2505 | | | | | 2510 | | | |
| Thr | Pro | Ser | Pro | Glu | Ser | Pro | Asp | Gln | Trp | Ser | Ser |
| | | 2515 | | | | 2520 | | | | | |
| Ser | Ser | Pro | His | Ser | Asn | Val | Ser | Asp | Trp | Ser | Glu |
| 2525 | | | | | 2530 | | | | | 2535 | |
| Gly | Val | Ser | Ser | Pro | Pro | Thr | Ser | Met | Gln | Ser | Gln |
| | | | 2540 | | | | | 2545 | | | |
| Ile | Ala | Arg | Ile | Pro | Glu | Ala | Phe | Lys | | | |
| | | 2550 | | | | | 2555 | | | | |

<210> SEQ ID NO 16
<211> LENGTH: 11433
<212> TYPE: DNA
<213> ORGANISM: Homo sapiens
<220> FEATURE:
<221> NAME/KEY: misc_feature
<223> OTHER INFORMATION: Notch-2

<400> SEQUENCE: 16

| | | |
|---|---|---|
| aggctgcttc gttgcacacc cgagaaagtt tcagccaaac ttcgggcggc ggctgaggcg | 60 |
| gcggccgagg agcggcggac tcggggcgcg gggagtcgag gcatttgcgc ctgggcttcg | 120 |
| gagcgtagcg ccagggcctg agcctttgaa gcaggaggag gggaggagag agtggggctc | 180 |
| ctctatcggg acccccctccc catgtggatc tgcccaggcg gcggcggcgg cggcggagga | 240 |
| ggaggcgacc gagaagatgc ccgccctgcg ccccgctctg ctgtgggcgc tgctggcgct | 300 |
| ctggctgtgc tgcgcggccc ccgcgcatgc attgcagtgt cgagatggct atgaaccctg | 360 |
| tgtaaatgaa ggaatgtgtg ttacctacca caatggcaca ggatactgca atgtccaga | 420 |
| aggcttcttg ggggaatatt gtcaacatcg agacccctgt gagaagaacc gctgccagaa | 480 |
| tggtgggact tgtgtggccc aggccatgct ggggaaagcc acgtgccgat gtgcctcagg | 540 |
| gtttacagga gaggactgcc agtactcaac atctcatcca tgctttgtgt ctcgaccctg | 600 |
| cctgaatggc ggcacatgcc atatgctcag ccgggatacc tatgagtgca cctgtcaagt | 660 |
| cgggtttaca ggtaaggagt gccaatggac ggatgcctgc ctgtctcatc cctgtgcaaa | 720 |
| tggaagtacc tgtaccactg tggccaacca gttctcctgc aaatgcctca caggcttcac | 780 |
| agggcagaaa tgtgagactg atgtcaatga gtgtgacatt ccaggacact gccagcatgg | 840 |
| tggcacctgc ctcaacctgc ctggttccta ccagtgccag tgccctcagg gcttcacagg | 900 |
| ccagtactgt gacagcctgt atgtgccctg tgcaccctca ccttgtgtca atggaggcac | 960 |
| ctgtcggcag actggtgact cactttttga gtgcaactgc cttccaggtt ttgaagggag | 1020 |
| cacctgtgag aggaatattg atgactgccc taaccacagg tgtcagaatg gaggggtttg | 1080 |

```
tgtggatggg gtcaacactt acaactgccg ctgtccccca caatggacag gacagttctg   1140
cacagaggat gtggatgaat gcctgctgca gcccaatgcc tgtcaaaatg ggggcacctg   1200
tgccaaccgc aatggaggct atggctgtgt atgtgtcaac ggctggagtg agatgactg    1260 cagtgagaac attgatgatt gtgccttcgc ctcctgtact ccaggctcca cctgcatcga   1320
ccgtgtggcc tccttctctt gcatgtgccc agaggggaag gcaggtctcc tgtgtcatct   1380
ggatgatgca tgcatcagca atccttgcca caagggggca ctgtgtgaca ccaacccccct 1440 aaatgggcaa tatatttgca cctgcccaca aggctacaaa ggggctgact gcacagaaga   1500
tgtggatgaa tgtgccatgg ccaatagcaa tccttgtgag catgcaggaa aatgtgtgaa   1560
cacggatggc gccttccact gtgagtgtct gaagggttat gcaggacctc gttgtgagat   1620
ggacatcaat gagtgccatt cagacccctg ccagaatgat gctacctgtc tggataagat   1680
tggaggcttc acatgtctgt gcatgccagg tttcaaaggt gtgcattgtg aattagaaat   1740
aaatgaatgt cagagcaacc cttgtgtgaa caatgggcag tgtgtggata aagtcaatcg   1800
tttccagtgc ctgtgtcctc ctggtttcac tgggccagtt tgccagattg atattgatga   1860
ctgttccagt actccgtgtc tgaatggggc aaagtgtatc gatcacccga atggctatga   1920
atgccagtgt gccacaggtt tcactggtgt gttgtgtgag gagaacattg acaactgtga   1980
ccccgatcct tgccaccatg gtcagtgtca ggatggtatt gattcctaca cctgcatctg   2040
caatcccggg tacatgggcg ccatctgcag tgaccagatt gatgaatgtt acagcagccc   2100
ttgcctgaac gatggtcgct gcattgacct ggtcaatggc taccagtgca actgccagcc   2160
aggcacgtca ggggttaatt gtgaaattaa ttttgatgac tgtgcaagta acccttgtat   2220
ccatggaatc tgtatggatg gcattaatcg ctacagttgt gtctgctcac caggattcac   2280
agggcagaga tgtaacattg acattgatga gtgtgcctcc aatccctgtc gcaagggtgc   2340
aacatgtatc aacggtgtga atggtttccg ctgtatatgc cccgaggggc cccatcaccc   2400
cagctgctac tcacaggtga acgaatgcct gagcaatccc tgcatccatg gaaactgtac   2460
tggaggtctc agtggatata gtgtctctg tgatgcaggc tgggttggca tcaactgtga   2520
agtggacaaa aatgaatgcc tttcgaatcc atgccagaat ggaggaactt gtgacaatct   2580
ggtgaatgga tacaggtgta cttgcaagaa gggctttaaa ggctataact gccaggtgaa   2640
tattgatgaa tgtgcctcaa atccatgcct gaaccaagga acctgctttg atgacataag   2700
tggctacact tgccactgtg tgctgccata cacaggcaag aattgtcaga cagtattggc   2760
tccctgttcc ccaaaccctt gtgagaatgc tgctgtttgc aaagagtcac caaattttga   2820
gagttatact tgcttgtgtg ctcctggctg gcaaggtcag cggtgtacca ttgacattga   2880
cgagtgtatc tccaagccct gcatgaacca tggtctctgc cataacaccc agggcagcta   2940
catgtgtgaa tgtccaccag gcttcagtgg tatggactgt gaggaggaca ttgatgactg   3000
ccttgccaat ccttgccaga atggaggttc ctgtatggat ggagtgaata ctttctcctg   3060
cctctgcctt ccgggtttca ctggggataa gtgccagaca gacatgaatg agtgtctgag   3120
tgaacccgtt aagaatggag ggacctgctc tgactacgtc aacagttaca cttgcaagtg   3180
ccagccagga tttgatggag tccattgtga gaacaacatc aatgagtgca ctgagagctc   3240
ctgtttcaat ggtggcacat gtgttgatgg gattaactcc ttctcttgct gtgccctgt    3300 gggtttcact ggatccttct gcctccatga gatcaatgaa tgcagctctc atccatgcct   3360
gaatgaggga acgtgtgttg atggcctggg tacctaccgc tgcagctgcc ccctgggcta   3420
cactgggaaa aactgtcaga ccctggtgaa tctctgcagt cggtctccat gtaaaaacaa   3480
```

-continued

| | |
|---|---|
| aggtacttgc gttcagaaaa aagcagagtc ccagtgccta tgtccatctg gatgggctgg | 3540 |
| tgcctattgt gacgtgccca atgtctcttg tgacatagca gcctccagga gaggtgtgct | 3600 |
| tgttgaacac ttgtgccagc actcaggtgt ctgcatcaat gctggcaaca cgcattactg | 3660 |
| tcagtgcccc ctgggctata ctgggagcta ctgtgaggag caactcgatg agtgtgcgtc | 3720 |
| caaccccctgc cagcacgggg caacatgcag tgacttcatt ggtggataca gatgcgagtg | 3780 |
| tgtcccaggc tatcagggtg tcaactgtga gtatgaagtg gatgagtgcc agaatcagcc | 3840 |
| ctgccagaat ggaggcacct gtattgacct tgtgaaccat ttcaagtgct cttgcccacc | 3900 |
| aggcactcgg ggcctactct gtgaagagaa cattgatgac tgtgcccggg tccccattg | 3960 |
| ccttaatggt ggtcagtgca tggataggat tggaggctac agttgtcgct gcttgcctgg | 4020 |
| ctttgctggg gagcgttgtg agggagacat caacgagtgc ctctccaacc cctgcagctc | 4080 |
| tgagggcagc ctggactgta tacagctcac caatgactac ctgtgtgttt gccgtagtgc | 4140 |
| ctttactggc cggcactgtg aaaccttcgt cgatgtgtgt ccccagatgc cctgcctgaa | 4200 |
| tggagggact tgtgctgtgg ccagtaacat gcctgatggt ttcatttgcc gttgtccccc | 4260 |
| gggattttcc ggggcaaggt gccagagcag ctgtggacaa gtgaaatgta ggaaggggga | 4320 |
| gcagtgtgtg cacaccgcct ctggaccccg ctgcttctgc cccagtcccc gggactgcga | 4380 |
| gtcaggctgt gccagtagcc cctgccagca cggggggcagc tgccaccctc agcgccagcc | 4440 |
| tccttattac tcctgccagt gtgccccacc attctcgggt agccgctgtg aactctacac | 4500 |
| ggcaccccc agcaccectc ctgccacctg tctgagccag tattgtgccg acaaagctcg | 4560 |
| ggatggcgtc tgtgatgagg cctgcaacag ccatgcctgc cagtgggatg ggggtgactg | 4620 |
| ttctctcacc atggagaacc cctgggccaa ctgctcctcc ccacttccct gctgggatta | 4680 |
| tatcaacaac cagtgtgatg agctgtgcaa cacggtcgag tgcctgtttg acaactttga | 4740 |
| atgccagggg aacagcaaga catgcaagta tgacaaatac tgtgcagacc acttcaaaga | 4800 |
| caaccactgt gaccaggggt gcaacagtga ggagtgtggt tgggatgggc tggactgtgc | 4860 |
| tgctgaccaa cctgagaacc tggcagaagg taccctggtt attgtggtat tgatgccacc | 4920 |
| tgaacaactg ctccaggatg ctcgcagctt cttgcgggca ctgggtaccc tgctccacac | 4980 |
| caacctgcgc attaagcggg actcccaggg ggaactcatg gtgtaccct attatggtga | 5040 |
| gaagtcagct gctatgaaga acagaggat gacacgcaga tcccttcctg gtgaacaaga | 5100 |
| acaggaggtg gctggctcta aagtctttct ggaaattgac aaccgccagt gtgttcaaga | 5160 |
| ctcagaccac tgcttcaaga acacggatgc agcagcagct ctcctggcct tcacgccat | 5220 |
| acagggggacc ctgtcatacc ctcttgtgtc tgtcgtcagt gaatccctga ctccagaacg | 5280 |
| cactcagctc ctctatctcc ttgctgttgc tgttgtcatc attctgtttta ttattctgct | 5340 |
| gggggtaatc atggcaaaac gaaagcgtaa gcatggctct ctctggctgc ctgaaggttt | 5400 |
| cactcttcgc cgagatgcaa gcaatcacaa gcgtcgtgag ccagtgggac aggatgctgt | 5460 |
| ggggctgaaa aatctctcag tgcaagtctc agaagctaac ctaattggta ctggaacaag | 5520 |
| tgaacactgg gtcgatgatg aagggcccca gccaaagaaa gtaaaggctg aagatgaggc | 5580 |
| cttactctca gaagaagatg accccattga tcgacggcca tggacacagc agcaccttga | 5640 |
| agctgcagac atccgtagga caccatcgct ggctctcacc cctcctcagg cagagcagga | 5700 |
| ggtggatgtg ttagatgtga atgtccgtgg cccagatggc tgcaccccat tgatgttggc | 5760 |
| ttctctccga ggaggcagct cagatttgag tgatgaagat gaagatgcag aggactcttc | 5820 |
| tgctaacatc atcacagact tggtctacca gggtgccagc ctccaggccc agacagaccg | 5880 |

```
gactggtgag atggccctgc accttgcagc ccgctactca cgggctgatg ctgccaagcg    5940
tctcctggat gcaggtgcag atgccaatgc ccaggacaac atgggccgct gtccactcca    6000
tgctgcagtg gcagctgatg cccaaggtgt cttccagatt ctgattcgca accgagtaac    6060
tgatctagat gccaggatga atgatggtac tacaccctg atcctggctg cccgcctggc     6120
tgtggaggga atggtggcag aactgatcaa ctgccaagcg gatgtgaatg cagtggatga    6180
ccatggaaaa tctgctcttc actgggcagc tgctgtcaat aatgtggagg caactctttt    6240
gttgttgaaa atggggcca accgagacat gcaggacaac aaggaagaga ccctctgtt      6300
tcttgctgcc cggaggga gctatgaagc agccaagatc ctgttagacc attttgccaa      6360
tcgagacatc acagaccata tggatcgtct tccccgggat gtggctcggg atcgcatgca    6420
ccatgacatt gtgcgccttc tggatgaata caatgtgacc ccaagccctc caggcaccgt    6480
gttgacttct gctctctcac ctgtcatctg tgggcccaac agatctttcc tcagcctgaa    6540
gcacaccccca tgggcaaga agtctagacg gcccagtgcc aagagtacca tgcctactag    6600
cctccctaac cttgccaagg aggcaaagga tgccaagggt agtaggagga agaagtctct    6660
gagtgagaag gtccaactgt ctgagagttc agtaacttta tccctgttg attccctaga     6720
atctcctcac acgtatgttt ccgacaccac atcctctcca atgattacat cccctgggat    6780
cttacaggcc tcacccaacc ctatgttggc cactgccgcc cctcctgccc cagtccatgc    6840
ccagcatgca ctatctttt ctaaccttca tgaaatgcag cctttggcac atggggccag     6900
cactgtgctt ccctcagtga gccagttgct atcccaccac acattgtgt ctccaggcag     6960
tggcagtgct ggaagcttga gtaggctcca tccagtccca gtcccagcag attggatgaa    7020
ccgcatggag gtgaatgaga cccagtacaa tgagatgttt ggtatggtcc tggctccagc    7080
tgagggcacc catcctggca tagctcccca gagcaggcca cctgaaggga agcacataac    7140
caccctcgg gagcccttgc cccccattgt gactttccag ctcatcccta aaggcagtat     7200
tgcccaacca gcgggggctc cccagcctca gtccacctgc cctccagctg ttgcgggccc    7260
cctgcccacc atgtaccaga ttccagaaat ggcccgtttg ccagtgtgg ctttccccac     7320
tgccatgatg ccccagcagg acgggcaggt agctcagacc attctcccag cctatcatcc    7380
tttcccagcc tctgtgggca agtaccccac accccttca cagcacagtt atgcttcctc     7440
aaatgctgct gagcgaacac ccagtcacag tggtcacctc cagggtgagc atccctacct    7500
gacaccatcc ccagagtctc ctgaccagtg gtcaagttca tcaccccact ctgcttctga    7560
ctggtcagat gtgaccacca gcctacccc tgggggtgct ggaggaggtc agcggggacc     7620
tgggacacac atgtctgagc caccacacaa caacatgcag gtttatgcgt gagagagtcc    7680
acctccagtg tagagacata actgactttt gtaaatgctg ctgaggaaca atgaaggtc     7740
atccgggaga gaaatgaaga aatctctgga gccagcttct agaggtagga agagaagat     7800
gttcttattc agataatgca agagaagcaa ttcgtcagtt tcactgggta tctgcaaggc    7860
ttattgatta ttctaatcta ataagacaag tttgtggaaa tgcaagatga atacaagcct    7920
tgggtccatg tttactctct tctatttgga gaataagatg gatgcttatt gaagcccaga    7980
cattcttgca gcttggactg catttaagc cctgcaggct tctgccatat ccatgagaag     8040
attctacact agcgtcctgt tgggaattat gccctgaat tctgcctgaa ttgacctacg     8100
catctcctcc tccttggaca ttcttttgtc ttcatttggt gcttttggtt ttgcacctct    8160
ccgtgattgt agccctacca gcatgttata gggcaagacc tttgtgcttt tgatcattct    8220
ggcccatgaa agcaactttg gtctcctttc ccctcctgtc ttcccggtat cccttggagt    8280
```

```
ctcacaaggt ttactttggt atggttctca gcacaaacct ttcaagtatg ttgtttcttt   8340
ggaaaatgga catactgtat tgtgttctcc tgcatatatc attcctggag agagaagggg   8400
agaagaatac ttttcttcaa caaattttgg gggcaggaga tcccttcaag aggctgcacc   8460 ttaattttc ttgtctgtgt gcaggtcttc atataaactt taccaggaag aagggtgtga   8520
gtttgttgtt tttctgtgta tgggcctggt cagtgtaaag ttttatcctt gatagtctag   8580
ttactatgac cctccccact tttttaaaac cagaaaaagg tttggaatgt tggaatgacc   8640
aagagacaag ttaactcgtg caagagccag ttacccaccc acaggtcccc ctacttcctg   8700
ccaagcattc cattgactgc ctgtatggaa cacatttgtc ccagatctga gcattctagg   8760
cctgtttcac tcactcaccc agcatatgaa actagtctta actgttgagc cttccttc   8820 atatccacag aagacactgt ctcaaatgtt gtacccttgc catttaggac tgaacttcc   8880 ttagcccaag ggacccagtg acagttgtct tccgtttgtc agatgatcag tctctactga   8940
ttatcttgct gctaaaggc ctgctcacca atctttcttt cacaccgtgt ggtccgtgtt   9000
actggtatac ccagtatgtt ctcactgaag acatggactt tatatgttca agtgcaggaa   9060
ttggaaagtt ggacttgttt tctatgatcc aaaacagccc tataagaagg ttggaaaagg   9120
aggaactata tagcagcctt tgctatttc tgctaccatt tcttttcctc tgaagcggcc   9180 atgcattcc ctttggcaac taacgtagaa actcaacaga acattttcct ttcctagagt   9240 cacctttag atgataatgg acaactatag acttgctcat tgttcagact gattgcccct   9300
cacctgaatc cactctctgt attcatgctc ttggcaattt ctttgacttt cttttaaggg   9360
cagaagcatt ttagttaatt gtagataaag aatagttttc ttcctcttct ccttgggcca   9420
gttaataatt ggtccatggc tacactgcaa cttccgtcca gtgctgtgat gcccatgaca   9480
cctgcaaaat aagttctgcc tgggcatttt gtagatatta acaggtgaat tcccgactct   9540
tttggtttga atgacagttc tcattccttc tatggctgca agtatgcatc agtgcttccc   9600
acttacctga tttgtctgtc ggtggcccca tatggaaacc ctgcgtgtct gttggcataa   9660
tagtttacaa atggttttt cagtcctatc caaatttatt gaaccaacaa aaataattac   9720
ttctgccctg agataagcag attaagtttg ttcattctct gctttattct ctccatgtgg   9780
caacattctg tcagcctctt tcatagtgtg caaacatttt atcattctaa atggtgactc   9840
tctgcccttg gacccattta ttattcacag atggggagaa cctatctgca tggacctctg   9900
tggaccacag cgtacctgcc cctttctgcc ctcctgctcc agcccacctt ctgaaagtat   9960
cagctactga tccagccact ggatatttta tatcctccct tttccttaag cacaatgtca  10020
gaccaaattg cttgtttctt tttcttggac tactttaatt tggatccttt gggtttggag  10080
aaagggaatg tgaaagctgt cattacagac aacaggtttc agtgatgagg aggacaacac  10140
tgcctttcaa actttttact gatctcttag attttaagaa ctcttgaatt gtgtggtatc  10200
taataaaagg gaaggtaaga tggataatca ctttctcatt tgggttctga attggagact  10260
cagtttttat gagacacatc ttttatgcca tgtatagatc ctcccctgct attttggtt  10320 tattttatt gttataaatg cttcttct ttgactcctc ttctgcctgc ctttgggat   10380 aggttttttt gtttgtttat ttgcttcctc tgttttgttt taagcatcat tttcttatgt  10440
gaggtgggga agggaaaggt atgagggaaa gagagtctga gaattaaaat atttagtat  10500 aagcaattgg ctgtgatgct caaatccatt gcatcctctt attgaatttg ccaatttgta  10560
atttttgcat aataaagaac caaaggtgta atgtttgtt gagaggtggt ttagggattt  10620
tggccctaac caatacattg aatgtatgat gactatttgg gaggacacat ttatgtaccc  10680
```

```
agaggcccc  actaataagt  ggtactatgg  ttacttcctt  gtgtacattt  ctcttaaaag    10740
tgatattata  tctgtttgta  tgagaaaccc  agtaaccaat  aaaatgaccg  catattcctg    10800
actaaacgta  gtaaggaaaa  tgcacacttt  gttttactt   ttccgtttca  ttctaaaggt    10860
agttaagatg  aaatttatat  gaaagcattt  ttatcacaaa  ataaaaaagg  tttgccaagc    10920
tcagtggtgt  tgtatttttt  attttccaat  actgcatcca  tggcctggca  gtgttacctc    10980
atgatgtcat  aatttgctga  gagagcaaat  tttcttttct  ttctgaatcc  cacaaagcct    11040
agcaccaaac  ttcttttttt  cttcctttaa  ttagatcata  aataaatgat  cctggggaaa    11100
aagcatctgt  caaataggaa  acatcacaaa  actgagcact  cttctgtgca  ctagccatag    11160
ctggtgacaa  acagatggtt  gctcagggac  aaggtgcctt  ccaatggaaa  tgcgaagtag    11220
ttgctatagc  aagaattggg  aactgggata  taagtcataa  tattaattat  gctgttatgt    11280
aaatgattgg  tttgtaacat  tccttaagtg  aaatttgtgt  agaacttaat  atacaggatt    11340
ataaaataat  attttgtgta  taaatttgtt  ataagttcac  attcatacat  ttatttataa    11400
agtcagtgag  atatttgaac  atgaaaaaaa  aaa                                   11433
```

<210> SEQ ID NO 17
<211> LENGTH: 2471
<212> TYPE: PRT
<213> ORGANISM: Homo sapiens
<220> FEATURE:
<221> NAME/KEY: misc_feature
<223> OTHER INFORMATION: Notch-2

<400> SEQUENCE: 17

```
Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
```

```
                225                 230                 235                 240
Asp Phe Thr Phe Glu Cys Asn Cys Leu Pro Gly Phe Glu Gly Ser Thr
                245                 250                 255
Cys Glu Arg Asn Ile Asp Asp Cys Pro Asn His Arg Cys Gln Asn Gly
                260                 265                 270
Gly Val Cys Val Asp Gly Val Asn Thr Tyr Asn Cys Arg Cys Pro Pro
                275                 280                 285
Gln Trp Thr Gly Gln Phe Cys Thr Glu Asp Val Asp Glu Cys Leu Leu
                290                 295                 300
Gln Pro Asn Ala Cys Gln Asn Gly Gly Thr Cys Ala Asn Arg Asn Gly
305                 310                 315                 320
Gly Tyr Gly Cys Val Cys Val Asn Gly Trp Ser Gly Asp Asp Cys Ser
                325                 330                 335
Glu Asn Ile Asp Asp Cys Ala Phe Ala Ser Cys Thr Pro Gly Ser Thr
                340                 345                 350
Cys Ile Asp Arg Val Ala Ser Phe Ser Cys Met Cys Pro Glu Gly Lys
                355                 360                 365
Ala Gly Leu Leu Cys His Leu Asp Asp Ala Cys Ile Ser Asn Pro Cys
                370                 375                 380
His Lys Gly Ala Leu Cys Asp Thr Asn Pro Leu Asn Gly Gln Tyr Ile
385                 390                 395                 400
Cys Thr Cys Pro Gln Gly Tyr Lys Gly Ala Asp Cys Thr Glu Asp Val
                405                 410                 415
Asp Glu Cys Ala Met Ala Asn Ser Asn Pro Cys Glu His Ala Gly Lys
                420                 425                 430
Cys Val Asn Thr Asp Gly Ala Phe His Cys Glu Cys Leu Lys Gly Tyr
                435                 440                 445
Ala Gly Pro Arg Cys Glu Met Asp Ile Asn Glu Cys His Ser Asp Pro
                450                 455                 460
Cys Gln Asn Asp Ala Thr Cys Leu Asp Lys Ile Gly Gly Phe Thr Cys
465                 470                 475                 480
Leu Cys Met Pro Gly Phe Lys Gly Val His Cys Glu Leu Glu Ile Asn
                485                 490                 495
Glu Cys Gln Ser Asn Pro Cys Val Asn Asn Gly Gln Cys Val Asp Lys
                500                 505                 510
Val Asn Arg Phe Gln Cys Leu Cys Pro Pro Gly Phe Thr Gly Pro Val
                515                 520                 525
Cys Gln Ile Asp Ile Asp Asp Cys Ser Ser Thr Pro Cys Leu Asn Gly
530                 535                 540
Ala Lys Cys Ile Asp His Pro Asn Gly Tyr Glu Cys Gln Cys Ala Thr
545                 550                 555                 560
Gly Phe Thr Gly Val Leu Cys Glu Glu Asn Ile Asp Asn Cys Asp Pro
                565                 570                 575
Asp Pro Cys His His Gly Gln Cys Gln Asp Gly Ile Asp Ser Tyr Thr
                580                 585                 590
Cys Ile Cys Asn Pro Gly Tyr Met Gly Ala Ile Cys Ser Asp Gln Ile
                595                 600                 605
Asp Glu Cys Tyr Ser Ser Pro Cys Leu Asn Asp Gly Arg Cys Ile Asp
                610                 615                 620
Leu Val Asn Gly Tyr Gln Cys Asn Cys Gln Pro Gly Thr Ser Gly Val
625                 630                 635                 640
Asn Cys Glu Ile Asn Phe Asp Asp Cys Ala Ser Asn Pro Cys Ile His
                645                 650                 655
```

-continued

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
            675                 680                 685

Asn Pro Cys Arg Lys Gly Ala Thr Cys Ile Asn Gly Val Asn Gly Phe
690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
            755                 760                 765

Gly Gly Thr Cys Asp Asn Leu Val Asn Gly Tyr Arg Cys Thr Cys Lys
            770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
            835                 840                 845

Lys Glu Ser Pro Asn Phe Glu Ser Tyr Thr Cys Leu Cys Ala Pro Gly
850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
            915                 920                 925

Gly Val Asn Thr Phe Ser Cys Leu Cys Leu Pro Gly Phe Thr Gly Asp
            930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
            980                 985                 990

Glu Ser Ser Cys Phe Asn Gly Gly Thr Cys Val Asp Gly Ile Asn Ser
            995                 1000                1005

Phe Ser Cys Leu Cys Pro Val Gly Phe Thr Gly Ser Phe Cys Leu
            1010                1015                1020

His Glu Ile Asn Glu Cys Ser Ser His Pro Cys Leu Asn Glu Gly
            1025                1030                1035

Thr Cys Val Asp Gly Leu Gly Thr Tyr Arg Cys Ser Cys Pro Leu
            1040                1045                1050

Gly Tyr Thr Gly Lys Asn Cys Gln Thr Leu Val Asn Leu Cys Ser
            1055                1060                1065

Arg Ser Pro Cys Lys Asn Lys Gly Thr Cys Val Gln Lys Lys Ala
            1070                1075                1080

```
Glu Ser Gln Cys Leu Cys Pro Ser Gly Trp Ala Gly Ala Tyr Cys
    1085            1090                1095

Asp Val Pro Asn Val Ser Cys Asp Ile Ala Ala Ser Arg Arg Gly
    1100            1105                1110

Val Leu Val Glu His Leu Cys Gln His Ser Gly Val Cys Ile Asn
    1115            1120                1125

Ala Gly Asn Thr His Tyr Cys Gln Cys Pro Leu Gly Tyr Thr Gly
    1130            1135                1140

Ser Tyr Cys Glu Glu Gln Leu Asp Glu Cys Ala Ser Asn Pro Cys
    1145            1150                1155

Gln His Gly Ala Thr Cys Ser Asp Phe Ile Gly Gly Tyr Arg Cys
    1160            1165                1170

Glu Cys Val Pro Gly Tyr Gln Gly Val Asn Cys Glu Tyr Glu Val
    1175            1180                1185

Asp Glu Cys Gln Asn Gln Pro Cys Gln Asn Gly Gly Thr Cys Ile
    1190            1195                1200

Asp Leu Val Asn His Phe Lys Cys Ser Cys Pro Pro Gly Thr Arg
    1205            1210                1215

Gly Leu Leu Cys Glu Glu Asn Ile Asp Asp Cys Ala Arg Gly Pro
    1220            1225                1230

His Cys Leu Asn Gly Gly Gln Cys Met Asp Arg Ile Gly Gly Tyr
    1235            1240                1245

Ser Cys Arg Cys Leu Pro Gly Phe Ala Gly Glu Arg Cys Glu Gly
    1250            1255                1260

Asp Ile Asn Glu Cys Leu Ser Asn Pro Cys Ser Ser Glu Gly Ser
    1265            1270                1275

Leu Asp Cys Ile Gln Leu Thr Asn Asp Tyr Leu Cys Val Cys Arg
    1280            1285                1290

Ser Ala Phe Thr Gly Arg His Cys Glu Thr Phe Val Asp Val Cys
    1295            1300                1305

Pro Gln Met Pro Cys Leu Asn Gly Gly Thr Cys Ala Val Ala Ser
    1310            1315                1320

Asn Met Pro Asp Gly Phe Ile Cys Arg Cys Pro Pro Gly Phe Ser
    1325            1330                1335

Gly Ala Arg Cys Gln Ser Ser Cys Gly Gln Val Lys Cys Arg Lys
    1340            1345                1350

Gly Glu Gln Cys Val His Thr Ala Ser Gly Pro Arg Cys Phe Cys
    1355            1360                1365

Pro Ser Pro Arg Asp Cys Glu Ser Gly Cys Ala Ser Ser Pro Cys
    1370            1375                1380

Gln His Gly Gly Ser Cys His Pro Gln Arg Gln Pro Pro Tyr Tyr
    1385            1390                1395

Ser Cys Gln Cys Ala Pro Pro Phe Ser Gly Ser Arg Cys Glu Leu
    1400            1405                1410

Tyr Thr Ala Pro Pro Ser Thr Pro Pro Ala Thr Cys Leu Ser Gln
    1415            1420                1425

Tyr Cys Ala Asp Lys Ala Arg Asp Gly Val Cys Asp Glu Ala Cys
    1430            1435                1440

Asn Ser His Ala Cys Gln Trp Asp Gly Gly Asp Cys Ser Leu Thr
    1445            1450                1455

Met Glu Asn Pro Trp Ala Asn Cys Ser Ser Pro Leu Pro Cys Trp
    1460            1465                1470

Asp Tyr Ile Asn Asn Gln Cys Asp Glu Leu Cys Asn Thr Val Glu
```

```
                    1475              1480              1485

Cys Leu Phe Asp Asn Phe Glu Cys Gln Gly Asn Ser Lys Thr Cys
    1490              1495              1500

Lys Tyr Asp Lys Tyr Cys Ala Asp His Phe Lys Asp Asn His Cys
    1505              1510              1515

Asp Gln Gly Cys Asn Ser Glu Glu Cys Gly Trp Asp Gly Leu Asp
    1520              1525              1530

Cys Ala Ala Asp Gln Pro Glu Asn Leu Ala Glu Gly Thr Leu Val
    1535              1540              1545

Ile Val Val Leu Met Pro Pro Glu Gln Leu Leu Gln Asp Ala Arg
    1550              1555              1560

Ser Phe Leu Arg Ala Leu Gly Thr Leu Leu His Thr Asn Leu Arg
    1565              1570              1575

Ile Lys Arg Asp Ser Gln Gly Glu Leu Met Val Tyr Pro Tyr Tyr
    1580              1585              1590

Gly Glu Lys Ser Ala Ala Met Lys Lys Gln Arg Met Thr Arg Arg
    1595              1600              1605

Ser Leu Pro Gly Glu Gln Glu Gln Glu Val Ala Gly Ser Lys Val
    1610              1615              1620

Phe Leu Glu Ile Asp Asn Arg Gln Cys Val Gln Asp Ser Asp His
    1625              1630              1635

Cys Phe Lys Asn Thr Asp Ala Ala Ala Ala Leu Leu Ala Ser His
    1640              1645              1650

Ala Ile Gln Gly Thr Leu Ser Tyr Pro Leu Val Ser Val Val Ser
    1655              1660              1665

Glu Ser Leu Thr Pro Glu Arg Thr Gln Leu Leu Tyr Leu Leu Ala
    1670              1675              1680

Val Ala Val Val Ile Ile Leu Phe Ile Ile Leu Leu Gly Val Ile
    1685              1690              1695

Met Ala Lys Arg Lys Arg Lys His Gly Ser Leu Trp Leu Pro Glu
    1700              1705              1710

Gly Phe Thr Leu Arg Arg Asp Ala Ser Asn His Lys Arg Arg Glu
    1715              1720              1725

Pro Val Gly Gln Asp Ala Val Gly Leu Lys Asn Leu Ser Val Gln
    1730              1735              1740

Val Ser Glu Ala Asn Leu Ile Gly Thr Gly Thr Ser Glu His Trp
    1745              1750              1755

Val Asp Asp Glu Gly Pro Gln Pro Lys Lys Val Lys Ala Glu Asp
    1760              1765              1770

Glu Ala Leu Leu Ser Glu Glu Asp Asp Pro Ile Asp Arg Arg Pro
    1775              1780              1785

Trp Thr Gln Gln His Leu Glu Ala Ala Asp Ile Arg Arg Thr Pro
    1790              1795              1800

Ser Leu Ala Leu Thr Pro Pro Gln Ala Glu Gln Glu Val Asp Val
    1805              1810              1815

Leu Asp Val Asn Val Arg Gly Pro Asp Gly Cys Thr Pro Leu Met
    1820              1825              1830

Leu Ala Ser Leu Arg Gly Gly Ser Ser Asp Leu Ser Asp Glu Asp
    1835              1840              1845

Glu Asp Ala Glu Asp Ser Ser Ala Asn Ile Ile Thr Asp Leu Val
    1850              1855              1860

Tyr Gln Gly Ala Ser Leu Gln Ala Gln Thr Asp Arg Thr Gly Glu
    1865              1870              1875
```

```
Met Ala Leu His Leu Ala Ala Arg Tyr Ser Arg Ala Asp Ala Ala
    1880            1885                1890

Lys Arg Leu Leu Asp Ala Gly Ala Asp Ala Asn Ala Gln Asp Asn
    1895            1900                1905

Met Gly Arg Cys Pro Leu His Ala Ala Val Ala Ala Asp Ala Gln
    1910            1915                1920

Gly Val Phe Gln Ile Leu Ile Arg Asn Arg Val Thr Asp Leu Asp
    1925            1930                1935

Ala Arg Met Asn Asp Gly Thr Thr Pro Leu Ile Leu Ala Ala Arg
    1940            1945                1950

Leu Ala Val Glu Gly Met Val Ala Glu Leu Ile Asn Cys Gln Ala
    1955            1960                1965

Asp Val Asn Ala Val Asp His Gly Lys Ser Ala Leu His Trp
    1970            1975                1980

Ala Ala Ala Val Asn Asn Val Glu Ala Thr Leu Leu Leu Leu Lys
    1985            1990                1995

Asn Gly Ala Asn Arg Asp Met Gln Asp Asn Lys Glu Glu Thr Pro
    2000            2005                2010

Leu Phe Leu Ala Ala Arg Glu Gly Ser Tyr Glu Ala Ala Lys Ile
    2015            2020                2025

Leu Leu Asp His Phe Ala Asn Arg Asp Ile Thr Asp His Met Asp
    2030            2035                2040

Arg Leu Pro Arg Asp Val Ala Arg Asp Arg Met His His Asp Ile
    2045            2050                2055

Val Arg Leu Leu Asp Glu Tyr Asn Val Thr Pro Ser Pro Pro Gly
    2060            2065                2070

Thr Val Leu Thr Ser Ala Leu Ser Pro Val Ile Cys Gly Pro Asn
    2075            2080                2085

Arg Ser Phe Leu Ser Leu Lys His Thr Pro Met Gly Lys Lys Ser
    2090            2095                2100

Arg Arg Pro Ser Ala Lys Ser Thr Met Pro Thr Ser Leu Pro Asn
    2105            2110                2115

Leu Ala Lys Glu Ala Lys Asp Ala Lys Gly Ser Arg Arg Lys Lys
    2120            2125                2130

Ser Leu Ser Glu Lys Val Gln Leu Ser Glu Ser Ser Val Thr Leu
    2135            2140                2145

Ser Pro Val Asp Ser Leu Glu Ser Pro His Thr Tyr Val Ser Asp
    2150            2155                2160

Thr Thr Ser Ser Pro Met Ile Thr Ser Pro Gly Ile Leu Gln Ala
    2165            2170                2175

Ser Pro Asn Pro Met Leu Ala Thr Ala Ala Pro Ala Pro Val
    2180            2185                2190

His Ala Gln His Ala Leu Ser Phe Ser Asn Leu His Glu Met Gln
    2195            2200                2205

Pro Leu Ala His Gly Ala Ser Thr Val Leu Pro Ser Val Ser Gln
    2210            2215                2220

Leu Leu Ser His His His Ile Val Ser Pro Gly Ser Gly Ser Ala
    2225            2230                2235

Gly Ser Leu Ser Arg Leu His Pro Val Pro Val Pro Ala Asp Trp
    2240            2245                2250

Met Asn Arg Met Glu Val Asn Glu Thr Gln Tyr Asn Glu Met Phe
    2255            2260                2265

Gly Met Val Leu Ala Pro Ala Glu Gly Thr His Pro Gly Ile Ala
    2270            2275                2280
```

```
Pro Gln Ser Arg Pro Pro Glu Gly Lys His Ile Thr Thr Pro Arg
    2285             2290                2295
Glu Pro Leu Pro Pro Ile Val Thr Phe Gln Leu Ile Pro Lys Gly
    2300             2305                2310
Ser Ile Ala Gln Pro Ala Gly Ala Pro Gln Pro Gln Ser Thr Cys
    2315             2320                2325
Pro Pro Ala Val Ala Gly Pro Leu Pro Thr Met Tyr Gln Ile Pro
    2330             2335                2340
Glu Met Ala Arg Leu Pro Ser Val Ala Phe Pro Thr Ala Met Met
    2345             2350                2355
Pro Gln Gln Asp Gly Gln Val Ala Gln Thr Ile Leu Pro Ala Tyr
    2360             2365                2370
His Pro Phe Pro Ala Ser Val Gly Lys Tyr Pro Thr Pro Pro Ser
    2375             2380                2385
Gln His Ser Tyr Ala Ser Ser Asn Ala Ala Glu Arg Thr Pro Ser
    2390             2395                2400
His Ser Gly His Leu Gln Gly Glu His Pro Tyr Leu Thr Pro Ser
    2405             2410                2415
Pro Glu Ser Pro Asp Gln Trp Ser Ser Ser Ser Pro His Ser Ala
    2420             2425                2430
Ser Asp Trp Ser Asp Val Thr Thr Ser Pro Thr Pro Gly Gly Ala
    2435             2440                2445
Gly Gly Gly Gln Arg Gly Pro Gly Thr His Met Ser Glu Pro Pro
    2450             2455                2460
His Asn Asn Met Gln Val Tyr Ala
    2465             2470

<210> SEQ ID NO 18
<211> LENGTH: 8091
<212> TYPE: DNA
<213> ORGANISM: Homo sapiens
<220> FEATURE:
<221> NAME/KEY: misc_feature
<223> OTHER INFORMATION: Notch-3

<400> SEQUENCE: 18
acgcggcgcg gaggctggcc cgggacgcgc ccggagccca gggaaggagg gaggagggga      60
gggtcgcggc cggccgccat ggggccgggg gcccgtggcc gccgccgccg ccgtcgcccg     120
atgtcgccgc caccgccacc gccacccgtg cgggcgctgc ccctgctgct gctgctagcg     180
gggccggggg ctgcagcccc cccttgcctg acggaagcc cgtgtgcaaa tggaggtcgt      240
tgcacccagc tgcccctccg ggaggctgcc tgcctgtgcc cgcctggctg ggtgggtgag     300
cggtgtcagc tggaggaccc ctgtcactca ggcccctgtg ctggccgtgg tgtctgccag     360
agttcagtgg tggctggcac cgcccgattc tcatgccggt gccccgtgg cttccgaggc      420 cctgactgct ccctgccaga tccctgcctc agcagcccct tgtcccacgg tgcccgctgc     480 tcagtgggc cgatggacg cttcctctgc tcctgccac ctggctacca gggccgcagc       540
tgccgaagcg acgtggatga gtgccgggtg ggtgagccct gccgcatgg tggcacctgc     600 ctcaacacac ctggctcctt ccgctgccag tgtccagctg gctacacagg gccactatgt     660
gagaaccccg cggtgccctg tgcgccctca ccatgccgta acggggcac tgcaggcag      720 agtggcgacc tcacttacga ctgtgcctgt cttcctgggt ttgagggtca gaattgtgaa    780
gtgaacgtgg acgactgtcc aggacaccga tgtctcaatg gggggacatg cgtggatggc    840
gtcaacacct ataactgcca gtgccctcct gagtggacag gccagttctg cacggaggac    900
```

```
gtggatgagt gtcagctgca gcccaacgcc tgccacaatg ggggtacctg cttcaacacg    960
ctgggtggcc acagctgcgt gtgtgtcaat ggctggacag gtgagagctg cagtcagaat   1020
atcgatgact gtgccacagc cgtgtgcttc catggggcca cctgccatga ccgcgtggct   1080
tctttctact gtgcctgccc catgggcaag actggcctcc tgtgtcacct ggatgacgcc   1140
tgtgtcagca cccctgcca cgaggatgct atctgtgaca caaatccggt gaacggccgg    1200
gccatttgca cctgtcctcc cggcttcacg ggtgggcat gtgaccagga tgtggacgag    1260
tgctctatcg gcgccaaccc ctgcgagcac ttgggcaggt gcgtgaacac gcagggctcc   1320
ttcctgtgcc agtgcggtcg tggctacact ggacctcgct gtgagaccga tgtcaacgag   1380
tgtctgtcgg ggccctgccg aaaccaggcc acgtgcctcg accgcatagg ccagttcacc   1440
tgtatctgta tggcaggctt cacaggaacc tattgcgagg tggacattga cgagtgtcag   1500
agtagcccct gtgtcaacgg tgggtctgc aaggaccgag tcaatggctt cagctgcacc   1560
tgcccctcgg gcttcagcgg ctccacgtgt cagctggacg tggacgaatg cgccagcacg   1620
ccctgcagga atggcgccaa atgcgtggac cagcccgatg gctacgagtg ccgctgtgcc   1680
gagggctttg agggcacgct gtgtgatcgc aacgtggacg actgctcccc tgacccatgc   1740
caccatggtc gctgcgtgga tggcatcgcc agcttctcat gtgcctgtgc tcctggctac   1800
acgggcacac gctgcgagag ccaggtggac gaatgccgca gccagccctg ccgccatggc   1860
ggcaaatgcc tagacctggt ggacaagtac ctctgccgct gccttctgg gaccacaggt   1920
gtgaactgcg aagtgaacat tgacgactgt gccagcaacc cctgcacctt ggagtctgc    1980
cgtgatggca tcaaccgcta cgactgtgtc tgccaacctg gcttcacagg gccccttgt    2040
aacgtggaga tcaatgagtg tgcttccagc ccatgcggcg agggaggttc ctgtgtggat   2100
ggggaaaatg gcttccgctg cctctgcccg cctggctcct tgcccccact ctgcctcccc   2160
ccgagccatc cctgtgccca tgagccctgc agtcacggca tctgctatga tgcacctggc   2220
gggttccgct gtgtgtgtga gcctggctgg agtggccccc gctgcagcca gagcctggcc   2280
cgagacgcct gtgagtccca gccgtgcagg gccggtggga catgcagcag cgatggaatg   2340
ggtttccact gcacctgccc gcctggtgtc cagggacgtc agtgtgaact cctctccccc   2400
tgcacccgga cccctgtga gcatggggc cgctgcgagt ctgcccctgg ccagctgcct   2460
gtctgctcct gccccaggg ctggcaaggc ccacgatgcc agcaggatgt ggacgagtgt   2520
gctggccccg caccctgtgg ccctcatggt atctgcacca acctggcagg gagtttcagc   2580
tgcacctgcc atggagggta cactggccct tcctgtgatc aggacatcaa tgactgtgac   2640
cccaacccat gcctgaacgg tggctcgtgc caagacggcg tgggctcctt ttcctgctcc   2700
tgcctccctg gtttcgccgg cccacgatgc gcccgcgatg tggatgagtg cctgagcaac   2760
ccctgcggcc cgggcacctg taccgaccac gtggcctcct tcacctgcac ctgcccgccg   2820
ggctacgag gcttccactg cgaacaggac ctgcccgact gcagcccag ctcctgcttc    2880
aatggcggga cctgtgtgga cggcgtgaac tcgttcagct gcctgtgccg tcccggctac   2940
acaggagccc actgccaaca tgaggcagac ccctgcctct cgcggccctg cctacacggg   3000
ggcgtctgca gcgccgccca ccctggcttc cgctgcacct gctcgagag cttcacgggc   3060
ccgcagtgcc agacgctggt ggattggtgc agccgccagc cttgtcaaaa cggggtcgc   3120
tgcgtccaga ctgggccta ttgccttttgt ccccctggat ggagcggacg cctctgtgac   3180
atccgaagct tgccctgcag ggaggccgca gcccagatcg gggtgcggct ggagcagctg   3240
tgtcaggcgg gtgggcagtg tgtggatgaa acagctcccc actactgcgt gtgcccagag   3300
```

```
ggccgtactg gtagccactg tgagcaggag gtggacccct gcttggccca gccctgccag      3360
catgggggga cctgccgtgg ctatatgggg ggctacatgt gtgagtgtct tcctggctac      3420
aatggtgata actgtgagga cgacgtgac gagtgtgcct cccagccctg ccagcacggg       3480
ggttcatgca ttgacctcgt ggcccgctat ctctgctcct gtccccagg aacgctgggg       3540 gtgctctgcg agattaatga ggatgactgc ggcccaggcc caccgctgga ctcagggccc      3600
cggtgcctac acaatggcac ctgcgtggac ctggtgggtg gtttccgctg cacctgtccc      3660
ccaggataca ctggtttgcg ctgcgaggca gacatcaatg agtgtcgctc aggtgcctgc      3720
cacgcggcac acacccggga ctgcctgcag gacccaggcg gaggtttccg ttgcctttgt      3780
catgctggct tctcaggtcc tcgctgtcag actgtcctgt ctccctgcga gtcccagcca      3840
tgccagcatg gaggccagtg ccgtcctagc ccgggtcctg ggggtgggct gaccttcacc      3900
tgtcactgtg cccagccgtt ctggggtcctg cgttgcgagc gggtggcgcg ctcctgccgg     3960
gagctgcagt gcccggtggg cgtcccatgc cagcagacgc cccgcgggcc gcgctgcgcc     4020 tgcccccag ggttgtcggg accctcctgc cgcagcttcc cggggtcgcc gccggggcc       4080 agcaacgcca gctgcgcggc cgcccctgt tccacgggg gctcctgccg ccccgcgccg       4140
ctcgcgccct tcttccgctg cgcttgcgcg cagggctgga ccgggccgcg ctgcgaggcg     4200
cccgccgcgg cacccgaggt ctcggaggag ccgcggtgcc cgcgcgccgc ctgccaggcc    4260
aagcgcgggg accagcgctg cgaccgcgag tgcaacagcc aggctgcgg ctgggacggc       4320 ggcgactgct cgctgagcgt gggcgacccc tggcggcaat gcgaggcgct gcagtgctgg      4380
cgcctcttca caacagccg ctgcgacccc gcctgcagct cgcccgcctg cctctacgac       4440
aacttcgact gccacgccgg tggccgcgag cgcacttgca accggtgta cgagaagtac       4500 tgccgccgacc acttttgccga cggccgctgc gaccagggct gcaacacgga ggagtgcggc    4560
tgggatgggc tggattgtgc cagcgaggtg ccggccctgc tggcccgcgg cgtgctggtg      4620
ctcacagtgc tgctgccgcc ggaggagcta ctgcgttcca gcgccgactt tctgcagcgg      4680
ctcagcgcca tcctgcgcac ctcgctgcgc ttccgcctgg acgcgcacgg ccaggccatg      4740
gtcttccctt accaccggcc tagtcctggc tccgaacccc gggcccgtcg ggagctggcc      4800
cccgaggtga tcggctcggt agtaatgctg gagattgaca accggctctg cctgcagtcg      4860
cctgagaatg atcactgctt ccccgatgcc cagagcgccg ctgactacct gggagcgttg      4920
tcagcggtgg agcgcctgga cttcccgtac ccactgcggg acgtgcgggg ggagccgctg     4980
gagcctccag aacccagcgt cccgctgctg ccactgctag tggcgggcgc tgtcttgctg      5040
ctggtcattc tcgtcctggg tgtcatggtg gccggcgca agcgcgagca cagcaccctc       5100
tggttccctg agggcttctc actgcacaag gacgtggcct ctggtcacaa gggccggcgg      5160
gaacccgtgg gccaggacgc gctgggcatg aagaacatgg ccaagggtga gagcctgatg      5220
ggggaggtgg ccacagactg gatggacaca gagtgcccag aggccaagcg gctaaaggta      5280
gaggagccag gcatggggc tgaggaggct gtggattgcc gtcagtggac tcaacaccat       5340
ctggttgctg ctgacatccg cgtggcacca gccatggcac tgacaccacc acagggcgac     5400
gcagatgctg atggcatgga tgtcaatgtg cgtggcccag atggcttcac cccgctaatg      5460
ctggcttcct tctgtggggg ggctctggag ccaatgccaa ctgaagagga tgaggcagat      5520
gacacatcag ctagcatcat ctccgacctg atctgccagg gggctcagct tggggcacgg     5580
actgaccgta ctgcgagac tgctttgcac ctggctgccc gttatgcccg tgctgatgca      5640
gccaagcggc tgctggatgc tggggcagac accaatgccc aggaccactc aggccgcact     5700
```

```
cccctgcaca cagctgtcac agccgatgcc cagggtgtct tccagattct catccgaaac   5760
cgctctacag acttggatgc ccgcatggca gatggctcaa cggcactgat cctggcggcc   5820
cgcctggcag tagagggcat ggtggaagag ctcatcgcca gccatgctga tgtcaatgct   5880
gtggatgagc ttgggaaatc agccttacac tgggctgcgg ctgtgaacaa cgtggaagcc   5940
actttggccc tgctcaaaaa tggagccaat aaggacatgc aggatagcaa ggaggagacc   6000
cccctattcc tggccgcccg cgagggcagc tatgaggctg ccaagctgct gttggaccac   6060
tttgccaacc gtgagatcac cgaccacctg gacaggctgc cgcgggacgt agcccaggag   6120
agactgcacc aggacatcgt gcgcttgctg gatcaaccca gtgggccccg cagcccccc    6180 ggtccccacg gcctgggcc tctgctctgt cctccagggg ccttcctccc tggcctcaaa    6240
gcggcacagt cggggtccaa gaagagcagg aggcccccg gaaggcggg gctggggccg     6300 caggggcccc gggggcgggg caagaagctg acgctggcct gcccgggccc cctggctgac   6360
agctcggtca cgctgtcgcc cgtggactcg ctggactccc cgcggccttt cggtgggccc   6420
cctgcttccc ctggtggctt ccccttgag gggccctatg cagctgccac tgccactgca    6480
gtgtctctgg cacagcttgg tggcccaggc cgggcaggtc tagggcgcca gcccctgga    6540 ggatgtgtac tcagcctggg cctgctgaac cctgtggctg tgccctcga ttgggcccgg    6600 ctgccccac ctgcccctcc aggccctcg ttcctgctgc cactggcgcc gggaccccag     6660
ctgctcaacc cagggacccc cgtctccccg caggagcggc cccgccctta cctggcagtc   6720
ccaggacatg gcgaggagta cccggtggct ggggcacaca gcagcccccc aaaggcccgc   6780
ttcctgcggg ttcccagtga gcacccttac ctgacccat ccccgaatc ccctgagcac      6840 tgggccagcc cctcacctcc ctccctctca gactggtccg aatccacgcc tagcccagcc   6900
actgccactg gggccatggc caccaccact ggggcactgc ctgcccagcc acttcccttg   6960
tctgttccca gctcccttgc tcaggccag acccagctgg ggcccagcc ggaagttacc     7020 cccaagaggc aagtgttggc ctgagacgct cgtcagttct tagatcttgg gggcctaaag   7080 agaccccgt cctgcctcct ttctttctct gtctcttcct tccttttagt cttttttcatc    7140 ctcttctctt tccaccaacc ctcctgcatc cttgccttgc agcgtgaccg agataggtca   7200
tcagcccagg gcttcagtct tccttttattt ataatgggtg ggggctacca cccacccctct  7260 cagtcttgtg aagagtctgg gacctccttc ttccccactt ctctcttccc tcattccttt    7320
ctctctcctt ctggcctctc atttccttac actctgacat gaatgaatta ttattatttt    7380
tcttttcttt ttttttttta cattttgtat agaaacaaat tcatttaaac aaacttatta   7440
ttattatttt ttacaaaata tatatatgga gatgctccct ccccctgtga acccccagt     7500 gcccccgtgg ggctgagtct gtgggcccat tcggccaagc tggattctgt gtacctagta   7560
cacaggcatg actgggatcc cgtgtaccga gtacacgacc caggtatgta ccaagtaggc   7620
acccttgggc gcacccactg ggccagggg tcgggggagt gttgggagcc tcctccccac    7680
cccacctccc tcacttcact gcattccaga ttgacatgt tccatagcct tgctggggaa    7740
gggcccactg ccaactccct ctgccccagc cccacccttg gccatctccc tttgggaact   7800 aggggggctgc tggtggga tgggagccag ggcagatgta tgcattcctt tatgtccctg     7860
taaatgtggg actacaagaa gaggagctgc ctgagtggta ctttctcttc ctggtaatcc    7920
tctggcccag ccttatggca gaatagaggt attttttaggc tattttttgta atatggcttc   7980 tggtcaaaat ccctgtgtag ctgaattccc aagccctgca ttgtacagcc ccccactccc    8040
ctcaccacct aataaaggaa tagttaacac tcaaaaaaaa aaaaaaaaa a             8091
```

<210> SEQ ID NO 19
<211> LENGTH: 2321
<212> TYPE: PRT
<213> ORGANISM: Homo sapiens
<220> FEATURE:
<221> NAME/KEY: misc_feature
<223> OTHER INFORMATION: Notch-3

<400> SEQUENCE: 19

```
Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu
            20                  25                  30

Leu Ala Gly Pro Gly Ala Ala Ala Pro Pro Cys Leu Asp Gly Ser Pro
        35                  40                  45

Cys Ala Asn Gly Gly Arg Cys Thr Gln Leu Pro Ser Arg Glu Ala Ala
    50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
            115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
            195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
            275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
            355                 360                 365
```

-continued

Asn Pro Val Asn Gly Arg Ala Ile Cys Thr Cys Pro Pro Gly Phe Thr
    370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
            435                 440                 445

Arg Ile Gly Gln Phe Thr Cys Ile Cys Met Ala Gly Phe Thr Gly Thr
    450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
            515                 520                 525

Tyr Glu Cys Arg Cys Ala Glu Gly Phe Glu Gly Thr Leu Cys Asp Arg
    530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Pro Pro Cys Arg
            580                 585                 590

His Gly Gly Lys Cys Leu Asp Leu Val Asp Lys Tyr Leu Cys Arg Cys
            595                 600                 605

Pro Ser Gly Thr Thr Gly Val Asn Cys Glu Val Asn Ile Asp Asp Cys
    610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
            675                 680                 685

Pro Pro Leu Cys Leu Pro Pro Ser His Pro Cys Ala His Glu Pro Cys
    690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
            755                 760                 765

Cys Glu Leu Leu Ser Pro Cys Thr Pro Asn Pro Cys Glu His Gly Gly
    770                 775                 780

Arg Cys Glu Ser Ala Pro Gly Gln Leu Pro Val Cys Ser Cys Pro Gln

-continued

```
            785                 790                 795                 800
Gly Trp Gln Gly Pro Arg Cys Gln Gln Asp Val Asp Glu Cys Ala Gly
                805                 810                 815
Pro Ala Pro Cys Gly Pro His Gly Ile Cys Thr Asn Leu Ala Gly Ser
                820                 825                 830
Phe Ser Cys Thr Cys His Gly Gly Tyr Thr Gly Pro Ser Cys Asp Gln
                835                 840                 845
Asp Ile Asn Asp Cys Asp Pro Asn Pro Cys Leu Asn Gly Gly Ser Cys
            850                 855                 860
Gln Asp Gly Val Gly Ser Phe Ser Cys Ser Cys Leu Pro Gly Phe Ala
865                 870                 875                 880
Gly Pro Arg Cys Ala Arg Asp Val Asp Glu Cys Leu Ser Asn Pro Cys
                885                 890                 895
Gly Pro Gly Thr Cys Thr Asp His Val Ala Ser Phe Thr Cys Thr Cys
                900                 905                 910
Pro Pro Gly Tyr Gly Gly Phe His Cys Glu Gln Asp Leu Pro Asp Cys
                915                 920                 925
Ser Pro Ser Ser Cys Phe Asn Gly Gly Thr Cys Val Asp Gly Val Asn
            930                 935                 940
Ser Phe Ser Cys Leu Cys Arg Pro Gly Tyr Thr Gly Ala His Cys Gln
945                 950                 955                 960
His Glu Ala Asp Pro Cys Leu Ser Arg Pro Cys Leu His Gly Gly Val
                965                 970                 975
Cys Ser Ala Ala His Pro Gly Phe Arg Cys Thr Cys Leu Glu Ser Phe
                980                 985                 990
Thr Gly Pro Gln Cys Gln Thr Leu Val Asp Trp Cys Ser Arg Gln Pro
            995                 1000                1005
Cys Gln Asn Gly Gly Arg Cys Val Gln Thr Gly Ala Tyr Cys Leu
    1010                1015                1020
Cys Pro Pro Gly Trp Ser Gly Arg Leu Cys Asp Ile Arg Ser Leu
    1025                1030                1035
Pro Cys Arg Glu Ala Ala Ala Gln Ile Gly Val Arg Leu Glu Gln
    1040                1045                1050
Leu Cys Gln Ala Gly Gly Gln Cys Val Asp Glu Asp Ser Ser His
    1055                1060                1065
Tyr Cys Val Cys Pro Glu Gly Arg Thr Gly Ser His Cys Glu Gln
    1070                1075                1080
Glu Val Asp Pro Cys Leu Ala Gln Pro Cys Gln His Gly Gly Thr
    1085                1090                1095
Cys Arg Gly Tyr Met Gly Gly Tyr Met Cys Glu Cys Leu Pro Gly
    1100                1105                1110
Tyr Asn Gly Asp Asn Cys Glu Asp Asp Val Asp Glu Cys Ala Ser
    1115                1120                1125
Gln Pro Cys Gln His Gly Gly Ser Cys Ile Asp Leu Val Ala Arg
    1130                1135                1140
Tyr Leu Cys Ser Cys Pro Pro Gly Thr Leu Gly Val Leu Cys Glu
    1145                1150                1155
Ile Asn Glu Asp Asp Cys Gly Pro Gly Pro Pro Leu Asp Ser Gly
    1160                1165                1170
Pro Arg Cys Leu His Asn Gly Thr Cys Val Asp Leu Val Gly Gly
    1175                1180                1185
Phe Arg Cys Thr Cys Pro Pro Gly Tyr Thr Gly Leu Arg Cys Glu
    1190                1195                1200
```

```
Ala Asp Ile Asn Glu Cys Arg Ser Gly Ala Cys His Ala Ala His
1205                1210                1215

Thr Arg Asp Cys Leu Gln Asp Pro Gly Gly Phe Arg Cys Leu
1220                1225                1230

Cys His Ala Gly Phe Ser Gly Pro Arg Cys Gln Thr Val Leu Ser
1235                1240                1245

Pro Cys Glu Ser Gln Pro Cys Gln His Gly Gly Gln Cys Arg Pro
1250                1255                1260

Ser Pro Gly Pro Gly Gly Leu Thr Phe Thr Cys His Cys Ala
1265                1270                1275

Gln Pro Phe Trp Gly Pro Arg Cys Glu Arg Val Ala Arg Ser Cys
1280                1285                1290

Arg Glu Leu Gln Cys Pro Val Gly Val Pro Cys Gln Gln Thr Pro
1295                1300                1305

Arg Gly Pro Arg Cys Ala Cys Pro Pro Gly Leu Ser Gly Pro Ser
1310                1315                1320

Cys Arg Ser Phe Pro Gly Ser Pro Pro Gly Ala Ser Asn Ala Ser
1325                1330                1335

Cys Ala Ala Ala Pro Cys Leu His Gly Gly Ser Cys Arg Pro Ala
1340                1345                1350

Pro Leu Ala Pro Phe Phe Arg Cys Ala Cys Ala Gln Gly Trp Thr
1355                1360                1365

Gly Pro Arg Cys Glu Ala Pro Ala Ala Ala Pro Glu Val Ser Glu
1370                1375                1380

Glu Pro Arg Cys Pro Arg Ala Ala Cys Gln Ala Lys Arg Gly Asp
1385                1390                1395

Gln Arg Cys Asp Arg Glu Cys Asn Ser Pro Gly Cys Gly Trp Asp
1400                1405                1410

Gly Gly Asp Cys Ser Leu Ser Val Gly Asp Pro Trp Arg Gln Cys
1415                1420                1425

Glu Ala Leu Gln Cys Trp Arg Leu Phe Asn Asn Ser Arg Cys Asp
1430                1435                1440

Pro Ala Cys Ser Ser Pro Ala Cys Leu Tyr Asp Asn Phe Asp Cys
1445                1450                1455

His Ala Gly Gly Arg Glu Arg Thr Cys Asn Pro Val Tyr Glu Lys
1460                1465                1470

Tyr Cys Ala Asp His Phe Ala Asp Gly Arg Cys Asp Gln Gly Cys
1475                1480                1485

Asn Thr Glu Glu Cys Gly Trp Asp Gly Leu Asp Cys Ala Ser Glu
1490                1495                1500

Val Pro Ala Leu Leu Ala Arg Gly Val Leu Val Leu Thr Val Leu
1505                1510                1515

Leu Pro Pro Glu Glu Leu Leu Arg Ser Ser Ala Asp Phe Leu Gln
1520                1525                1530

Arg Leu Ser Ala Ile Leu Arg Thr Ser Leu Arg Phe Arg Leu Asp
1535                1540                1545

Ala His Gly Gln Ala Met Val Phe Pro Tyr His Arg Pro Ser Pro
1550                1555                1560

Gly Ser Glu Pro Arg Ala Arg Arg Glu Leu Ala Pro Glu Val Ile
1565                1570                1575

Gly Ser Val Val Met Leu Glu Ile Asp Asn Arg Leu Cys Leu Gln
1580                1585                1590

Ser Pro Glu Asn Asp His Cys Phe Pro Asp Ala Gln Ser Ala Ala
1595                1600                1605
```

-continued

Asp Tyr Leu Gly Ala Leu Ser Ala Val Glu Arg Leu Asp Phe Pro
1610             1615                 1620

Tyr Pro Leu Arg Asp Val Arg Gly Glu Pro Leu Glu Pro Pro Glu
1625             1630                 1635

Pro Ser Val Pro Leu Leu Pro Leu Leu Val Ala Gly Ala Val Leu
1640             1645                 1650

Leu Leu Val Ile Leu Val Leu Gly Val Met Val Ala Arg Arg Lys
1655             1660                 1665

Arg Glu His Ser Thr Leu Trp Phe Pro Glu Gly Phe Ser Leu His
1670             1675                 1680

Lys Asp Val Ala Ser Gly His Lys Gly Arg Arg Glu Pro Val Gly
1685             1690                 1695

Gln Asp Ala Leu Gly Met Lys Asn Met Ala Lys Gly Glu Ser Leu
1700             1705                 1710

Met Gly Glu Val Ala Thr Asp Trp Met Asp Thr Glu Cys Pro Glu
1715             1720                 1725

Ala Lys Arg Leu Lys Val Glu Glu Pro Gly Met Gly Ala Glu Glu
1730             1735                 1740

Ala Val Asp Cys Arg Gln Trp Thr Gln His His Leu Val Ala Ala
1745             1750                 1755

Asp Ile Arg Val Ala Pro Ala Met Ala Leu Thr Pro Pro Gln Gly
1760             1765                 1770

Asp Ala Asp Ala Asp Gly Met Asp Val Asn Val Arg Gly Pro Asp
1775             1780                 1785

Gly Phe Thr Pro Leu Met Leu Ala Ser Phe Cys Gly Gly Ala Leu
1790             1795                 1800

Glu Pro Met Pro Thr Glu Glu Asp Glu Ala Asp Asp Thr Ser Ala
1805             1810                 1815

Ser Ile Ile Ser Asp Leu Ile Cys Gln Gly Ala Gln Leu Gly Ala
1820             1825                 1830

Arg Thr Asp Arg Thr Gly Glu Thr Ala Leu His Leu Ala Ala Arg
1835             1840                 1845

Tyr Ala Arg Ala Asp Ala Ala Lys Arg Leu Leu Asp Ala Gly Ala
1850             1855                 1860

Asp Thr Asn Ala Gln Asp His Ser Gly Arg Thr Pro Leu His Thr
1865             1870                 1875

Ala Val Thr Ala Asp Ala Gln Gly Val Phe Gln Ile Leu Ile Arg
1880             1885                 1890

Asn Arg Ser Thr Asp Leu Asp Ala Arg Met Ala Asp Gly Ser Thr
1895             1900                 1905

Ala Leu Ile Leu Ala Ala Arg Leu Ala Val Glu Gly Met Val Glu
1910             1915                 1920

Glu Leu Ile Ala Ser His Ala Asp Val Asn Ala Val Asp Glu Leu
1925             1930                 1935

Gly Lys Ser Ala Leu His Trp Ala Ala Ala Val Asn Asn Val Glu
1940             1945                 1950

Ala Thr Leu Ala Leu Leu Lys Asn Gly Ala Asn Lys Asp Met Gln
1955             1960                 1965

Asp Ser Lys Glu Glu Thr Pro Leu Phe Leu Ala Ala Arg Glu Gly
1970             1975                 1980

Ser Tyr Glu Ala Ala Lys Leu Leu Leu Asp His Phe Ala Asn Arg
1985             1990                 1995

Glu Ile Thr Asp His Leu Asp Arg Leu Pro Arg Asp Val Ala Gln

```
                2000                2005                2010

Glu  Arg  Leu  His  Gln  Asp  Ile  Val  Arg  Leu  Leu  Asp  Gln  Pro  Ser
     2015                2020                2025

Gly  Pro  Arg  Ser  Pro  Pro  Gly  Pro  His  Gly  Leu  Gly  Pro  Leu  Leu
     2030                2035                2040

Cys  Pro  Pro  Gly  Ala  Phe  Leu  Pro  Gly  Leu  Lys  Ala  Ala  Gln  Ser
     2045                2050                2055

Gly  Ser  Lys  Lys  Ser  Arg  Arg  Pro  Pro  Gly  Lys  Ala  Gly  Leu  Gly
     2060                2065                2070

Pro  Gln  Gly  Pro  Arg  Gly  Arg  Gly  Lys  Lys  Leu  Thr  Leu  Ala  Cys
     2075                2080                2085

Pro  Gly  Pro  Leu  Ala  Asp  Ser  Ser  Val  Thr  Leu  Ser  Pro  Val  Asp
     2090                2095                2100

Ser  Leu  Asp  Ser  Pro  Arg  Pro  Phe  Gly  Gly  Pro  Pro  Ala  Ser  Pro
     2105                2110                2115

Gly  Gly  Phe  Pro  Leu  Glu  Gly  Pro  Tyr  Ala  Ala  Ala  Thr  Ala  Thr
     2120                2125                2130

Ala  Val  Ser  Leu  Ala  Gln  Leu  Gly  Gly  Pro  Gly  Arg  Ala  Gly  Leu
     2135                2140                2145

Gly  Arg  Gln  Pro  Pro  Gly  Gly  Cys  Val  Leu  Ser  Leu  Gly  Leu  Leu
     2150                2155                2160

Asn  Pro  Val  Ala  Val  Pro  Leu  Asp  Trp  Ala  Arg  Leu  Pro  Pro  Pro
     2165                2170                2175

Ala  Pro  Pro  Gly  Pro  Ser  Phe  Leu  Leu  Pro  Leu  Ala  Pro  Gly  Pro
     2180                2185                2190

Gln  Leu  Leu  Asn  Pro  Gly  Thr  Pro  Val  Ser  Pro  Gln  Glu  Arg  Pro
     2195                2200                2205

Pro  Pro  Tyr  Leu  Ala  Val  Pro  Gly  His  Gly  Glu  Glu  Tyr  Pro  Val
     2210                2215                2220

Ala  Gly  Ala  His  Ser  Ser  Pro  Pro  Lys  Ala  Arg  Phe  Leu  Arg  Val
     2225                2230                2235

Pro  Ser  Glu  His  Pro  Tyr  Leu  Thr  Pro  Ser  Pro  Glu  Ser  Pro  Glu
     2240                2245                2250

His  Trp  Ala  Ser  Pro  Ser  Pro  Ser  Leu  Ser  Asp  Trp  Ser  Glu
     2255                2260                2265

Ser  Thr  Pro  Ser  Pro  Ala  Thr  Ala  Thr  Gly  Ala  Met  Ala  Thr  Thr
     2270                2275                2280

Thr  Gly  Ala  Leu  Pro  Ala  Gln  Pro  Leu  Pro  Leu  Ser  Val  Pro  Ser
     2285                2290                2295

Ser  Leu  Ala  Gln  Ala  Gln  Thr  Gln  Leu  Gly  Pro  Gln  Pro  Glu  Val
     2300                2305                2310

Thr  Pro  Lys  Arg  Gln  Val  Leu  Ala
     2315                2320

<210> SEQ ID NO 20
<211> LENGTH: 6836
<212> TYPE: DNA
<213> ORGANISM: Homo sapiens
<220> FEATURE:
<221> NAME/KEY: misc_feature
<223> OTHER INFORMATION: Notch-4

<400> SEQUENCE: 20
agacgtgagg cttgcagcag gccgaggagg aagaagaggg gcagtgggag cagaggaggt    60
ggctcctgcc ccagtgagag ctctgagggt ccctgcctga agaggacag ggactggggc    120
```

-continued

```
ttggagaagg ggctgtggaa tgcagccccc ttcactgctg ctgctgctgc tgctgctgct    180
gctatgtgtc tcagtggtca gacccagagg gctgctgtgt gggagtttcc cagaaccctg    240
tgccaatgga ggcacctgcc tgagcctgtc tctgggacaa gggacctgcc agtgtgcccc    300
tggcttcctg ggtgagacgt gccagtttcc tgacccctgc cagaacgccc agctctgcca    360
aaatggaggc agctgccaag ccctgcttcc cgctccccta gggctcccca gctctccctc    420
tccattgaca cccagcttct tgtgcacttg cctccctggc ttcactggtg agagatgcca    480
ggccaagctt gaagaccctt gtcctccctc cttctgttcc aaaaggggcc gctgccacat    540
ccaggcctcg ggccgccac agtgctcctg catgcctgga tggacaggtg agcagtgcca    600
gcttcgggac ttctgttcag ccaacccatg tgttaatgga ggggtgtgtc tggccacgta    660
cccccagatc cagtgccact gcccaccggg cttcgagggc catgcctgtg aacgtgatgt    720
caacgagtgc ttccaggacc caggaccctg ccccaaaggc acctcctgcc ataacaccct    780
gggctccttc cagtgcctct gccctgtggg gcaggagggt ccacgttgtg agctgcgggc    840
aggaccctgc cctcctaggg gctgttcgaa tgggggcacc tgccagctga tgccagagaa    900
agactccacc tttcacctct gcctctgtcc cccaggtttc ataggcccgg gctgtgaggt    960
gaatccagac aactgtgtca gccaccaatg tcagaatggg ggcacttgcc aggatgggct   1020
ggacacctac acctgcctct gcccagaaac ctggacaggc tgggactgct ccgaagatgt   1080
ggatgagtgt gaggcccagg gtccccctca ctgcagaaac gggggcacct gccagaactc   1140
tgctggtagc tttcactgcg tgtgtgtgag tggctggggg ggcacaagct gtgaggagaa   1200
cctggatgac tgtattgctg ccacctgtgc cccgggatcc acctgcattg accgggtggg   1260
ctctttctcc tgcctctgcc cacctggacg cacaggactc ctgtgccact ggaagacat   1320 gtgtctgagc cagccgtgcc atggggatgc ccaatgcagc accaaccccc tcacaggctc   1380
cacactctgc ctgtgtcagc ctggctattc ggggcccacc tgccaccagg acctggacga   1440
gtgtctgatg gcccagcaag gcccaagtcc ctgtgaacat ggcggttcct gcctcaacac   1500
tcctggctcc ttcaactgcc tctgtccacc tggctacaca ggctcccgtt gtgaggctga   1560
tcacaatgag tgcctctccc agccctgcca cccaggaagc acctgtctgg acctacttgc   1620
caccttccac tgcctctgcc cgccaggctt agaagggcag ctctgtgagg tggagaccaa   1680
cgagtgtgcc tcagctccct gcctgaacca cgcggattgc catgacctgc tcaacggctt   1740
ccagtgcatc tgcctgcctg gattctccgg cacccgatgt gaggaggata tcgatgagtg   1800
cagaagctct ccctgtgcca atggtgggca gtgccaggac cagcctggag ccttccactg   1860
caagtgtctc ccaggctttg aagggccacg ctgtcaaaca gaggtggatg agtgcctgag   1920

tgacccatgt cccgttggag ccagctgcct tgatcttcca ggagccttct tttgcctctg   1980
cccctctggt ttcacaggcc agctctgtga gttcccctg tgtgctccca actgtgcca   2040 gcccaagcag atatgtaagg accagaaaga caaggccaac tgcctctgtc ctgatggaag   2100
ccctggctgt gccccacctg aggacaactg cacctgccac cacgggcact gccagagatc   2160
ctcatgtgtg tgtgacgtgg gttggacggg ccagagtgt gaggcagagc taggggctg   2220 catctctgca ccctgtgccc atggggggac ctgctacccc cagccctctg ctacaactg   2280 cacctgccct acaggctaca caggacccac ctgtagtgag gagatgacag cttgtcactc   2340
agggccatgt ctcaatggcg gctcctgcaa ccctagccct ggaggctact actgcacctg   2400
ccctccaagc cacacagggc cccagtgcca aaccagcact gactactgtg tgtctgcccc   2460
gtgcttcaat ggggtacct gtgtgaacag gcctggcacc ttctcctgcc tctgtgccat   2520
```

```
gggcttccag ggcccgcgct gtgagggaaa gctccgcccc agctgtgcag acagcccctg   2580
taggaatagg gcaacctgcc aggacagccc tcagggtccc cgctgcctct gccccactgg   2640
ctacaccgga ggcagctgcc agactctgat ggacttatgt gcccagaagc cctgcccacg   2700
caattcccac tgcctccaga ctgggccctc cttccactgc ttgtgcctcc agggatggac   2760
cgggcctctc tgcaaccttc cactgtcctc ctgccagaag gctgcactga gccaaggcat   2820
agacgtctct tcccttttgcc acaatggagg cctctgtgtc gacagcggcc cctcctattt   2880
ctgccactgc cccctggat tccaaggcag cctgtgccag gatcacgtga acccatgtga   2940
gtccaggcct tgccagaacg gggccacctg catggcccag cccagtgggt atctctgcca   3000
gtgtgcccca ggctacgatg gacagaactg ctcaaaggaa ctcgatgctt gtcagtccca   3060
accctgtcac aaccatggaa cctgtactcc caaacctgga ggcttccact gtgcctgccc   3120
tccaggcttt gtggggctac gctgtgaggg agacgtggac gagtgtctgg accagccctg   3180 ccacccccaca ggcactgcag cctgccactc tctggccaat gccttctact gccagtgtct   3240
gcctggacac acaggccagt ggtgtgaggt ggagatagac ccctgccaca gccaaccctg   3300
ctttcatgga gggaccctgtg aggccacagc aggatcaccc ctgggtttca tctgccactg   3360
ccccaagggt tttgaaggcc ccacctgcag ccacagggcc ccttcctgcg gcttccatca   3420
ctgccaccac ggaggcctgt gtctgccctc ccctaagcca ggcttcccac cacgctgtgc   3480
ctgcctcagt ggctatgggg gtcctgactg cctgacccca ccagctccta aaggctgtgg   3540
ccctccctcc ccatgcctat acaatggcag ctgctcagag accacgggct ggggggccc   3600 aggctttcga tgctcctgcc ctcacagctc tccagggccc cggtgtcaga acccggagc   3660 caagggtgt gagggcagaa gtggagatgg ggcctgcgat gctggctgca gtggcccggg   3720
aggaaactgg gatggagggg actgctctct gggagtccca gacccctgga agggctgccc   3780
ctcccactct cggtgctggc ttctcttccg ggacgggcag tgccaccac agtgtgactc   3840 tgaagagtgt ctgtttgatg gctacgactg tgagacccct ccagcctgca ctccagccta   3900
tgaccagtac tgccatgatc acttccacaa cgggcactgt gagaaaggct gcaacactgc   3960
agagtgtggc tgggatggag gtgactgcag gcctgaagat ggggacccag agtggggcc   4020 ctccctggcc ctgctggtgg tactgagccc cccagcccta gaccagcagc tgtttgccct   4080
ggcccgggtg ctgtccctga ctctgagggt aggactctgg gtaaggaagg atcgtgatgg   4140
cagggacatg gtgtacccct atcctggggc ccgggctgaa gaaaagctag gaggaactcg   4200
ggaccccacc tatcaggaga gagcagcccc tcaaacacag cccctgggca aggagaccga   4260
ctccctcagt gctgggtttg tggtggtcat gggtgtggat ttgtcccgct gtggccctga   4320
ccacccggca tcccgctgtc cctgggaccc tgggcttcta ctccgcttcc ttgctgcgat   4380
ggctgcagtg ggagccctgg agccctgct gcctggacca ctgctggctg tccaccctca   4440
tgcagggacc gcacccctg ccaaccagct tccctggcct gtgctgtgct ccccagtggc   4500
cggggtgatt ctcctggccc tagggctct tctcgtcctc cagctcatcc ggcgtcgacg   4560
ccgagagcat ggagctctct ggctgccccc tggtttcact cgacggcctc ggactcagtc   4620
agctccccac cgacgccggc ccccactagg cgaggacagc attggtctca aggcactgaa   4680
gccaaaggca gaagttgatg aggatggagt tgtgatgtgc tcaggccctg aggagggaga   4740
ggaggtgggc caggctgaag aaacaggccc accctccacg tgccagctct ggtctctgag   4800
tggtggctgt ggggcgctcc ctcaggcagc catgctaact cctccccagg aatctgagat   4860
ggaagcccct gacctggaca cccgtggacc tgatgggggtg acacccctga tgtcagcagt   4920
```

```
ttgctgtggg gaagtacagt ccgggacctt ccaaggggca tggttgggat gtcctgagcc    4980
ctgggaacct ctgctggatg aggggcctg tccccaggct cacaccgtgg gcactgggga    5040 gaccccctg cacctggctg cccgattctc ccggccaacc gctgcccgcc gcctccttga    5100
ggctggagcc aaccccaacc agccagaccg ggcaggcgc acacccttc atgctgctgt    5160 ggctgctgat gctcgggagg tctgccagct tctgctccgt agcagacaaa ctgcagtgga    5220
cgctcgcaca gaggacggga ccacacccctt gatgctggct gccaggctgg cggtggaaga    5280
cctggttgaa gaactgattg cagcccaagc agacgtgggg gccagagata aatgggggaa    5340
aactgcgctg cactgggctg ctgccgtgaa caacgcccga gccgcccgct cgcttctcca    5400
ggccggagcc gataaagatg cccaggacaa cagggagcag acgccgctat tcctggcggc    5460
gcgggaagga gcggtggaag tagcccagct actgctgggg ctgggggcag cccgagagct    5520
gcgggaccag gctgggctag cgccggcgga cgtcgctcac caacgtaacc actgggatct    5580
gctgacgctg ctggaagggg ctgggccacc agaggcccgt cacaaagcca cgccgggccg    5640
cgaggctggg cccttccgc gcgcacggac ggtgtcagta agcgtgcccc cgcatggggg    5700
cggggctctg ccgcgctgcc ggacgctgtc agccggagca ggccctcgtg ggggcggagc    5760
ttgtctgcag gctcggactt ggtccgtaga cttggctgcg cgggggggcg gggcctattc    5820
tcattgccgg agcctctcgg gagtaggagc aggaggaggc ccgaccctc gcggccgtag    5880 gttttctgca ggcatgcgcg ggcctcggcc caaccctgcg ataatgcgag gaagatacgg    5940
agtggctgcc gggcgcggag gcagggtctc aacggatgac tggccctgtg attgggtggc    6000
cctgggagct tgcggttctg cctccaacat tccgatcccg cctccttgcc ttactccgtc    6060
cccggagcgg ggatcacctc aacttgactg tggtccccca gccctccaag aaatgcccat    6120
aaaccaagga ggagagggta aaaatagaa gaatacatgg tagggaggaa ttccaaaaat    6180
gattacccat taaaggcag gctggaaggc cttcctggtt ttaagatgga tcccccaaaa    6240
tgaagggttg tgagtttagt ttctctccta aaatgaatgt atgcccacca gagcagacat    6300
cttccacgtg gagaagctgc agctctggaa agagggttta agatgctagg atgaggcagg    6360
cccagtcctc ctccagaaaa taagacaggc acaggaggg cagagtggag tggaaatacc    6420
cctaagttgg aaccaagaat tgcaggcata tgggatgtaa gatgttcttt cctatatatg    6480
gtttccaaag ggtgccccta tgatccattg tccccactgc ccacaaatgg ctgacaaata    6540
tttattgggc acctactatg tgccaggcac tgtgtaggtg ctgaaaagtg gccaagggcc    6600 accccgctg atgactcctt gcattccctc ccctcacaac aaagaactcc actgtgggga    6660
tgaagcgctt cttctagcca ctgctatcgc tatttaagaa ccctaaatct gtcacccata    6720
ataaagctga tttgaagtgt taaaaaaaaa aaaaaaaaaa aaaaaaaaaa aaaaaaaaaa    6780
aaaaaaaaaa aaaaaaaaaa aaaaaaaaaa aaaaaaaaaa aaaaaaaaaa aaaaaa       6836
```

<210> SEQ ID NO 21
<211> LENGTH: 2002
<212> TYPE: PRT
<213> ORGANISM: Homo sapiens
<220> FEATURE:
<221> NAME/KEY: misc_feature
<223> OTHER INFORMATION: Notch-4

<400> SEQUENCE: 21

Met Gln Pro Pro Ser Leu Leu Leu Leu Leu Leu Leu Leu Leu Leu Cys
1               5                   10                  15

Val Ser Val Val Arg Pro Arg Gly Leu Leu Cys Gly Ser Phe Pro Glu
            20                  25                  30

```
Pro Cys Ala Asn Gly Gly Thr Cys Leu Ser Leu Ser Leu Gly Gln Gly
            35                  40                  45

Thr Cys Gln Cys Ala Pro Gly Phe Leu Gly Glu Thr Cys Gln Phe Pro
         50                  55                  60

Asp Pro Cys Gln Asn Ala Gln Leu Cys Gln Asn Gly Gly Ser Cys Gln
 65                  70                  75                  80

Ala Leu Leu Pro Ala Pro Leu Gly Leu Pro Ser Ser Pro Ser Pro Leu
                 85                  90                  95

Thr Pro Ser Phe Leu Cys Thr Cys Leu Pro Gly Phe Thr Gly Glu Arg
            100                 105                 110

Cys Gln Ala Lys Leu Glu Asp Pro Cys Pro Ser Phe Cys Ser Lys
            115                 120                 125

Arg Gly Arg Cys His Ile Gln Ala Ser Gly Arg Pro Gln Cys Ser Cys
            130                 135                 140

Met Pro Gly Trp Thr Gly Glu Gln Cys Gln Leu Arg Asp Phe Cys Ser
145                 150                 155                 160

Ala Asn Pro Cys Val Asn Gly Gly Val Cys Leu Ala Thr Tyr Pro Gln
                165                 170                 175

Ile Gln Cys His Cys Pro Pro Gly Phe Glu Gly His Ala Cys Glu Arg
            180                 185                 190

Asp Val Asn Glu Cys Phe Gln Asp Pro Gly Pro Cys Pro Lys Gly Thr
            195                 200                 205

Ser Cys His Asn Thr Leu Gly Ser Phe Gln Cys Leu Cys Pro Val Gly
            210                 215                 220

Gln Glu Gly Pro Arg Cys Glu Leu Arg Ala Gly Pro Cys Pro Pro Arg
225                 230                 235                 240

Gly Cys Ser Asn Gly Gly Thr Cys Gln Leu Met Pro Glu Lys Asp Ser
            245                 250                 255

Thr Phe His Leu Cys Leu Cys Pro Pro Gly Phe Ile Gly Pro Gly Cys
            260                 265                 270

Glu Val Asn Pro Asp Asn Cys Val Ser His Gln Cys Gln Asn Gly Gly
            275                 280                 285

Thr Cys Gln Asp Gly Leu Asp Thr Tyr Thr Cys Leu Cys Pro Glu Thr
            290                 295                 300

Trp Thr Gly Trp Asp Cys Ser Glu Asp Val Asp Glu Cys Glu Ala Gln
305                 310                 315                 320

Gly Pro Pro His Cys Arg Asn Gly Gly Thr Cys Gln Asn Ser Ala Gly
            325                 330                 335

Ser Phe His Cys Val Cys Val Ser Gly Trp Gly Gly Thr Ser Cys Glu
            340                 345                 350

Glu Asn Leu Asp Asp Cys Ile Ala Ala Thr Cys Ala Pro Gly Ser Thr
            355                 360                 365

Cys Ile Asp Arg Val Gly Ser Phe Ser Cys Leu Cys Pro Pro Gly Arg
            370                 375                 380

Thr Gly Leu Leu Cys His Leu Glu Asp Met Cys Leu Ser Gln Pro Cys
385                 390                 395                 400

His Gly Asp Ala Gln Cys Ser Thr Asn Pro Leu Thr Gly Ser Thr Leu
            405                 410                 415

Cys Leu Cys Gln Pro Gly Tyr Ser Gly Pro Thr Cys His Gln Asp Leu
            420                 425                 430

Asp Glu Cys Leu Met Ala Gln Gln Gly Pro Ser Pro Cys Glu His Gly
            435                 440                 445

Gly Ser Cys Leu Asn Thr Pro Gly Ser Phe Asn Cys Leu Cys Pro Pro
```

```
                450                 455                 460
Gly Tyr Thr Gly Ser Arg Cys Glu Ala Asp His Asn Glu Cys Leu Ser
465                 470                 475                 480

Gln Pro Cys His Pro Gly Ser Thr Cys Leu Asp Leu Ala Thr Phe
                485                 490                 495

His Cys Leu Cys Pro Gly Leu Glu Gly Gln Leu Cys Glu Val Glu
                500                 505                 510

Thr Asn Glu Cys Ala Ser Ala Pro Cys Leu Asn His Ala Asp Cys His
                515                 520                 525

Asp Leu Leu Asn Gly Phe Gln Cys Ile Cys Leu Pro Gly Phe Ser Gly
            530                 535                 540

Thr Arg Cys Glu Glu Asp Ile Asp Glu Cys Arg Ser Ser Pro Cys Ala
545                 550                 555                 560

Asn Gly Gly Gln Cys Gln Asp Gln Pro Gly Ala Phe His Cys Lys Cys
                565                 570                 575

Leu Pro Gly Phe Glu Gly Pro Arg Cys Gln Thr Glu Val Asp Glu Cys
                580                 585                 590

Leu Ser Asp Pro Cys Pro Val Gly Ala Ser Cys Leu Asp Leu Pro Gly
            595                 600                 605

Ala Phe Phe Cys Leu Cys Pro Ser Gly Phe Thr Gly Gln Leu Cys Glu
            610                 615                 620

Val Pro Leu Cys Ala Pro Asn Leu Cys Gln Pro Lys Gln Ile Cys Lys
625                 630                 635                 640

Asp Gln Lys Asp Lys Ala Asn Cys Leu Cys Pro Asp Gly Ser Pro Gly
                645                 650                 655

Cys Ala Pro Pro Glu Asp Asn Cys Thr Cys His His Gly His Cys Gln
                660                 665                 670

Arg Ser Ser Cys Val Cys Asp Val Gly Trp Thr Gly Pro Glu Cys Glu
            675                 680                 685

Ala Glu Leu Gly Gly Cys Ile Ser Ala Pro Cys Ala His Gly Gly Thr
            690                 695                 700

Cys Tyr Pro Gln Pro Ser Gly Tyr Asn Cys Thr Cys Pro Thr Gly Tyr
705                 710                 715                 720

Thr Gly Pro Thr Cys Ser Glu Glu Met Thr Ala Cys His Ser Gly Pro
                725                 730                 735

Cys Leu Asn Gly Gly Ser Cys Asn Pro Ser Pro Gly Gly Tyr Tyr Cys
                740                 745                 750

Thr Cys Pro Pro Ser His Thr Gly Pro Gln Cys Gln Thr Ser Thr Asp
            755                 760                 765

Tyr Cys Val Ser Ala Pro Cys Phe Asn Gly Gly Thr Cys Val Asn Arg
770                 775                 780

Pro Gly Thr Phe Ser Cys Leu Cys Ala Met Gly Phe Gln Gly Pro Arg
785                 790                 795                 800

Cys Glu Gly Lys Leu Arg Pro Ser Cys Ala Asp Ser Pro Cys Arg Asn
                805                 810                 815

Arg Ala Thr Cys Gln Asp Ser Pro Gln Gly Pro Arg Cys Leu Cys Pro
                820                 825                 830

Thr Gly Tyr Thr Gly Gly Ser Cys Gln Thr Leu Met Asp Leu Cys Ala
            835                 840                 845

Gln Lys Pro Cys Pro Arg Asn Ser His Cys Leu Gln Thr Gly Pro Ser
            850                 855                 860

Phe His Cys Leu Cys Leu Gln Gly Trp Thr Gly Pro Leu Cys Asn Leu
865                 870                 875                 880
```

```
Pro Leu Ser Ser Cys Gln Lys Ala Ala Leu Ser Gln Gly Ile Asp Val
            885                 890                 895

Ser Ser Leu Cys His Asn Gly Gly Leu Cys Val Asp Ser Gly Pro Ser
        900                 905                 910

Tyr Phe Cys His Cys Pro Pro Gly Phe Gln Gly Ser Leu Cys Gln Asp
        915                 920                 925

His Val Asn Pro Cys Glu Ser Arg Pro Cys Gln Asn Gly Ala Thr Cys
        930                 935                 940

Met Ala Gln Pro Ser Gly Tyr Leu Cys Gln Cys Ala Pro Gly Tyr Asp
945                 950                 955                 960

Gly Gln Asn Cys Ser Lys Glu Leu Asp Ala Cys Gln Ser Gln Pro Cys
        965                 970                 975

His Asn His Gly Thr Cys Thr Pro Lys Pro Gly Gly Phe His Cys Ala
        980                 985                 990

Cys Pro Pro Gly Phe Val Gly Leu Arg Cys Glu Gly Asp Val Asp Glu
        995                 1000                1005

Cys Leu Asp Gln Pro Cys His Pro Thr Gly Thr Ala Ala Cys His
        1010                1015                1020

Ser Leu Ala Asn Ala Phe Tyr Cys Gln Cys Leu Pro Gly His Thr
        1025                1030                1035

Gly Gln Trp Cys Glu Val Glu Ile Asp Pro Cys His Ser Gln Pro
        1040                1045                1050

Cys Phe His Gly Gly Thr Cys Glu Ala Thr Ala Gly Ser Pro Leu
        1055                1060                1065

Gly Phe Ile Cys His Cys Pro Lys Gly Phe Glu Gly Pro Thr Cys
        1070                1075                1080

Ser His Arg Ala Pro Ser Cys Gly Phe His His Cys His His Gly
        1085                1090                1095

Gly Leu Cys Leu Pro Ser Pro Lys Pro Gly Phe Pro Pro Arg Cys
        1100                1105                1110

Ala Cys Leu Ser Gly Tyr Gly Gly Pro Asp Cys Leu Thr Pro Pro
        1115                1120                1125

Ala Pro Lys Gly Cys Gly Pro Pro Ser Pro Cys Leu Tyr Asn Gly
        1130                1135                1140

Ser Cys Ser Glu Thr Thr Gly Leu Gly Gly Pro Gly Phe Arg Cys
        1145                1150                1155

Ser Cys Pro His Ser Ser Pro Gly Pro Arg Cys Gln Lys Pro Gly
        1160                1165                1170

Ala Lys Gly Cys Glu Gly Arg Ser Gly Asp Gly Ala Cys Asp Ala
        1175                1180                1185

Gly Cys Ser Gly Pro Gly Gly Asn Trp Asp Gly Gly Asp Cys Ser
        1190                1195                1200

Leu Gly Val Pro Asp Pro Trp Lys Gly Cys Pro Ser His Ser Arg
        1205                1210                1215

Cys Trp Leu Leu Phe Arg Asp Gly Gln Cys His Pro Gln Cys Asp
        1220                1225                1230

Ser Glu Glu Cys Leu Phe Asp Gly Tyr Asp Cys Glu Thr Pro Pro
        1235                1240                1245

Ala Cys Thr Pro Ala Tyr Asp Gln Tyr Cys His Asp His Phe His
        1250                1255                1260

Asn Gly His Cys Glu Lys Gly Cys Asn Thr Ala Glu Cys Gly Trp
        1265                1270                1275

Asp Gly Gly Asp Cys Arg Pro Glu Asp Gly Asp Pro Glu Trp Gly
        1280                1285                1290
```

-continued

```
Pro Ser Leu Ala Leu Leu Val Val Leu Ser Pro Pro Ala Leu Asp
    1295                1300            1305

Gln Gln Leu Phe Ala Leu Ala Arg Val Leu Ser Leu Thr Leu Arg
    1310                1315            1320

Val Gly Leu Trp Val Arg Lys Asp Arg Asp Gly Arg Asp Met Val
    1325                1330            1335

Tyr Pro Tyr Pro Gly Ala Arg Ala Glu Glu Lys Leu Gly Gly Thr
    1340                1345            1350

Arg Asp Pro Thr Tyr Gln Glu Arg Ala Ala Pro Gln Thr Gln Pro
    1355                1360            1365

Leu Gly Lys Glu Thr Asp Ser Leu Ser Ala Gly Phe Val Val Val
    1370                1375            1380

Met Gly Val Asp Leu Ser Arg Cys Gly Pro Asp His Pro Ala Ser
    1385                1390            1395

Arg Cys Pro Trp Asp Pro Gly Leu Leu Leu Arg Phe Leu Ala Ala
    1400                1405            1410

Met Ala Ala Val Gly Ala Leu Glu Pro Leu Leu Pro Gly Pro Leu
    1415                1420            1425

Leu Ala Val His Pro His Ala Gly Thr Ala Pro Pro Ala Asn Gln
    1430                1435            1440

Leu Pro Trp Pro Val Leu Cys Ser Pro Val Ala Gly Val Ile Leu
    1445                1450            1455

Leu Ala Leu Gly Ala Leu Leu Val Leu Gln Leu Ile Arg Arg Arg
    1460                1465            1470

Arg Arg Glu His Gly Ala Leu Trp Leu Pro Pro Gly Phe Thr Arg
    1475                1480            1485

Arg Pro Arg Thr Gln Ser Ala Pro His Arg Arg Arg Pro Pro Leu
    1490                1495            1500

Gly Glu Asp Ser Ile Gly Leu Lys Ala Leu Lys Pro Lys Ala Glu
    1505                1510            1515

Val Asp Glu Asp Gly Val Val Met Cys Ser Gly Pro Glu Glu Gly
    1520                1525            1530

Glu Glu Val Gly Gln Ala Glu Glu Thr Gly Pro Pro Ser Thr Cys
    1535                1540            1545

Gln Leu Trp Ser Leu Ser Gly Gly Cys Gly Ala Leu Pro Gln Ala
    1550                1555            1560

Ala Met Leu Thr Pro Pro Gln Glu Ser Glu Met Glu Ala Pro Asp
    1565                1570            1575

Leu Asp Thr Arg Gly Pro Asp Gly Val Thr Pro Leu Met Ser Ala
    1580                1585            1590

Val Cys Cys Gly Glu Val Gln Ser Gly Thr Phe Gln Gly Ala Trp
    1595                1600            1605

Leu Gly Cys Pro Glu Pro Trp Glu Pro Leu Leu Asp Gly Gly Ala
    1610                1615            1620

Cys Pro Gln Ala His Thr Val Gly Thr Gly Glu Thr Pro Leu His
    1625                1630            1635

Leu Ala Ala Arg Phe Ser Arg Pro Thr Ala Ala Arg Arg Leu Leu
    1640                1645            1650

Glu Ala Gly Ala Asn Pro Asn Gln Pro Asp Arg Ala Gly Arg Thr
    1655                1660            1665

Pro Leu His Ala Ala Val Ala Ala Asp Ala Arg Glu Val Cys Gln
    1670                1675            1680

Leu Leu Leu Arg Ser Arg Gln Thr Ala Val Asp Ala Arg Thr Glu
```

```
                        1685                1690                1695

Asp  Gly  Thr  Thr  Pro  Leu  Met  Leu  Ala  Ala  Arg  Leu  Ala  Val  Glu
          1700                1705                1710

Asp  Leu  Val  Glu  Glu  Leu  Ile  Ala  Ala  Gln  Ala  Asp  Val  Gly  Ala
     1715                1720                1725

Arg  Asp  Lys  Trp  Gly  Lys  Thr  Ala  Leu  His  Trp  Ala  Ala  Ala  Val
1730                1735                1740

Asn  Asn  Ala  Arg  Ala  Ala  Arg  Ser  Leu  Leu  Gln  Ala  Gly  Ala  Asp
1745                1750                1755

Lys  Asp  Ala  Gln  Asp  Asn  Arg  Glu  Gln  Thr  Pro  Leu  Phe  Leu  Ala
1760                1765                1770

Ala  Arg  Glu  Gly  Ala  Val  Glu  Val  Ala  Gln  Leu  Leu  Leu  Gly  Leu
     1775                1780                1785

Gly  Ala  Ala  Arg  Glu  Leu  Arg  Asp  Gln  Ala  Gly  Leu  Ala  Pro  Ala
     1790                1795                1800

Asp  Val  Ala  His  Gln  Arg  Asn  His  Trp  Asp  Leu  Leu  Thr  Leu  Leu
     1805                1810                1815

Glu  Gly  Ala  Gly  Pro  Pro  Glu  Ala  Arg  His  Lys  Ala  Thr  Pro  Gly
     1820                1825                1830

Arg  Glu  Ala  Gly  Pro  Phe  Pro  Arg  Ala  Arg  Thr  Val  Ser  Val  Ser
     1835                1840                1845

Val  Pro  Pro  His  Gly  Gly  Ala  Leu  Pro  Arg  Cys  Arg  Thr  Leu
     1850                1855                1860

Ser  Ala  Gly  Ala  Gly  Pro  Arg  Gly  Gly  Gly  Ala  Cys  Leu  Gln  Ala
     1865                1870                1875

Arg  Thr  Trp  Ser  Val  Asp  Leu  Ala  Ala  Arg  Gly  Gly  Ala  Tyr
     1880                1885                1890

Ser  His  Cys  Arg  Ser  Leu  Ser  Gly  Val  Gly  Ala  Gly  Gly  Gly  Pro
     1895                1900                1905

Thr  Pro  Arg  Gly  Arg  Phe  Ser  Ala  Gly  Met  Arg  Gly  Pro  Arg
     1910                1915                1920

Pro  Asn  Pro  Ala  Ile  Met  Arg  Gly  Arg  Tyr  Gly  Val  Ala  Ala  Gly
     1925                1930                1935

Arg  Gly  Gly  Arg  Val  Ser  Thr  Asp  Asp  Trp  Pro  Cys  Asp  Trp  Val
     1940                1945                1950

Ala  Leu  Gly  Ala  Cys  Gly  Ser  Ala  Ser  Asn  Ile  Pro  Ile  Pro  Pro
     1955                1960                1965

Pro  Cys  Leu  Thr  Pro  Ser  Pro  Glu  Arg  Gly  Ser  Pro  Gln  Leu  Asp
     1970                1975                1980

Cys  Gly  Pro  Pro  Ala  Leu  Gln  Glu  Met  Pro  Ile  Asn  Gln  Gly  Gly
     1985                1990                1995

Glu  Gly  Lys  Lys
     2000

<210> SEQ ID NO 22
<211> LENGTH: 5896
<212> TYPE: DNA
<213> ORGANISM: Homo sapiens
<220> FEATURE:
<221> NAME/KEY: misc_feature
<223> OTHER INFORMATION: Jagged-1

<400> SEQUENCE: 22
ctgcggccgg cccgcgagct aggctgggtt tttttttttc tccctccct cccccctttt      60 tccatgcagc tgatctaaaa gggaataaaa ggctgcgcat aatcataata ataaagaag     120
```

-continued

```
gggagcgcga gagaaggaaa gaaagccggg aggtggaaga ggaggggggag cgtctcaaag    180 aagcgatcag aataataaaa ggaggccggg ctctttgcct tctggaacgg gccgctcttg    240
aaagggcttt tgaaaagtgg tgttgttttc cagtcgtgca tgctccaatc ggcggagtat    300
attagagccg ggacgcggcg gccgcagggg cagcggcgac ggcagcaccg gcggcagcac    360
cagcgcgaac agcagcggcg gcgtcccgag tgcccgcggc gcgcggcgca gcgatgcgtt    420
ccccacggac gcgcggccgg tccgggcgcc cctaagcct cctgctcgcc ctgctctgtg     480
ccctgcgagc caaggtgtgt ggggcctcgg gtcagttcga gttggagatc ctgtccatgc    540
agaacgtgaa cggggagctg cagaacggga actgctgcgg cggcgcccgg aacccgggag    600
accgcaagtg caccgcgac gagtgtgaca catacttcaa agtgtgcctc aaggagtatc     660
agtcccgcgt cacggccggg gggccctgca gcttcggctc agggtccacg cctgtcatcg    720
ggggcaacac cttcaacctc aaggccagcc gcggcaacga ccgcaaccgc atcgtgctgc    780
ctttcagttt cgcctggccg aggtcctata cgttgcttgt ggaggcgtgg gattccagta    840
atgacaccgt tcaacctgac agtattattg aaaaggcttc tcactcgggc atgatcaacc    900
ccagccggca gtggcagacg ctgaagcaga acacgggcgt tgcccacttt gagtatcaga    960
tccgcgtgac ctgtgatgac tactactatg gctttggctg caataagttc tgccgcccca   1020
gagatgactt ctttggacac tatgcctgtg accagaatgg caacaaaact tgcatggaag   1080
gctggatggg cccccgaatgt aacagagcta tttgccgaca aggctgcagt cctaagcatg   1140
ggtcttgcaa actcccaggt gactgcaggt gccagtatgg ctggcaaggc ctgtactgtg   1200
ataagtgcat cccacacccg ggatgcgtcc acggcatctg taatgagccc tggcagtgcc   1260
tctgtgagac caactggggc ggccagctct gtgacaaaga tctcaattac tgtgggactc   1320
atcagccgtg tctcaacggg ggaacttgta gcaacacagg ccctgacaaa tatcagtgtt   1380
cctgccctga ggggtattca ggacccaact gtgaaattgc tgagcacgcc tgcctctctg   1440
atccctgtca caacagaggc agctgtaagg agacctccct gggctttgag tgtgagtgtt   1500
ccccaggctg gaccggcccc acatgctcta caaacattga tgactgttct cctaataact   1560
gttcccacgg gggcacctgc caggacctgg ttaacggatt taagtgtgtg tgccccccac   1620
agtggactgg gaaaacgtgc cagttagatg caaatgaatg tgaggccaaa ccttgtgtaa   1680
acgccaaatc ctgtaagaat ctcattgcca gctactactg cgactgtctt cccggctgga   1740
tgggtcagaa ttgtgacata aatattaatg actgccttgg ccagtgtcag aatgacgcct   1800
cctgtcggga tttggttaat ggttatcgct gtatctgtcc acctggctat gcaggcgatc   1860
actgtgagag agacatcgat gaatgtgcca gcaacccctg tttgaatggg ggtcactgtc   1920
agaatgaaat caacagattc cagtgtctgt gtcccactgg tttctctgga aacctctgtc   1980
agctggacat cgattattgt gagcctaatc cctgccagaa cggtgcccag tgctacaacc   2040
gtgccagtga ctatttctgc aagtgccccg aggactatga gggcaagaac tgctcacacc   2100
tgaaagacca ctgccgcacg accccctgtg aagtgattga cagctgcaca gtggccatgg   2160
cttccaacga cacacctgaa ggggtgcggt atattttcctc caacgtctgt ggtcctcacg   2220
ggaagtgcaa gagtcagtcg ggaggcaaat tcacctgtga ctgtaacaaa ggcttcacgg   2280
gaacatactg ccatgaaaat attaatgact gtgagagcaa cccttgtaga aacggtggca   2340
cttgcatcga tggtgtcaac tcctacaagt gcatctgtag tgacggctgg gagggggcct   2400
actgtgaaac caatattaat gactgcagcc agaacccctg ccacaatggg ggcacgtgtc   2460
gcgacctggt caatgacttc tactgtgact gtaaaaatgg gtggaaagga aagacctgcc   2520
```

```
actcacgtga cagtcagtgt gatgaggcca cgtgcaacaa cggtggcacc tgctatgatg    2580
agggggatgc ttttaagtgc atgtgtcctg cggctgggaa aggaacaacc tgtaacatag    2640
cccgaaacag tagctgcctg cccaacccct gccataatgg gggcacatgt gtggtcaacg    2700
gcgagtcctt tacgtgcgtc tgcaaggaag gctgggaggg gcccatctgt gctcagaata    2760
ccaatgactg cagccctcat ccctgttaca acagcggcac ctgtgtggat ggagacaact    2820
ggtaccggtc cgaatgtgcc ccgggttttg ctgggcccga ctgcagaata aacatcaatg    2880
aatgccagtc ttcaccttgt gcctttggag cgacctgtgt ggatgagatc aatggctacc    2940
ggtgtgtctg ccctccaggg cacagtggtg ccaagtgcca ggaagtttca gggagacctt    3000
gcatcaccat ggggagtgtg ataccagatg gggccaaatg ggatgatgac tgtaatacct    3060
gccagtgcct gaatggacgg atcgcctgct caaaggtctg gtgtggccct cgaccttgcc    3120
tgctccacaa agggcacagc gagtgcccca gcgggcagag ctgcatcccc atcctggacg    3180
accagtgctt cgtccacccc tgcactggtg tgggcgagtc tcggtcttcc agtctccagc    3240
cggtgaagac aaagtgcacc tctgactcct attaccagga taactgtgcg aacatcacat    3300
ttacctttaa caaggagatg atgtcaccag gtcttactac ggagcacatt tgcagtgaat    3360
tgaggaattt gaatattttg aagaatgttt ccgctgaata ttcaatctac atcgcttgcg    3420
agccttcccc ttcagcgaac aatgaaatac atgtggccat ttctgctgaa gatatacggg    3480
atgatgggaa cccgatcaag gaaatcactg acaaaataat cgatcttgtt agtaaacgtg    3540
atggaaacag ctcgctgatt gctgccgttg cagaagtaag agttcagagg cggcctctga    3600
agaacagaac agatttcctt gttcccttgc tgagctctgt cttaactgtg cttggatct    3660
gttgcttggt gacggccttc tactggtgcc tgcggaagcg gcggaagccg ggcagccaca    3720
cacactcagc ctctgaggac aacaccacca acaacgtgcg ggacagctg aaccagatca    3780
aaaaccccat tgagaaacat ggggccaaca cggtccccat caaggattac gagaacaaga    3840
actccaaaat gtctaaaata aggacacaca attctgaagt agaagaggac gacatggaca    3900
aacaccagca gaaagcccgg tttgccaagc agcggcgta tacgctggta gacagagaag    3960
agaagcccc caacggcacg ccgacaaaac acccaaactg gacaaacaaa caggacaaca    4020
gagacttgga aagtgcccag agcttaaacc gaatggagta catcgtatag cagaccgcgg    4080
gcactgccgc cgctaggtag agtctgaggg cttgtagttc tttaaactgt cgtgtcatac    4140
tcgagtctga ggccgttgct gacttagaat ccctgtgtta atttaagttt tgacaagctg    4200
gcttacactg gcaatggtag tttctgtggt tggctgggaa atcgagtgcc gcatctcaca    4260
gctatgcaaa aagctagtca acagtaccct ggttgtgtgt ccccttgcag ccgacacggt    4320
ctcggatcag gctcccagga gcctgcccag ccccctggtc tttgagctcc cacttctgcc    4380
agatgtccta atggtgatgc agtcttagat catagtttta tttatatta ttgactcttg    4440
agttgttttt gtatattggt tttatgatga cgtacaagta gttctgtatt tgaaagtgcc    4500
tttgcagctc agaaccacag caacgatcac aaatgacttt attatttatt ttttaattg    4560
tatttttgtt gttgggggag gggagacttt gatgtcagca gttgctggta aaatgaagaa    4620
tttaagaaa aaaatgtcaa aagtagaact ttgtatagtt atgtaaataa ttctttttta    4680
ttaatcactg tgtatatttg atttattaac ttaataatca agagccttaa acatcattc    4740
cтттттатттт atatgtatgt gtttagaatt gaaggttttt gatagcattg taagcgtatg    4800
gctttatttt tttgaactct tctcatact tgttgcctat aagccaaaat таaggтgтттт    4860
gaaaatagtt татттттаааа caataggatg ggcttctgtg cccagaatac tgatggaatt    4920
```

```
tttttttgtac gacgtcagat gtttaaaaca ccttctatag catcacttaa aacacgtttt    4980
aaggactgac tgaggcagtt tgaggattag tttagaacag gttttttttgt ttgtttgttt    5040 tttgttttc tgctttagac ttgaaaagag acaggcaggt gatctgctgc agagcagtaa      5100
gggaacaagt tgagctatga cttaacatag ccaaaatgtg agtggttgaa tatgattaaa      5160
aatatcaaat taattgtgtg aacttggaag cacaccaatc tgactttgta aattctgatt     5220
tcttttcacc attcgtacat aatactgaac cacttgtaga tttgattttt ttttttaatct   5280 actgcattta gggagtattc taataagcta gttgaatact tgaaccataa aatgtccagt     5340
aagatcactg tttagatttg ccatagagta cactgcctgc cttaagtgag gaaatcaaag     5400
tgctattacg aagttcaaga tcaaaaggc ttataaaaca gagtaatctt gttggttcac      5460
cattgagacc gtgaagatac tttgtattgt cctattagtg ttatatgaac atacaaatgc    5520
atctttgatg tgttgttctt ggcaataaat tttgaaaagt aatatttatt aaatttttt     5580 gtatgaaaac atgaacagt gtggctcttc tgagcttacg tagttctacc ggcttttgccg   5640 tgtgcttctg ccaccctgct gagtctgttc tggtaatcgg ggtataatag gctctgcctg    5700
acagagggat ggaggaagaa ctgaaaggct tttcaaccac aaaactcatc tggagttctc   5760
aaagacctgg ggctgctgtg aagctggaac tgcgggagcc ccatctaggg gagccttgat   5820
tcccttgtta ttcaacagca agtgtgaata ctgcttgaat aaacaccact ggattaatgg    5880
aaaaaaaaaa aaaaaa                                                    5896

<210> SEQ ID NO 23
<211> LENGTH: 1218
<212> TYPE: PRT
<213> ORGANISM: Homo sapiens
<220> FEATURE:
<221> NAME/KEY: misc_feature
<223> OTHER INFORMATION: Jagged-1

<400> SEQUENCE: 23

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190
```

```
Gly Phe Gly Cys Asn Lys Phe Cys Arg Pro Arg Asp Phe Phe Gly
            195                 200                 205

His Tyr Ala Cys Asp Gln Asn Gly Asn Lys Thr Cys Met Glu Gly Trp
            210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
            275                 280                 285

Gly Gly Gln Leu Cys Asp Lys Asp Leu Asn Tyr Cys Gly Thr His Gln
            290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
            355                 360                 365

Pro Thr Cys Ser Thr Asn Ile Asp Asp Cys Ser Pro Asn Asn Cys Ser
370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
            435                 440                 445

Ile Asn Ile Asn Asp Cys Leu Gly Gln Cys Gln Asn Asp Ala Ser Cys
            450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
            515                 520                 525

Cys Glu Pro Asn Pro Cys Gln Asn Gly Ala Gln Cys Tyr Asn Arg Ala
530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
            595                 600                 605

Ser Gly Gly Lys Phe Thr Cys Asp Cys Asn Lys Gly Phe Thr Gly Thr
```

-continued

```
            610                 615                 620
Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
                660                 665                 670

Gln Asn Pro Cys His Asn Gly Gly Thr Cys Arg Asp Leu Val Asn Asp
                675                 680                 685

Phe Tyr Cys Asp Cys Lys Asn Gly Trp Lys Gly Lys Thr Cys His Ser
        690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
                740                 745                 750

Cys His Asn Gly Gly Thr Cys Val Val Asn Gly Glu Ser Phe Thr Cys
            755                 760                 765

Val Cys Lys Glu Gly Trp Glu Gly Pro Ile Cys Ala Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
                820                 825                 830

Ala Thr Cys Val Asp Glu Ile Asn Gly Tyr Arg Cys Val Cys Pro Pro
            835                 840                 845

Gly His Ser Gly Ala Lys Cys Gln Glu Val Ser Gly Arg Pro Cys Ile
            850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
                900                 905                 910

Ser Gly Gln Ser Cys Ile Pro Ile Leu Asp Asp Gln Cys Phe Val His
            915                 920                 925

Pro Cys Thr Gly Val Gly Glu Cys Arg Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
            995                 1000                1005

Asn Asn Glu Ile His Val Ala Ile Ser Ala Glu Asp Ile Arg Asp
        1010                1015                1020

Asp Gly Asn Pro Ile Lys Glu Ile Thr Asp Lys Ile Ile Asp Leu
    1025                1030                1035
```

| | | | | | | | | | |
|---|---|---|---|---|---|---|---|---|---|
|Val|Ser|Lys|Arg|Asp|Gly|Asn|Ser|Ser|Leu|Ile|Ala|Ala|Val|Ala|

Val Ser Lys Arg Asp Gly Asn Ser Ser Leu Ile Ala Ala Val Ala
1040                1045               1050

Glu Val Arg Val Gln Arg Arg Pro Leu Lys Asn Arg Thr Asp Phe
1055                1060               1065

Leu Val Pro Leu Leu Ser Ser Val Leu Thr Val Ala Trp Ile Cys
1070                1075               1080

Cys Leu Val Thr Ala Phe Tyr Trp Cys Leu Arg Lys Arg Arg Lys
1085                1090               1095

Pro Gly Ser His Thr His Ser Ala Ser Glu Asp Asn Thr Thr Asn
1100                1105               1110

Asn Val Arg Glu Gln Leu Asn Gln Ile Lys Asn Pro Ile Glu Lys
1115                1120               1125

His Gly Ala Asn Thr Val Pro Ile Lys Asp Tyr Glu Asn Lys Asn
1130                1135               1140

Ser Lys Met Ser Lys Ile Arg Thr His Asn Ser Glu Val Glu Glu
1145                1150               1155

Asp Asp Met Asp Lys His Gln Gln Lys Ala Arg Phe Ala Lys Gln
1160                1165               1170

Pro Ala Tyr Thr Leu Val Asp Arg Glu Glu Lys Pro Pro Asn Gly
1175                1180               1185

Thr Pro Thr Lys His Pro Asn Trp Thr Asn Lys Gln Asp Asn Arg
1190                1195               1200

Asp Leu Glu Ser Ala Gln Ser Leu Asn Arg Met Glu Tyr Ile Val
1205                1210               1215

<210> SEQ ID NO 24
<211> LENGTH: 5077
<212> TYPE: DNA
<213> ORGANISM: Homo sapiens
<220> FEATURE:
<221> NAME/KEY: misc_feature
<223> OTHER INFORMATION: Jagged-2

<400> SEQUENCE: 24

```
ctcatgcata tgcaggtgcg cgggtgacga atgggcgagc gagctgtcag tctcgttccg      60
aacttgttgg ctgcggtgcc gggagcgcgg gcgcgcagag ccgaggccgg acccgctgc      120 cttcaccgcc gccgccgtcg ccgccgggtg ggagccgggc cgggcagccg gagcgcggcc      180
gccagcgagc cggagctgcc gccgccctg cacgcccgcc gccaggccc gcgcgccgcg      240 gcgctgcgct cgaccccgcc cgcgccgccg ccgccgccgc ctctgccgct gccgctgcct      300
ctgcgggcgc tcggagggcg gcggggcgct gggaggccgg cgcggcggct gggagccggg      360
cgcgggcggc ggcggcgggg ccgggcgggc ggtcgcggg ggcaatgcgg gcgcagggcc      420
gggggcgcct tccccggcgg ctgctgctgc tgctggcgct ctgggtgcag gcggcgcggc      480
ccatgggcta tttcgagctg cagctgagcg cgctgcggaa cgtgaacggg gagctgctga      540
gcggcgcctg ctgtgacggc gacggccgga caacgcgcgc gggggctgc ggccacgacg      600 agtgcgacac gtacgtgcgc gtgtgcctta aggagtacca ggccaaggtg acgcccacgg      660
ggccctgcag ctacggccac ggcgccacgc ccgtgctggg cggcaactcc ttctacctgc      720
cgccggcggg cgctgcgggg gaccgagcgc gggcgcgggc ccgggccggc ggcgaccagg      780
acccgggcct cgtcgtcatc cccttccagt tcgcctggcc gcgctccttt accctcatcg      840
tggaggcctg ggactgggac aacgatacca ccccgaatga ggagctgctg atcgagcgag      900
tgtcgcatgc cggcatgatc aacccggagg accgctggaa gagcctgcac ttcagcggcc      960
acgtggcgca cctggagctg cagatccgcg tgcgctgcga cgagaactac tacagcgcca     1020
```

```
cttgcaacaa gttctgccgg ccccgcaacg acttttttcgg ccactacacc tgcgaccagt   1080
acggcaacaa ggcctgcatg gacggctgga tgggcaagga gtgcaaggaa gctgtgtgta   1140
aacaagggtg taatttgctc cacggggat gcaccgtgcc tggggagtgc aggtgcagct    1200
acggctggca agggaggttc tgcgatgagt gtgtcccta ccccggctgc gtgcatggca    1260
gttgtgtgga ccctggcag tgcaactgtg agaccaactg gggcggcctg ctctgtgaca    1320
aagacctgaa ctactgtggc agccaccacc cctgcaccaa cggaggcacg tgcatcaacg   1380
ccgagcctga ccagtaccgc tgcacctgcc ctgacggcta ctcgggcagg aactgtgaga   1440
aggctgagca cgcctgcacc tccaacccgt gtgccaacgg gggctcttgc catgaggtgc   1500
cgtccggctt cgaatgccac tgcccatcgg gctggagcgg gcccacctgt gcccttgaca   1560
tcgatgagtg tgcttcgaac ccgtgtgcgg ccggtgcac ctgtgtggac caggtggacg    1620
gctttgagtg catctgcccc gagcagtggg tgggggccac ctgccagctg gacgccaatg   1680
agtgtgaagg gaagccatgc cttaacgctt tttcttgcaa aaacctgatt ggcggctatt   1740
actgtgattg catcccgggc tggaagggca tcaactgcca tatcaacgtc aacgactgtc   1800
gcgggcagtg tcagcatggg ggcacctgca aggacctggt gaacgggtac cagtgtgtgt   1860
gcccacgggg cttcggaggc cggcattgcg agctggaacg agacgagtgt gccagcagcc   1920
cctgccacag cggcggcctc tgcgaggacc tggccgacgg cttccactgc cactgccccc   1980
agggcttctc cgggcctctc tgtgaggtgg atgtcgacct tgtgagcca agcccctgcc    2040 ggaacggcgc tcgctgctat aacctggagg gtgactatta ctgcgcctgc cctgatgact   2100
ttggtggcaa gaactgctcc gtgccccgcg agccgtgccc tggcggggcc tgcagagtga   2160 tcgatgctc cgggtcagac gcggggcctg ggatgcctgg cacagcagcc tccggcgtgt   2220 gtggcccca tggacgctgc gtcagccagc cagggggcaa cttttcctgc atctgtgaca   2280 gtggcttttac tggcacctac tgccatgaga acattgacga ctgcctgggc cagccctgcc   2340
gcaatggggg cacatgcatc gatgaggtgg acgccttccg ctgcttctgc cccagcggct   2400
gggagggcga gctctgcgac accaatccca acgactgcct tcccgatccc tgccacagcc   2460
gcggccgctg ctacgacctg gtcaatgact tctactgtgc gtgcgacgac ggctggaagg   2520
gcaagacctg ccactcacgc gagttccagt gcgatgccta cacctgcagc aacggtggca   2580
cctgctacga cagcggcgac accttccgct gcgcctgccc ccccggctgg aagggcagca   2640
cctgcgccgt cgccaagaac agcagctgcc tgcccaaccc ctgtgtgaat ggtggcacct   2700
gcgtgggcag cggggcctcc ttctcctgca tctgccggga cggctgggag gtcgtacttt   2760
gcactcacaa taccaacgac tgcaaccctc tgccttgcta caatggtggc atctgtgttg   2820
acggcgtcaa ctggttccgc tgcgagtgtg cacctggctt cgcggggcct gactgccgca   2880
tcaacatcga cgagtgccag tcctcgcccct gtgcctacgg ggccacgtgt gtggatgaga   2940
tcaacgggta tcgctgtagc tgcccacccg gccgagccgg ccccggtgc caggaagtga   3000 tcgggttcgg gagatcctgc tggtcccggg gcactccgtt cccacacgga agctcctggg   3060
tggaagactg caacagctgc cgctgcctgg atggccgccg tgactgcagc aaggtgtggt   3120
gcggatggaa gccttgtctg ctggccggcc agcccgaggc cctgagcgcc cagtgcccac   3180
tggggcaaag gtgcctggag aaggcccag gccagtgtct gcgaccaccc tgtgaggcct   3240
ggggggagtg cggcgcagaa gagccaccga gcacccctg cctgccacgc tccggccacc   3300
tggacaataa ctgtgcccgc ctcaccttgc atttcaaccg tgaccacgtg ccccagggca   3360
ccacggtggg cgccatttgc tccgggatcc gctccctgcc agccacaagg gctgtggcac   3420
```

-continued

```
gggaccgcct gctggtgttg ctttgcgacc gggcgtcctc gggggccagt gccgtggagg    3480
tggccgtgtc cttcagccct gccagggacc tgcctgacag cagcctgatc cagggcgcgg    3540
cccacgccat cgtggccgcc atcacccagc ggggggaacag ctcactgctc ctggctgtca    3600
ccgaggtcaa ggtggagacg gttgttacgg gcggctcttc cacaggtctg ctggtgcctg    3660
tgctgtgtgg tgccttcagc gtgctgtggc tggcgtgcgt ggtcctgtgc gtgtggtgga    3720
cacgcaagcg caggaaagag cgggagagga gccggctgcc gcgggaggag agcgccaaca    3780
accagtgggc cccgctcaac cccatccgca accccatcga gcggccgggg ggccacaagg    3840
acgtgctcta ccagtgcaag aacttcacgc cgccgccgcg cagggcggac gaggcgctgc    3900
ccgggccggc cggccacgcg gccgtcaggg aggatgagga ggacgaggat ctgggccgcg    3960
gtgaggagga ctccctggag gcggagaagt tcctctcaca caaattcacc aaagatcctg    4020
gccgctcgcc ggggaggccg gcccactggg cctcaggccc caaagtggac aaccgcgcgg    4080
tcaggagcat caatgaggcc cgctacgccg gcaaggagta ggggcggctg ccagctgggc    4140
cgggacccag ggccctcggt gggagccatg ccgtctgccg gacccggagg ccgaggccat    4200
gtgcatagtt tctttatttt gtgtaaaaaa accaccaaaa acaaaaacca aatgtttatt    4260
ttctacgttt cttttaacctt gtataaatta ttcagtaact gtcaggctga aaacaatgga    4320
gtattctcgg atagttgcta tttttgtaaa gtttccgtgc gtggcactcg ctgtatgaaa    4380
ggagagagca aagggtgtct gcgtcgtcac caaatcgtag cgtttgttac cagaggttgt    4440
gcactgttta cagaatcttc cttttattcc tcactcgggt ttctctgtgg ctccaggcca    4500
aagtgccggt gagacccatg gctgtgttgg tgtggcccat ggctgttggt gggacccgtg    4560
gctgatggtg tggcctgtgg ctgtcggtgg gactcgtggc tgtcaatggg acctgtggct    4620
gtcggtggga cctacggtgg tcggtgggac cctggttatt gatgtggccc tggctgccgg    4680
cacggcccgt ggctgttgac gcacctgtgg ttgttagtgg ggcctgaggt catcggcgtg    4740
gcccaaggcc ggcaggtcaa cctcgcgctt gctggccagt ccaccctgcc tgccgtctgt    4800
gcttcctcct gcccagaacg cccgctccag cgatctctcc actgtgcttt cagaagtgcc    4860
cttcctgctg cgcagttctc ccatcctggg acggcggcag tattgaagct cgtgacaagt    4920
gccttcacac agacccctcg caactgtcca cgcgtgccgt ggcaccaggc gctgcccacc    4980
tgccggcccc ggccgcccct cctcgtgaaa gtgcattttt gtaaatgtgt acatattaaa    5040
ggaagcactc tgtatatttg attgaataat gccacca                             5077
```

<210> SEQ ID NO 25
<211> LENGTH: 1238
<212> TYPE: PRT
<213> ORGANISM: Homo sapiens
<220> FEATURE:
<221> NAME/KEY: misc_feature
<223> OTHER INFORMATION: Jagged-2

<400> SEQUENCE: 25

```
Met Arg Ala Gln Gly Arg Gly Arg Leu Pro Arg Leu Leu Leu Leu
  1               5                  10                  15

Leu Ala Leu Trp Val Gln Ala Ala Arg Pro Met Gly Tyr Phe Glu Leu
                 20                  25                  30

Gln Leu Ser Ala Leu Arg Asn Val Asn Gly Glu Leu Leu Ser Gly Ala
             35                  40                  45

Cys Cys Asp Gly Asp Gly Arg Thr Thr Arg Ala Gly Gly Cys Gly His
         50                  55                  60
```

```
Asp Glu Cys Asp Thr Tyr Val Arg Val Cys Leu Lys Glu Tyr Gln Ala
 65                  70                  75                  80

Lys Val Thr Pro Thr Gly Pro Cys Ser Tyr Gly His Gly Ala Thr Pro
                 85                  90                  95

Val Leu Gly Gly Asn Ser Phe Tyr Leu Pro Ala Gly Ala Ala Gly
            100                 105                 110

Asp Arg Ala Arg Ala Arg Ala Arg Ala Gly Gly Asp Gln Asp Pro Gly
            115                 120                 125

Leu Val Val Ile Pro Phe Gln Phe Ala Trp Pro Arg Ser Phe Thr Leu
            130                 135                 140

Ile Val Glu Ala Trp Asp Trp Asp Asn Asp Thr Thr Pro Asn Glu Glu
145                 150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
                180                 185                 190

Gln Ile Arg Val Arg Cys Asp Glu Asn Tyr Tyr Ser Ala Thr Cys Asn
                195                 200                 205

Lys Phe Cys Arg Pro Arg Asn Asp Phe Phe Gly His Tyr Thr Cys Asp
210                 215                 220

Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
                245                 250                 255

Thr Val Pro Gly Glu Cys Arg Cys Ser Tyr Gly Trp Gln Gly Arg Phe
                260                 265                 270

Cys Asp Glu Cys Val Pro Tyr Pro Gly Cys Val His Gly Ser Cys Val
                275                 280                 285

Glu Pro Trp Gln Cys Asn Cys Glu Thr Asn Trp Gly Gly Leu Leu Cys
                290                 295                 300

Asp Lys Asp Leu Asn Tyr Cys Gly Ser His His Pro Cys Thr Asn Gly
305                 310                 315                 320

Gly Thr Cys Ile Asn Ala Glu Pro Asp Gln Tyr Arg Cys Thr Cys Pro
                325                 330                 335

Asp Gly Tyr Ser Gly Arg Asn Cys Glu Lys Ala Glu His Ala Cys Thr
                340                 345                 350

Ser Asn Pro Cys Ala Asn Gly Gly Ser Cys His Glu Val Pro Ser Gly
                355                 360                 365

Phe Glu Cys His Cys Pro Ser Gly Trp Ser Gly Pro Thr Cys Ala Leu
                370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                405                 410                 415

Gly Ala Thr Cys Gln Leu Asp Ala Asn Glu Cys Glu Gly Lys Pro Cys
                420                 425                 430

Leu Asn Ala Phe Ser Cys Lys Asn Leu Ile Gly Gly Tyr Tyr Cys Asp
                435                 440                 445

Cys Ile Pro Gly Trp Lys Gly Ile Asn Cys His Ile Asn Val Asn Asp
                450                 455                 460

Cys Arg Gly Gln Cys Gln His Gly Gly Thr Cys Lys Asp Leu Val Asn
465                 470                 475                 480

Gly Tyr Gln Cys Val Cys Pro Arg Gly Phe Gly Gly Arg His Cys Glu
                485                 490                 495
```

Leu Glu Arg Asp Glu Cys Ala Ser Ser Pro Cys His Ser Gly Gly Leu
        500                 505                 510

Cys Glu Asp Leu Ala Asp Gly Phe His Cys His Cys Pro Gln Gly Phe
        515                 520                 525

Ser Gly Pro Leu Cys Glu Val Asp Val Asp Leu Cys Glu Pro Ser Pro
        530                 535                 540

Cys Arg Asn Gly Ala Arg Cys Tyr Asn Leu Glu Gly Asp Tyr Tyr Cys
545                 550                 555                 560

Ala Cys Pro Asp Asp Phe Gly Gly Lys Asn Cys Ser Val Pro Arg Glu
                565                 570                 575

Pro Cys Pro Gly Gly Ala Cys Arg Val Ile Asp Gly Cys Gly Ser Asp
            580                 585                 590

Ala Gly Pro Gly Met Pro Gly Thr Ala Ala Ser Gly Val Cys Gly Pro
            595                 600                 605

His Gly Arg Cys Val Ser Gln Pro Gly Gly Asn Phe Ser Cys Ile Cys
        610                 615                 620

Asp Ser Gly Phe Thr Gly Thr Tyr Cys His Glu Asn Ile Asp Asp Cys
625                 630                 635                 640

Leu Gly Gln Pro Cys Arg Asn Gly Gly Thr Cys Ile Asp Glu Val Asp
                645                 650                 655

Ala Phe Arg Cys Phe Cys Pro Ser Gly Trp Glu Gly Glu Leu Cys Asp
            660                 665                 670

Thr Asn Pro Asn Asp Cys Leu Pro Asp Pro Cys His Ser Arg Gly Arg
        675                 680                 685

Cys Tyr Asp Leu Val Asn Asp Phe Tyr Cys Ala Cys Asp Asp Gly Trp
690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
            725                 730                 735

Ala Cys Pro Pro Gly Trp Lys Gly Ser Thr Cys Ala Val Ala Lys Asn
            740                 745                 750

Ser Ser Cys Leu Pro Asn Pro Cys Val Asn Gly Gly Thr Cys Val Gly
        755                 760                 765

Ser Gly Ala Ser Phe Ser Cys Ile Cys Arg Asp Gly Trp Glu Gly Arg
        770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
            805                 810                 815

Pro Gly Phe Ala Gly Pro Asp Cys Arg Ile Asn Ile Asp Glu Cys Gln
            820                 825                 830

Ser Ser Pro Cys Ala Tyr Gly Ala Thr Cys Val Asp Glu Ile Asn Gly
        835                 840                 845

Tyr Arg Cys Ser Cys Pro Pro Gly Arg Ala Gly Pro Arg Cys Gln Glu
        850                 855                 860

Val Ile Gly Phe Gly Arg Ser Cys Trp Ser Arg Gly Thr Pro Phe Pro
865                 870                 875                 880

His Gly Ser Ser Trp Val Glu Asp Cys Asn Ser Cys Arg Cys Leu Asp
            885                 890                 895

Gly Arg Arg Asp Cys Ser Lys Val Trp Cys Gly Trp Lys Pro Cys Leu
            900                 905                 910

Leu Ala Gly Gln Pro Glu Ala Leu Ser Ala Gln Cys Pro Leu Gly Gln 915              920              925
Arg Cys Leu Glu Lys Ala Pro Gly Gln Cys Leu Arg Pro Cys Glu
    930              935              940

Ala Trp Gly Glu Cys Gly Ala Glu Pro Pro Ser Thr Pro Cys Leu
945              950              955              960

Pro Arg Ser Gly His Leu Asp Asn Asn Cys Ala Arg Leu Thr Leu His
                 965              970              975

Phe Asn Arg Asp His Val Pro Gln Gly Thr Thr Val Gly Ala Ile Cys
            980              985              990

Ser Gly Ile Arg Ser Leu Pro Ala  Thr Arg Ala Val Ala  Arg Asp Arg
        995              1000             1005

Leu Leu  Val Leu Leu Cys  Asp Arg Ala Ser Ser Gly  Ala Ser Ala
    1010             1015             1020

Val Glu  Val Ala Val Ser  Phe Ser Pro Ala Arg Asp  Leu Pro Asp
    1025             1030             1035

Ser Ser  Leu Ile Gln Gly  Ala Ala His Ala Ile Val  Ala Ala Ile
    1040             1045             1050

Thr Gln  Arg Gly Asn Ser  Ser Leu Leu Leu Ala Val  Thr Glu Val
    1055             1060             1065

Lys Val  Glu Thr Val Val  Thr Gly Ser Ser Thr  Gly Leu Leu
    1070             1075             1080

Val Pro  Val Leu Cys Gly  Ala Phe Ser Val Leu Trp  Leu Ala Cys
    1085             1090             1095

Val Val  Leu Cys Val Trp  Trp Thr Arg Lys Arg  Lys Glu Arg
    1100             1105             1110

Glu Arg  Ser Arg Leu Pro  Arg Glu Glu Ser Ala Asn  Asn Gln Trp
    1115             1120             1125

Ala Pro  Leu Asn Pro Ile Arg  Asn Pro Ile Glu Arg  Pro Gly Gly
    1130             1135             1140

His Lys  Asp Val Leu Tyr Gln  Cys Lys Asn Phe Thr  Pro Pro Pro
    1145             1150             1155

Arg Arg  Ala Asp Glu Ala Leu  Pro Gly Pro Ala Gly  His Ala Ala
    1160             1165             1170

Val Arg  Glu Asp Glu Glu  Asp Glu Asp Leu Gly Arg  Gly Glu Glu
    1175             1180             1185

Asp Ser  Leu Glu Ala Glu Lys  Phe Leu Ser His Lys  Phe Thr Lys
    1190             1195             1200

Asp Pro  Gly Arg Ser Pro Gly  Arg Pro Ala His Trp  Ala Ser Gly
    1205             1210             1215

Pro Lys  Val Asp Asn Arg Ala  Val Arg Ser Ile Asn  Glu Ala Arg
    1220             1225             1230

Tyr Ala  Gly Lys Glu
    1235

<210> SEQ ID NO 26
<211> LENGTH: 4963
<212> TYPE: DNA
<213> ORGANISM: Homo sapiens
<220> FEATURE:
<221> NAME/KEY: misc_feature
<223> OTHER INFORMATION: Jagged2, transcript variant 2

<400> SEQUENCE: 26
ctcatgcata tgcaggtgcg cgggtgacga atgggcgagc gagctgtcag tctcgttccg    60
aacttgttgg ctgcggtgcc gggagcgcgg gcgcgcagag ccgaggccgg acccgctgc   120

```
cttcaccgcc gccgccgtcg ccgccgggtg ggagccgggc cgggcagccg gagcgcggcc    180
gccagcgagc cggagctgcc gccgcccctg cacgcccgcc gcccaggccc gcgcgccgcg    240
gcgctgcgct cgaccccgcc cgcgccgccg ccgccgccgc tctgccgct gccgctgcct     300 ctgcgggcgc tcggagggcg ggcgggcgct gggaggccgg cgcggcggct gggagccggg    360
cgcgggcggc ggcggcgggg ccgggcgggc gggtcgcggg ggcaatgcgg gcgcagggcc    420
gggggcgcct tccccggcgg ctgctgctgc tgctggcgct ctgggtgcag gcggcgcggc    480
ccatgggcta tttcgagctg cagctgagcg cgctgcggaa cgtgaacggg gagctgctga    540
gcggcgcctg ctgtgacggc gacggccgga caacgcgcgc gggggctgc ggccacgacg     600 agtgcgacac gtacgtgcgc gtgtgccta aggagtacca ggccaaggtg acgcccacgg     660
ggccctgcag ctacgccac ggcgccacgc ccgtgctggg cggcaactcc ttctacctgc     720
cgccggcggg cgctgcgggg gaccgagcgc gggcgcgggc ccgggccggc ggcgaccagg    780
acccgggcct cgtcgtcatc cccttccagt tcgcctggcc gcgctccttt accctcatcg    840
tggaggcctg ggactgggac aacgatacca ccccgaatga ggagctgctg atcgagcgag    900
tgtcgcatgc cggcatgatc aacccggagg accgctggaa gagcctgcac ttcagcggcc    960
acgtggcgca cctggagctg cagatccgcg tgcgctgcga cgagaactac tacagcgcca    1020
cttgcaacaa gttctgccgg ccccgcaacg acttttttcgg ccactacacc tgcgaccagt   1080
acggcaacaa ggcctgcatg gacggctgga tgggcaagga gtgcaaggaa gctgtgtgta    1140
aacaagggtg taatttgctc cacggggat gcaccgtgcc tggggagtgc aggtgcagct     1200
acggctggca agggaggttc tgcgatgagt gtgtccccta ccccggctgc gtgcatggca    1260
gttgtgtgga gccctggcag tgcaactgtg agaccaactg gggcggcctg ctctgtgaca    1320
aagacctgaa ctactgtggc agccaccacc cctgcaccaa cggaggcacg tgcatcaacg    1380
ccgagcctga ccagtaccgc tgcacctgcc ctgacggcta ctcgggcagg aactgtgaga    1440
aggctgagca cgcctgcacc tccaacccgt gtgccaacgg gggctcttgc catgaggtgc    1500
cgtccggctt cgaatgccac tgcccatcgg gctggagcgg gcccacctgt gcccttgaca    1560
tcgatgagtg tgcttcgaac ccgtgtgcgg ccggtgcac ctgtgtggac caggtggacg     1620
gctttgagtg catctgcccc gagcagtggg tggggccac ctgccagctg acgtcaacg      1680 actgtcgcgg gcagtgtcag catggggca cctgcaagga cctggtgaac gggtaccagt    1740
gtgtgtgccc acgggcttc ggaggccggc attgcgagct ggaacgagac gagtgtgcca    1800 gcagccctg ccacacgcgg ggcctctgcg aggacctggc cgacggcttc cactgccact    1860 gccccaggg cttctccggg cctctctgtg aggtggatgt cgacctttgt gagccaagcc    1920
cctgccggaa cggcgctcgc tgctataacc tggagggtga ctattactgc gcctgccctg    1980
atgactttgg tggcaagaac tgctccgtgc ccgcgagcc gtgccctggc ggggcctgca    2040
gagtgatcga tggctgcggg tcagacgcgg ggcctgggat gcctggcaca gcagcctccg    2100
gcgtgtgtgg cccccatgga cgctgcgtca gccagccagg gggcaacttt tcctgcatct    2160
gtgacagtgg ctttactggc acctactgcc atgagaacat tgacgactgc ctgggccagc    2220
cctgccgcaa tggggggcaca tgcatcgatg aggtggacgc cttccgctgc ttctgcccca    2280
gcggctggga gggcgagctc tgcgacacca atcccaacga ctgccttccc gatccctgcc    2340
acagccgcgg ccgctgctac gacctggtca atgacttcta ctgtgcgtgc gacgacggct    2400
ggaagggcaa gacctgccac tcacgcgagt ccagtgcga tgcctacacc tgcagcaacg    2460
gtggcacctg ctacgacagc ggcgacacct tccgctgcgc ctgcccccc ggctggaagg    2520
```

```
gcagcacctg cgccgtcgcc aagaacagca gctgcctgcc caacccctgt gtgaatggtg    2580
gcacctgcgt gggcagcggg gcctccttct cctgcatctg ccgggacggc tgggagggtc    2640
gtacttgcac tcacaatacc aacgactgca accctctgcc ttgctacaat ggtggcatct    2700
gtgttgacgg cgtcaactgg ttccgctgcg agtgtgcacc tggcttcgcg gggcctgact    2760
gccgcatcaa catcgacgag tgccagtcct cgccctgtgc ctacggggcc acgtgtgtgg    2820
atgagatcaa cgggtatcgc tgtagctgcc caccccgccg agccggcccc cggtgccagg    2880
aagtgatcgg gttcgggaga tcctgctggt cccggggcac tccgttccca cacggaagct    2940
cctgggtgga agactgcaac agctgccgct gcctggatgg ccgccgtgac tgcagcaagg    3000
tgtggtgcgg atggaagcct tgtctgctgg ccggccagcc cgaggccctg agcgcccagt    3060
gcccactggg gcaaaggtgc ctggagaagg ccccaggcca gtgtctgcga ccaccctgtg    3120
aggcctgggg ggagtgcggc gcagaagagc caccgagcac cccctgcctg ccacgctccg    3180
gccacctgga caataactgt gcccgcctca ccttgcattt caaccgtgac cacgtgcccc    3240
agggcaccac ggtgggcgcc atttgctccg ggatccgctc cctgccagcc acaagggctg    3300
tggcacggga ccgcctgctg gtgttgcttt cgaccgggc gtcctcgggg gccagtgccg    3360
tggaggtggc cgtgtccttc agccctgcca gggacctgcc tgacagcagc ctgatccagg    3420
gcgcggccca cgccatcgtg gccgccatca cccagcgggg gaacagctca ctgctcctgg    3480
ctgtcaccga ggtcaaggtg gagacggttg ttacgggcgg ctcttccaca ggtctgctgg    3540
tgcctgtgct gtgtggtgcc ttcagcgtgc tgtggctggc gtgcgtggtc ctgtgcgtgt    3600
ggtggacacg caagcgcagg aaagagcggg agaggagccg gctgccgcgg gaggagagcg    3660
ccaacaacca gtgggcccg ctcaaccca tccgcaaccc catcgagcgg ccgggggggcc    3720 acaaggacgt gctctaccag tgcaagaact tcacgccgcc gccgcgcagg gcggacgagg    3780
cgctgcccgg gccggccggc cacgcggccg tcagggagga tgaggaggac gaggatctgg    3840
gccgcggtga ggaggactcc ctggaggcgg agaagttcct ctcacacaaa ttcaccaaag    3900
atcctggccg ctcgccgggg aggcggccc actgggcctc aggcccaa gtggacaacc    3960 gcgcggtcag gagcatcaat gaggcccgct acgccggcaa ggagtagggg cggctgccag    4020
ctgggccggg acccagggcc ctcggtggga gccatgccgt ctgccggacc cggaggccga    4080
ggccatgtgc atagtttctt tattttgtgt aaaaaaacca ccaaaaacaa aaaccaaatg    4140
tttattttct acgtttcttt aaccttgtat aaattattca gtaactgtca ggctgaaaac    4200 aatgagtat tctcggatag ttgctatttt tgtaaagttt ccgtgcgtgg cactcgctgt    4260
atgaaaggag agagcaaagg gtgtctgcgt cgtcaccaaa tcgtagcgtt tgttaccaga    4320
ggttgtgcac tgtttacaga atcttccttt tattcctcac tcgggtttct ctgtggctcc    4380
aggccaaagt gccggtgaga cccatggctg tgttggtgtg gcccatggct gttggtggga    4440
cccgtggctg atggtgtggc ctgtggctgt cggtgggact cgtggctgtc aatgggacct    4500
gtggctgtcg gtgggaccta cggtggtcgg tgggaccctg gttattgatg tggccctggc    4560
tgccggcacg gcccgtggct gttgacgcac ctgtggttgt tagtggggcc tgaggtcatc    4620
ggcgtggccc aaggccggca ggtcaacctc gcgcttgctg gccagtccac cctgcctgcc    4680
gtctgtgctt cctcctgccc agaacgcccg ctccagcgat ctctccactg tgctttcaga    4740
agtgcccttc ctgctgcgca gttctcccat cctgggacgg cggcagtatt gaagctcgtg    4800
acaagtgcct tcacacagac ccctcgcaac tgtccacgcg tgccgtggca ccaggcgctg    4860
cccacctgcc ggccccggcc gccctcctc gtgaaagtgc atttttgtaa atgtgtacat    4920
```
attaaaggaa gcactctgta tatttgattg aataatgcca cca         4963

<210> SEQ ID NO 27
<211> LENGTH: 1200
<212> TYPE: PRT
<213> ORGANISM: Homo sapiens
<220> FEATURE:
<221> NAME/KEY: misc_feature
<223> OTHER INFORMATION: Jagged2, transcript variant 2

<400> SEQUENCE: 27

```
Met Arg Ala Gln Gly Arg Gly Arg Leu Pro Arg Arg Leu Leu Leu
1               5                   10                  15

Leu Ala Leu Trp Val Gln Ala Ala Arg Pro Met Gly Tyr Phe Glu Leu
            20                  25                  30

Gln Leu Ser Ala Leu Arg Asn Val Asn Gly Glu Leu Leu Ser Gly Ala
            35                  40                      45

Cys Cys Asp Gly Asp Gly Arg Thr Thr Arg Ala Gly Gly Cys Gly His
        50                  55                      60

Asp Glu Cys Asp Thr Tyr Val Arg Val Cys Leu Lys Glu Tyr Gln Ala
65                  70                      75                  80

Lys Val Thr Pro Thr Gly Pro Cys Ser Tyr Gly His Gly Ala Thr Pro
                85                      90                      95

Val Leu Gly Gly Asn Ser Phe Tyr Leu Pro Pro Ala Gly Ala Ala Gly
                100                     105                     110

Asp Arg Ala Arg Ala Arg Ala Arg Ala Gly Gly Asp Gln Asp Pro Gly
            115                     120                     125

Leu Val Val Ile Pro Phe Gln Phe Ala Trp Pro Arg Ser Phe Thr Leu
        130                     135                     140

Ile Val Glu Ala Trp Asp Trp Asp Asn Asp Thr Thr Pro Asn Glu Glu
145                     150                     155                     160

Leu Leu Ile Glu Arg Val Ser His Ala Gly Met Ile Asn Pro Glu Asp
                165                     170                     175

Arg Trp Lys Ser Leu His Phe Ser Gly His Val Ala His Leu Glu Leu
                180                     185                     190

Gln Ile Arg Val Arg Cys Asp Glu Asn Tyr Tyr Ser Ala Thr Cys Asn
            195                     200                     205

Lys Phe Cys Arg Pro Arg Asn Asp Phe Phe Gly His Tyr Thr Cys Asp
210                     215                     220

Gln Tyr Gly Asn Lys Ala Cys Met Asp Gly Trp Met Gly Lys Glu Cys
225                     230                     235                     240

Lys Glu Ala Val Cys Lys Gln Gly Cys Asn Leu Leu His Gly Gly Cys
                245                     250                     255

Thr Val Pro Gly Glu Cys Arg Cys Ser Tyr Gly Trp Gln Gly Arg Phe
                260                     265                     270

Cys Asp Glu Cys Val Pro Tyr Pro Gly Cys Val His Gly Ser Cys Val
            275                     280                     285

Glu Pro Trp Gln Cys Asn Cys Glu Thr Asn Trp Gly Gly Leu Leu Cys
        290                     295                     300

Asp Lys Asp Leu Asn Tyr Cys Gly Ser His His Pro Cys Thr Asn Gly
305                     310                     315                     320

Gly Thr Cys Ile Asn Ala Glu Pro Asp Gln Tyr Arg Cys Thr Cys Pro
                325                     330                     335

Asp Gly Tyr Ser Gly Arg Asn Cys Glu Lys Ala Glu His Ala Cys Thr
            340                     345                     350

Ser Asn Pro Cys Ala Asn Gly Gly Ser Cys His Glu Val Pro Ser Gly
```

-continued

```
            355                 360                 365
Phe Glu Cys His Cys Pro Ser Gly Trp Ser Gly Pro Thr Cys Ala Leu
        370                 375                 380
Asp Ile Asp Glu Cys Ala Ser Asn Pro Cys Ala Ala Gly Gly Thr Cys
385                 390                 395                 400
Val Asp Gln Val Asp Gly Phe Glu Cys Ile Cys Pro Glu Gln Trp Val
                405                 410                 415
Gly Ala Thr Cys Gln Leu Asp Val Asn Asp Cys Arg Gly Gln Cys Gln
                420                 425                 430
His Gly Gly Thr Cys Lys Asp Leu Val Asn Gly Tyr Gln Cys Val Cys
            435                 440                 445
Pro Arg Gly Phe Gly Gly Arg His Cys Glu Leu Glu Arg Asp Glu Cys
        450                 455                 460
Ala Ser Ser Pro Cys His Ser Gly Gly Leu Cys Glu Asp Leu Ala Asp
465                 470                 475                 480
Gly Phe His Cys His Cys Pro Gln Gly Phe Ser Gly Pro Leu Cys Glu
                485                 490                 495
Val Asp Val Asp Leu Cys Glu Pro Ser Pro Cys Arg Asn Gly Ala Arg
                500                 505                 510
Cys Tyr Asn Leu Glu Gly Asp Tyr Tyr Cys Ala Cys Pro Asp Asp Phe
            515                 520                 525
Gly Gly Lys Asn Cys Ser Val Pro Arg Glu Pro Cys Pro Gly Gly Ala
        530                 535                 540
Cys Arg Val Ile Asp Gly Cys Gly Ser Asp Ala Gly Pro Gly Met Pro
545                 550                 555                 560
Gly Thr Ala Ala Ser Gly Val Cys Gly Pro His Gly Arg Cys Val Ser
                565                 570                 575
Gln Pro Gly Gly Asn Phe Ser Cys Ile Cys Asp Ser Gly Phe Thr Gly
                580                 585                 590
Thr Tyr Cys His Glu Asn Ile Asp Asp Cys Leu Gly Gln Pro Cys Arg
            595                 600                 605
Asn Gly Gly Thr Cys Ile Asp Glu Val Asp Ala Phe Arg Cys Phe Cys
        610                 615                 620
Pro Ser Gly Trp Glu Gly Glu Leu Cys Asp Thr Asn Pro Asn Asp Cys
625                 630                 635                 640
Leu Pro Asp Pro Cys His Ser Arg Gly Arg Cys Tyr Asp Leu Val Asn
                645                 650                 655
Asp Phe Tyr Cys Ala Cys Asp Asp Gly Trp Lys Gly Lys Thr Cys His
                660                 665                 670
Ser Arg Glu Phe Gln Cys Asp Ala Tyr Thr Cys Ser Asn Gly Gly Thr
            675                 680                 685
Cys Tyr Asp Ser Gly Asp Thr Phe Arg Cys Ala Cys Pro Pro Gly Trp
        690                 695                 700
Lys Gly Ser Thr Cys Ala Val Ala Lys Asn Ser Ser Cys Leu Pro Asn
705                 710                 715                 720
Pro Cys Val Asn Gly Gly Thr Cys Val Gly Ser Gly Ala Ser Phe Ser
                725                 730                 735
Cys Ile Cys Arg Asp Gly Trp Glu Gly Arg Thr Cys Thr His Asn Thr
                740                 745                 750
Asn Asp Cys Asn Pro Leu Pro Cys Tyr Asn Gly Gly Ile Cys Val Asp
            755                 760                 765
Gly Val Asn Trp Phe Arg Cys Glu Cys Ala Pro Gly Phe Ala Gly Pro
        770                 775                 780
```

-continued

```
Asp Cys Arg Ile Asn Ile Asp Glu Cys Gln Ser Ser Pro Cys Ala Tyr
785                 790                 795                 800

Gly Ala Thr Cys Val Asp Glu Ile Asn Gly Tyr Arg Cys Ser Cys Pro
            805                 810                 815

Pro Gly Arg Ala Gly Pro Arg Cys Gln Glu Val Ile Gly Phe Gly Arg
        820                 825                 830

Ser Cys Trp Ser Arg Gly Thr Pro Phe Pro His Gly Ser Ser Trp Val
    835                 840                 845

Glu Asp Cys Asn Ser Cys Arg Cys Leu Asp Gly Arg Arg Asp Cys Ser
850                 855                 860

Lys Val Trp Cys Gly Trp Lys Pro Cys Leu Leu Ala Gly Gln Pro Glu
865                 870                 875                 880

Ala Leu Ser Ala Gln Cys Pro Leu Gly Gln Arg Cys Leu Glu Lys Ala
                885                 890                 895

Pro Gly Gln Cys Leu Arg Pro Cys Glu Ala Trp Gly Glu Cys Gly
            900                 905                 910

Ala Glu Glu Pro Pro Ser Thr Pro Cys Leu Pro Arg Ser Gly His Leu
        915                 920                 925

Asp Asn Asn Cys Ala Arg Leu Thr Leu His Phe Asn Arg Asp His Val
930                 935                 940

Pro Gln Gly Thr Thr Val Gly Ala Ile Cys Ser Gly Ile Arg Ser Leu
945                 950                 955                 960

Pro Ala Thr Arg Ala Val Ala Arg Asp Arg Leu Val Leu Leu Cys
            965                 970                 975

Asp Arg Ala Ser Ser Gly Ala Ser Ala Val Glu Val Ala Val Ser Phe
        980                 985                 990

Ser Pro Ala Arg Asp Leu Pro Asp Ser Ser Leu Ile Gln Gly Ala Ala
    995                 1000                1005

His Ala Ile Val Ala Ala Ile Thr Gln Arg Gly Asn Ser Ser Leu
    1010                1015                1020

Leu Leu Ala Val Thr Glu Val Lys Val Glu Thr Val Val Thr Gly
    1025                1030                1035

Gly Ser Ser Thr Gly Leu Leu Val Pro Val Leu Cys Gly Ala Phe
    1040                1045                1050

Ser Val Leu Trp Leu Ala Cys Val Val Leu Cys Val Trp Trp Thr
    1055                1060                1065

Arg Lys Arg Arg Lys Arg Glu Arg Ser Arg Leu Pro Arg Glu
    1070                1075                1080

Glu Ser Ala Asn Asn Gln Trp Ala Pro Leu Asn Pro Ile Arg Asn
    1085                1090                1095

Pro Ile Glu Arg Pro Gly Gly His Lys Asp Val Leu Tyr Gln Cys
    1100                1105                1110

Lys Asn Phe Thr Pro Pro Arg Arg Ala Asp Glu Ala Leu Pro
    1115                1120                1125

Gly Pro Ala Gly His Ala Ala Val Arg Glu Asp Glu Glu Asp Glu
    1130                1135                1140

Asp Leu Gly Arg Gly Glu Glu Asp Ser Leu Glu Ala Glu Lys Phe
    1145                1150                1155

Leu Ser His Lys Phe Thr Lys Asp Pro Gly Arg Ser Pro Gly Arg
    1160                1165                1170

Pro Ala His Trp Ala Ser Gly Pro Lys Val Asp Asn Arg Ala Val
    1175                1180                1185

Arg Ser Ile Asn Glu Ala Arg Tyr Ala Gly Lys Glu
    1190                1195                1200
```

<210> SEQ ID NO 28
<211> LENGTH: 3158
<212> TYPE: DNA
<213> ORGANISM: Homo sapiens
<220> FEATURE:
<221> NAME/KEY: misc_feature
<223> OTHER INFORMATION: Delta like 1 (Notch ligand)

<400> SEQUENCE: 28

```
aaaccggaac ggggcccaac ttctggggcc tggagaaggg aaacgaagtc ccccccggtt      60
tcccgaggtt gcctttcctc gggcatcctt ggtttcggcg ggacttcgca gggcggatat     120
aaagaacggc gcctttggga agaggcggag accggcttta agaaagaag tcttggtcct     180
gcggcttggg cgaggcaagg gcgaggcaag ggcgctttct gccgacgctc cccgtggccc     240
tacgatcccc cgcgcgtccg ccgctgttct aaggagagaa gtgggggccc cccaggctcg     300
cgcgtggagc gaagcagcat gggcagtcgg tgcgcgctgg ccctggcggt gctctcggcc     360
ttgctgtgtc aggtctggag ctctggggtg ttcgaactga agctgcagga gttcgtcaac     420
aagaaggggc tgctggggaa ccgcaactgc tgccgcgggg gcgcggggcc accgcgtgc     480
gcctgccgga ccttcttccg cgtgtgcctc aagcactacc aggccagcgt gtccccgag     540
ccgcccctgca cctacggcag cgccgtcacc cccgtgctgg gcgtcgactc cttcagtctg     600
cccgacggcg ggggcgccga ctccgcgttc agcaacccca tccgcttccc cttcggcttc     660
acctggccgg gcaccttctc tctgattatt gaagctctcc acacagattc tcctgatgac     720
ctcgcaacag aaaacccaga aagactcatc agccgcctgg ccacccagag gcacctgacg     780
gtgggcgagg agtggtccca ggacctgcac agcagcggcc gcacggacct caagtactcc     840
taccgcttcg tgtgtgacga acactactac ggagagggct gctccgtttt ctgccgtccc     900
cgggacgatg ccttcggcca cttcacctgt gggggagcgtg gggagaaagt gtgcaaccct     960
ggctggaaag ggcctactgc acagagccg atctgcctgc ctggatgtga tgagcagcat    1020
ggatttttgtg acaaaccagg gaatgcaag tgcagagtgg gctggcaggg ccggtactgt    1080
gacgagtgta tccgctatcc aggctgtctc catggcacct gccagcagcc tggcagtgc    1140
aactgccagg aaggctgggg gggctttttc tgcaaccagg acctgaacta ctgcacacac    1200
cataagccct gcaagaatgg agccaccctgc accaacacgg gccaggggag ctacacttgc    1260
tcttgccggc tgggtacac aggtgccacc tgcgagctgg ggattgacga gtgtgaccc    1320
agcccttgta agaacggagg gagctgcacg gatctcgaga cagctactc ctgtacctgc    1380
ccacccggct tctacggcaa atctgtgaa ttgagtgcca tgacctgtgc ggacggccct    1440
tgctttaacg gggtcggtg ctcagacagc cccgatggag ggtacagctg ccgctgcccc    1500
gtgggctact ccggcttcaa ctgtgagaag aaaattgact actgcagctc ttcaccctgt    1560
tctaatggtg ccaagtgtgt ggacctcggt gatgcctacc tgtgccgctg ccaggccggc    1620
ttctcgggga ggcactgtga cgacaacgtg gacgactgcg cctcctcccc gtgcgccaac    1680
gggggcacct gccgggatgg cgtgaacgac ttctcctgca cctgcccgcc tggctacacg    1740
ggcaggaact gcagtgcccc cgtcagcagg tgcgagcacg cccctgcca caatggggcc    1800
acctgccacc agagggggcca cggctatgtg tgcgaatgtg cccgaagcta cggggtccc    1860
aactgccagt tcctgctccc cgagctgccc ccgggcccag cggtggtgga cctcactgag    1920
aagctagagg gccagggcgg gccattcccc tgggtggccg tgtgcgccgg ggtcatcctt    1980
gtcctcatgc tgctgctggg ctgtgccgct gtggtggtct cgtccggct gaggctgcag    2040
```

-continued

```
aagcaccggc ccccagccga cccctgccgg ggggagacgg agaccatgaa caacctggcc    2100
aactgccagt gtgagaagga catctcagtc agcatcatcg ggccacgca gatcaagaac     2160 accaacaaga aggcggactt ccacggggac acagcgccg acaagaatgg cttcaaggcc     2220
cgctacccag cggtggacta taacctcgtg caggacctca agggtgacga caccgccgtc    2280
agggacgcgc acagcaagcg tgacaccaag tgccagcccc agggctcctc aggggaggag    2340
aaggggaccc cgaccacact cagggggtgga gaagcatctg aaagaaaaag gccggactcg    2400
ggctgttcaa cttcaaaaga caccaagtac cagtcggtgt acgtcatatc cgaggagaag    2460
gatgagtgcg tcatagcaac tgaggtgtaa aatggaagtg agatggcaag actcccgttt    2520
ctcttaaaat aagtaaaatt ccaaggatat atgccccaac gaatgctgct gaagaggagg    2580
gaggcctcgt ggactgctgc tgagaaaccg agttcagacc gagcaggttc tcctcctgag    2640
gtcctcgacg cctgccgaca gcctgtcgcg gcccggccgc ctgcggcact gccttccgtg    2700
acgtcgccgt tgcactatgg acagttgctc ttaagagaat atatatttaa atgggtgaac    2760
tgaattacgc ctaagaagca tgcactgcct gagtgtatat tttggattct tatgagccag    2820
tcttttcttg aattagaaac acaaacactg cctttattgt ccttttttgat acgaagatgt    2880 gcttttttcta gatggaaaag atgtgtgtta tttttttggat ttgtaaaaat attttttcatg    2940 atatctgtaa agcttgagta ttttgtgatg ttcgttttttt ataatttaaa ttttggtaaa    3000
tatgtacaaa ggcacttcgg gtctatgtga ctatatttttt ttgtatataa atgtatttat    3060
ggaatattgt gccaatgtta tttgagtttt ttactgtttt gttaatgaag aaattccttt    3120
ttaaaatatt tttccaaaat aaattttatg aggaattc                          3158
```

<210> SEQ ID NO 29
<211> LENGTH: 723
<212> TYPE: PRT
<213> ORGANISM: Homo sapiens
<220> FEATURE:
<221> NAME/KEY: misc_feature
<223> OTHER INFORMATION: Delta like 1 (Notch ligand)

<400> SEQUENCE: 29

```
Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
```

-continued

```
                165                 170                 175
Phe Val Cys Asp Glu His Tyr Tyr Gly Glu Gly Cys Ser Val Phe Cys
            180                 185                 190
Arg Pro Arg Asp Asp Ala Phe Gly His Phe Thr Cys Gly Glu Arg Gly
            195                 200                 205
Glu Lys Val Cys Asn Pro Gly Trp Lys Gly Pro Tyr Cys Thr Glu Pro
            210                 215                 220
Ile Cys Leu Pro Gly Cys Asp Glu Gln His Gly Phe Cys Asp Lys Pro
225                 230                 235                 240
Gly Glu Cys Lys Cys Arg Val Gly Trp Gln Gly Arg Tyr Cys Asp Glu
            245                 250                 255
Cys Ile Arg Tyr Pro Gly Cys Leu His Gly Thr Cys Gln Gln Pro Trp
            260                 265                 270
Gln Cys Asn Cys Gln Glu Gly Trp Gly Gly Leu Phe Cys Asn Gln Asp
            275                 280                 285
Leu Asn Tyr Cys Thr His His Lys Pro Cys Lys Asn Gly Ala Thr Cys
            290                 295                 300
Thr Asn Thr Gly Gln Gly Ser Tyr Thr Cys Ser Cys Arg Pro Gly Tyr
305                 310                 315                 320
Thr Gly Ala Thr Cys Glu Leu Gly Ile Asp Glu Cys Asp Pro Ser Pro
            325                 330                 335
Cys Lys Asn Gly Gly Ser Cys Thr Asp Leu Glu Asn Ser Tyr Ser Cys
            340                 345                 350
Thr Cys Pro Pro Gly Phe Tyr Gly Lys Ile Cys Glu Leu Ser Ala Met
            355                 360                 365
Thr Cys Ala Asp Gly Pro Cys Phe Asn Gly Gly Arg Cys Ser Asp Ser
            370                 375                 380
Pro Asp Gly Gly Tyr Ser Cys Arg Cys Pro Val Gly Tyr Ser Gly Phe
385                 390                 395                 400
Asn Cys Glu Lys Lys Ile Asp Tyr Cys Ser Ser Pro Cys Ser Asn
            405                 410                 415
Gly Ala Lys Cys Val Asp Leu Gly Asp Ala Tyr Leu Cys Arg Cys Gln
            420                 425                 430
Ala Gly Phe Ser Gly Arg His Cys Asp Asp Asn Val Asp Asp Cys Ala
            435                 440                 445
Ser Ser Pro Cys Ala Asn Gly Gly Thr Cys Arg Asp Gly Val Asn Asp
450                 455                 460
Phe Ser Cys Thr Cys Pro Pro Gly Tyr Thr Gly Arg Asn Cys Ser Ala
465                 470                 475                 480
Pro Val Ser Arg Cys Glu His Ala Pro Cys His Asn Gly Ala Thr Cys
            485                 490                 495
His Gln Arg Gly His Gly Tyr Val Cys Glu Cys Ala Arg Ser Tyr Gly
            500                 505                 510
Gly Pro Asn Cys Gln Phe Leu Leu Pro Glu Leu Pro Pro Gly Pro Ala
            515                 520                 525
Val Val Asp Leu Thr Glu Lys Leu Glu Gly Gln Gly Gly Pro Phe Pro
            530                 535                 540
Trp Val Ala Val Cys Ala Gly Val Ile Leu Val Leu Met Leu Leu Leu
545                 550                 555                 560
Gly Cys Ala Ala Val Val Val Cys Val Arg Leu Arg Leu Gln Lys His
            565                 570                 575
Arg Pro Pro Ala Asp Pro Cys Arg Gly Glu Thr Glu Thr Met Asn Asn
            580                 585                 590
```

```
Leu Ala Asn Cys Gln Arg Glu Lys Asp Ile Ser Val Ser Ile Ile Gly
        595                 600                 605
Ala Thr Gln Ile Lys Asn Thr Asn Lys Lys Ala Asp Phe His Gly Asp
    610                 615                 620
His Ser Ala Asp Lys Asn Gly Phe Lys Ala Arg Tyr Pro Ala Val Asp
625                 630                 635                 640
Tyr Asn Leu Val Gln Asp Leu Lys Gly Asp Asp Thr Ala Val Arg Asp
                645                 650                 655
Ala His Ser Lys Arg Asp Thr Lys Cys Gln Pro Gln Gly Ser Ser Gly
            660                 665                 670
Glu Glu Lys Gly Thr Pro Thr Thr Leu Arg Gly Gly Glu Ala Ser Glu
        675                 680                 685
Arg Lys Arg Pro Asp Ser Gly Cys Ser Thr Ser Lys Asp Thr Lys Tyr
    690                 695                 700
Gln Ser Val Tyr Val Ile Ser Glu Glu Lys Asp Glu Cys Val Ile Ala
705                 710                 715                 720
Thr Glu Val

<210> SEQ ID NO 30
<211> LENGTH: 1971
<212> TYPE: DNA
<213> ORGANISM: Homo sapiens
<220> FEATURE:
<221> NAME/KEY: misc_feature
<223> OTHER INFORMATION: Delta like 3 (Notch ligand)

<400> SEQUENCE: 30
gaaggccatg gtctccccac ggatgtccgg gctcctctcc cagactgtga tcctagcgct      60
cattttcctc cccagacac ggcccgctgg cgtcttcgag ctgcagatcc actctttcgg     120
gccgggtcca ggccctgggg ccccgcggtc ccctgcagc gcccggctcc cctgccgcct     180
cttcttcaga gtctgcctga agcctgggct ctcagaggag gccgccgagt ccccgtgcgc     240
cctgggcgcg gcgctgagtg cgcgcggacc ggtctacacc gagcagcccg gagcgcccgc     300
gcctgatctc ccactgcccg acgggctctt gcaggtgccc ttccgggacg cctggcctgg     360
cacctctct ttcatcatcg aaacctggag agaggagtta ggagaccaga ttggagggcc     420
cgcctggagc ctgctggcgc gcgtggctgg caggcggcgc ttggcagccg gaggcccgtg     480
ggcccgggac attcagcgcg caggcgcctg ggagctgcgc ttctcgtacc gcgcgcgctg     540
cgagccgcct gccgtcggga ccgcgtgcac gcgcctctgc cgtccgcgca gcgcccctc     600
gcggtgcggt ccgggactgc gcccctgcgc accgctcgag gacgaatgtg aggcgccgct     660
ggtgtgccga gcaggctgca gccctgagca tggcttctgt aacagcccg gtgaatgccg     720
atgcctagag ggctggactg gacccctctg cacggtccct gtctccacca gcagctgcct     780
cagccccagg ggcccgtcct ctgctaccac cggatgcctt gtccctgggc ctgggccctg     840
tgacgggaac ccgtgtgcca atggaggcag ctgtagtgag acacccaggt cctttgaatg     900
cacctgcccg cgtgggttct acgggctgcg gtgtgaggtg agcggggtga catgtgcaga     960
tggaccctgc ttcaacggcg gcttgtgtgt cggggtgca gacctgact ctgcctacat    1020
ctgccactgc ccacctggtt tccaaggctc aactgtgag aagagggtgg accggtgcag    1080
cctgcagcca tgccgcaatg gcggactctg cctggacctg ggcacgccc tgcgctgccg    1140
ctgccgcgcc ggcttcgcgg gtcctcgctg cgagcacgac ctggacgact gcgcgggccg    1200
cgcctgcgct aacggcggca cgtgtgtgga gggcggcggc gcgcaccgct gctcctgcgc    1260
gctgggcttc ggcggccgcg actgccgcga gcgcgccgac ccgtgcgccg cgcgcccctg    1320
```

-continued

```
tgctcacggc ggccgctgct acgcccactt ctccggcctc gtctgcgctt cgcgctcccg    1380
g
ctacatggga gcgcggtgtg agttcccagt gcaccccgac ggcgcaagcg ccttgcccgc    1440
ggccccgccg ggcctcaggc ccggggaccc tcagcgctac cttttgcctc cggctctggg    1500
actgctcgtg gccgcgggcg tggccggcgc tgcgctcttg ctggtccacg tgcgccgccg    1560
tggccactcc caggatgctg ggtctcgctt gctggctggg accccggagc cgtcagtcca    1620
cgcactcccg gatgcactca acaacctaag gacgcaggag ggttccgggg atggtccgag    1680
ctcgtccgta gattggaatc gccctgaaga tgtagaccct caagggattt atgtcatatc    1740
tgctccttcc atctacgctc gggaggtagc gacgccccct tccccccgc tacacactgg     1800
gcgcgctggg cagaggcagc acctgctttt tccctaccct tcctcgattc tgtccgtgaa    1860
atgaattggg tagagtctct ggaaggtttt aagcccattt tcagttctaa cttactttca    1920
tcctattttg catccctctt atcgttttga gctacctgcc atcttctctt t             1971
```

<210> SEQ ID NO 31
<211> LENGTH: 618
<212> TYPE: PRT
<213> ORGANISM: Homo sapiens
<220> FEATURE:
<221> NAME/KEY: misc_feature
<223> OTHER INFORMATION: Delta like 3  (Notch ligand)

<400> SEQUENCE: 31

```
Met Val Ser Pro Arg Met Ser Gly Leu Leu Ser Gln Thr Val Ile Leu
1               5                  10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Ala Pro Arg Ser
        35                  40                  45

Pro Cys Ser Ala Arg Leu Pro Cys Arg Leu Phe Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
```

```
                245                 250                 255
Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Ala Asp Pro Asp Ser Ala
            325                 330                 335

Tyr Ile Cys His Cys Pro Gly Phe Gln Gly Ser Asn Cys Glu Lys
            340                 345                 350

Arg Val Asp Arg Cys Ser Leu Gln Pro Cys Arg Asn Gly Gly Leu Cys
                355                 360                 365

Leu Asp Leu Gly His Ala Leu Arg Cys Arg Cys Arg Ala Gly Phe Ala
    370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Ala His Arg Cys Ser
                405                 410                 415

Cys Ala Leu Gly Phe Gly Gly Arg Asp Cys Arg Glu Arg Ala Asp Pro
            420                 425                 430

Cys Ala Ala Arg Pro Cys Ala His Gly Gly Arg Cys Tyr Ala His Phe
                435                 440                 445

Ser Gly Leu Val Cys Ala Cys Ala Pro Gly Tyr Met Gly Ala Arg Cys
    450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Leu Pro Pro Ala
                485                 490                 495

Leu Gly Leu Leu Val Ala Ala Gly Val Ala Gly Ala Ala Leu Leu Leu
            500                 505                 510

Val His Val Arg Arg Arg Gly His Ser Gln Asp Ala Gly Ser Arg Leu
    515                 520                 525

Leu Ala Gly Thr Pro Glu Pro Ser Val His Ala Leu Pro Asp Ala Leu
    530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Val Ala Thr Pro Leu Phe
            580                 585                 590

Pro Pro Leu His Thr Gly Arg Ala Gly Gln Arg Gln His Leu Leu Phe
                595                 600                 605

Pro Tyr Pro Ser Ser Ile Leu Ser Val Lys
    610                 615

<210> SEQ ID NO 32
<211> LENGTH: 3383
<212> TYPE: DNA
<213> ORGANISM: Homo sapiens
<220> FEATURE:
<221> NAME/KEY: misc_feature
<223> OTHER INFORMATION: Delta like 4 (Notch ligand)
```

```
<400> SEQUENCE: 32
gctgcgcgca ggccgggaac acgaggccaa gagccgcagc cccagccgcc ttggtgcagc    60
gtacaccggc actagcccgc ttgcagcccc aggattagac agaagacgcg tcctcggcgc   120
ggtcgccgcc cagccgtagt cacctggatt acctacagcg gcagctgcag cggagccagc   180
gagaaggcca aggggagca gcgtcccgag aggagcgcct cttttcaggg accccgccgg    240
ctggcggacg cgcgggaaag cggcgtcgcg aacagagcca gattgagggc ccgcgggtgg   300
agagagcgac gcccgagggg atggcggcag cgtcccggag cgcctctggc tgggcgctac   360
tgctgctggt ggcactttgg cagcagcgcg cggccggctc cggcgtcttc cagctgcagc   420
tgcaggagtt catcaacgag cgcggcgtac tggccagtgg gcggccttgc gagcccggct   480
gccggacttt cttccgcgtc tgccttaagc acttccaggc ggtcgtctcg cccggaccct   540
gcaccttcgg gaccgtctcc acgccggtat tgggcaccaa ctccttcgct gtccgggacg   600
acagtagcgg cggggggcgc aaccctctcc aactgcccct tcaatttcacc tggccgggta   660 ccttctcgct catcatcgaa gcttggcacg cgccaggaga cgacctgcgg ccagaggcct   720
tgccaccaga tgcactcatc agcaagatcg ccatccaggg ctccctagct gtgggtcaga   780
actggttatt ggatgagcaa accagcaccc tcacaaggct gcgctactct taccgggtca   840
tctgcagtga caactactat ggagacaact gctcccgcct gtgcaagaag cgcaatgacc   900
acttcggcca ctatgtgtgc cagccagatg gcaacttgtc ctgcctgccc ggttggactg   960
gggaatattg ccaacagcct atctgtcttt cgggctgtca tgaacagaat ggctactgca  1020
gcaagccagc agagtgcctc tgccgcccag gctggcaggg ccggctgtgt aacgaatgca  1080 tccccccacaa tggctgtcgc cacggcacct gcagcactcc ctggcaatgt acttgtgatg  1140
agggctgggg aggcctgttt tgtgaccaag atctcaacta ctgcacccac cactcccat   1200 gcaagaatgg ggcaacgtgc tccaacagtg ggcagcgaag ctacacctgc acctgtcgcc  1260
caggctacac tggtgtggac tgtgagctgg agctcagcga gtgtgacagc aaccctgtc   1320 gcaatggagg cagctgtaag gaccaggagg atggctacca ctgcctgtgt cctccgggct  1380
actatggcct gcattgtgaa cacagcacct tgagctgcgc cgactccccc tgcttcaatg  1440
ggggctcctg ccgggagcgc aaccaggggg ccaactatgc ttgtgaatgt ccccccaact  1500
tcaccggctc caactgcgag aagaaagtgg acaggtgcac cagcaaccccc tgtgccaacg  1560 ggggacagtg cctgaaccga ggtccaagcc gcatgtgccg ctgccgtcct ggattcacgg  1620
gcacctactg tgaactccac gtcagcgact gtgcccgtaa cccttgcgcc cacggtggca  1680
cttgccatga cctggagaat gggctcatgt gcacctgccc tgccggcttc tctggccgac  1740
gctgtgaggt gcggacatcc atcgatgcct gtgcctcgag tccctgcttc aacagggcca  1800
cctgctacac cgacctctcc acagacacct ttgtgtgcaa ctgcccttat ggctttgtgg  1860
gcagccgctg cgagttcccc gtgggcttgc cgccccagctt ccctgggtg gccgtctcgc  1920 tgggtgtggg gctggcagtg ctgctggtac tgctgggcat ggtggcagtg gctgtgcggc  1980
agctgcggct tcgacggccg gacgacggca gcagggaagc catgaacaac ttgtcggact  2040
tccagaagga caacctgatt cctgccgccc agcttaaaaa cacaaaccag aagaaggagc  2100
tggaagtgga ctgtggcctg gacaagtcca actgtggcaa acagcaaaac cacacattgg  2160
actataatct ggccccaggg cccctggggc ggggaccat gccaggaaag tttcccccaca  2220 gtgcacaagag cttaggagag aaggcgccac tgcggttaca cagtgaaaag ccagagtgtc  2280
ggatatcagc gatatgctcc cccagggact ccatgtacca gtctgtgtgt ttgatatcag  2340
```

```
aggagaggaa tgaatgtgtc attgccacgg aggtataagg caggagccta cctggacatc    2400
cctgctcagc cccgcggctg gaccttcctt ctgcattgtt tacattgcat cctggatggg    2460 acgttttca tatgcaacgt gctgctctca ggaggaggag ggaatggcag gaaccggaca     2520
gactgtgaac ttgccaagag atgcaatacc cttccacacc tttgggtgtc tgtctggcat    2580
cagattggca gctgcaccaa ccagaggaac agaagagaag agagatgcca ctgggcactg    2640
ccctgccagt agtggccttc aggggctcc ttccgggct ccggcctgtt ttccagagag      2700
agtggcagta gccccatggg gcccggagct gctgtggcct ccactggcat ccgtgtttcc    2760
aaaagtgcct ttggcccagg ctccacggcg acagttgggc ccaaatcaga aggagagag    2820 ggggccaatg agggcagggc ctcctgtggg ctggaaaacc actgggtgcg tctcttgctg    2880
gggtttgccc tggaggtgag gtgagtgctc gagggagggg agtgctttct gccccatgcc    2940
tccaactact gtatgcaggc ctggctctct ggtctaggcc ctttgggcaa gaatgtccgt    3000 ctaccggct tccaccaccc tctggccctg ggcttctgta agcagacagg cagagggcct    3060 gccctccca ccagccaagg gtgccaggcc taactggggc actcagggca gtgtgttgga    3120
aattccactg aggggaaat caggtgctgc ggccgcctgg gccctttcct ccctcaagcc    3180
catctccaca acctcgagcc tgggctctgg tccactactg ccccagacca ccctcaaagc    3240
tggtcttcag aaatcaataa tatgagtttt tattttgttt tttttttttt ttttgtagtt    3300
tattttggag tctagtattt caataattta agaatcagaa gcactgacct ttctacattt    3360
tataacatta ttttgtatat aat                                            3383

<210> SEQ ID NO 33
<211> LENGTH: 685
<212> TYPE: PRT
<213> ORGANISM: Homo sapiens
<220> FEATURE:
<221> NAME/KEY: misc_feature
<223> OTHER INFORMATION: Delta like 4 (Notch ligand)

<400> SEQUENCE: 33

Met Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175
```

```
Asp Asn Tyr Tyr Gly Asp Asn Cys Ser Arg Leu Cys Lys Lys Arg Asn
                180                 185                 190

Asp His Phe Gly His Tyr Val Cys Gln Pro Asp Gly Asn Leu Ser Cys
            195                 200                 205

Leu Pro Gly Trp Thr Gly Glu Tyr Cys Gln Gln Pro Ile Cys Leu Ser
        210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605
```

```
Gln Asn His Thr Leu Asp Tyr Asn Leu Ala Pro Gly Pro Leu Gly Arg
    610                 615                 620
Gly Thr Met Pro Gly Lys Phe Pro His Ser Asp Lys Ser Leu Gly Glu
625                 630                 635                 640
Lys Ala Pro Leu Arg Leu His Ser Glu Lys Pro Glu Cys Arg Ile Ser
                645                 650                 655
Ala Ile Cys Ser Pro Arg Asp Ser Met Tyr Gln Ser Val Cys Leu Ile
            660                 665                 670
Ser Glu Glu Arg Asn Glu Cys Val Ile Ala Thr Glu Val
        675                 680                 685

<210> SEQ ID NO 34
<211> LENGTH: 5077
<212> TYPE: DNA
<213> ORGANISM: Homo sapiens
<220> FEATURE:
<221> NAME/KEY: misc_feature
<223> OTHER INFORMATION: Jagged2, transcript variant 1

<400> SEQUENCE: 34
```

| | | | | | |
|---|---|---|---|---|---|
| ctcatgcata | tgcaggtgcg | cgggtgacga | atgggcgagc | gagctgtcag | tctcgttccg | 60 |
| aacttgttgg | ctgcggtgcc | gggagcgcgg | gcgcgcagag | ccgaggccgg | gacccgctgc | 120 |
| cttcaccgcc | gccgccgtcg | ccgccgggtg | ggagccgggc | cgggcagccg | gagcgcggcc | 180 |
| gccagcgagc | cggagctgcc | gccgcccctg | cacgcccgcc | gcccaggccc | gcgcgccgcg | 240 |
| gcgctgcgct | cgaccccgcc | cgcgccgccg | ccgccgccgc | ctctgccgct | gccgctgcct | 300 |
| ctgcgggcgc | tcggagggcg | ggcgggcgct | gggaggccgg | cgcggcggct | gggagccggg | 360 |
| cgcgggcggc | ggcggcgggg | ccgggcggc | gggtcgcggg | ggcaatgcgg | gcgcagggcc | 420 |
| gggggcgcct | tccccggcgg | ctgctgctgc | tgctggcgct | ctgggtgcag | gcggcgcggc | 480 |
| ccatgggcta | tttcgagctg | cagctgagcg | cgctgcggaa | cgtgaacggg | gagctgctga | 540 |
| gcggcgcctg | ctgtgacggc | gacggccgga | caacgcgcgc | gggggctgc | ggccacgacg | 600 |
| agtgcgacac | gtacgtgcgc | gtgtgcctta | aggagtacca | ggccaaggtg | acgcccacgg | 660 |
| ggccctgcag | ctacggccac | ggcgccacgc | ccgtgctggg | cggcaactcc | ttctacctgc | 720 |
| cgccggcggg | cgctgcgggg | gaccgagcgc | gggcgcgggc | ccgggccggc | ggcgaccagg | 780 |
| acccgggcct | cgtcgtcatc | cccttccagt | tcgcctggcc | gcgctccttt | accctcatcg | 840 |
| tggaggcctg | ggactgggac | aacgatacca | ccccgaatga | ggagctgctg | atcgagcgag | 900 |
| tgtcgcatgc | cggcatgatc | aacccggagg | accgctggaa | gagcctgcac | ttcagcggcc | 960 |
| acgtggcgca | cctggagctg | cagatccgcg | tgcgctgcga | cgagaactac | tacagcgcca | 1020 |
| cttgcaacaa | gttctgccgg | ccccgcaacg | acttttttcgg | ccactacacc | tgcgaccagt | 1080 |
| acggcaacaa | ggcctgcatg | gacggctgga | tgggcaagga | gtgcaaggaa | gctgtgtgta | 1140 |
| aacaagggtg | taatttgctc | cacggggat | gcaccgtgcc | tggggagtgc | aggtgcagct | 1200 |
| acggctggca | agggaggttc | tgcgatgagt | gtgtccccta | ccccggctgc | gtgcatggca | 1260 |
| gttgtgtgga | gccctggcag | tgcaactgtg | agaccaactg | gggcggcctg | ctctgtgaca | 1320 |
| aagacctgaa | ctactgtggc | agccaccacc | cctgcaccaa | cggaggcacg | tgcatcaacg | 1380 |
| ccgagcctga | ccagtaccgc | tgcacctgcc | ctgacggcta | ctcgggcagg | aactgtgaga | 1440 |
| aggctgagca | cgcctgcacc | tccaacccgt | gtgccaacgg | ggctcttgc | catgaggtgc | 1500 |
| cgtccggctt | cgaatgccac | tgcccatcgg | gctgagcgg | gcccacctgt | gcccttgaca | 1560 |
| tcgatgagtg | tgcttcgaac | ccgtgtgcgg | ccggtggcac | ctgtgtggac | caggtggacg | 1620 |

```
gctttgagtg catctgcccc gagcagtggg tggggggccac ctgccagctg gacgccaatg    1680
agtgtgaagg gaagccatgc cttaacgctt tttcttgcaa aaacctgatt ggcggctatt    1740
actgtgattg catcccgggc tggaagggca tcaactgcca tatcaacgtc aacgactgtc    1800
gcgggcagtg tcagcatggg ggcacctgca aggacctggt gaacgggtac cagtgtgtgt    1860
gcccacgggg cttcggaggc cggcattgcg agctggaacg agacgagtgt gccagcagcc    1920
cctgccacag cggcggcctc tgcgaggacc tggccgacgg cttccactgc cactgccccc    1980
agggcttctc cgggcctctc tgtgaggtgg atgtcgacct tgtgagcca agccctgcc     2040 ggaacggcgc tcgctgctat aacctggagg gtgactatta ctgcgcctgc cctgatgact    2100
ttggtggcaa gaactgctcc gtgccccgcg agcgtgccc tggcggggcc tgcagagtga    2160
tcgatggctg cgggtcagac gcggggcctg ggatgcctgg cacagcagcc tccggcgtgt    2220
gtggccccca tggacgctgc gtcagccagc caggggcaa cttttcctgc atctgtgaca    2280
gtggctttac tggcacctac tgccatgaga acattgacga ctgcctgggc cagccctgcc    2340
gcaatggggg cacatgcatc gatgaggtgg acgccttccg ctgcttctgc cccagcggct    2400
gggagggcga gctctgcgac accaatccca acgactgcc tcccgatccc tgccacagcc    2460
gcggccgctg ctacgacctg gtcaatgact ctactgtgc gtgcgacgac ggctggaagg    2520
gcaagacctg ccactcacgc gagttccagt gcgatgccta cacctgcagc aacgtgca    2580 cctgctacga cagcggcgac accttccgct gcgcctgccc cccggctgg aagggcagca    2640 cctgcgccgt cgccaagaac agcagctgcc tgcccaaccc ctgtgtgaat ggtggcacct    2700
gcgtgggcag cggggcctcc ttctcctgca tctgccggga cggctgggag ggtcgtactt    2760
gcactcacaa taccaacgac tgcaaccctc tgccttgcta caatggtggc atctgtgttg    2820
acggcgtcaa ctggttccgc tgcgagtgtg cacctggctt cgcggggcct gactgccgca    2880
tcaacatcga cgagtgccag tcctcgcccct gtgcctacgg ggccacgtgt gtggatgaga    2940
tcaacgggta tcgctgtagc tgcccaccccg gccgagccgg ccccggtgc caggaagtga    3000 tcgggttcgg gagatcctgc tggtcccggg gcactccgtt cccacacgga agctcctggg    3060
tggaagactg caacagctgc cgctgcctgg atggccgccg tgactgcagc aaggtgtggt    3120
gcggatggaa gccttgtctg ctggccggcc agcccgaggc cctgagcgcc cagtgcccac    3180
tgggcaaaag gtgcctggag aaggccccag gccagtgtct gcgaccaccc tgtgaggcct    3240
ggggggagtg cggcgcagaa gagccaccga gcacccctg cctgccacgc tccgccacc    3300 tggacaataa ctgtgcccgc ctcaccttgc atttcaaccg tgaccacgtg ccccagggca    3360
ccacggtggg cgccatttgc tccgggatcc gctccctgcc agccacaagg gctgtggcac    3420
gggaccgcct gctggtgttg ctttgcgacc gggcgtcctc ggggggccagt gccgtggagg    3480 tggccgtgtc cttcagccct gccagggacc tgcctgacag cagcctgatc cagggcgcgg    3540
cccacgccat cgtggccgcc atcacccagc ggggaacag ctcactgctc ctggctgtca    3600
ccgaggtcaa ggtggagacg gttgttacgg gcggctcttc cacaggtctg ctggtgcctg    3660
tgctgtgtgg tgccttcagc gtgctgtggc tggcgtgcgt ggtcctgtgc gtgtggtgga    3720
cacgcaagcg caggaaagag cgggagagga gccggctgcc gcgggaggag agcgccaaca    3780
accagtgggc cccgctcaac cccatccgca acccatcga gcggccgggg ggccacaagg    3840
acgtgctcta ccagtgcaag aacttcacgc cgccgccgcg cagggcggac gaggcgctgc    3900
ccgggccggc cggccacgcg gccgtcaggg aggatgagga ggacgaggat ctgggccgcg    3960
gtgaggagga ctccctggag gcggagaagt tcctctcaca caaattcacc aaagatcctg    4020
```

```
gccgctcgcc ggggaggccg gcccactggg cctcaggccc caaagtggac aaccgcgcgg      4080
tcaggagcat caatgaggcc cgctacgccg gcaaggagta ggggcggctg ccagctgggc      4140
cgggacccag ggccctcggt gggagccatg ccgtctgccg gacccggagg ccgaggccat      4200
gtgcatagtt tctttatttt gtgtaaaaaa accaccaaaa acaaaaacca aatgtttatt      4260
ttctacgttt ctttaacctt gtataaatta ttcagtaact gtcaggctga aaacaatgga      4320
gtattctcgg atagttgcta ttttgtaaa gtttccgtgc gtggcactcg ctgtatgaaa       4380
ggagagagca aagggtgtct gcgtcgtcac caaatcgtag cgtttgttac cagaggttgt      4440
gcactgttta cagaatcttc cttttattcc tcactcgggt ttctctgtgg ctccaggcca      4500
aagtgccggt gagacccatg gctgtgttgg tgtggcccat ggctgttggt gggacccgtg      4560
gctgatggtg tggcctgtgg ctgtcggtgg gactcgtggc tgtcaatggg acctgtggct      4620
gtcggtggga cctacggtgg tcggtgggac cctggttatt gatgtggccc tggctgccgg      4680
cacggcccgt ggctgttgac gcacctgtgg ttgttagtgg ggcctgaggt catcggcgtg      4740
gcccaaggcc ggcaggtcaa cctcgcgctt gctggccagt ccaccctgcc tgccgtctgt      4800
gcttcctcct gcccagaacg cccgctccag cgatctctcc actgtgcttt cagaagtgcc      4860
cttcctgctg cgcagttctc ccatcctggg acggcggcag tattgaagct cgtgacaagt      4920
gccttcacac agacccctcg caactgtcca cgcgtgccgt ggcaccaggc gctgcccacc      4980
tgccggcccc ggccgcccct cctcgtgaaa gtgcatttt gtaaatgtgt acatattaaa       5040
ggaagcactc tgtatatttg attgaataat gccacca                              5077
```

<210> SEQ ID NO 35
<211> LENGTH: 1238
<212> TYPE: PRT
<213> ORGANISM: Homo sapiens
<220> FEATURE:
<221> NAME/KEY: misc_feature
<223> OTHER INFORMATION: Jagged2, transcript variant 1

<400> SEQUENCE: 35

| | | | | | | | | | | | | | | |
|---|---|---|---|---|---|---|---|---|---|---|---|---|---|---|
| Met | Arg | Ala | Gln | Gly | Arg | Gly | Arg | Leu | Pro | Arg | Leu | Leu | Leu | Leu |
| 1 | | | | 5 | | | | | 10 | | | | | 15 |
| Leu | Ala | Leu | Trp | Val | Gln | Ala | Ala | Arg | Pro | Met | Gly | Tyr | Phe | Glu | Leu |
| | | | 20 | | | | | 25 | | | | | 30 | |
| Gln | Leu | Ser | Ala | Leu | Arg | Asn | Val | Asn | Gly | Glu | Leu | Leu | Ser | Gly | Ala |
| | | | | 35 | | | | | 40 | | | | | 45 | |
| Cys | Cys | Asp | Gly | Asp | Gly | Arg | Thr | Thr | Arg | Ala | Gly | Gly | Cys | Gly | His |
| 50 | | | | | 55 | | | | | 60 | | | | | |
| Asp | Glu | Cys | Asp | Thr | Tyr | Val | Arg | Val | Cys | Leu | Lys | Glu | Tyr | Gln | Ala |
| 65 | | | | | 70 | | | | | 75 | | | | | 80 |
| Lys | Val | Thr | Pro | Thr | Gly | Pro | Cys | Ser | Tyr | Gly | His | Gly | Ala | Thr | Pro |
| | | | | 85 | | | | | 90 | | | | | 95 | |
| Val | Leu | Gly | Gly | Asn | Ser | Phe | Tyr | Leu | Pro | Pro | Ala | Gly | Ala | Ala | Gly |
| | | | | 100 | | | | | 105 | | | | | 110 | |
| Asp | Arg | Ala | Arg | Ala | Arg | Ala | Arg | Ala | Gly | Gly | Asp | Gln | Asp | Pro | Gly |
| | | | 115 | | | | | 120 | | | | | 125 | | |
| Leu | Val | Val | Ile | Pro | Phe | Gln | Phe | Ala | Trp | Pro | Arg | Ser | Phe | Thr | Leu |
| | 130 | | | | | 135 | | | | | 140 | | | | |
| Ile | Val | Glu | Ala | Trp | Asp | Trp | Asp | Asn | Asp | Thr | Thr | Pro | Asn | Glu | Glu |
| 145 | | | | | 150 | | | | | 155 | | | | | 160 |
| Leu | Leu | Ile | Glu | Arg | Val | Ser | His | Ala | Gly | Met | Ile | Asn | Pro | Glu | Asp |
| | | | | 165 | | | | | 170 | | | | | 175 | |

```
Arg Trp Lys Ser Leu His Phe Ser Gly His Val Ala His Leu Glu Leu
            180                 185                 190
Gln Ile Arg Val Arg Cys Asp Glu Asn Tyr Tyr Ser Ala Thr Cys Asn
            195                 200                 205
Lys Phe Cys Arg Pro Arg Asn Asp Phe Phe Gly His Tyr Thr Cys Asp
210                 215                 220
Gln Tyr Gly Asn Lys Ala Cys Met Asp Gly Trp Met Gly Lys Glu Cys
225                 230                 235                 240
Lys Glu Ala Val Cys Lys Gln Gly Cys Asn Leu Leu His Gly Gly Cys
                245                 250                 255
Thr Val Pro Gly Glu Cys Arg Cys Ser Tyr Gly Trp Gln Gly Arg Phe
            260                 265                 270
Cys Asp Glu Cys Val Pro Tyr Pro Gly Cys Val His Gly Ser Cys Val
            275                 280                 285
Glu Pro Trp Gln Cys Asn Cys Glu Thr Asn Trp Gly Gly Leu Leu Cys
            290                 295                 300
Asp Lys Asp Leu Asn Tyr Cys Gly Ser His His Pro Cys Thr Asn Gly
305                 310                 315                 320
Gly Thr Cys Ile Asn Ala Glu Pro Asp Gln Tyr Arg Cys Thr Cys Pro
                325                 330                 335
Asp Gly Tyr Ser Gly Arg Asn Cys Glu Lys Ala Glu His Ala Cys Thr
            340                 345                 350
Ser Asn Pro Cys Ala Asn Gly Gly Ser Cys His Glu Val Pro Ser Gly
            355                 360                 365
Phe Glu Cys His Cys Pro Ser Gly Trp Ser Gly Pro Thr Cys Ala Leu
            370                 375                 380
Asp Ile Asp Glu Cys Ala Ser Asn Pro Cys Ala Ala Gly Gly Thr Cys
385                 390                 395                 400
Val Asp Gln Val Asp Gly Phe Glu Cys Ile Cys Pro Glu Gln Trp Val
                405                 410                 415
Gly Ala Thr Cys Gln Leu Asp Ala Asn Glu Cys Glu Gly Lys Pro Cys
            420                 425                 430
Leu Asn Ala Phe Ser Cys Lys Asn Leu Ile Gly Gly Tyr Tyr Cys Asp
            435                 440                 445
Cys Ile Pro Gly Trp Lys Gly Ile Asn Cys His Ile Asn Val Asn Asp
450                 455                 460
Cys Arg Gly Gln Cys Gln His Gly Gly Thr Cys Lys Asp Leu Val Asn
465                 470                 475                 480
Gly Tyr Gln Cys Val Cys Pro Arg Gly Phe Gly Gly Arg His Cys Glu
                485                 490                 495
Leu Glu Arg Asp Glu Cys Ala Ser Ser Pro Cys His Ser Gly Gly Leu
            500                 505                 510
Cys Glu Asp Leu Ala Asp Gly Phe His Cys His Cys Pro Gln Gly Phe
            515                 520                 525
Ser Gly Pro Leu Cys Glu Val Asp Val Asp Leu Cys Glu Pro Ser Pro
            530                 535                 540
Cys Arg Asn Gly Ala Arg Cys Tyr Asn Leu Glu Gly Asp Tyr Tyr Cys
545                 550                 555                 560
Ala Cys Pro Asp Asp Phe Gly Lys Asn Cys Ser Val Pro Arg Glu
                565                 570                 575
Pro Cys Pro Gly Gly Ala Cys Arg Val Ile Asp Gly Cys Gly Ser Asp
            580                 585                 590
Ala Gly Pro Gly Met Pro Gly Thr Ala Ala Ser Gly Val Cys Gly Pro
```

```
                 595                 600                 605
His Gly Arg Cys Val Ser Gln Pro Gly Gly Asn Phe Ser Cys Ile Cys
610                     615                 620

Asp Ser Gly Phe Thr Gly Thr Tyr Cys His Glu Asn Ile Asp Asp Cys
625                     630                 635                 640

Leu Gly Gln Pro Cys Arg Asn Gly Gly Thr Cys Ile Asp Glu Val Asp
                    645                 650                 655

Ala Phe Arg Cys Phe Cys Pro Ser Gly Trp Glu Gly Glu Leu Cys Asp
                660                 665                 670

Thr Asn Pro Asn Asp Cys Leu Pro Asp Pro Cys His Ser Arg Gly Arg
            675                 680                 685

Cys Tyr Asp Leu Val Asn Asp Phe Tyr Cys Ala Cys Asp Asp Gly Trp
        690                 695                 700

Lys Gly Lys Thr Cys His Ser Arg Glu Phe Gln Cys Asp Ala Tyr Thr
705                     710                 715                 720

Cys Ser Asn Gly Gly Thr Cys Tyr Asp Ser Gly Asp Thr Phe Arg Cys
                    725                 730                 735

Ala Cys Pro Pro Gly Trp Lys Gly Ser Thr Cys Ala Val Ala Lys Asn
                740                 745                 750

Ser Ser Cys Leu Pro Asn Pro Cys Val Asn Gly Gly Thr Cys Val Gly
            755                 760                 765

Ser Gly Ala Ser Phe Ser Cys Ile Cys Arg Asp Gly Trp Glu Gly Arg
        770                 775                 780

Thr Cys Thr His Asn Thr Asn Asp Cys Asn Pro Leu Pro Cys Tyr Asn
785                     790                 795                 800

Gly Gly Ile Cys Val Asp Gly Val Asn Trp Phe Arg Cys Glu Cys Ala
                    805                 810                 815

Pro Gly Phe Ala Gly Pro Asp Cys Arg Ile Asn Ile Asp Glu Cys Gln
                820                 825                 830

Ser Ser Pro Cys Ala Tyr Gly Ala Thr Cys Val Asp Glu Ile Asn Gly
            835                 840                 845

Tyr Arg Cys Ser Cys Pro Pro Gly Arg Ala Gly Pro Arg Cys Gln Glu
        850                 855                 860

Val Ile Gly Phe Gly Arg Ser Cys Trp Ser Arg Gly Thr Pro Phe Pro
865                     870                 875                 880

His Gly Ser Ser Trp Val Glu Asp Cys Asn Ser Cys Arg Cys Leu Asp
                    885                 890                 895

Gly Arg Arg Asp Cys Ser Lys Val Trp Cys Gly Trp Lys Pro Cys Leu
                900                 905                 910

Leu Ala Gly Gln Pro Glu Ala Leu Ser Ala Gln Cys Pro Leu Gly Gln
            915                 920                 925

Arg Cys Leu Glu Lys Ala Pro Gly Gln Cys Leu Arg Pro Pro Cys Glu
        930                 935                 940

Ala Trp Gly Glu Cys Gly Ala Glu Glu Pro Ser Thr Pro Cys Leu
945                     950                 955                 960

Pro Arg Ser Gly His Leu Asp Asn Asn Cys Ala Arg Leu Thr Leu His
                    965                 970                 975

Phe Asn Arg Asp His Val Pro Gln Gly Thr Thr Val Gly Ala Ile Cys
                980                 985                 990

Ser Gly Ile Arg Ser Leu Pro  Ala  Thr Arg Ala Val Ala  Arg Asp Arg
            995                 1000                1005

Leu Leu Val Leu Leu Cys Asp  Arg Ala Ser Ser Gly  Ala Ser Ala
    1010                1015                1020
```

| | | | | | | | | | | | |
|---|---|---|---|---|---|---|---|---|---|---|---|
| Val | Glu | Val | Ala | Val | Ser | Phe | Ser | Pro | Ala | Arg | Asp | Leu | Pro | Asp |
| 1025 | | | | 1030 | | | | | 1035 | | | | | |

Val Glu Val Ala Val Ser Phe Ser Pro Ala Arg Asp Leu Pro Asp
1025                1030                1035

Ser Ser Leu Ile Gln Gly Ala Ala His Ala Ile Val Ala Ala Ile
1040                1045                1050

Thr Gln Arg Gly Asn Ser Ser Leu Leu Leu Ala Val Thr Glu Val
1055                1060                1065

Lys Val Glu Thr Val Val Thr Gly Gly Ser Ser Thr Gly Leu Leu
1070                1075                1080

Val Pro Val Leu Cys Gly Ala Phe Ser Val Leu Trp Leu Ala Cys
1085                1090                1095

Val Val Leu Cys Val Trp Trp Thr Arg Lys Arg Lys Glu Arg
1100                1105                1110

Glu Arg Ser Arg Leu Pro Arg Glu Glu Ser Ala Asn Asn Gln Trp
1115                1120                1125

Ala Pro Leu Asn Pro Ile Arg Asn Pro Ile Glu Arg Pro Gly Gly
1130                1135                1140

His Lys Asp Val Leu Tyr Gln Cys Lys Asn Phe Thr Pro Pro Pro
1145                1150                1155

Arg Arg Ala Asp Glu Ala Leu Pro Gly Pro Ala Gly His Ala Ala
1160                1165                1170

Val Arg Glu Asp Glu Glu Asp Glu Asp Leu Gly Arg Gly Glu Glu
1175                1180                1185

Asp Ser Leu Glu Ala Glu Lys Phe Leu Ser His Lys Phe Thr Lys
1190                1195                1200

Asp Pro Gly Arg Ser Pro Gly Arg Pro Ala His Trp Ala Ser Gly
1205                1210                1215

Pro Lys Val Asp Asn Arg Ala Val Arg Ser Ile Asn Glu Ala Arg
1220                1225                1230

Tyr Ala Gly Lys Glu
1235

```
<210> SEQ ID NO 36
<211> LENGTH: 2223
<212> TYPE: DNA
<213> ORGANISM: Homo sapiens
<220> FEATURE:
<221> NAME/KEY: misc_feature
<223> OTHER INFORMATION: Hey-1

<400> SEQUENCE: 36
tcagtgtgtg cggaacgcaa gcagccgaga gcggagaggc gccgctgtag ttaactcctc      60
cctgcccgcc gcgccgaccc tccccaggaa cccccaggga gccagcatga agcgagctca     120
ccccgagtac agctcctcgg acagcgagct ggacgagacc atcgaggtgg agaaggagag     180
tgcggacgag aatggaaact tgagttcggc tctaggttcc atgtccccaa ctacatcttc     240
ccagattttg gccagaaaaa gacggagagg aataattgag aagcgccgac gagaccggat     300
caataacagt ttgtctgagc tgagaaggct ggtacccagt gcttttgaga gcagggatc     360 tgctaagcta gaaaaagccg agatcctgca gatgaccgtg gatcacctga aaatgctgca     420
tacggcagga gggaaaggtt actttgacgc gcacgcccct gctatggact atcggagttt     480
gggatttcgg gaatgcctgg cagaagttgc gcgttatctg agcatcattg aaggactaga     540
tgcctctgac ccgcttcgag ttcgactggt ttcgcatctc aacaactacg cttcccagcg     600
ggaagccgcg agcggcgccc acgcgggcct cggacacatt ccctggggga ccgtcttcgg     660
acatcacccg cacatcgcgc accgctgtt gctgccccag aacggccacg ggaacgcggg     720
```

```
caccacggcc tcacccacgg aaccgcacca ccagggcagg ctgggctcgg cacatccgga      780
ggcgcctgct ttgcgagcgc ccctagcgg cagcttcgga ccgtgctcc ctgtggtcac        840
ctccgcctcc aaactgtcgc tgcctctgct ctcctcagtg gcctccctgt cggccttccc      900
cttctctttc ggctccttcc acttactgtc tcccaatgca ctgagccctt cagcacccac      960
gcaggctgca aaccttggca agccctatag accttggggg acggagatcg gagcttttta    1020
aagaactgat gtagaatgag ggaggggaaa gtttaaaatc ccagctgggc tggactgttg    1080
ccaacatcac cttaaagtcg tcagtaaaag taaaaaggaa aaaggtacac tttcagataa    1140
tttttttttt aaagactaaa ggtttgttgg tttactttta tcttttttaa tgttttttc     1200
atcatgtcat gtattagcag ttttaaaaa ctagttgtta aattttgttc aagacattaa      1260
attgaaatag tgagtataag ccaacacttt gtgataggtt tgtactgtgc ctaatttact    1320
ttgtaaacca gaatgattcc gttttttgcct caaaatttgg ggaatcttaa catttaggta   1380
tttttggtct gtttttctcc ttgtatagtt atggtctgtt tttagaatta attttccaaa   1440
ccactatgct taatgttaac atgattctgt ttgttaatat tttgacagat taaggtgttg   1500
tataaataat attcttttgg ggggagggga actatattga attttatatt tctgagcaaa   1560
gcgttgacaa atcagatgat cagctttatc caagaaagaa gactagtaaa ttgtctgcct    1620
cctatagcag aaaggtgaat gtacaaactg ttggtggcct gaatccatct gaccagctgc    1680
tggtatctgc caggactggc agttctgatt tagttaggag gaccgctgat aggttaggtc    1740
tcatttggag tgttggtgga aaggaaactg aaggtaattg aatagaatac gcctgcattt   1800
accagcccca gcaacacaaa gaattttttaa tcacacggat ctcaaattca caaatgttaa   1860
catggataag tgatcatggt gtgcgagtgg tcaattgagt agtacagtgg aaactgttaa   1920
atgcataacc taattttcct gggactgcca tattttcttt taactggaaa tttttatgtg   1980
agttttcctt ttggtgcatg gaactgtggt tgccaaggta tttaaaaggg ctttcctgcc    2040
tccttctctt tgatttattt aatttgattt gggctataaa atatcatttt tcaggtttat   2100
tcttttagca ggtgtagtta aacgacctcc actgaactgg gtttgacctc tgttgtactg   2160
atgtgttgtg actaaataaa aagaaagaa caaagtaaaa aaaaaaaaa aaaaaaaaa      2220
aaa                                                                  2223
```

<210> SEQ ID NO 37
<211> LENGTH: 304
<212> TYPE: PRT
<213> ORGANISM: Homo sapiens
<220> FEATURE:
<221> NAME/KEY: misc_feature
<223> OTHER INFORMATION: Hey-1

<400> SEQUENCE: 37

```
Met Lys Arg Ala His Pro Glu Tyr Ser Ser Asp Ser Glu Leu Asp
1               5                   10                  15

Glu Thr Ile Glu Val Glu Lys Glu Ser Ala Asp Glu Asn Gly Asn Leu
            20                  25                  30

Ser Ser Ala Leu Gly Ser Met Ser Pro Thr Thr Ser Ser Gln Ile Leu
        35                  40                  45

Ala Arg Lys Arg Arg Arg Gly Ile Ile Glu Lys Arg Arg Arg Asp Arg
    50                  55                  60

Ile Asn Asn Ser Leu Ser Glu Leu Arg Arg Leu Val Pro Ser Ala Phe
65                  70                  75                  80

Glu Lys Gln Gly Ser Ala Lys Leu Glu Lys Ala Glu Ile Leu Gln Met
            85                  90                  95
```

```
Thr Val Asp His Leu Lys Met Leu His Thr Ala Gly Gly Lys Gly Tyr
            100                 105                 110
Phe Asp Ala His Ala Leu Ala Met Asp Tyr Arg Ser Leu Gly Phe Arg
        115                 120                 125
Glu Cys Leu Ala Glu Val Ala Arg Tyr Leu Ser Ile Ile Glu Gly Leu
    130                 135                 140
Asp Ala Ser Asp Pro Leu Arg Val Arg Leu Val Ser His Leu Asn Asn
145                 150                 155                 160
Tyr Ala Ser Gln Arg Glu Ala Ala Ser Gly Ala His Ala Gly Leu Gly
                165                 170                 175
His Ile Pro Trp Gly Thr Val Phe Gly His His Pro His Ile Ala His
            180                 185                 190
Pro Leu Leu Leu Pro Gln Asn Gly His Gly Asn Ala Gly Thr Thr Ala
        195                 200                 205
Ser Pro Thr Glu Pro His His Gln Gly Arg Leu Gly Ser Ala His Pro
    210                 215                 220
Glu Ala Pro Ala Leu Arg Ala Pro Pro Ser Gly Ser Phe Gly Pro Val
225                 230                 235                 240
Leu Pro Val Val Thr Ser Ala Ser Lys Leu Ser Leu Pro Leu Leu Ser
                245                 250                 255
Ser Val Ala Ser Leu Ser Ala Phe Pro Phe Ser Phe Gly Ser Phe His
            260                 265                 270
Leu Leu Ser Pro Asn Ala Leu Ser Pro Ser Ala Pro Thr Gln Ala Ala
        275                 280                 285
Asn Leu Gly Lys Pro Tyr Arg Pro Trp Gly Thr Glu Ile Gly Ala Phe
    290                 295                 300

<210> SEQ ID NO 38
<211> LENGTH: 2533
<212> TYPE: DNA
<213> ORGANISM: Homo sapiens
<220> FEATURE:
<221> NAME/KEY: misc_feature
<223> OTHER INFORMATION: Hey-2

<400> SEQUENCE: 38
tcggcgtccg agcttccggc cgggctgtgc cccgcgcggt cttcgccggg atgaagcgcc      60
cctgcgagga gacgacctcc gagagcgaca tggacgagac catcgacgtg gggagcgaga     120
acaattactc ggggcaaagt actagctctg tgattagatt gaattctcca acaacaacat     180
ctcagattat ggcaagaaag aaaaggagag ggattataga gaaaaggcgt cgggatcgga     240
taaataacag tttatctgag ttgagaagac ttgtgccaac tgcttttgaa aaacaaggat     300
ctgcaaagtt agaaaaagct gaaatattgc aaatgacagt ggatcatttg aagatgcttc     360
aggcaacagg gggtaaaggc tactttgacg cacacgctct tgccatggac ttcatgagca     420
taggattccg agagtgccta acagaagttg cgcggtacct gagctccgtg gaaggcctgg     480
actcctcgga tccgctgcgg gtgcggcttg tgtctcatct cagcacttgc gccacccagc     540
gggaggcggc ggccatgaca tcctccatgg cccaccacca tcatccgctc cacccgcatc     600
actgggccgc cgccttccac cacctgcccg cagccctgct ccagcccaac ggcctccatg     660
cctcagagtc aacccttgt cgcctctcca caacttcaga agtgcctcct gcccacggct     720
ctgctctcct cacggccacg tttgccatg cggattcagc cctccgaatg ccatccacgg     780
gcagcgtcgc ccctgcgtg ccactctct ccacctctct cttgtccctc tctgccaccg     840
tccacgccgc agccgcagca gccaccgcgg ctgcacacag cttccctctg tccttcgcgg     900
```

```
gggcattccc catgcttccc ccaaacgcag cagcagcagt ggccgcggcc acagccatca    960
gcccgcccct tgtcagtatca gccacgtcca gtcctcagca gaccagcagt ggaacaaaca   1020
ataaacctta ccgaccctgg gggacagaag ttggagcttt ttaaattttt cttgaacttc   1080
ttgcaatagt aactgaatgt cctccatttc agagtcagct taaaacctct gcaccctgaa   1140
ggtagccata cagatgccga cagatccaca aaggaacaat aaagctattt gagacacaaa   1200
cctcacgagt ggaaatgtgg tattctcttt tttttctctc ccttttttgt ttggttcaag   1260
gcagctcggt aactgacatc agcaactttt gaaaacttca cacttgttac catttagaag   1320
tttcctggaa aatatatgga ccgtaccatc cagcagtgca tcagtatgtc tgaattgggg   1380
aagtaaaatg ccctgactga attctcttga gactagatgg gacatacata tagagaga    1440
gagtgagaga gtcgtgtttc gtaagtgcct gagcttagga agttttcttc tggatatata   1500
acattgcaca agggaagacg agtgtggagg ataggttaag aaaggaaagg gacagaagtc   1560
ttgcaatagg ctgcagacat tttaatacca tgccagagaa gagtattctg ctgaaaccaa   1620
caggttttac tggtcaaaat gactgctgaa ataatttttc aagttgaaag atctagtttt   1680
atcttagttt gccttctttg tacagacatg ccaagaggtg acatttagca gtgcattggt   1740
ataagcaatt atttcatcag ttctcagatt aacaagcatt tctgctctgc ctgcaggccc   1800
ccaggcactt tttttttttgg atggctcaaa atatggtgct gctttatata aaccttacat   1860
ttatatagtg cacctatgag cagttgccta ccatgtgtcc accagaggct atttaattca   1920
tgccaacttg aaaactctcc agtttgtagg agtttggttt aatttattca gtttcattag   1980
gactatttt atatatttat cctcttcatt ttctcctaat gatgcaacat ctattcttgt   2040
caccctttgg gagaagttac atttctggag gtgatgaagc aaggagggag cactaggaag   2100
agaaaagcta caatttttaa agctctttgt caagttagtg attgcatttg atcccaaaac   2160
aagatgaatg tatgcaatgg gatgtacata agttatttttt gcccatgcct aaactagtgc   2220
tatgtaatgg ggttgtggtt tgttttttttt cgatttcgtt taatgacaaa ataatctctt   2280
aatatgctga aatcaagcac gtgagagttt tgtttaaaa gataagagac acagcatgta   2340
ttatgcactt catttctcta ctgtgtggag aaagcaataa acattatgag aatgttaaac   2400
gttatgcaaa attatacttt taaatatttg ttttgaaatt actgtaccta gtctttttg    2460
cattactttg taacctttt ctatgcaaga gtctttacat accactaatt aaatgaagtc   2520
ctttttgact att                                                     2533
```

<210> SEQ ID NO 39
<211> LENGTH: 337
<212> TYPE: PRT
<213> ORGANISM: Homo sapiens
<220> FEATURE:
<221> NAME/KEY: misc_feature
<223> OTHER INFORMATION: Hey-2

<400> SEQUENCE: 39

```
Met Lys Arg Pro Cys Glu Glu Thr Thr Ser Glu Ser Asp Met Asp Glu
1               5                   10                  15

Thr Ile Asp Val Gly Ser Glu Asn Asn Tyr Ser Gly Gln Ser Thr Ser
            20                  25                  30

Ser Val Ile Arg Leu Asn Ser Pro Thr Thr Thr Ser Gln Ile Met Ala
        35                  40                  45

Arg Lys Lys Arg Arg Gly Ile Ile Glu Lys Arg Arg Arg Asp Arg Ile
    50                  55                  60
```

```
Asn Asn Ser Leu Ser Glu Leu Arg Arg Leu Val Pro Thr Ala Phe Glu
 65                  70                  75                  80

Lys Gln Gly Ser Ala Lys Leu Glu Lys Ala Glu Ile Leu Gln Met Thr
             85                  90                  95

Val Asp His Leu Lys Met Leu Gln Ala Thr Gly Gly Lys Gly Tyr Phe
        100                 105                 110

Asp Ala His Ala Leu Ala Met Asp Phe Met Ser Ile Gly Phe Arg Glu
        115                 120                 125

Cys Leu Thr Glu Val Ala Arg Tyr Leu Ser Ser Val Glu Gly Leu Asp
130                 135                 140

Ser Ser Asp Pro Leu Arg Val Arg Leu Val Ser His Leu Ser Thr Cys
145                 150                 155                 160

Ala Thr Gln Arg Glu Ala Ala Ala Met Thr Ser Ser Met Ala His His
                165                 170                 175

His His Pro Leu His Pro His His Trp Ala Ala Ala Phe His His Leu
            180                 185                 190

Pro Ala Ala Leu Leu Gln Pro Asn Gly Leu His Ala Ser Glu Ser Thr
            195                 200                 205

Pro Cys Arg Leu Ser Thr Thr Ser Glu Val Pro Ala His Gly Ser
210                 215                 220

Ala Leu Leu Thr Ala Thr Phe Ala His Ala Asp Ser Ala Leu Arg Met
225                 230                 235                 240

Pro Ser Thr Gly Ser Val Ala Pro Cys Val Pro Pro Leu Ser Thr Ser
                245                 250                 255

Leu Leu Ser Leu Ser Ala Thr Val His Ala Ala Ala Ala Ala Ala Thr
            260                 265                 270

Ala Ala Ala His Ser Phe Pro Leu Ser Phe Ala Gly Ala Phe Pro Met
            275                 280                 285

Leu Pro Pro Asn Ala Ala Ala Val Ala Ala Thr Ala Ile Ser
290                 295                 300

Pro Pro Leu Ser Val Ser Ala Thr Ser Ser Pro Gln Gln Thr Ser Ser
305                 310                 315                 320

Gly Thr Asn Asn Lys Pro Tyr Arg Pro Trp Gly Thr Glu Val Gly Ala
                325                 330                 335

Phe
```

<210> SEQ ID NO 40
<211> LENGTH: 1471
<212> TYPE: DNA
<213> ORGANISM: Homo sapiens
<220> FEATURE:
<221> NAME/KEY: misc_feature
<223> OTHER INFORMATION: Hes-1

<400> SEQUENCE: 40

```
atcacacagg atccggagct ggtgctgata acagcggaat ccccgtctca cctctctcct      60
tggtcctgga acagcgctac tgatcaccaa gtagccacaa aatataataa accctcagca     120
cttgctcagt agttttgtga agtctcaag taaaagagac acaaacaaaa aattcttttt      180
cgtgaagaac tccaaaaata aaattctcta gagataaaaa aaaaaaaaaa aggaaaatgc     240
cagctgatat aatggagaaa aattcctcgt ccccggtggc tgctacccca gccagtgtca     300
acacgacacc ggataaacca agacagcat ctgagcacag aaagtcatca aagcctatta      360
tggagaaaag acgaagagca agaataaatg aaagtctgag ccagctgaaa acactgattt     420
tggatgctct gaagaaagat agctcgcggc attccaagct ggagaaggcg acattctggg     480
```

```
aaatgacagt gaagcacctc cggaacctgc agcgggcgca gatgacggct gcgctgagca      540
cagacccaag tgtgctgggg aagtaccgag ccggcttcag cgagtgcatg aacgaggtga      600
cccgcttcct gtccacgtgc gagggcgtta ataccgaggt gcgcactcgg ctgctcggcc      660
acctggccaa ctgcatgacc cagatcaatg ccatgaccta ccccgggcag ccgcaccccg      720
ccttgcaggc gccgccaccg cccccaccgg gacccggcgg ccccagcac gcgccgttcg       780
cgccgccgcc gccactcgtg cccatccccg ggggcgcggc gcccctccc ggcggcgccc       840
cctgcaagct gggcagccag gctggagagg cggctaaggt gtttggaggc ttccaggtgg      900
taccggctcc cgatggccag tttgctttcc tcattcccaa cggggccttc gcgcacagcg      960
gccctgtcat ccccgtctac accagcaaca gcggcacctc cgtgggcccc aacgcagtgt     1020
caccttccag cggcccctcg cttacggcgg actccatgtg gaggccgtgg cggaactgag     1080
ggggctcagg ccaccctcc tcctaaactc cccaacccac ctctcttccc tccggactct      1140
aaacaggaac ttgaatactg ggagagaaga ggactttttt gattaagtgg ttactttgtg     1200
tttttttaat ttctaagaag ttacttttg tagagagagc tgtattaagt gactgaccat      1260
gcactatatt tgtatatatt ttatatgttc atattggatt gcgcctttgt attataaaag     1320
ctcagatgac atttcgtttt ttacacgaga tttctttttt atgtgatgcc aaagatgttt     1380
gaaaatgctc ttaaaatatc ttcctttggg gaagtttatt tgagaaaata taataaaaga     1440
aaaaagtaaa ggcaaaaaaa aaaaaaaaaa a                                     1471

<210> SEQ ID NO 41
<211> LENGTH: 280
<212> TYPE: PRT
<213> ORGANISM: Homo sapiens
<220> FEATURE:
<221> NAME/KEY: misc_feature
<223> OTHER INFORMATION: Hes-1

<400> SEQUENCE: 41

Met Pro Ala Asp Ile Met Glu Lys Asn Ser Ser Pro Val Ala Ala
1               5                   10                  15

Thr Pro Ala Ser Val Asn Thr Thr Pro Asp Lys Pro Lys Thr Ala Ser
            20                  25                  30

Glu His Arg Lys Ser Ser Lys Pro Ile Met Glu Lys Arg Arg Arg Ala
        35                  40                  45

Arg Ile Asn Glu Ser Leu Ser Gln Leu Lys Thr Leu Ile Leu Asp Ala
    50                  55                  60

Leu Lys Lys Asp Ser Ser Arg His Ser Lys Leu Glu Lys Ala Asp Ile
65                  70                  75                  80

Leu Glu Met Thr Val Lys His Leu Arg Asn Leu Gln Arg Ala Gln Met
                85                  90                  95

Thr Ala Ala Leu Ser Thr Asp Pro Ser Val Leu Gly Lys Tyr Arg Ala
            100                 105                 110

Gly Phe Ser Glu Cys Met Asn Glu Val Thr Arg Phe Leu Ser Thr Cys
        115                 120                 125

Glu Gly Val Asn Thr Glu Val Arg Thr Arg Leu Leu Gly His Leu Ala
    130                 135                 140

Asn Cys Met Thr Gln Ile Asn Ala Met Thr Tyr Pro Gly Gln Pro His
145                 150                 155                 160

Pro Ala Leu Gln Ala Pro Pro Pro Pro Pro Gly Pro Gly Gly Pro
                165                 170                 175

Gln His Ala Pro Phe Ala Pro Pro Pro Leu Val Pro Ile Pro Gly
            180                 185                 190
```

```
Gly Ala Ala Pro Pro Gly Gly Ala Pro Cys Lys Leu Gly Ser Gln
            195                 200                 205

Ala Gly Glu Ala Ala Lys Val Phe Gly Gly Phe Gln Val Val Pro Ala
        210                 215                 220

Pro Asp Gly Gln Phe Ala Phe Leu Ile Pro Asn Gly Ala Phe Ala His
225                 230                 235                 240

Ser Gly Pro Val Ile Pro Val Tyr Thr Ser Asn Ser Gly Thr Ser Val
            245                 250                 255

Gly Pro Asn Ala Val Ser Pro Ser Ser Gly Pro Ser Leu Thr Ala Asp
            260                 265                 270

Ser Met Trp Arg Pro Trp Arg Asn
            275                 280

<210> SEQ ID NO 42
<211> LENGTH: 10386
<212> TYPE: DNA
<213> ORGANISM: Homo sapiens
<220> FEATURE:
<221> NAME/KEY: misc_feature
<223> OTHER INFORMATION: APC
<220> FEATURE:
<221> NAME/KEY: misc_feature
<222> LOCATION: (9521)..(9521)
<223> OTHER INFORMATION: n is a, c, g, or t

<400> SEQUENCE: 42
attgaggact cggaaatgag gtccaagggt agccaaggat ggctgcagct tcatatgatc      60
agttgttaaa gcaagttgag gcactgaaga tggagaactc aaatcttcga caagagctag     120
aagataattc caatcatctt acaaaactgg aaactgaggc atctaatatg aaggaagtac     180
ttaaacaact acaaggaagt attgaagatg aagctatggc ttcttctgga cagattgatt     240
tattgagcgt tcttaaagag cttaacttag atagcagtaa tttccctgga gtaaaactgc     300
ggtcaaaaat gtccctccgt tcttatggaa gccgggaagg atctgtatca agccgttctg     360
gagagtgcag tcctgttcct atgggttcat ttccaagaag agggtttgta aatggaagca     420
gagaaagtac tggatattta gaagaacttg agaaagagag gtcattgctt cttgctgatc     480
ttgacaaaga agaaaaggaa aaagactggt attacgctca acttcagaat ctcactaaaa     540
gaatagatag tcttcctta actgaaaatt tttccttaca aacagatatg accagaaggc     600
aattggaata tgaagcaagg caaatcagag ttgcgatgga agaacaacta ggtacctgcc     660
aggatatgga aaaacgagca cagcgaagaa tagccagaat tcagcaaatc gaaaaggaca     720
tacttcgtat acgacagctt ttacagtccc aagcaacaga agcagagagg tcatctcaga     780
acaagcatga aaccggctca catgatgctg agcggcagaa tgaaggtcaa ggagtgggag     840
aaatcaacat ggcaacttct ggtaatggtc agggttcaac tacacgaatg gaccatgaaa     900
cagccagtgt tttgagttct agtagcacac actctgcacc tcgaaggctg acaagtcatc     960
tgggaaccaa ggtggaaatg gtgtattcat tgttgtcaat gcttggtact catgataagg    1020
atgatatgtc gcgaacttgg ctagctatgt ctagctccca agcacagctg tatatccatg    1080
gacagtctgg atgtcttcct ctcctcatcc agcttttaca tggcaatgac aaagactctg    1140
tattgttggg aaattccggg ggcagtaaag aggctcgggc cagggccagt gcagcactcc    1200
acaacatcat tcactcacag cctgatgaca agagaggcag gcgtgaaatc cgagtccttc    1260
atcttttgga acagatacgc gcttactgtg aaacctgttg ggagtggcag gaagctcatg    1320
aaccaggcat ggaccaggac aaaaatccaa tgccagctcc tgttgaacat cagatctgtc    1380
```

```
ctgctgtgtg tgttctaatg aaactttcat ttgatgaaga gcatagacat gcaatgaatg    1440
aactaggggg actacaggcc attgcagaat tattgcaagt ggactgtgaa atgtacgggc    1500
ttactaatga ccactacagt attacactaa gacgatatgc tggaatggct ttgacaaact    1560 tgactttttgg agatgtagcc aacaaggcta cgctatgctc tatgaaaggc tgcatgagag    1620
cacttgtggc ccaactaaaa tctgaaagtg aagacttaca gcaggttatt gcaagtgttt    1680
tgaggaattt gtcttggcga gcagatgtaa atagtaaaaa gacgttgcga gaagttggaa    1740
gtgtgaaagc attgatggaa tgtgctttag aagttaaaaa ggaatcaacc ctcaaaagcg    1800
tattgagtgc cttatggaat ttgtcagcac attgcactga gaataaagct gatatatgtg    1860
ctgtagatgg tgcacttgca ttttttggttg gcactcttac ttaccggagc cagacaaaca    1920
ctttagccat tattgaaagt ggaggtggga tattacggaa tgtgtccagc ttgatagcta    1980
caaatgagga ccacaggcaa atcctaagag agaacaactg tctacaaact ttattacaac    2040
acttaaaatc tcatagtttg acaatagtca gtaatgcatg tggaactttg tggaatctct    2100
cagcaagaaa tcctaaagac caggaagcat tatgggacat gggggcagtt agcatgctca    2160
agaacctcat tcattcaaag cacaaaatga ttgctatggg aagtgctgca gcttaaagga    2220
atctcatggc aaataggcct gcgaagtaca aggatgccaa tattatgtct cctggctcaa    2280
gcttgccatc tcttcatgtt aggaaacaaa aagccctaga agcagaatta gatgctcagc    2340
acttatcaga aacttttgac aatatagaca atttaagtcc caaggcatct catcgtagta    2400
agcagagaca caagcaaagt ctctatggtg attatgtttt tgacaccaat cgacatgatg    2460
ataataggtc agacaatttt aatactggca acatgactgt cctttcacca tatttgaata    2520
ctacagtgtt acccagctcc tcttcatcaa gaggaagctt agatagttct cgttctgaaa    2580
aagatagaag tttggagaga gaacgcggaa ttggtctagg caactaccat ccagcaacag    2640
aaaatccagg aacttcttca aagcgaggtt gcagatctc caccactgca gcccagattg    2700
ccaaagtcat ggaagaagtg tcagccattc atacctctca ggaagacaga agttctgggt    2760
ctaccactga attacattgt gtgacagatg agagaaatgc acttagaaga agctctgctg    2820
cccatacaca ttcaaacact tacaatttca ctaagtcgga aaattcaaat aggacatgtt    2880
ctatgcctta tgccaaatta gaatacaaga gatcttcaaa tgatagttta aatagtgtca    2940
gtagtagtga tggttatggt aaaagaggtc aaatgaaacc ctcgattgaa tcctattctg    3000
aagatgatga agtaagtttt gcagttatg gtcaataccc agccgaccta gcccataaaa    3060
tacatagtgc aaatcatatg gatgataatg atggagaact agatacacca ataaattata    3120
gtcttaaata ttcagatgag cagttgaact ctggaaggca aagtccttca cagaatgaaa    3180
gatgggcaag acccaaacac ataatagaag atgaaataaa acaaagtgag caagacaat    3240 caaggaatca agtacaact tatcctgttt atactgagag cactgatgat aaacacctca    3300
agttccaacc acatttttgga cagcaggaat gtgtttctcc atacaggtca cggggagcca    3360
atggttcaga aacaaatcga gtgggttcta atcatggaat taatcaaaat gtaagccagt    3420
ctttgtgtca agaagatgac tatgaagatg ataagcctac caattatagt gaacgttact    3480
ctgaagaaga acagcatgaa gaagaagaga gaccaacaaa ttatagcata aaatataatg    3540
aagagaaacg tcatgtggat cagcctattg attatagttt aaaatatgcc acagatattc    3600
cttcatcaca gaaacagtca ttttcattct caaagagttc atctggacaa agcagtaaaa    3660
ccgaacatat gtcttcaagc agtgagaata cgtccacacc ttcatctaat gccaagaggc    3720
agaatcagct ccatccaagt tctgcacaga gtagaagtgg tcagcctcaa aaggctgcca    3780
```

```
cttgcaaagt ttcttctatt aaccaagaaa caatacagac ttattgtgta gaagatactc    3840
caatatgttt ttcaagatgt agttcattat catctttgtc atcagctgaa gatgaaatag    3900
gatgtaatca gacgacacag gaagcagatt ctgctaatac cctgcaaata gcagaaataa    3960
aagaaaagat tggaactagg tcagctgaag atcctgtgag cgaagttcca gcagtgtcac    4020
agcaccctag aaccaaatcc agcagactgc agggttctag tttatcttca gaatcagcca    4080
ggcacaaagc tgttgaattt tcttcaggag cgaaatctcc ctccaaaagt ggtgctcaga    4140
cacccaaaag tccacctgaa cactatgttc aggagacccc actcatgttt agcagatgta    4200
cttctgtcag ttcacttgat agttttgaga gtcgttcgat tgccagctcc gttcagagtg    4260
aaccatgcag tggaatggta agtggcatta taagccccag tgatcttcca gatagccctg    4320
gacaaaccat gccaccaagc agaagtaaaa cacctccacc acctcctcaa acagctcaaa    4380
ccaagcgaga agtacctaaa aataaagcac ctactgctga aaagagagag agtggaccta    4440
agcaagctgc agtaaatgct gcagttcaga gggtccaggt tcttccagat gctgatactt    4500
tattacattt tgccacggaa agtactccag atggattttc ttgttcatcc agcctgagtg    4560
ctctgagcct cgatgagcca tttatacaga aagatgtgga attaagaata atgcctccag    4620
ttcaggaaaa tgacaatggg aatgaaacag aatcagagca gcctaaagaa tcaaatgaaa    4680
accaagagaa agaggcagaa aaaactattg attctgaaaa ggacctatta gatgattcag    4740
atgatgatga tattgaaata ctagaagaat gtattatttc tgccatgcca acaaagtcat    4800
cacgtaaagc aaaaaagcca gcccagactg cttcaaaatt acctccacct gtggcaagga    4860
aaccaagtca gctgcctgtg tacaaacttc taccatcaca aaacaggttg caaccccaaa    4920
agcatgttag ttttacaccg ggggatgata tgccacgggt gtattgtgtt gaagggacac    4980
ctataaactt ttccacagct acatctctaa gtgatctaac aatcgaatcc cctccaaatg    5040
agttagctgc tggagaagga gttagaggag gagcacagtc aggtgaattt gaaaaacgag    5100
ataccattcc tacagaaggc agaagtacag atgaggctca aggaggaaaa acctcatctg    5160
taaccatacc tgaattggat gacaataaag cagaggaagg tgatattctt gcagaatgca    5220
ttaattctgc tatgcccaaa gggaaaagtc acaagccttt ccgtgtgaaa aagataatgg    5280
accaggtcca gcaagcatct gcgtcgtctt ctgcacccaa caaaaatcag ttagatggta    5340
agaaaaagaa accaacttca ccagtaaaac ctataccaca aaatactgaa tataggacac    5400
gtgtaagaaa aaatgcagac tcaaaaaata atttaaatgc tgagagagtt ttctcagaca    5460
acaaagattc aaagaaacag aatttgaaaa ataattccaa ggacttcaat gataagctcc    5520
caaataatga agatagagtc agaggaagtt ttgcttttga ttcacctcat cattacacgc    5580
ctattgaagg aactccttac tgttttttcac gaaatgattc tttgagttct ctagattttg    5640
atgatgatga tgttgaccct tccagggaaa aggctgaatt aagaaaggca aaagaaaata    5700
aggaatcaga ggctaaagtt accagccaca cagaactaac ctccaaccaa caatcagcta    5760
ataagacaca agctattgca aagcagccaa taaatcgagg tcagcctaaa cccatacttc    5820
agaaacaatc cactttttccc cagtcatcca aagacatacc agacagaggg gcagcaactg    5880
atgaaaagtt acagaatttt gctattgaaa atactccagt ttgcttttct cataattcct    5940
ctctgagttc tctcagtgac attgaccaag aaaacaacaa taagaaaaat gaacctatca    6000
aagagactga gcccctgac tcacagggag aaccaagtaa acctcaagca tcaggctatg    6060
ctcctaaatc atttcatgtt gaagataccc cagtttgttt tcaagaaac agttctctca    6120 gttctcttag tattgactct gaagatgacc tgttgcagga atgtataagc tccgcaatgc    6180
```

```
caaaaaagaa aaagccttca agactcaagg gtgataatga aaaacatagt cccagaaata    6240
tgggtggcat attaggtgaa gatctgacac ttgatttgaa agatatacag agaccagatt    6300
cagaacatgg tctatcccct gattcagaaa attttgattg gaaagctatt caggaaggtg    6360
caaattccat agtaagtagt ttacatcaag ctgctgctgc tgcatgttta tctagacaag    6420
cttcgtctga ttcagattcc atcctttccc tgaaatcagg aatctctctg ggatcaccat    6480
ttcatcttac acctgatcaa gaagaaaaac cctttacaag taataaaggc ccacgaattc    6540
taaaaccagg ggagaaaagt acattggaaa ctaaaagat agaatctgaa agtaaaggaa    6600
tcaaaggagg aaaaaaagtt tataaaagtt tgattactgg aaaagttcga tctaattcag    6660
aaatttcagg ccaaatgaaa cagccccttc aagcaaacat gccttcaatc tctcgaggca    6720
ggacaatgat tcatattcca ggagttcgaa atagctcctc aagtacaagt cctgtttcta    6780
aaaaaggccc acccttaag actccagcct ccaaaagccc tagtgaaggt caaacagcca    6840
ccacttctcc tagaggagcc aagccatctg tgaaatcaga attaagccct gttgccaggc    6900
agacatccca ataggtgggt tcaagtaaag caccttctag atcaggatct agagattcga    6960 cccccttcaag acctgcccag caaccattaa gtagacctat acagtctcct ggccgaaact    7020
caatttcccc tggtagaaat ggaataagtc ctcctaacaa attatctcaa cttccaagga    7080
catcatcccc tagtactgct tcaactaagt cctcaggttc tggaaaaatg tcatatacat    7140
ctccaggtag acagatgagc caacagaacc ttaccaaaca aacaggttta tccaagaatg    7200
ccagtagtat tccaagaagt gagtctgcct ccaaaggact aaatcagatg aataatggta    7260
atggagccaa taaaaaggta gaactttcta gaatgtcttc aactaaatca gtggaagtg     7320 aatctgatag atcagaaaga cctgtattag tacgccagtc aactttcatc aaagaagctc    7380
caagcccaac cttaagaaga aaattggagg aatctgcttc atttgaatct ctttctccat    7440
catctagacc agcttctccc actaggtccc aggcacaaac tccagttta agtccttccc     7500 ttcctgatat gtctctatcc acacattcgt ctgttcaggc tggtggatgg cgaaaactcc    7560
cacctaatct cagtcccact atagagtata atgatggaag accagcaaag cgccatgata    7620
ttgcacggtc tcattctgaa agtccttcta gacttccaat caataggtca ggaacctgga    7680
aacgtgagca cagcaaacat tcatcatccc ttcctcgagt aagcacttgg agaagaactg    7740
gaagttcatc ttcaattctt tctgcttcat cagaatccag tgaaaagca aaaagtgagg     7800 atgaaaaaca tgtgaactct atttcaggaa ccaaacaaag taaagaaaac caagtatccg    7860 caaaggaac atggagaaaa ataaagaaa atgaattttc tcccacaaat agtacttctc      7920
agaccgtttc ctcaggtgct acaaatggtg ctgaatcaaa gactctaatt tatcaaatgg    7980
cacctgctgt ttctaaaaca gaggatgttt gggtgagaat tgaggactgt cccattaaca    8040
atcctagatc tggaagatct cccacaggta atactccccc ggtgattgac agtgtttcag    8100
aaaaggcaaa tccaaacatt aaagattcaa aagataatca ggcaaaacaa aatgtgggta    8160
atggcagtgt tcccatgcgt accgtgggtt tggaaaatcg cctgaactcc tttattcagg    8220
tggatgcccc tgaccaaaaa ggaactgaga taaaaccagg acaaaataat cctgtccctg    8280
tatcagagac taatgaaagt tctatagtgg aacgtacccc attcagttct agcagctcaa    8340
gcaaacacag ttcacctagt gggactgttg ctgccagagt gactcctttt aattacaacc    8400
caagccctag gaaaagcagc gcagatagca cttcagctcg gccatctcag atcccaactc    8460
cagtgaataa caacacaaag aagcgagatt ccaaaactga cagcacagaa tccagtggaa    8520
cccaaagtcc taagcgccat tctgggtctt accttgtgac atctgtttaa aagagaggaa    8580
```

-continued

| | | | | | |
|---|---|---|---|---|---|
| gaatgaaact | aagaaaattc | tatgttaatt | acaactgcta | tatagacatt | ttgtttcaaa | 8640 |
| tgaaacttta | aaagactgaa | aaattttgta | aataggtttg | attcttgtta | gagggttttt | 8700 |
| gttctggaag | ccatatttga | tagtatactt | tgtcttcact | ggtcttatt | tgggaggcac | 8760 |
| tcttgatggt | taggaaaaaa | atagtaaagc | caagtatgtt | tgtacagtat | gttttacatg | 8820 |
| tatttaaagt | agcatcccat | cccaacttcc | tttaattatt | gcttgtctta | aataatgaa | 8880 |
| cactacagat | agaaaatatg | atatattgct | gttatcaatc | atttctagat | tataaactga | 8940 |
| ctaaacttac | atcagggaaa | aattggtatt | tatgcaaaaa | aaatgtttt | tgtccttgtg | 9000 |
| agtccatcta | acatcataat | taatcatgtg | gctgtgaaat | tcacagtaat | atggttcccg | 9060 |
| atgaacaagc | tttacccagc | ctgtttgctt | tactgcatga | atgaaactga | tggttcaatt | 9120 |
| tcagaagtaa | tgattaacag | ttatgtggtc | acatgatgtg | catagagata | gctacagtgt | 9180 |
| aataatttac | actattttgt | gctccaaaca | aaacaaaaat | ctgtgtaact | gtaaaacatt | 9240 |
| gaatgaaact | attttacctg | aactagattt | tatctgaaag | taggtagaat | ttttgctatg | 9300 |
| ctgtaatttg | ttgtatattc | tggtatttga | ggtgagatgg | ctgctctttt | attaatgaga | 9360 |
| catgaattgt | gtctcaacag | aaactaaatg | aacatttcag | aataaattat | tgctgtatgt | 9420 |
| aaactgttac | tgaaattggt | atttgtttga | agggtcttgt | ttcacatttg | tattaataat | 9480 |
| tgtttaaaat | gcctcttta | aaagcttata | taaatttttt | ncttcagctt | ctatgcatta | 9540 |
| agagtaaaat | tcctcttact | gtaataaaaa | caattgaaga | agactgttgc | cacttaacca | 9600 |
| ttccatgcgt | tggcacttat | ctattcctga | aattctttta | tgtgattagc | tcatcttgat | 9660 |
| ttttaacatt | tttccactta | aactttttt | tcttactcca | ctggagctca | gtaaaagtaa | 9720 |
| attcatgtaa | tagcaatgca | agcagcctag | cacagactaa | gcattgagca | taataggccc | 9780 |
| acataatttc | ctctttctta | atattataga | aattctgtac | ttgaaattga | ttcttagaca | 9840 |
| ttgcagtctc | ttcgaggctt | tacagtgtaa | actgtcttgc | cccttcatct | tcttgttgca | 9900 |
| actgggtctg | acatgaacac | tttttatcac | cctgtatgtt | agggcaagat | ctcagcagtg | 9960 |
| aagtataatc | agcactttgc | catgctcaga | aaattcaaat | cacatggaac | tttagaggta | 10020 |
| gatttaatac | gattaagata | ttcagaagta | tattttgaaa | tccctgcctg | ttaaggaaac | 10080 |
| tttatttgtg | gtaggtacag | ttctggggta | catgttaagt | gtccccttat | acagtggagg | 10140 |
| gaagtcttcc | ttcctgaagg | aaaataaact | gacacttatt | aactaagata | atttacttaa | 10200 |
| tatatcttcc | ctgatttgtt | ttaaaagatc | agagggtgac | tgatgataca | tgcatacata | 10260 |
| tttgttgaat | aaatgaaaat | ttattttag | tgataagatt | catacactct | gtatttgggg | 10320 |
| agagaaaacc | tttttaagca | tggtggggca | ctcagatagg | agtgaataca | cctacctggt | 10380 |
| ggtcat | | | | | 10386 |

<210> SEQ ID NO 43
<211> LENGTH: 2843
<212> TYPE: PRT
<213> ORGANISM: Homo sapiens
<220> FEATURE:
<221> NAME/KEY: misc_feature
<223> OTHER INFORMATION: APC

<400> SEQUENCE: 43

Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu

```
                35                  40                  45
Lys Gln Leu Gln Gly Ser Ile Glu Asp Glu Ala Met Ala Ser Ser Gly
 50                  55                  60
Gln Ile Asp Leu Leu Glu Arg Leu Lys Glu Leu Asn Leu Asp Ser Ser
 65                  70                  75                  80
Asn Phe Pro Gly Val Lys Leu Arg Ser Lys Met Ser Leu Arg Ser Tyr
                 85                  90                  95
Gly Ser Arg Glu Gly Ser Val Ser Arg Ser Gly Glu Cys Ser Pro
                100                 105                 110
Val Pro Met Gly Ser Phe Pro Arg Arg Gly Phe Val Asn Gly Ser Arg
                115                 120                 125
Glu Ser Thr Gly Tyr Leu Glu Glu Leu Glu Lys Glu Arg Ser Leu Leu
                130                 135                 140
Leu Ala Asp Leu Asp Lys Glu Glu Lys Glu Lys Asp Trp Tyr Tyr Ala
145                 150                 155                 160
Gln Leu Gln Asn Leu Thr Lys Arg Ile Asp Ser Leu Pro Leu Thr Glu
                165                 170                 175
Asn Phe Ser Leu Gln Thr Asp Met Thr Arg Arg Gln Leu Glu Tyr Glu
                180                 185                 190
Ala Arg Gln Ile Arg Val Ala Met Glu Glu Gln Leu Gly Thr Cys Gln
                195                 200                 205
Asp Met Glu Lys Arg Ala Gln Arg Arg Ile Ala Arg Ile Gln Gln Ile
                210                 215                 220
Glu Lys Asp Ile Leu Arg Ile Arg Gln Leu Leu Gln Ser Gln Ala Thr
225                 230                 235                 240
Glu Ala Glu Arg Ser Ser Gln Asn Lys His Glu Thr Gly Ser His Asp
                245                 250                 255
Ala Glu Arg Gln Asn Glu Gly Gln Gly Val Gly Glu Ile Asn Met Ala
                260                 265                 270
Thr Ser Gly Asn Gly Gln Gly Ser Thr Thr Arg Met Asp His Glu Thr
                275                 280                 285
Ala Ser Val Leu Ser Ser Ser Thr His Ser Ala Pro Arg Arg Leu
290                 295                 300
Thr Ser His Leu Gly Thr Lys Val Glu Met Val Tyr Ser Leu Leu Ser
305                 310                 315                 320
Met Leu Gly Thr His Asp Lys Asp Asp Met Ser Arg Thr Leu Leu Ala
                325                 330                 335
Met Ser Ser Ser Gln Asp Ser Cys Ile Ser Met Arg Gln Ser Gly Cys
                340                 345                 350
Leu Pro Leu Leu Ile Gln Leu Leu His Gly Asn Asp Lys Asp Ser Val
                355                 360                 365
Leu Leu Gly Asn Ser Arg Gly Ser Lys Glu Ala Arg Ala Arg Ala Ser
                370                 375                 380
Ala Ala Leu His Asn Ile Ile His Ser Gln Pro Asp Asp Lys Arg Gly
385                 390                 395                 400
Arg Arg Glu Ile Arg Val Leu His Leu Leu Glu Gln Ile Arg Ala Tyr
                405                 410                 415
Cys Glu Thr Cys Trp Glu Trp Gln Glu Ala His Glu Pro Gly Met Asp
                420                 425                 430
Gln Asp Lys Asn Pro Met Pro Ala Pro Val Glu His Gln Ile Cys Pro
                435                 440                 445
Ala Val Cys Val Leu Met Lys Leu Ser Phe Asp Glu Glu His Arg His
                450                 455                 460
```

```
                                -continued

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
            485                 490                 495

Leu Arg Arg Tyr Ala Gly Met Ala Leu Thr Asn Leu Thr Phe Gly Asp
        500                 505                 510

Val Ala Asn Lys Ala Thr Leu Cys Ser Met Lys Gly Cys Met Arg Ala
    515                 520                 525

Leu Val Ala Gln Leu Lys Ser Glu Ser Glu Asp Leu Gln Gln Val Ile
530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
            565                 570                 575

Leu Glu Val Lys Lys Glu Ser Thr Leu Lys Ser Val Leu Ser Ala Leu
        580                 585                 590

Trp Asn Leu Ser Ala His Cys Thr Glu Asn Lys Ala Asp Ile Cys Ala
    595                 600                 605

Val Asp Gly Ala Leu Ala Phe Leu Val Gly Thr Leu Thr Tyr Arg Ser
610                 615                 620

Gln Thr Asn Thr Leu Ala Ile Ile Glu Ser Gly Gly Ile Leu Arg
625                 630                 635                 640

Asn Val Ser Ser Leu Ile Ala Thr Asn Glu Asp His Arg Gln Ile Leu
            645                 650                 655

Arg Glu Asn Asn Cys Leu Gln Thr Leu Leu Gln His Leu Lys Ser His
        660                 665                 670

Ser Leu Thr Ile Val Ser Asn Ala Cys Gly Thr Leu Trp Asn Leu Ser
    675                 680                 685

Ala Arg Asn Pro Lys Asp Gln Glu Ala Leu Trp Asp Met Gly Ala Val
690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
            725                 730                 735

Tyr Lys Asp Ala Asn Ile Met Ser Pro Gly Ser Ser Leu Pro Ser Leu
        740                 745                 750

His Val Arg Lys Gln Lys Ala Leu Glu Ala Glu Leu Asp Ala Gln His
    755                 760                 765

Leu Ser Glu Thr Phe Asp Asn Ile Asp Asn Leu Ser Pro Lys Ala Ser
770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
            805                 810                 815

Gly Asn Met Thr Val Leu Ser Pro Tyr Leu Asn Thr Thr Val Leu Pro
        820                 825                 830

Ser Ser Ser Ser Ser Arg Gly Ser Leu Asp Ser Ser Arg Ser Glu Lys
    835                 840                 845

Asp Arg Ser Leu Glu Arg Glu Arg Gly Ile Gly Leu Gly Asn Tyr His
850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
            885                 890                 895
```

```
Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
            915                 920                 925

His Thr His Ser Asn Thr Tyr Asn Phe Thr Lys Ser Glu Asn Ser Asn
            930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asp Gly Tyr Gly Lys Arg
                965                 970                 975

Gly Gln Met Lys Pro Ser Ile Glu Ser Tyr Ser Glu Asp Glu Ser
            980                 985                 990

Lys Phe Cys Ser Tyr Gly Gln Tyr Pro Ala Asp Leu Ala His Lys Ile
            995                 1000                1005

His Ser Ala Asn His Met Asp Asp Asn Asp Gly Glu Leu Asp Thr
            1010                1015                1020

Pro Ile Asn Tyr Ser Leu Lys Tyr Ser Asp Glu Gln Leu Asn Ser
            1025                1030                1035

Gly Arg Gln Ser Pro Ser Gln Asn Glu Arg Trp Ala Arg Pro Lys
            1040                1045                1050

His Ile Ile Glu Asp Glu Ile Lys Gln Ser Glu Gln Arg Gln Ser
            1055                1060                1065

Arg Asn Gln Ser Thr Thr Tyr Pro Val Tyr Thr Glu Ser Thr Asp
            1070                1075                1080

Asp Lys His Leu Lys Phe Gln Pro His Phe Gly Gln Gln Glu Cys
            1085                1090                1095

Val Ser Pro Tyr Arg Ser Arg Gly Ala Asn Gly Ser Glu Thr Asn
            1100                1105                1110

Arg Val Gly Ser Asn His Gly Ile Asn Gln Asn Val Ser Gln Ser
            1115                1120                1125

Leu Cys Gln Glu Asp Asp Tyr Glu Asp Asp Lys Pro Thr Asn Tyr
            1130                1135                1140

Ser Glu Arg Tyr Ser Glu Glu Gln His Glu Glu Glu Glu Glu Arg
            1145                1150                1155

Pro Thr Asn Tyr Ser Ile Lys Tyr Asn Glu Glu Lys Arg His Val
            1160                1165                1170

Asp Gln Pro Ile Asp Tyr Ser Leu Lys Tyr Ala Thr Asp Ile Pro
            1175                1180                1185

Ser Ser Gln Lys Gln Ser Phe Ser Phe Ser Lys Ser Ser Ser Gly
            1190                1195                1200

Gln Ser Ser Lys Thr Glu His Met Ser Ser Ser Glu Asn Thr
            1205                1210                1215

Ser Thr Pro Ser Ser Asn Ala Lys Arg Gln Asn Gln Leu His Pro
            1220                1225                1230

Ser Ser Ala Gln Ser Arg Ser Gly Gln Pro Gln Lys Ala Ala Thr
            1235                1240                1245

Cys Lys Val Ser Ser Ile Asn Gln Glu Thr Ile Gln Thr Tyr Cys
            1250                1255                1260

Val Glu Asp Thr Pro Ile Cys Phe Ser Arg Cys Ser Ser Leu Ser
            1265                1270                1275

Ser Leu Ser Ser Ala Glu Asp Glu Ile Gly Cys Asn Gln Thr Thr
            1280                1285                1290

Gln Glu Ala Asp Ser Ala Asn Thr Leu Gln Ile Ala Glu Ile Lys
```

```
            1295                1300                1305

Glu Lys Ile Gly Thr Arg Ser Ala Glu Asp Pro Val Ser Glu Val
    1310                1315                1320

Pro Ala Val Ser Gln His Pro Arg Thr Lys Ser Ser Arg Leu Gln
    1325                1330                1335

Gly Ser Ser Leu Ser Ser Glu Ser Ala Arg His Lys Ala Val Glu
    1340                1345                1350

Phe Ser Ser Gly Ala Lys Ser Pro Ser Lys Ser Gly Ala Gln Thr
    1355                1360                1365

Pro Lys Ser Pro Pro Glu His Tyr Val Gln Glu Thr Pro Leu Met
    1370                1375                1380

Phe Ser Arg Cys Thr Ser Val Ser Ser Leu Asp Ser Phe Glu Ser
    1385                1390                1395

Arg Ser Ile Ala Ser Ser Val Gln Ser Glu Pro Cys Ser Gly Met
    1400                1405                1410

Val Ser Gly Ile Ile Ser Pro Ser Asp Leu Pro Asp Ser Pro Gly
    1415                1420                1425

Gln Thr Met Pro Pro Ser Arg Ser Lys Thr Pro Pro Pro Pro Pro
    1430                1435                1440

Gln Thr Ala Gln Thr Lys Arg Glu Val Pro Lys Asn Lys Ala Pro
    1445                1450                1455

Thr Ala Glu Lys Arg Glu Ser Gly Pro Lys Gln Ala Ala Val Asn
    1460                1465                1470

Ala Ala Val Gln Arg Val Gln Val Leu Pro Asp Ala Asp Thr Leu
    1475                1480                1485

Leu His Phe Ala Thr Glu Ser Thr Pro Asp Gly Phe Ser Cys Ser
    1490                1495                1500

Ser Ser Leu Ser Ala Leu Ser Leu Asp Glu Pro Phe Ile Gln Lys
    1505                1510                1515

Asp Val Glu Leu Arg Ile Met Pro Pro Val Gln Glu Asn Asp Asn
    1520                1525                1530

Gly Asn Glu Thr Glu Ser Glu Gln Pro Lys Glu Ser Asn Glu Asn
    1535                1540                1545

Gln Glu Lys Glu Ala Glu Lys Thr Ile Asp Ser Glu Lys Asp Leu
    1550                1555                1560

Leu Asp Asp Ser Asp Asp Asp Ile Glu Ile Leu Glu Glu Cys
    1565                1570                1575

Ile Ile Ser Ala Met Pro Thr Lys Ser Ser Arg Lys Ala Lys Lys
    1580                1585                1590

Pro Ala Gln Thr Ala Ser Lys Leu Pro Pro Val Ala Arg Lys
    1595                1600                1605

Pro Ser Gln Leu Pro Val Tyr Lys Leu Leu Pro Ser Gln Asn Arg
    1610                1615                1620

Leu Gln Pro Gln Lys His Val Ser Phe Thr Pro Gly Asp Asp Met
    1625                1630                1635

Pro Arg Val Tyr Cys Val Glu Gly Thr Pro Ile Asn Phe Ser Thr
    1640                1645                1650

Ala Thr Ser Leu Ser Asp Leu Thr Ile Glu Ser Pro Pro Asn Glu
    1655                1660                1665

Leu Ala Ala Gly Glu Gly Val Arg Gly Gly Ala Gln Ser Gly Glu
    1670                1675                1680

Phe Glu Lys Arg Asp Thr Ile Pro Thr Glu Gly Arg Ser Thr Asp
    1685                1690                1695
```

```
Glu Ala Gln Gly Gly Lys Thr Ser Ser Val Thr Ile Pro Glu Leu
1700                1705                1710

Asp Asp Asn Lys Ala Glu Glu Gly Asp Ile Leu Ala Glu Cys Ile
1715                1720                1725

Asn Ser Ala Met Pro Lys Gly Lys Ser His Lys Pro Phe Arg Val
1730                1735                1740

Lys Lys Ile Met Asp Gln Val Gln Gln Ala Ser Ala Ser Ser Ser
1745                1750                1755

Ala Pro Asn Lys Asn Gln Leu Asp Gly Lys Lys Lys Lys Pro Thr
1760                1765                1770

Ser Pro Val Lys Pro Ile Pro Gln Asn Thr Glu Tyr Arg Thr Arg
1775                1780                1785

Val Arg Lys Asn Ala Asp Ser Lys Asn Asn Leu Asn Ala Glu Arg
1790                1795                1800

Val Phe Ser Asp Asn Lys Asp Ser Lys Lys Gln Asn Leu Lys Asn
1805                1810                1815

Asn Ser Lys Asp Phe Asn Asp Lys Leu Pro Asn Asn Glu Asp Arg
1820                1825                1830

Val Arg Gly Ser Phe Ala Phe Asp Ser Pro His His Tyr Thr Pro
1835                1840                1845

Ile Glu Gly Thr Pro Tyr Cys Phe Ser Arg Asn Asp Ser Leu Ser
1850                1855                1860

Ser Leu Asp Phe Asp Asp Asp Val Asp Leu Ser Arg Glu Lys
1865                1870                1875

Ala Glu Leu Arg Lys Ala Lys Glu Asn Lys Glu Ser Glu Ala Lys
1880                1885                1890

Val Thr Ser His Thr Glu Leu Thr Ser Asn Gln Gln Ser Ala Asn
1895                1900                1905

Lys Thr Gln Ala Ile Ala Lys Gln Pro Ile Asn Arg Gly Gln Pro
1910                1915                1920

Lys Pro Ile Leu Gln Lys Gln Ser Thr Phe Pro Gln Ser Ser Lys
1925                1930                1935

Asp Ile Pro Asp Arg Gly Ala Ala Thr Asp Glu Lys Leu Gln Asn
1940                1945                1950

Phe Ala Ile Glu Asn Thr Pro Val Cys Phe Ser His Asn Ser Ser
1955                1960                1965

Leu Ser Ser Leu Ser Asp Ile Asp Gln Glu Asn Asn Asn Lys Glu
1970                1975                1980

Asn Glu Pro Ile Lys Glu Thr Glu Pro Pro Asp Ser Gln Gly Glu
1985                1990                1995

Pro Ser Lys Pro Gln Ala Ser Gly Tyr Ala Pro Lys Ser Phe His
2000                2005                2010

Val Glu Asp Thr Pro Val Cys Phe Ser Arg Asn Ser Ser Leu Ser
2015                2020                2025

Ser Leu Ser Ile Asp Ser Glu Asp Asp Leu Leu Gln Glu Cys Ile
2030                2035                2040

Ser Ser Ala Met Pro Lys Lys Lys Lys Pro Ser Arg Leu Lys Gly
2045                2050                2055

Asp Asn Glu Lys His Ser Pro Arg Asn Met Gly Gly Ile Leu Gly
2060                2065                2070

Glu Asp Leu Thr Leu Asp Leu Lys Asp Ile Gln Arg Pro Asp Ser
2075                2080                2085

Glu His Gly Leu Ser Pro Asp Ser Glu Asn Phe Asp Trp Lys Ala
2090                2095                2100
```

-continued

```
Ile Gln Glu Gly Ala Asn Ser Ile Val Ser Ser Leu His Gln Ala
    2105                2110                2115
Ala Ala Ala Ala Cys Leu Ser Arg Gln Ala Ser Ser Asp Ser Asp
    2120                2125                2130
Ser Ile Leu Ser Leu Lys Ser Gly Ile Ser Leu Gly Ser Pro Phe
    2135                2140                2145
His Leu Thr Pro Asp Gln Glu Glu Lys Pro Phe Thr Ser Asn Lys
    2150                2155                2160
Gly Pro Arg Ile Leu Lys Pro Gly Glu Lys Ser Thr Leu Glu Thr
    2165                2170                2175
Lys Lys Ile Glu Ser Glu Ser Lys Gly Ile Lys Gly Gly Lys Lys
    2180                2185                2190
Val Tyr Lys Ser Leu Ile Thr Gly Lys Val Arg Ser Asn Ser Glu
    2195                2200                2205
Ile Ser Gly Gln Met Lys Gln Pro Leu Gln Ala Asn Met Pro Ser
    2210                2215                2220
Ile Ser Arg Gly Arg Thr Met Ile His Ile Pro Gly Val Arg Asn
    2225                2230                2235
Ser Ser Ser Ser Thr Ser Pro Val Ser Lys Lys Gly Pro Pro Leu
    2240                2245                2250
Lys Thr Pro Ala Ser Lys Ser Pro Ser Glu Gly Gln Thr Ala Thr
    2255                2260                2265
Thr Ser Pro Arg Gly Ala Lys Pro Ser Val Lys Ser Glu Leu Ser
    2270                2275                2280
Pro Val Ala Arg Gln Thr Ser Gln Ile Gly Gly Ser Ser Lys Ala
    2285                2290                2295
Pro Ser Arg Ser Gly Ser Arg Asp Ser Thr Pro Ser Arg Pro Ala
    2300                2305                2310
Gln Gln Pro Leu Ser Arg Pro Ile Gln Ser Pro Gly Arg Asn Ser
    2315                2320                2325
Ile Ser Pro Gly Arg Asn Gly Ile Ser Pro Pro Asn Lys Leu Ser
    2330                2335                2340
Gln Leu Pro Arg Thr Ser Ser Pro Ser Thr Ala Ser Thr Lys Ser
    2345                2350                2355
Ser Gly Ser Gly Lys Met Ser Tyr Thr Ser Pro Gly Arg Gln Met
    2360                2365                2370
Ser Gln Gln Asn Leu Thr Lys Gln Thr Gly Leu Ser Lys Asn Ala
    2375                2380                2385
Ser Ser Ile Pro Arg Ser Glu Ser Ala Ser Lys Gly Leu Asn Gln
    2390                2395                2400
Met Asn Asn Gly Asn Gly Ala Asn Lys Lys Val Glu Leu Ser Arg
    2405                2410                2415
Met Ser Ser Thr Lys Ser Ser Gly Ser Glu Ser Asp Arg Ser Glu
    2420                2425                2430
Arg Pro Val Leu Val Arg Gln Ser Thr Phe Ile Lys Glu Ala Pro
    2435                2440                2445
Ser Pro Thr Leu Arg Arg Lys Leu Glu Glu Ser Ala Ser Phe Glu
    2450                2455                2460
Ser Leu Ser Pro Ser Ser Arg Pro Ala Ser Pro Thr Arg Ser Gln
    2465                2470                2475
Ala Gln Thr Pro Val Leu Ser Pro Ser Leu Pro Asp Met Ser Leu
    2480                2485                2490
Ser Thr His Ser Ser Val Gln Ala Gly Gly Trp Arg Lys Leu Pro
```

```
               2495                 2500                 2505

Pro Asn Leu Ser Pro Thr Ile Glu Tyr Asn Asp Gly Arg Pro Ala
    2510                 2515                 2520

Lys Arg His Asp Ile Ala Arg Ser His Ser Glu Ser Pro Ser Arg
    2525                 2530                 2535

Leu Pro Ile Asn Arg Ser Gly Thr Trp Lys Arg Glu His Ser Lys
    2540                 2545                 2550

His Ser Ser Ser Leu Pro Arg Val Ser Thr Trp Arg Arg Thr Gly
    2555                 2560                 2565

Ser Ser Ser Ser Ile Leu Ser Ala Ser Ser Glu Ser Ser Glu Lys
    2570                 2575                 2580

Ala Lys Ser Glu Asp Glu Lys His Val Asn Ser Ile Ser Gly Thr
    2585                 2590                 2595

Lys Gln Ser Lys Glu Asn Gln Val Ser Ala Lys Gly Thr Trp Arg
    2600                 2605                 2610

Lys Ile Lys Glu Asn Glu Phe Ser Pro Thr Asn Ser Thr Ser Gln
    2615                 2620                 2625

Thr Val Ser Ser Gly Ala Thr Asn Gly Ala Glu Ser Lys Thr Leu
    2630                 2635                 2640

Ile Tyr Gln Met Ala Pro Ala Val Ser Lys Thr Glu Asp Val Trp
    2645                 2650                 2655

Val Arg Ile Glu Asp Cys Pro Ile Asn Asn Pro Arg Ser Gly Arg
    2660                 2665                 2670

Ser Pro Thr Gly Asn Thr Pro Pro Val Ile Asp Ser Val Ser Glu
    2675                 2680                 2685

Lys Ala Asn Pro Asn Ile Lys Asp Ser Lys Asp Asn Gln Ala Lys
    2690                 2695                 2700

Gln Asn Val Gly Asn Gly Ser Val Pro Met Arg Thr Val Gly Leu
    2705                 2710                 2715

Glu Asn Arg Leu Asn Ser Phe Ile Gln Val Asp Ala Pro Asp Gln
    2720                 2725                 2730

Lys Gly Thr Glu Ile Lys Pro Gly Gln Asn Asn Pro Val Pro Val
    2735                 2740                 2745

Ser Glu Thr Asn Glu Ser Ser Ile Val Glu Arg Thr Pro Phe Ser
    2750                 2755                 2760

Ser Ser Ser Ser Lys His Ser Ser Pro Ser Gly Thr Val Ala
    2765                 2770                 2775

Ala Arg Val Thr Pro Phe Asn Tyr Asn Pro Ser Pro Arg Lys Ser
    2780                 2785                 2790

Ser Ala Asp Ser Thr Ser Ala Arg Pro Ser Gln Ile Pro Thr Pro
    2795                 2800                 2805

Val Asn Asn Asn Thr Lys Lys Arg Asp Ser Lys Thr Asp Ser Thr
    2810                 2815                 2820

Glu Ser Ser Gly Thr Gln Ser Pro Lys Arg His Ser Gly Ser Tyr
    2825                 2830                 2835

Leu Val Thr Ser Val
    2840

<210> SEQ ID NO 44
<211> LENGTH: 2121
<212> TYPE: DNA
<213> ORGANISM: Homo sapiens
<220> FEATURE:
<221> NAME/KEY: misc_feature
<223> OTHER INFORMATION: C-myc
```

<400> SEQUENCE: 44

```
ctgctcgcgg ccgccaccgc cgggccccgg ccgtccctgg ctcccctcct gcctcgagaa      60
gggcagggct tctcagaggc ttggcgggaa aaagaacgg agggagggat cgcgctgagt     120
ataaaagccg gttttcgggg ctttatctaa ctcgctgtag taattccagc gagaggcaga    180
gggagcgagc gggcggccgg ctagggtgga agagccgggc gagcagagct gcgctgcggg    240
cgtcctggga agggagatcc ggagcgaata ggggcttcg cctctggccc agccctcccg     300
cttgatcccc caggccagcg gtccgcaacc cttgccgcat ccacgaaact tgcccatag     360
cagcgggcgg gcactttgca ctggaactta caacacccga gcaaggacgc gactctcccg    420
acgcggggag gctattctgc ccatttgggg acacttcccc gccgctgcca ggacccgctt    480
ctctgaaagg ctctccttgc agctgcttag acgctggatt tttttcgggt agtggaaaac    540
cagcagcctc ccgcgacgat gccctcaac gttagcttca ccaacaggaa ctatgacctc     600
gactacgact cggtgcagcc gtatttctac tgcgacgagg aggagaactt ctaccagcag    660
cagcagcaga gcgagctgca gccccggcg cccagcgagg atatctggaa gaaattcgag     720
ctgctgccca ccccgcccct gtcccctagc cgccgctccg ggctctgctc gccctcctac    780
gttgcggtca caccttctc ccttcgggga acaacgacg gcggtggcgg gagcttctcc      840
acggccgacc agctggagat ggtgaccgag ctgctgggag gagacatggt gaaccagagt    900
ttcatctgcg acccggacga cgagaccttc atcaaaaaca tcatcatcca ggactgtatg    960
tggagcggct tctcggccgc cgccaagctc gtctcagaga agctggcctc ctaccaggct   1020
gcgcgcaaag acagcggcag cccgaacccc gcccgcggcc acagcgtctg ctccacctcc   1080
agcttgtacc tgcaggatct gagcgccgcc gcctcagagt gcatcgaccc ctcggtggtc   1140
ttccctacc ctctcaacga cagcagctcg cccagtcct gcgcctcgca agactccagc    1200
gccttctctc cgtcctcgga ttctctgctc tcctcgacgg agtcctcccc gcagggcagc   1260
cccgagcccc tggtgctcca tgaggagaca ccgcccacca ccagcagcga ctctgaggag   1320
gaacaagaag atgaggaaga aatcgatgtt gtttctgtgg aaaagaggca ggctcctggc   1380
aaaaggtcag agtctggatc accttctgct ggaggccaca gcaaacctcc tcacagccca   1440
ctggtcctca gaggtgcca cgtctccaca catcagcaca actacgcagc gcctccctcc   1500
actcggaagg actatcctgc tgccaagagg gtcaagttgg acagtgtcag agtcctgaga   1560
cagatcagca caaccgaaa atgcaccagc cccaggtcct cggacaccga ggagaatgtc   1620
aagaggcgaa cacacaacgt cttggagcgc cagaggagga acgagctaaa acggagcttt   1680
tttgcccctgc gtgaccagat cccggagttg gaaaacaatg aaaaggcccc caaggtagtt   1740
atccttaaaa aagccacagc atacatcctg tccgtccaag cagaggagca aaagctcatt   1800
tctgaagagg acttgttgcg gaaacgacga gaacagttga acacaaaact gaacagcta    1860
cggaactctt gtgcgtaagg aaaagtaagg aaaacgattc cttctaacag aaatgtcctg   1920
agcaatcacc tatgaacttg tttcaaatgc atgatcaaat gcaacctcac aaccttggct   1980
gagtcttgag actgaaagat ttagccataa tgtaaactgc ctcaaattgg actttgggca   2040
taaaagaact tttttatgct taccatcttt tttttttctt taacagattt gtatttaaga   2100
attgttttta aaaattttta a                                             2121
```

<210> SEQ ID NO 45
<211> LENGTH: 439
<212> TYPE: PRT
<213> ORGANISM: Homo sapiens
<220> FEATURE:

```
<221> NAME/KEY: misc_feature
<223> OTHER INFORMATION: C-myc

<400> SEQUENCE: 45

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Ser Phe Ser Thr Ala
                85                  90                  95

Asp Gln Leu Glu Met Val Thr Glu Leu Leu Gly Gly Asp Met Val Asn
                100                 105                 110

Gln Ser Phe Ile Cys Asp Pro Asp Asp Glu Thr Phe Ile Lys Asn Ile
            115                 120                 125

Ile Ile Gln Asp Cys Met Trp Ser Gly Phe Ser Ala Ala Lys Leu
130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ser Glu Cys Ile Asp Pro Ser
                180                 185                 190

Val Val Phe Pro Tyr Pro Leu Asn Asp Ser Ser Ser Pro Lys Ser Cys
            195                 200                 205

Ala Ser Gln Asp Ser Ser Ala Phe Ser Pro Ser Ser Asp Ser Leu Leu
            210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
                260                 265                 270

Pro Gly Lys Arg Ser Glu Ser Gly Ser Pro Ser Ala Gly Gly His Ser
            275                 280                 285

Lys Pro Pro His Ser Pro Leu Val Leu Lys Arg Cys His Val Ser Thr
            290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
            340                 345                 350

Asn Val Lys Arg Arg Thr His Asn Val Leu Glu Arg Gln Arg Arg Asn
            355                 360                 365

Glu Leu Lys Arg Ser Phe Phe Ala Leu Arg Asp Gln Ile Pro Glu Leu
        370                 375                 380

Glu Asn Asn Glu Lys Ala Pro Lys Val Val Ile Leu Lys Lys Ala Thr
385                 390                 395                 400
```

Ala Tyr Ile Leu Ser Val Gln Ala Glu Glu Gln Lys Leu Ile Ser Glu
            405                 410                 415

Glu Asp Leu Leu Arg Lys Arg Arg Glu Gln Leu Lys His Lys Leu Glu
        420                 425                 430

Gln Leu Arg Asn Ser Cys Ala
    435

<210> SEQ ID NO 46
<211> LENGTH: 11
<212> TYPE: PRT
<213> ORGANISM: HIV
<220> FEATURE:
<221> NAME/KEY: misc_feature
<223> OTHER INFORMATION: TAT protein

<400> SEQUENCE: 46

Tyr Gly Arg Lys Lys Arg Arg Gln Arg Arg Arg
1               5                   10

<210> SEQ ID NO 47
<211> LENGTH: 54
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: Prox-1 sense

<400> SEQUENCE: 47
tggtcatctg caagctggat tcaagagaa tccagcttgc agatgacctt tttc         54

<210> SEQ ID NO 48
<211> LENGTH: 58
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: Prox-1 anti-sense

<400> SEQUENCE: 48
tcgagaaaaa aggtcatctg caagctggat tctcttgaaa tccagcttgc agtgacca    58

<210> SEQ ID NO 49
<211> LENGTH: 55
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: Prox-2 sense

<400> SEQUENCE: 49
tgagccagtt tgatatggat ttcaagagaa tccatatcaa actggctctt ttttc       55

<210> SEQ ID NO 50
<211> LENGTH: 58
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<223> OTHER INFORMATION: Prox-2 anti-sense

```
<400> SEQUENCE: 50
tcgagaaaaa agagccagtt tgatatggat tctcttgaaa tccatatcaa actgctca        58
```

MATERIALS AND METHODS FOR COLORECTAL CANCER SCREENING, DIAGNOSIS AND THERAPY

This application is a U.S. National Phase of PCT/EP2004/008819, filed Aug. 6, 2004, which claims the benefit of priority to U.S. Application Ser. No. 60/494,221, which was filed on Aug. 8, 2003. The contents of all priority applications are incorporated herein by reference in their entireties.

The file copy of the sequence listing is submitted on a Compact-Disc Read Only Memory (CD-ROM). The sequence listing is saved as an ASCII DOS text file named 39467A.txt (375 KB), which was created on Feb. 8, 2006. The contents of the CD-ROM are incorporated herein by reference in its entirety.

FIELD OF THE INVENTION

The present invention relates generally to methods and materials for altering colorectal cancer progression. The present invention also relates to techniques for screening for colon cancer and/or premalignancies.

BACKGROUND

The transcription factor Prox-1 is expressed in a number of tissues during embryonic development, including lens fiber cells, subpopulation of neurons in brains and neural tube, skeletal muscle, heart, liver, pancreas and lymphatic endothelial cells. Targeted inactivation of Prox-1 results in the defects of eye development because of the failure of lens fiber cells to elongate (Wigle et al., Nat. Genet. 21: 318-22, 1999). Prox-1 is also necessary for the migration of hepatocytes during liver development (Sosa-Pineda et al., Nat. Genet. 25: 254-5, 2000). In addition, Prox-1 deficient embryos lack lymphatic vasculature, while the blood vessel development is not affected (Wigle et al., Cell 98: 769-778, 1999).

Recently, others and we have demonstrated the essential role of Prox-1 in the regulation of the lymphatic endothelial phenotype. Overexpression of Prox-1 in blood vascular endothelial cells, where it is otherwise absent, leads to the increased expression of lymphatic endothelial markers and to the suppression of the genes characteristic for the blood vascular endothelial lineage (Petrova et al., Embo J. 21: 4593-9, 2002; Hong et al., Dev. Dyn. 225: 351-7, 2002).

Notch is a transmembrane protein that acts as a receptor in a cell-cell signaling mechanism, and in combination with other cellular factors, influences differentiation, proliferation and apoptotic events at all stages of development (Artavanis-Tsakonas, Science 284: 770-776, 1999). In animal models, mutations in the Notch receptor have resulted in developmental abnormalities (Joutel et al., Nature 383: 707, 1996; Li. et al., Nature Genet. 16:243, 1997).

Cancer treatments generally promote tumor regression by inhibiting tumor cell proliferation, inhibiting angiogenesis (growth of new blood vessels that is necessary to support tumor growth) and/or prohibiting metastasis by reducing tumor cell motility or invasiveness. Colon cancers are a very common malignancy and colon cancers are typically adenocarcinomas, or sometimes carcinoid tumors. Treatment is primarily surgical resection of the colon, although chemotherapy has been found to be beneficial in some cases. These treatment options for colon cancer are of unpredictable and sometimes limited value, especially if the cancer has not been identified and removed at early stages. There continues to exist a need for novel therapies and diagnostic methods for cancer conditions.

SUMMARY OF THE INVENTION

The present invention addresses one or more ongoing needs by providing materials and methods for screening for and treating cancerous and precancerous conditions, especially colorectal in nature.

As one aspect, the invention provides materials and methods to screen a mammalian subject for a cancerous or precancerous condition based on analysis of Prox-1 expression in cells from the mammalian subject. In particular, materials and methods are provided for screening colon tissue for signs of cancerous or precancerous pathology.

For example, the method includes a method of screening colon tissue for a pathological condition, said method comprising:

measuring Prox-1 expression in a biological sample that comprises colon tissue from a mammalian subject, wherein elevated Prox-1 expression in the colon tissue correlates with a pathological phenotype. The determination of elevated Prox-1 expression is generally made by way of a comparison, e.g., to a measurement of Prox-1 expression in healthy colon tissue (from the same subject or others of the same species, preferably matched for sex, age, race, or other characteristics); or to a measurement of Prox-1 expression in diseased (especially neoplastic) colon tissue. When comparing Prox-1 expression in the colon tissue to Prox-1 expression in healthy colon tissue, an increased (e.g., elevated) Prox-1 expression in the colon tissue from the mammalian subject correlates with a pathological phenotype. When comparing to diseased tissue, comparable levels of expression in the tissue from the subject correlates with a pathological phenotype.

In another, related example, the invention includes a method of screening colon tissue for a pathological condition, the method comprising steps of:

(a) obtaining a biological sample comprising colon tissue from a mammalian subject;
(b) measuring Prox-1 expression in the colon tissue; and (c) screening for the presence or absence of a pathological condition from the measurement of Prox-1 in the sample.

Similarly, the invention includes a method of screening colon tissue for a pathological condition, the method comprising steps of: (a) obtaining a biological sample comprising colon tissue from a mammalian subject; (b) measuring Prox-1 expression in the colon tissue; and (c) comparing Prox-1 expression in the colon tissue to Prox-1 expression in healthy colon tissue, wherein increased Prox-1 expression in the colon tissue correlates with a pathological phenotype.

For this type of method, the term "pathological condition" is intended to include any abnormality or evidence of disease that warrants medical treatment or monitoring due to concern of developing disease. Cancers and precancerous changes in tissue are particularly contemplated. Thus, in preferred embodiments, the method can be characterized as a screen for colon cancer or colorectal cancers, and increased Prox-1 expression in the colon tissue is scored as being indicative of a cancerous or precancerous condition.

The method can be combined with any other molecular, cellular, pathological, or patient symptom criteria to assist a medical practitioner in early diagnosis and therapeutic or prophylactic therapy. For example, in one variation, the method further comprises measuring expression of at least one gene or protein selected from the group consisting of CD44, Enc1, and ID2 in the colon tissue, wherein elevated Prox-1 expression and elevated expression of the at least one gene/protein in the colon tissue correlate with a pathological phenotype. In another variation, the method further comprising measuring activation of -catenin/TCF pathway in the colon tissue, wherein activation of the -catenin/TCF pathway and elevated Prox-1 expression in the colon tissue correlate with a pathological phenotype. Activation of the -catenin/TCF pathway can be measured by a variety of indicators, including mutations in an APC gene; mutations in a -catenin gene; and nuclear localization of -catenin.

The biological sample is any tissue or fluid sample obtained in any way from a mammalian subject that includes cells from the large intestine. Biopsies or other surgically removed specimens are preferred. Stool or feces may contain sufficient colon tissue for some embodiments of the assay.

The assay may be performed on any mammalian subject, including laboratory animals used in cancer research, livestock, and domestic pets. Humans are most preferred.

Any available technique can be used for measuring Prox-1 expression, including direct and indirect techniques. For example, in one variation, the measuring comprises measuring Prox-1 protein in the biological sample. Preferred techniques for measuring amounts or concentrations of Prox-1 protein in a sample are immunological techniques that involve use of a polyclonal or monoclonal antibody that specifically binds Prox-1, or use of a Prox-1-binding fragment of such an antibody. For example, the measuring comprises contacting the colon tissue with a Prox-1 antibody or antigen-binding fragment thereof. Quantification of the amount of bound antibody (e.g., using a label or second, labeled antibody) provides a measurement of Prox-1 protein expressed in the sample. Immunoassays such as radioimmunoassay, immunoradiometric assay (labeled antibody), or an enzyme-linked immunosorbent assay (ELISA) are contemplated.

In another variation, the measuring comprises measuring Prox-1 mRNA in the colon tissue. Elevated levels of Prox-1 mRNA in the sample are scored as elevated Prox-1 expression. Any available assay for measuring specific oligonucleotides is suitable. Preferred materials for such measurements are oligonucleotide probes complementary to all or a portion of the Prox-1 mRNA sequence. Probes of at least 14 and more preferably 18 nucleotides are preferred to assure specificity. One technique for measuring Prox-1 mRNA comprises in situ hybridization to measure Prox-1 mRNA in the colon sample. Other techniques involve steps of isolating mRNA from the colon tissue and measuring Prox-1 mRNA in the isolated mRNA, for example, by Northern hybridization procedures. In still another variation, quantitative reverse transcriptase polymerase chain reaction (PCR), real-time PCR, or other PCR techniques are employed to quantitatively amplify Prox-1 mRNA (relative to control samples) to provide a quantitative measurement of Prox-1 mRNA in the colon tissue.

In yet another embodiment, Prox-1 expression is measured indirectly by measuring a functional property of Prox-1, such as measuring Prox-1 binding to DNA or downstream Prox-1 transcription factor effects.

The screening method further includes a comparing step whereby Prox-1 expression in the colon tissue is compared to Prox-1 expression in healthy colon tissue, wherein increased Prox-1 expression in the colon tissue correlates with a pathological phenotype. As described herein, Prox-1 expression is elevated in a statistically significant manner in pathological specimens studied, compared to healthy colon tissue samples. In one variation, the comparison is performed by taking simultaneous or sequential measurements of a test sample and a sample of colon tissue that is known to be taken from healthy tissue. In another variation, data is accumulated on the quantity of Prox-1 mRNA or protein in healthy tissues, and the amount that is measured in the colon tissue from the biological sample is compared to this predetermined amount. It will be appreciated that comparing Prox-1 measurements from a test sample to measurements from a cancerous or precancerous condition can provide an equivalent indication of the presence or absence of the pathological condition, wherein a test sample with Prox-1 expression comparable to the elevated level observed in a cancer correlates with a pathological phenotype.

For measurement comparisons, a database of Prox-1 measurements from colon tissues can be developed, preferably containing information about healthiness or disease of the tissue; age, sex, race/ethnicity of the donor, and location from which the sample was taken. With a database of samples, comparisons can be analyzed using statistical analysis to determine the statistical significance of a measurement's deviation from a mean, optionally selecting entries from the database by selecting for the patient's age, sex, ethnicity, and other factors to best match the patient (mammalian subject) being tested. Such statistical analysis permits establishment of one or more "cutoff" values for the Prox-1 measurement that are correlated with a likelihood of having, or developing, a cancerous condition.

If elevated Prox-1 is detected, then in a preferred embodiment, the method further comprises a step of administering to a human subject identified as having a pathological condition characterized by increased Prox-1 expression in colon tissue a composition comprising a Prox-1 inhibitor.

In a related embodiment, the invention provides a method of inhibiting the growth of colon cancer cells, such as colon carcinoma cells, colon adenoma cells, or colon adenocarcinoma cells in a mammalian subject comprising a step of:

administering to the subject a composition comprising a molecule that suppresses expression of Prox-1, thereby inhibiting the growth of colon carcinoma cells.

For reasons of cost, safety, and efficacy, it is becoming increasingly preferred to attempt to identify patients most likely to benefit from a therapeutic regimen before administering it. This is especially true with cancers where it is known that not all patients respond the same to all therapies. Thus, in a preferred variation of the method, steps are taken to identify patients most likely to benefit from this regimen. For example, the method further comprises a step of identifying a mammalian subject with a colon cancer characterized by increased Prox-1 expression. The composition is administered to such a patient after the identifying step, because cancers characterized by the elevated expression are expected to be the cancers most likely to respond to the inhibitors. Exemplary cancers (neoplasms) in which Prox-1 elevation has been observed include colorectal adenomas and colorectal carcinomas, as described below in greater detail.

The composition to be administered preferably includes, in addition to the Prox-1 inhibitor, a pharmaceutically acceptable diluent, adjuvant, or carrier medium. The composition optionally includes additional antineoplastic agents.

Administration of any Prox-1 inhibitors, alone or in combination, is contemplated for this invention, either alone or in combination with other Prox-1 inhibitors or other antineoplastic agents. Exemplary inhibitor molecules include antisense oligonucleotides that inhibit Prox-1 expression; microRNA that inhibits Prox-1 expression; small (short) interfering RNA (siRNA) that inhibit Prox-1 expression (e.g., siRNA that comprise at least one nucleotide sequence set forth in SEQ ID NOS: 4, 5, 6, and 7); zinc finger proteins that inhibit Prox-1 expression; polypeptides that act as dominant negative form of Prox-1 protein, such as Prox-1 forms that have a disrupted DNA binding domain or transactivation domain(s); polynucleotides that encode dominant-negative Prox-1 proteins; Prox-1 antibodies and fragments thereof; polynucleotides that encode Prox-1 antibodies or encode polypeptides that comprise Prox-1 binding domains; small molecules discovered and designed through screening based on the teachings herein, and so on. U.S. Patent Application Publication No. 2003/0224516 discloses exemplary molecules for inhibiting Prox-1 expression and is incorporated herein by reference.

The inhibitor is preferably administered in an amount and in a regimen that halts or inhibits neoplastic growth of the affected colorectal tissue. As another benchmark, the tissue itself preferably reverts to a non-transformed, more healthy looking phenotype. As described herein, one apparent benchmark of beneficial administration is an increase in Notch-1 signaling. Thus, in one variation, the composition is administered in an amount effective to suppress Prox-1 expression and increase Notch 1 signaling.

Other indications of efficacy relate to modulation of prostaglandin synthesis. Thus, in another variation, the composition is administered in an amount effective to increase 15-PDGH activity or decrease prostaglandin D2 synthase activity.

As described herein and in literature, colorectal cancers also are often characterized by increases in the -catenin/TCF signaling pathway, relative to what is observable in healthy colorectal tissue. Thus, in a preferred variation, in addition to administering a Prox-1 inhibitor composition, the regimen further comprises administering to the subject an inhibitor of the -catenin/TCF signaling pathway. (Optionally, the patient's diseased tissue is first pre-screened for elevated expression/signaling of this pathway.) The categories of inhibitors described above for Prox-1 are specifically contemplated for the -catenin/TCF pathway as well. In one variation, the inhibitor of the -catenin/TCF signaling pathway is dominant negative form of TCF-4. The inhibitor optionally targets (inhibits) TCF-4, β-catenin, or c-myc expression or activity.

In yet another variation, administration of the Prox-1 inhibitor is combined with administration of a COX-2 inhibitor, such as any of the increasing class of non-steroidal anti-inflammatory agents.

In still another variation, administration of the Prox-1 inhibitor is combined with administration of a Notch signaling pathway agonist, such as a Notch ligand or expression vector to cause expression of a Notch ligand. Exemplary Notch ligands include Jagged1, Jagged2, Delta1, Delta3, Delta4, or Serrate.

Also contemplated is administration of a molecule that comprises an inhibitor of DNA methyltransferases. Such inhibitors are themselves contemplated as efficacious for inhibiting Prox-1 expression, and can be combined with any other Prox-1 inhibitor described herein for combination therapy. An exemplary methyltransferase inhibitor is 5-aza-2'-deoxycytidine.

In still another variation, the Prox-1 inhibitor composition is administered in combination with any known antineoplastic agent that is used in cancer therapy.

In still another variation, the Prox-1 inhibitor and/or Cox-2 inhibitor are combined (in a medicament or as a combination therapy) with an agent that induces differentiation in colorectal cancer cell lines. Exemplary agents include 1,25-dihydroxyvitamin D3 and analogs thereof; butyrate; and retinoids.

With respect to any combination treatment or therapy regimens described herein, the Prox-1 inhibitor composition can be administered simultaneously with the other active agents, which may be in admixture with the Prox-1 inhibitor, or may be in a separate composition. Each composition preferably includes a pharmaceutically acceptable diluent, adjuvant, or carrier. When the agents are separately administered, they may be administered in any order.

In still another embodiment, the invention includes a method of inhibiting Prox-1 function in a mammalian subject having a disease characterized by of Prox-1 over-expression in cells, comprising the step of administering to said mammalian subject a composition, said composition comprising a compound effective to inhibit Prox-1 function in cells.

In still another variation, the invention includes the use of a Prox-1 inhibitor in the manufacture of a medicament for the treatment of a disease characterized by Prox-1 over-expression in cells, especially cancerous or precancerous cells of colorectal origin. The medicament optionally includes the additional agents described above, either in admixture with the Prox-1 inhibitor or separated, yet packaged together (preferably with instructions for treating the disease).

In yet another embodiment, the invention provides a method of screening for Prox-1 modulators comprising the steps of: (a) contacting a test molecule with Prox-1 protein, or a nucleic acid comprising a nucleotide sequence that encodes Prox-1 protein, under conditions which permit the interaction of the test molecule with the Prox-1 protein or nucleic acid; and (b) measuring the interaction between the test molecule and Prox-1 protein or the nucleic acid, wherein a test molecule that binds the Prox-1 protein or nucleic acid is identified as a Prox-1 modulator.

"Test molecule" refers to the molecule that is under evaluation for the ability to modulate (i.e., increase or decrease) the activity of Prox-1 protein. Most commonly, a test molecule that is a Prox-1 modulator will interact directly with Prox-1. However, the screens described herein can identify test molecules that modulate Prox-1 protein activity indirectly, such as by affecting Prox-1 gene expression. The screens work with essentially any test molecule, and the invention is not limited in this manner. In preferred embodiments, the test molecule is a protein, a carbohydrate, a lipid, or a nucleic acid. Molecules which regulate Prox-1 expression include nucleic acids which are complementary to nucleic acids encoding a Prox-1 protein, or are complementary to nucleic acid sequences which direct or control the expression of Prox-1 protein, and which act as anti-sense regulators of expression. The test molecule may be a member of a chemical library, such as libraries commonly maintained in large pharmaceutical companies or libraries generated combinatorially. In alternate embodiments, the test molecule interacts with Prox-1 by binding to the Prox-1 DNA binding domain, thereby effecting Prox-1 activity.

With respect to the screening methods described herein, it may be desirable to evaluate two or more test compounds together for their ability to increase or decrease the Prox-1 protein activity or expression. The assays set forth herein can be readily modified by adding such additional test compounds either simultaneous with, or subsequent to, or prior to, the first test compound. In additional embodiments, the measurement of the interaction of test molecules with Prox-1 may is carried out using solution-phase assays or immunoassays. In other embodiments, measurement of the interaction of test molecules with Prox-1 is carried out by evaluating biological activity of Prox-1.

In a related embodiment, the invention provides a method of screening for modulators of binding between a DNA and Prox-1 protein comprising steps of: (a) contacting a DNA with a Prox-1 protein in the presence and in the absence of a putative modulator compound; (b) detecting binding between the DNA and the Prox-1 protein in the presence and absence of the putative modulator compound; and (c) identifying a modulator compound based on a decrease or increase in binding between the DNA and the Prox-1 protein in the presence of the putative modulator compound, as compared to binding in the absence of the putative modulator compound.

In a related variation, molecules that modulate binding between DNA and Prox-1 are formulated into a composition or a growth media for contacting a cell from a colorectal cancer or colorectal cancer cell line, and a modulator that inhibits growth of the cell is selected as a preferred modulator for development as a therapeutic.

In yet another related embodiment, the invention provides a method of screening for modulators of binding between a DNA and Prox-1 protein comprising steps of: (a) contacting a DNA with a Prox-1 protein in the presence and in the absence of a putative modulator compound; (b) detecting binding between the DNA and the Prox-1 protein in the presence and absence of the putative modulator compound; and (c) identifying a modulator compound based on a decrease or increase in differentiation in the presence of the putative modulator compound, as compared to differentiation in the absence of the putative modulator compound.

In vivo screening also is contemplated, either in addition to or in place of in vitro screening. The test compound preferably is formulated into a pharmaceutically acceptable diluent, adjuvant, or carrier. In a preferred variation, this formulation is administered to a mammal with pathological (e.g., cancerous) Prox-1 expressing colon tissue, and the efficacy of the formulation at inhibiting disease progression is monitored. For example, a method described above optionally further comprises steps of formulating a composition comprising the selected Prox-1 modulator and a pharmaceutically acceptable carrier; administering the composition to a mammalian subject having a colorectal cancer; and monitoring the mammalian subject for growth, metastasis, shrinkage, or disappearance of the colorectal cancer.

"Putative modulator compounds" are analogous to the "test molecules" described above in that they are alleged to have an effect on Prox-1 protein activity and are being identified as such using the methods described herein. In certain embodiments detecting DNA binding to Prox-1 protein and identifying an increase or decrease of DNA binding to Prox-1 protein employs immuno-based assays or various other assays that measure biological activity. Likewise, embodied by the invention are methods wherein identifying a modulator compound the use of proliferation and/or differentiation assays.

In still another variation of the invention, provided are short interfering RNA (siRNA) molecules that down regulate expression of Prox-1 by RNA interference. The siRNA molecule can be adapted for use to treat colorectal cancer and any other indications that respond to the level of Prox-1. The siRNA molecule comprises a sense region and an antisense region. The antisense region comprises sequence complementary to an RNA sequence encoding Prox-1, or a fragment thereof, and the sense region comprise sequence complementary to the antisense region. In additional embodiments, the siRNA molecule can comprise two nucleic acid fragments, wherein one fragment comprises the sense region and the second fragment comprises the antisense region of said siRNA molecule.

In one embodiment, a siRNA molecule of the invention can comprise any contiguous Prox-1 sequence. Preferably, the siRNA constructs are between 18 and 100 nucleotides in length. More preferably, the siRNA constructs are 21 nucleotides in length. In still another embodiment, the sense region of a siRNA molecule of the invention comprises a 3'-terminal overhang and the antisense region comprises a 3'-terminal overhang. The 3'-terminal overhangs each are preferably from 1 to 5 nucleotides. More preferably, the 3'-terminal overhangs are 2 nucleotides. In a preferred embodiment, the antisense region of the 3'-terminal nucleotide overhang is complementary to RNA encoding Prox-1.

With respect to the antisense region of the siRNA constructs, the antisense region of Prox-1 siRNA constructs can comprise a sequence complementary to sequence having any of SEQ ID NOs. 4 and 6. Further, the antisense region of Prox-1 siRNA constructs can comprise a having any of SEQ ID NOs. 5 and 7.

In yet an additional embodiment of the invention, compounds, particularly antisense oligonucleotides, which are targeted to a nucleic acid encoding Prox-1, and which modulate the expression of Prox-1 are provided. The antisense oligonucleotides of the invention are preferably complementary to (at least a segment of) the genomic Prox-1 sequence set forth as SEQ ID NO: 1. mRNA splice sites, i.e., intron-exon junctions, may be preferred target regions. Accordingly, in another embodiment, the antisense oligonucleotides of the invention comprise a region complementary to a promoter or other control region, an exon, an intron, or an exon-intron boundary. Also embodied by the present invention are antisense oligonucleotides that are complementary to a region within 20-200 bases of an exon-intron splice junction. As detailed herein, pharmaceutical compositions comprising antisense oligonucleotides are also provided.

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. Where protein therapy is described, embodiments involving polynucleotide therapy (using polynucleotides that encode the protein) are specifically contemplated, and the reverse also is true.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 1C illustrates the quantification of dot blot in FIG. 1A, the asterisk indicating tumor samples in which Prox-1 expression is significantly different from that of the normal tissue ($P<0.005$).

FIG. 2C and FIG. 2I show high power magnification of adenoma and normal colon sections.

DETAILED DESCRIPTION

Figure 1:
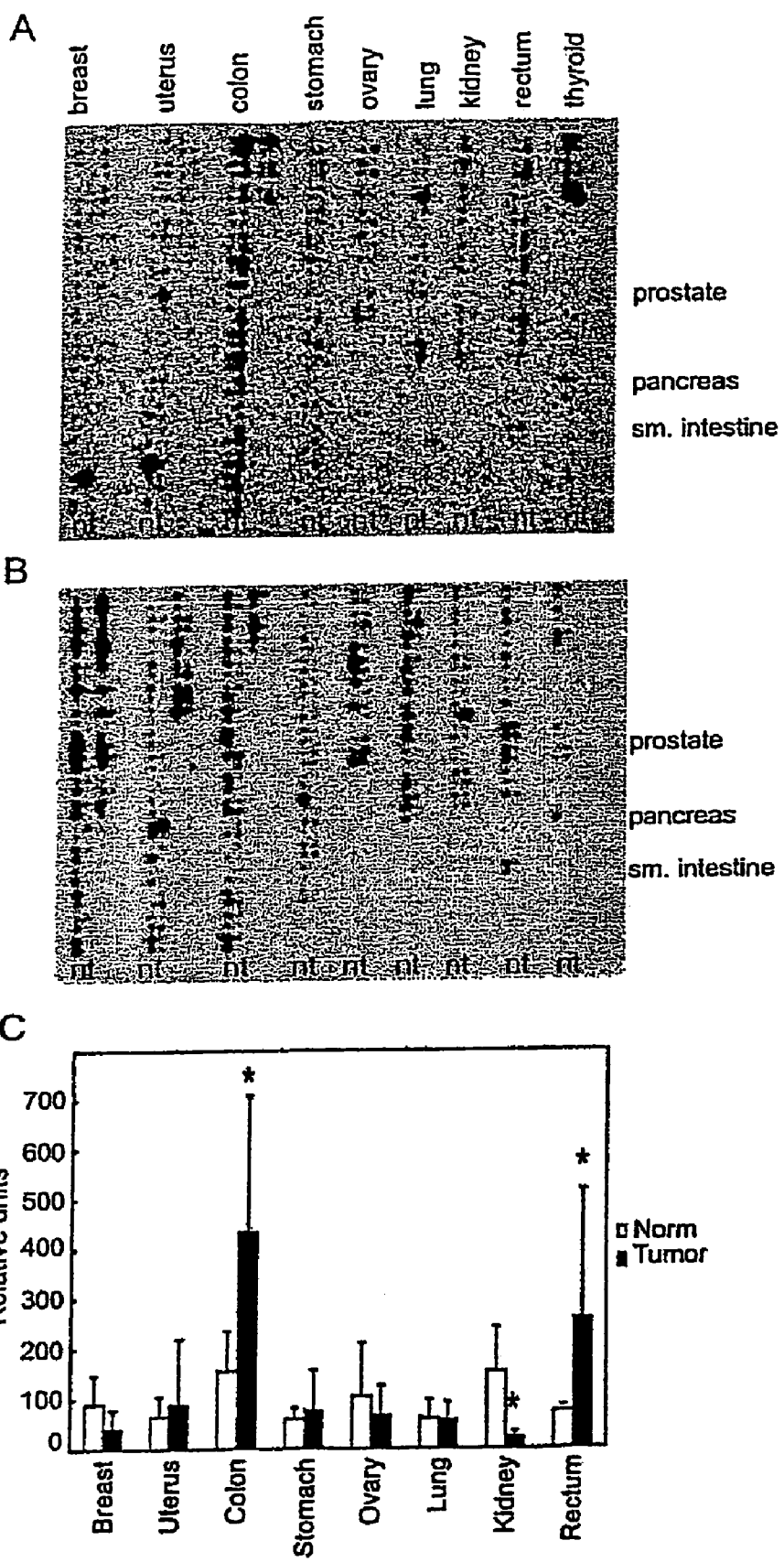
FIGS. 1A, 1B, and 1C depict the elevated Prox-1 mRNA levels in colorectal tumors. A cancer RNA profiling array was hybridized to probes for Prox-1 (FIG. 1A) and the lymphatic endothelial marker LYVE-1 (FIG. 1B).
Figure 2:
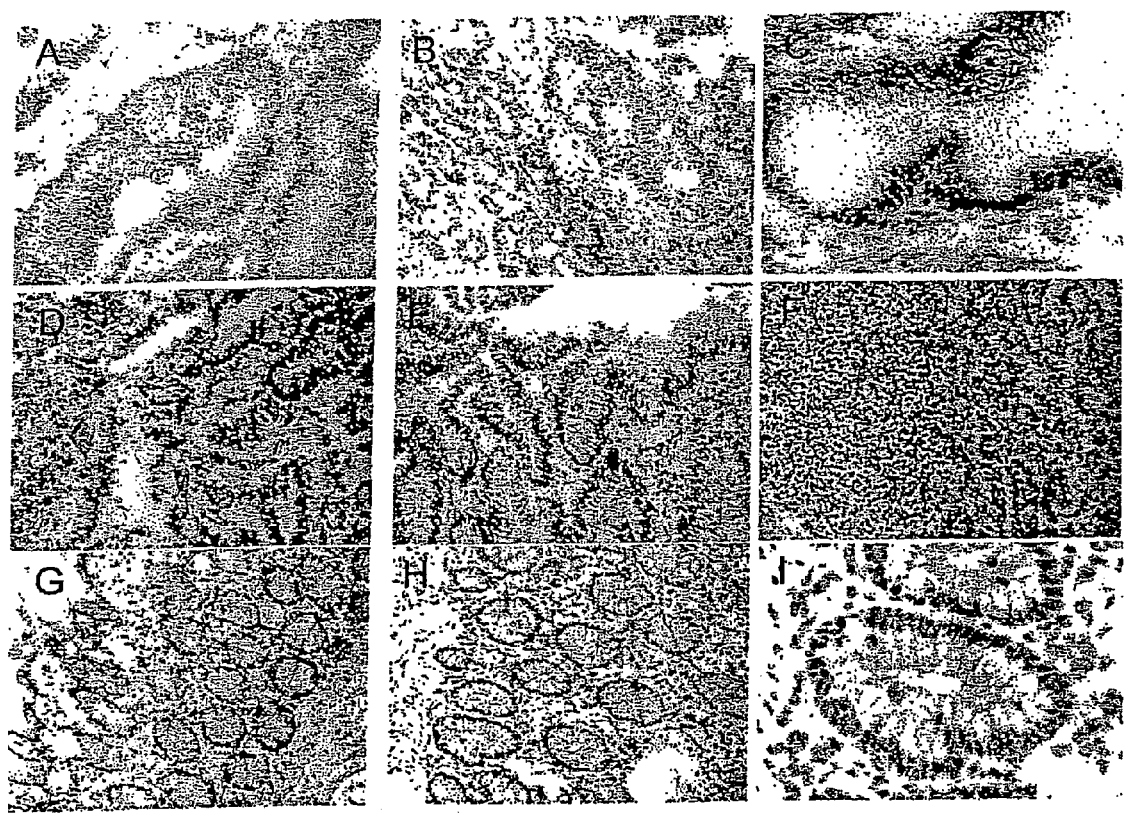
FIGS. 2A-2I depict Prox-1 expression patterns in colon cancer and normal colonic epithelium. Frozen sections of colon adenomas (FIG. 2A-C) or adenocarcinomas (FIG. 2D-F) and the corresponding normal tissues (FIG. 2H-I) were stained for Prox-1.

Demonstrated herein for the first time is the importance of Prox-1 in cancer. The Prox-1 gene and protein is overexpressed in colorectal cancers, as compared to healthy colon tissue and other cancer tissues. Prox-1 was overexpressed in 68% of colorectal carcinomas and in 80% of premalignant lesions that were examined, indicating that Prox-1 is important for tumorigenesis, and therefore a useful marker for screening and a useful target for intervention. In normal colonic epithelium, Prox-1 expression was restricted to two cell types, neuroendocrine cells and non-proliferating cells at the very base of the colonic crypts, a location that corresponds to the stem cell compartment. Contemplated and provided for in the present invention are polynucleotides and polypeptides for screening and diagnosis of colorectal cancer and/or premalignancies.

Intervention to suppress Prox-1 expression in colorectal cells resulted in increased activation of Notch signal transduction. Specifically, ablation of Prox-1 resulted in cell growth arrest and increased expression of epithelial markers. This was accompanied by an upregulation of the cell cycle inhibitor p21cip1, which has been shown to be important for the differentiation of intestinal epithelia (Quaroni et al., Am. J. Physiol. Cell Physiol. 279: C1045-57, 2000; Yang et al., Cancer Res. 61, 565-9, 2001), and by an increased expression of components of the Notch signaling pathway. Unexpectedly, this phenotype persisted for up to two weeks after transient transfection with Prox-1 siRNAs, demonstrating profound changes in the transcriptional program induced in the absence of Prox-1. Without intending to be limited to a particular theory or mechanism, Prox-1 may be involved in the maintenance of an undifferentiated state of colonic intestinal stem cells, and overexpression of Prox-1 in cancer cells and resulting inhibition of the Notch signaling pathway may lead to the de-differentiation frequently observed upon malignant transformation. The suppression of Prox-1 expression also negatively regulates prostaglandin activity in the tumor cell lines studied. It is, therefore, contemplated that suppression of Prox-1 or activation of Notch signaling in tumor cells can provide a differentiation therapy for colon carcinoma. The present invention, more specifically, provides compositions and methods for suppressing Prox-1 expression.

A. Inhibitory Nucleic Acid Constructs for the Suppression of Prox-1 Expression As discussed herein, Prox-1 is overexpressed in colorectal cancer cells and suppression of Prox-1 expression results in increased Notch signal transduction and modified expression of enzymes of the prostaglandin biosynthetic pathway. This data provides an indication to disrupt the expression or activity of Prox-1 as a method of alleviating the symptoms of and/or inhibiting the growth or metastasis of colon cancer. Such disruption is achieved using any materials or methods available to inhibit Prox-1 mRNA or protein expression, or inhibit Prox-1 binding, and any Prox-1 activity. The present section discusses nucleic acid-based methods of disrupting the expression of Prox-1. Polynucleotide products which are useful in this endeavor include antisense polynucleotides, ribozymes, small interfering RNAs, natural or designed microRNAs, triple helix polynucleotides, and novel transcription factors that modulate the expression of Prox-1 protein.

Techniques for making and delivering antisense polynucleotides and ribozymes are well known to those in the art and have been extensively described in scientific, patent, and trade literature. (PCT Publication No. WO 00/32765; (J Biol Chem; 272:626-38. 1997); Kurreck et al., (Nucleic Acids Res.; 30:1911-8. 2002); Crooke and B. Lebleu, eds. Antisense Research and Applications (1993) CRC Press; and Antisense RNA and DNA (1988) D. A. Melton, Ed. Cold Spring Harbor Laboratory Cold Spring Harbor, N.Y.) Anti-sense RNA and DNA molecules act to directly block the translation of mRNA by binding to targeted mRNA and preventing protein translation. An example of an antisense polynucleotide is an oligodeoxyribonucleotide derived from the translation initiation site, e.g., between −10 and +10 regions of the relevant nucleotide sequence. Antisense oligonucleotides of 8-200 nucleotides in length that include at least a portion of this region of the Prox-1 cDNA or genomic sequences set forth as SEQ ID NOs: 1 and 2 (or are complementary to) are preferred Prox-1 inhibitors of the invention.

Antisense polynucleotides are typically generated within the cell by expression from antisense constructs that contain the antisense nucleic acid strand as the transcribed strand. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. Highly effective antisense constructs include regions complementary to intron/exon splice junctions. Thus, a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

For purposes of making antisense oligonucleotides, polynucleotide sequences that are substantially complementary over their entire length and have zero or very few base mismatches are preferred. For example, sequences of fifteen bases in length preferably have complementary nucleotides at thirteen or fourteen or fifteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozymes) could be designed. These molecules, though having less than 50% homology, would bind to target sequences under appropriate conditions.

Methods for designing and optimizing antisense nucleotides are described in Lima et al., (J Biol Chem; 272:626-38. 1997) and Kurreck et al., (Nucleic Acids Res.; 30:1911-8. 2002). Additionally, commercial software and online resources are available to optimize antisense sequence selection and also to compare selected sequences to known genomic sequences to help ensure uniqueness/specificity for a chosen gene. (See, e.g., world wide web at sfold.wadsworth.org/index.pl.) Such uniqueness can be further confirmed by hybridization analyses. Antisense nucleic acids are introduced into cells (e.g., by a viral vector or colloidal dispersion system such as a liposome).

The genomic contig of chromosome 1 (where Prox-1 is located), cDNA for Prox-1, and protein sequences for Prox-1 (SEQ ID NOs: 1, 2, and 3, respectively) are published and disclosed as Genbank Accession Numbers NT_021877, NM_002763, and NM_002763, respectively. The Genbank Database is accessible on the world wide web at ncbi.nlm.nih.gov. Related Prox-1 protein and/or nucleic acid sequences from other sources may be identified using probes directed at these sequences. Such additional sequences may be useful in certain aspects of the present invention. Although antisense sequences may be full length genomic or cDNA copies, they also may be shorter fragments or oligonucleotides e.g., polynucleotides of 100 or less bases. Although shorter oligomers (8-20) are easier to make and more easily permeable in vivo, other factors also are involved in determining the specificity of base pairing. For example, the binding affinity and sequence specificity of an oligonucleotide to its complementary target increases with increasing length. It is contemplated that oligonucleotides of 8, 9, 10, 11, 12, 13, 14, 15, 16, 17, 18, 19, 20, 25, 30, 35, 40, 45, 50, or more base pairs will be used.

Ribozymes are enzymatic RNA molecules capable of catalyzing the specific cleavage of RNA. The cleavage event renders the mRNA unstable and prevents protein expression. The mechanism of ribozyme action involves sequence specific interaction of the ribozyme molecule to complementary target RNA, followed by an endonucleolytic cleavage. Within the scope of the invention are engineered hammerhead, for which the substrate sequence requirements are minimal, or other motif ribozyme molecules that specifically and efficiently catalyze endonucleolytic cleavage of RNA sequences encoding protein complex components. Design of the hammerhead ribozyme and the therapeutic uses of ribozymes are disclosed in Usman et al., Current Opin. Struct. Biol. (1996) 6:527-533. Ribozymes can also be prepared and used as described in Long et al., FASEB J. (1993) 7:25; Symons, Ann. Rev. Biochem. (1992) 61:641; Perrotta et al., Biochem. (1992) 31:16-17; Ojwang et al., Proc. Natl. Acad. Sci. (USA) (1992) 89:10802-10806; and U.S. Pat. No. 5,254,678. Methods of cleaving RNA using ribozymes is described in U.S. Pat. No. 5,116,742; and methods for increasing the specificity of ribozymes are described in U.S. Pat. No. 5,225,337 and Koizumi et al., Nucleic Acid Res. (1989) 17:7059-7071. Preparation and use of ribozyme fragments in a hairpin structure are described by Chowrira and Burke, Nucleic Acids Res. (1992) 20:2835. Ribozymes can also be made by rolling transcription (Daubendiek and Kool, Nat. Biotechnol. (1997) 15(3):273-277).

The full-length gene need not be known in order to design and use specific inhibitory ribozymes. Specific ribozyme cleavage sites within any potential RNA target are initially identified by scanning the target molecule for ribozyme cleavage sites which include the following sequences, GUA, GUU, and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays (Draper PCT WO 93/23569; and U.S. Pat. No. 5,093,246, incorporated herein by reference). Using the nucleic acid sequences disclosed herein and methods known in the art, ribozymes can be designed to specifically bind and cut the corresponding mRNA species. Ribozymes, therefore, provide a means to inhibit the expression Prox-1.

Alternatively, endogenous gene expression can be reduced by inactivating or "knocking out" the gene or its promoter using targeted homologous recombination. (E.g., see Smithies et al., 1985, Nature 317:230-234; Thomas & Capecchi, 1987, Cell 51:503-512; Thompson et al., 1989 Cell 5:313-321). For example, a mutant, non-functional gene (or a completely unrelated DNA sequence) flanked by DNA homologous to the endogenous gene (either the coding regions or regulatory regions of the gene) can be used to transfect cells that express that gene in vivo. Insertion of the DNA construct, via targeted homologous recombination, results in inactivation of the gene.

Gene expression can also be reduced by targeting deoxyribonucleotide sequences complementary to the regulatory region of the target gene (i.e., the gene promoter and/or enhancers) to form triple helical structures that prevent transcription of the gene in target cells in the body. (See generally, Helene, C. 1991, Anticancer Drug Des., 6(6):569-84; Helene, C., et al., 1992, Ann, N.Y. Acad. Sci., 660:27-36; and Maher, L. J., 1992, Bioassays 14(12):807-15). Nucleic acid molecules used in triple helix formation for the inhibition of transcription are generally single stranded deoxyribonucleotides. The base composition must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Another technique for inhibiting the expression of a gene involves the use of RNA for induction of RNA interference (RNAi), using double stranded (dsRNA) (Fire et al, *Nature* 391: 806-811. 1998) or small interfering RNA (siRNA) sequences (Elbashir et al, Nature 411, 494-498 (2001)); Yu et al., *Proc Natl Acad Sci USA*. 99:6047-52 (2002). "RNAi" is the process by which dsRNA induces homology-dependent degradation of complimentary mRNA. The presence of dsRNA in cells triggers the RNAi response though a mechanism that has yet to be fully characterized. In one embodiment, a synthetic antisense nucleic acid molecule is hybridized by complementary base pairing with a "sense" ribonucleic acid to form a double stranded RNA. The presence of long dsRNAs in cells stimulates the activity of a ribonuclease III enzyme. The dsRNA antisense and sense nucleic acid molecules are provided that correspond to at least about 20, 25, 50, 100, 250 or 500 nucleotides or an entire Prox-1 coding strand, or to only a portion thereof. In an alternative embodiment, the siRNAs are 30 nucleotides or less in length, and more preferably 21- to 23-nucleotides, with characteristic 2- to 3-nucleotide 3'-overhanging ends, which are generated by ribonuclease III cleavage from longer dsRNAs. (See e.g. Tuschl T. *Nat Biotechnol.* 20:446-48. 2002). At notably higher concentrations single stranded 21 nucleotide RNA molecules have been also shown to function as siRNAs (i.e., enter the RNAi pathway and specifically target mRNA for degradation in mammalian cells (Martinez et al., Cell 110, 563-574,2002). Cleavage of the target RNA takes place in the middle of the region complementary to the antisense strand of the siRNA duplex (Elbashir et al., 2001, Genes Dev., 15, 188).

Intracellular transcription of small RNA molecules can be achieved by cloning the siRNA templates into RNA polymerase III (Pol III) transcription units, which normally encode the small nuclear RNA (snRNA) U6 or the human RNAse P RNA H1. Two approaches can be used to express siRNAs: in one embodiment, sense and antisense strands constituting the siRNA duplex are transcribed using constructs with individual promoters (Lee, et al. *Nat. Biotechnol.* 20, 500-505. 2002); in an alternative embodiment, siRNAs are expressed as stem-loop hairpin RNA structures that give rise to siRNAs after intracellular processing (Brummelkamp et al. *Science* 296:550-553. 2002, herein incorporated by reference). Alternatively, a stem loop hairpin can be expressed within an unrelated Pol II transcribed mRNA transcript. A stem-loop hairpin designed to contain the siRNA sequence also contains conserved microRNA sequences within the loop and stem regions, thus resembling a natural precursor mRNA structure. Subsequently, the precursor can be processed by the cellular RNAi components to yield mature, functional siRNA/miRNA. (See, generally, Zeng et al., Mol Cell 9, 1327-1333 (2002); Hutvagner et al., Science 297, 2056-2060 (2002); Kawasake et al., Nature 423, 838-842 (2003)).

RNAi has been studied in a variety of systems. Work in *Drosophila* embryonic lysates (Elbashir et al., 2001, EMBO J, 20, 6877) has revealed certain requirements for siRNA length, structure, chemical composition, and sequence that are essential to mediate efficient RNAi activity. Twenty-one nucleotide siRNA duplexes are most active when containing two nucleotide 3'-overhangs. Replacing the 3'-overhanging segments of a 21-mer siRNA duplex having 2 nucleotide 3' overhangs with deoxyribonucleotides has no adverse effect on RNAi activity, while, replacing up to 4 nucleotides on each end of the siRNA with deoxyribonucleotides may be well tolerated. Complete substitution with deoxyribonucleotides results in no RNAi activity (Elbashir et al., 2001, EMBO J., 20, 6877).

Furthermore, complete substitution of one or both siRNA strands with 2'-deoxy (2'-H) or 2'-O-methyl nucleotides results in no RNAi activity, whereas substitution of the 3'-terminal siRNA overhang nucleotides with deoxy nucleotides (2'-H) is tolerated. Single mismatch sequences in the center of the siRNA duplex may abolish RNAi activity. In addition, studies indicate that the position of the cleavage site in the target RNA is defined by the 5'-end of the siRNA guide sequence rather than the 3'-end (Elbashir et al., 2001, EMBO J, 20, 6877). Other studies indicate that a 5'-phosphate on the target-complementary strand of a siRNA duplex is required for siRNA activity and that ATP is utilized to maintain the 5'-phosphate moiety on the siRNA (Nykanen et al., 2001, Cell, 107, 309).

The dsRNA/siRNA is most commonly administered by annealing sense and antisense RNA strands in vitro before delivery to the organism. In an alternate embodiment, RNAi may be carried out by administering sense and antisense nucleic acids of the invention in the same solution without annealing prior to administration, and may even be performed by administering the nucleic acids in separate vehicles within a very close timeframe.

Genetic control can also be achieved through the design of novel transcription factors for modulating expression of the gene of interest in native cells and animals. For example, the Cys2-His2 zinc finger proteins, which bind DNA via their zinc finger domains, have been shown to be amenable to structural changes that lead to the recognition of different target sequences. These artificial zinc finger proteins recognize specific target sites with high affinity and low dissociation constants, and are able to act as gene switches to modulate gene expression. Knowledge of the particular target sequence of the present invention facilitates the engineering of zinc finger proteins specific for the target sequence using known methods such as a combination of structure-based modeling and screening of phage display libraries (Segal et al., (1999) Proc Natl Acad Sci USA 96:2758-2763; Liu et al., (1997) Proc Natl Acad Sci USA 94:5525-30; Greisman and Pabo (1997) Science 275:657-61; Choo et al., (1997) J Mol Biol 273:525-32). Each zinc finger domain usually recognizes three or more base pairs. Since a recognition sequence of 18 base pairs is generally sufficient in length to render it unique in any known genome, a zinc finger protein consisting of 6 tandem repeats of zinc fingers would be expected to ensure specificity for a particular sequence (Segal et al., (1999) Proc Natl Acad Sci USA 96:2758-2763). The artificial zinc finger repeats, designed based on target sequences, are fused to activation or repression domains to promote or suppress gene expression (Liu et al., (1997) Proc Natl Acad Sci USA 94:5525-30). Alternatively, the zinc finger domains can be fused to the TATA box-binding factor (TBP) with varying lengths of linker region between the zinc finger peptide and the TBP to create either transcriptional activators or repressors (Kim et al., (1997) Proc Natl Acad Sci USA 94:3616-3620). Such proteins, and polynucleotides that encode them, have utility for modulating expression in vivo in both native cells, animals and humans. The novel transcription factor can be delivered to the target cells by transfecting constructs that express the transcription factor (gene therapy), or by introducing the protein. Engineered zinc finger proteins can also be designed to bind RNA sequences for use in therapeutics as alternatives to antisense or catalytic RNA methods (McColl et al., (1999) Proc Natl Acad Sci USA 96:9521-6; Wu et al., (1995) Proc Natl Acad Sci USA 92:344-348).

Inactivation of Prox-1 function can also be accomplished using an overexpressed dominant negative form of Prox-1. As used herein a "dominant negative protein" is a mutant form of a protein which has the property of inhibiting the function of the endogenous, wild type form of the protein which corresponds to the mutant protein. Typically, dominant negative proteins have amino acid substitutions or are truncated forms of the wild type protein. The mutation may be in a substrate-binding domain (or DNA binding domain), a catalytic domain, or a cellular localization domain. For instance, a dominant negative form of Prox-1 may include a mutant truncated with respect to the DNA binding domain or trans-activation domain. Disruption of the DNA binding domain entails truncation of the protein to exclude amino acids 572-634 of SEQ ID NO. 3, based on homology to Prospero (Drosophila). Disruption of the transactivation domain entails the deletion of amino acids 635-737. Other dominant negatives may include truncated forms of Prox-1 lacking the last 60 amino acids or the first 575 amino acids. Preferably, the mutant polypeptide will be overproduced. Point mutations can be made that have such an effect. In addition, fusion of different polypeptides of various lengths to the terminus of a protein can yield dominant negative mutants. General strategies for making dominant negative mutants are described in Herskowitz, Nature (1987) 329:219-222.

Anti-sense RNA and DNA molecules, ribozymes, RNAi, triple helix polynucleotides, and novel transcription factors can be prepared by any method known in the art for the synthesis of DNA and RNA molecules. These include techniques for chemically synthesizing oligodeoxyribonucleotides well known in the art including, but not limited to, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably or transiently into cells.

B. Gene Therapy

As described n detail in the preceding section, a variety of genetic manipulations to achieve modulation of Prox-1 protein expression or activity are contemplated. Additionally, where administration of proteins is contemplated, such as zinc finger proteins targeted to Prox-1, administration of a gene therapy vector to cause the protein of interest to be produced in vivo also is contemplated. Where inhibition of proteins is contemplated (e.g., through use of antibodies or small molecule inhibitors), inhibition of protein expression in vivo by genetic techniques, such as knock-out techniques or anti-sense therapy, is contemplated.

It is now widely recognized that DNA may be introduced into a cell using a variety of viral vectors. Exemplary vectors that have been described in the literature include replication-deficient retroviral vectors, including but not limited to lentivirus vectors (Kim et al., J. Virol., 72(1): 811-816 (1998); Kingsman & Johnson, Scrip Magazine, October, 1998, pp. 43-46.); adenoviral (see, for example, U.S. Pat. No. 5,824, 544; U.S. Pat. No. 5,707,618; U.S. Pat. No. 5,792,453; U.S. Pat. No. 5,693,509; U.S. Pat. No. 5,670,488; U.S. Pat. No. 5,585,362; Quantin et al., Proc. Natl. Acad. Sci. USA, 89: 2581-2584 (1992); Stratford-Perricadet et al., J. Clin. Invest., 90: 626-630 (1992); and Rosenfeld et al., Cell, 68: 143-155 (1992)), retroviral (see, for example, U.S. Pat. No. 5,888,502; U.S. Pat. No. 5,830,725; U.S. Pat. No. 5,770,414; U.S. Pat. No. 5,686,278; U.S. Pat. No. 4,861,719), adeno-associated viral (see, for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851, 521; U.S. Pat. No. 5,252,479; Gnatenko et al., J. Investig. Med., 45: 87-98 (1997), an adenoviral-adenoassociated viral hybrid (see, for example, U.S. Pat. No. 5,856,152) or a vaccinia viral or a herpesviral (see, for example, U.S. Pat. No. 5,879,934; U.S. Pat. No. 5,849,571; U.S. Pat. No. 5,830,727; U.S. Pat. No. 5,661,033; U.S. Pat. No. 5,328,688); Lipofectin-mediated gene transfer (BRL); liposomal vectors (See, e.g., U.S. Pat. No. 5,631,237 (Liposomes comprising Sendai virus proteins)); and combinations thereof. All of the foregoing documents are incorporated herein by reference in the entirety. Replication-deficient adenoviral vectors and adeno-associated viral vectors constitute preferred embodiments.

In embodiments employing a viral vector, preferred polynucleotides include a suitable promoter and polyadenylation sequence to promote expression in the target tissue of interest. For many applications of the present invention, suitable promoters/enhancers for mammalian cell expression include, e.g., cytomegalovirus promoter/enhancer (Lehner et al., J. Clin. Microbiol., 29:2494-2502 (1991); Boshart et al., Cell, 41:521-530 (1985)); Rous sarcoma virus promoter (Davis et al., Hum. Gene Ther., 4:151 (1993)); simian virus 40 promoter, long terminal repeat (LTR) of retroviruses, keratin 14 promoter, and myosin heavy chain promoter.

In other embodiments, non-viral delivery is contemplated. These include calcium phosphate precipitation (Graham and Van Der Eb, Virology, 52:456-467 (1973); Chen and Okayama, Mol Cell Biol., 7:2745-2752, (1987); Rippe, et al., Mol. Cell Biol., 10:689-695 (1990)), DEAE-dextran (Gopal, Mol. Cell Biol., 5:1188-1190 (1985)), electroporation (Tur-Kaspa, et al., Mol. Cell Biol., 6:716-718, (1986); Potter, et al., Proc. Nat. Acad Sci. USA, 81:7161-7165, (1984)), direct microinjection (Harland and Weintraub, J. Cell Biol., 101: 1094-1099 (1985)), DNA-loaded liposomes (Nicolau and Sene, Biochim. Biophys. Acta, 721:185-190 (1982); Fraley, et al., Proc. Natl. Acad. Sci. USA, 76:3348-3352 (1979); Felgner, Sci. Am., 276(6):102-6 (1997); Felgner, Hum. Gene Ther., 7(15):1791-3, (1996)), cell sonication (Fechheimer, et al., Proc. Natl. Acad. Sci. USA, 84:8463-8467 (1987)), gene bombardment using high velocity microprojectiles (Yang, et al., Proc. Natl. Acad. Sci. USA, 87:9568-9572 (1990)), and receptor-mediated transfection (Wu and Wu, J. Biol. Chem., 262:4429-4432 (1987); Wu and Wu, Biochemistry, 27:887-892 (1988); Wu and Wu, Adv. Drug Delivery Rev., 12:159-167 (1993)).

In a particular embodiment of the invention, the expression construct (or indeed the peptides discussed above) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, "In Liver Diseases, Targeted Diagnosis And Therapy Using Specific Receptors And Ligands," Wu, G., Wu, C., ed., New York: Marcel Dekker, pp.

87-104 (1991)). The addition of DNA to cationic liposomes causes a topological transition from liposomes to optically birefringent liquid-crystalline condensed globules (Radler, et al., *Science,* 275(5301):810-4, (1997)). These DNA-lipid complexes are potential non-viral vectors for use in gene therapy and delivery.

Liposome-mediated nucleic acid delivery and expression of foreign DNA in vitro has been very successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda, et al., *Science,* 243:375-378 (1989)). In other embodiments, the liposome may be complexed or employed in conjunction with nuclear nonhistone chromosomal proteins (HMG-1) (Kato, et al., *J. Biol. Chem,* 266:3361-3364 (1991)). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993), supra).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu (1987), supra) and transferrin (Wagner, et al., *Proc. Nat'l. Acad Sci. USA,* 87(9):3410-3414 (1990)). Recently, a synthetic neoglycoprotein, which recognizes the same receptor as ASOR, has been used as a gene delivery vehicle (Ferkol, et al., *FASEB J.,* 7:1081-1091 (1993); Perales, et al., *Proc. Natl. Acad. Sci., USA* 91:4086-4090 (1994)) and epidermal growth factor (EGF) has also been used to deliver genes to squamous carcinoma cells (Myers, EPO 0273085).

In other embodiments, the delivery vehicle may comprise a ligand and a liposome. For example, Nicolau, et al., *Methods Enzymol.,* 149:157-176 (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky, et al., *Proc. Nat. Acad. Sci. USA,* 81:7529-7533 (1984) successfully injected polyomavirus DNA in the form of $CaPO_4$ precipitates into liver and spleen of adult and newborn mice demonstrating active viral replication and acute infection. Benvenisty and Neshif, *Proc. Nat. Acad. Sci. USA,* 83:9551-9555 (1986) also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein, et al., *Nature,* 327:70-73 (1987)). Several devices for accelerating small particles have been developed. One such device relies on a high voltage discharge to generate an electrical current, which in turn provides the motive force (Yang, et al., *Proc. Natl. Acad. Sci USA,* 87:9568-9572 (1990)). The microprojectiles used have consisted of biologically inert substances such as tungsten or gold beads.

Well-known techniques exist for gene delivery to in vivo and ex vivo situations. For viral vectors, one generally will prepare a viral vector stock. Depending on the type of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector or protein. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In an ex vivo embodiment, cells from the patient are removed and maintained outside the body for at least some period of time. During this period, a therapy is delivered, after which the cells are reintroduced into the patient; preferably, any tumor cells in the sample have been killed.

C. Antibodies Immunoreactive with Prox-1 Protein

In another aspect, the present invention contemplates an antibody that is immunoreactive with a Prox-1 protein molecule of the present invention, or any portion thereof. Such antibodies include, but are not limited to, polyclonal, monoclonal, chimeric, single chain, Fab fragments and fragments produced by a Fab expression library, bifunctional/bispecific antibodies, humanized antibodies, CDR grafted antibodies, human antibodies and antibodies which include portions of CDR sequences specific for Prox-1 protein. The antibodies are useful as diagnostic reagents for measuring Prox-1 expression in a biological sample (e.g., a biopsy of colon tissue), and are useful for binding to Prox-1 protein to inhibit Prox-1 activity where the antibodies are delivered into cells.

Neutralizing antibodies, i.e., those which may suppress Prox-1 expression, are especially preferred for therapeutic embodiments. In a preferred embodiment, an antibody is a monoclonal antibody. The invention provides for a pharmaceutical composition comprising a therapeutically effective amount of an antibody directed against Prox-1 protein. The antibody may bind to and neutralize the apoptotic effects of the Prox-1 protein. The antibody may be formulated with a pharmaceutical acceptable adjuvant. Means for preparing and characterizing antibodies are well known in the art (see, e.g., Harlow and Lane, ANTIBODIES: A LABORATORY MANUAL, Cold Spring Harbor Laboratory, Cold Spring Harbor, N.Y., 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, goat, sheep, pigs or horses. Because of the relatively large blood volume of rabbits, a rabbit is a preferred choice for production of polyclonal antibodies.

Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Antibodies, both polyclonal and monoclonal, specific for isoforms of antigen may be prepared using conventional immunization techniques, as will be generally known to those of skill in the art. As used herein, the term "specific for" is intended to mean that the variable regions of the antibodies recognize and bind Prox-1 protein and are capable of distinguishing Prox-1 protein from other antigens, for example other secreted proapoptotic factors. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

Monoclonal antibodies to Prox-1 protein may be prepared using any technique which provides for the production of antibody molecules by continuous cell lines in culture. These include but are not limited to the hybridoma technique originally described by Koehler and Milstein (Nature 256: 495-497, 1975), the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985).

When the hybridoma technique is employed, myeloma cell lines may be used. Such cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions. It should be noted that the hybridomas and cell lines produced by such techniques for producing the monoclonal antibodies are contemplated to be novel compositions of the present invention. An exemplary method for producing monoclonal antibodies against Prox-1 is provided in Example 1. Those of skill in the art will appreciate that such a method may be modified using techniques well known to those of skill in the art and still produce antibodies within the scope of the present invention.

In addition to the production of monoclonal antibodies, techniques developed for the production of "chimeric antibodies", the splicing of mouse antibody genes to human antibody genes to obtain a molecule with appropriate antigen specificity and biological activity can be used (Morrison et al., Proc Natl Acad Sci 81: 6851-6855, 1984; Neuberger et al., Nature 312: 604-608, 1984; Takeda et al., Nature 314: 452-454; 1985). Alternatively, techniques described for the production of single chain antibodies (U.S. Pat. No. 4,946,778) can be adapted to produce Prox-1 protein-specific single chain antibodies.

Antibodies may also be produced by inducing in vivo production in the lymphocyte population or by screening recombinant immunoglobulin libraries or panels of highly specific binding reagents as disclosed in Orlandi et al (Proc Natl Acad Sci 86: 3833-3837; 1989), and Winter G and Milstein C (Nature 349: 293-299, 1991).

Fully human antibodies relate to antibody molecules in which essentially the entire sequences of both the light chain and the heavy chain, including the CDRs, arise from human genes. Such antibodies are termed "human antibodies," or "fully human antibodies" herein. Human monoclonal antibodies can be prepared by the trioma technique; the human B-cell hybridoma technique (see Kozbor, et al., *Immunol Today* 4: 72 (1983)) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., *Proc Natl Acad Sci USA* 80: 2026-2030 (1983)) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, *J. Mol. Biol.* 227:381 (1991); Marks et al., *J. Mol. Biol.* 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10, 779-783 (1992)); Lonberg et al. (*Nature* 368 856-859 (1994)); Morrison (*Nature* 368:812-13 (1994)); Fishwild et al, (Nature Biotechnology 14, 845-51 (1996)); Neuberger (*Nature Biotechnology* 14:826 (1996)); and Lonberg and Huszar (*Intern. Rev. Inmunol*. 13:65-93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

Antibodies as described herein are useful in standard immunochemical procedures, such as ELISA, radioimmuno assays, and Western blot methods and in immunohistochemical procedures such as tissue staining, as well as in other procedures which may utilize antibodies specific to Prox-1 protein -related antigen epitopes. Additionally, it is proposed that monoclonal antibodies specific to the particular Prox-1 protein of different species may be utilized in other useful applications.

In general, both polyclonal and monoclonal antibodies against Prox-1 protein may be used in a variety of embodiments. In certain aspects, the antibodies may be employed for therapeutic purposes in which the inhibition of Prox-1 protein activity is desired (e.g., to reduce apoptosis in neuronal cells). Antibodies may be used to block Prox-1 protein action.

Antibodies of the present invention also may prove useful in diagnostic purposes in order, for example, to detect increases or decreases in Prox-1 protein in tissue samples including samples for sites of inflammation, or fluid samples including blood serum, plasma and exudate samples. Additional aspects will employ the antibodies of the present invention in antibody cloning protocols to obtain cDNAs or genes encoding other Prox-1 protein. They may also be used in inhibition studies to analyze the effects of Prox-1 related peptides in cells or animals. Anti-Prox-1 protein antibodies will also be useful in immunolocalization studies to analyze the distribution of Prox-1 protein during various cellular events, for example, to determine the cellular or tissue-specific distribution of Prox-1 protein polypeptides under different points in the cell cycle. A particularly useful application of such antibodies is in purifying native or recombinant Prox-1 protein, for example, using an antibody affinity column. The operation of all such immunological techniques will be known to those of skill in the art in light of the present disclosure.

D. Assaying for Other Modulators of Prox-1 Activity and/or Expression

In some situations, it may be desirable to identify molecules that are modulators, i.e., agonists or antagonists, of the activity of Prox-1 protein. Natural or synthetic molecules that modulate Prox-1 protein may be identified using one or more screening assays, such as those described herein. Such molecules may be administered either in an ex vivo manner, or in an in vivo manner by injection, or by oral delivery, implantation device or the like.

"Test molecule(s)" refers to the molecule(s) that is/are under evaluation for the ability to modulate (i.e., increase or decrease) the activity of Prox-1 protein. Most commonly, a molecule that modulates Prox-1 activity will interact directly with Prox-1. However, it is also contemplated that a molecule may also modulate Prox-1 protein activity indirectly, such as by affecting Prox-1 gene expression, or by binding to a Prox-1 binding partner. In one embodiment, a test molecule will bind to a Prox-1 protein with an affinity constant of at least about $10^{-6}$ M, preferably about $10^{-8}$ M, more preferably about $10^{-9}$ M, and even more preferably about $10^{-10}$ M.

Methods for identifying compounds which interact with Prox-1 protein are encompassed by the present invention. In certain embodiments, a Prox-1 protein is incubated with a test molecule under conditions which permit the interaction of the test molecule with a Prox-1 protein, and the extent of the interaction can be measured. The test molecule(s) can be screened in a substantially purified form or in a crude mixture.

In certain embodiments, a Prox-1 protein agonist or antagonist may be a protein, peptide, carbohydrate, lipid or small molecular weight molecule which interacts with Prox-1 to regulate its activity. Molecules which regulate Prox-1 expression include nucleic acids which are complementary to nucleic acids encoding a Prox-1 protein, or are complementary to nucleic acid sequences which direct or control the expression of Prox-1 protein, and which act as anti-sense regulators of expression.

Once a set of test molecules has been identified as interacting with Prox-1 protein, the molecules may be further evaluated for their ability to increase or decrease Prox-1 activity. The measurement of the interaction of test molecules with Prox-1 may be carried out in several formats, including solution-phase assays and immunoassays. In general, test molecules are incubated with Prox-1 for a specified period of time, and Prox-1 protein activity is determined by one or more assays for measuring biological activity.

In the event that Prox-1 displays biological activity through an interaction with a binding partner, a variety of in vitro assays may be used to measure the binding of Prox-1 to the corresponding binding partner. These assays may be used to screen test molecules for their ability to increase or decrease the rate and/or the extent of binding of Prox-1 to its binding partner. In one assay, a Prox-1 polypeptide is immobilized in the wells of a microtiter plate. Radiolabeled Prox-1 binding partner and the test molecule(s) can then be added either one at a time (in either order) or simultaneously to the wells. After incubation, the wells can be washed and counted (using a scintillation counter) for radioactivity to determine the extent to which the binding partner bound to Prox-1 polypeptide. Typically, the molecules will be tested over a range of concentrations, and a series of control wells lacking one or more elements of the test assays can be used for accuracy in the evaluation of the results. An alternative to this method involves reversing the "positions" of the proteins, i.e., immobilizing Prox-1 binding partner to the microtiter plate wells, incubating with the test molecule and radiolabeled Prox-1 polypeptide, and determining the extent of Prox-1 polypeptide binding. See, for example, chapter 18, *Current Protocols in Molecular Biology*, Ausubel et al., eds., John Wiley & Sons, New York, N.Y. (1995).

As an alternative to radiolabeling, Prox-1 protein or its binding partner may be conjugated to biotin and the presence of biotinylated protein can then be detected using streptavidin linked to an enzyme, such as horseradish peroxidase (HRP) or alkaline phosphatase (AP), that can be detected colorometrically or by fluorescent tagging of streptavidin. An antibody directed to Prox-1 or to a Prox-1 binding partner and conjugated to biotin may also be used and can be detected after incubation with enzyme-linked streptavidin linked to AP or HRP.

A Prox-1 protein or Prox-1 binding partner can also be immobilized by attachment to agarose beads, acrylic beads or other types of such inert solid phase substrates. The substrate-protein complex can be placed in a solution containing the complementary protein and the test compound. After incubation the beads can be precipitated by centrifugation, and the amount of binding between Prox-1 protein and its binding partner can be assessed using the methods described herein. Alternatively, the substrate-protein complex can be immobilized in a column, and the test molecule and complementary protein are passed through the column. The formation of a complex between an Prox-1 protein and its binding partner can then be assessed using any of the techniques set forth herein, i.e., radiolabeling, antibody binding or the like.

Another in vitro assay that is useful for identifying a test molecule which increases or decreases the formation of a complex between Prox-1 and a Prox-1 binding partner is a surface plasmon resonance detector system such as the BIAcore assay system (Pharmacia, Piscataway, N.J.). The BIAcore system may be carried out using the manufacturer's protocol. This assay essentially involves the covalent binding of either Prox-1 or a Prox-1 binding partner to a dextran-coated sensor chip which is located in a detector. The test compound and the other complementary protein can then be injected, either simultaneously or sequentially, into the chamber containing the sensor chip. The amount of complementary protein that binds can be assessed based on the change in molecular mass which is physically associated with the dextran-coated side of the sensor chip; the change in molecular mass can be measured by the detector system.

In some cases, it may be desirable to evaluate two or more test compounds together for their ability to increase or decrease the formation of a complex between Prox-1 polypeptide and a Prox-1 binding partner. In these cases, the assays set forth herein can be readily modified by adding such additional test compound(s) either simultaneous with, or subsequent to, the first test compound. The remainder of the steps in the assay are as set forth herein.

In vitro assays such as those described herein may be used advantageously to screen large numbers of compounds for effects on complex formation by Prox-1 polypeptide and a Prox-1 binding partner. The assays may be automated to screen compounds generated in phage display, synthetic peptide, and chemical synthesis libraries.

Compounds which increase or decrease the formation of a complex between a Prox-1 polypeptide and a Prox-1 binding partner may also be screened in cell culture using cells and cell lines expressing either Prox-1 polypeptide or a Prox-1 binding partner. Cells and cell lines may be obtained from any mammal. The binding of a Prox-1 protein to cells expressing a Prox-1 binding partner at the surface is evaluated in the presence or absence of test molecules, and the extent of binding may be determined by, for example, flow cytometry using a biotinylated antibody to a Prox-1 binding partner. Cell culture assays can be used advantageously to further evaluate compounds that score positive in protein binding assays described herein.

Cell cultures can also be used to screen the impact of a drug candidate. For example, drug candidates may decrease or increase the expression of the Prox-1 like gene. In certain embodiments, the amount of Prox-1 protein that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide may result in, or be associated with, a disease or pathological condition. In such cases, one may test a drug candidate's ability to decrease the production of such a metabolic product in a cell culture.

E. Internalizing Proteins

The tat protein sequence (from HIV) can be used to internalize proteins into a cell. See e.g., Falwell et al., *Proc. Natl. Acad. Sci. USA,* 91:664-668 (1994). For example, an 11 amino acid sequence (YGRKKRRQRRR; SEQ ID NO: 46) of the HIV tat protein (termed the "protein transduction domain", or TAT PDT) has been described as mediating delivery across the cytoplasmic membrane and the nuclear membrane of a cell. See Schwarze et al., *Science,* 285:1569-1572 (1999); and Nagahara et al., *Nature Medicine,* 4:1449-1452 (1998). In these procedures, FITC-constructs are prepared which bind to cells as observed by fluorescence-activated cell sorting (FACS) analysis, and these constructs penetrate tissues after i.p. adminstration.—Next, tat-bgal fusion proteins are constructed. Cells treated with this construct demonstrate b-gal activity. Following injection, a number of tissues, including liver, kidney, lung, heart and brain tissue, have been found to demonstrate expression using these procedures. It is believed that these constructions underwent some degree of unfolding in order to enter the cell; as such, refolding may be required after entering the cell.

It will thus be appreciated that the tat protein sequence may be used to internalize a desired protein or polypeptide into a cell. For example, using the tat protein sequence, Prox-1 antagonist (such as an anti-Prox-1 binding agent, small molecule, or antisense oligonucleotide) can be administered intracellularly to inhibit the activity of a Prox-1 molecule. See also, Strauss, E., *Science,* 285:1466-1467 (1999).

F. Rational Drug Design

The goal of rational drug design is to produce structural analogs of biologically active polypeptides or compounds with which they interact (agonists, antagonists, inhibitors, peptidomimetics, binding partners, etc.). By creating such analogs, it is possible to fashion drugs which are more active or stable than the natural molecules, which have different susceptibility to alteration or which may affect the function of various other molecules. In one approach, one generates a three-dimensional structure for Prox-1 protein or a fragment thereof. This is accomplished by x-ray crystallography, computer modeling or by a combination of both approaches. An alternative approach, "alanine scan," involves the random replacement of residues throughout molecule with alanine, and the resulting affect on function determined.

It also is possible to isolate a specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have activity as stimulators, inhibitors, agonists, antagonists of Prox-1 protein or molecules affected by Prox-1 protein function. Such rational drug design may start with lead compounds identified by the present invention. By virtue of the availability of cloned Prox-1 protein sequences, sufficient amounts of the related proteins can be produced to perform crystallographic studies. In addition, knowledge of the polypeptide sequences permits computer employed predictions of structure-function relationships.

G. Therapeutic Methods

As discussed herein, polynucleotides or modulators of Prox-1 (including inhibitors of Prox-1) are administered to treat cancer. Therapeutic compositions can be administered in therapeutically effective dosages alone or in combination with adjuvant cancer therapy such as surgery, chemotherapy, radiotherapy, thermotherapy, and laser therapy, and may provide a beneficial effect, e.g. reducing tumor size, slowing rate of tumor growth, inhibiting metastasis, or otherwise improving overall clinical condition, without necessarily eradicating the cancer.

The composition can also be administered in therapeutically effective amounts as a portion of an anti-cancer cocktail. An anti-cancer cocktail is a mixture of the polypeptide or modulator of the invention with one or more anti-cancer drugs in addition to a pharmaceutically acceptable carrier for delivery. Any anti-cancer drugs can be used as a treatment in combination with the polypeptide or modulator of the invention, including: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate.

In addition, therapeutic compositions of the invention may be used for prophylactic treatment of cancer. There are hereditary conditions and/or environmental situations (e.g. exposure to carcinogens) known in the art that predispose an individual to developing cancers. Under these circumstances, it may be beneficial to treat these individuals with therapeutically effective doses of compositions of the invention to reduce the risk of developing cancers.

In vitro and in vivo models can be used to determine the effective doses of the compositions of the invention for cancer treatment. These in vitro models include proliferation and differentiation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921-30 (1974), mobility and invasive potential of tumor cells in Boyden Chamber assays as described in Pilkington et al., Anticancer Res., 17: 4107-9 (1997), and angiogenesis assays such as induction of vascularization of the chick chorioallantoic membrane or induction of vascular endothelial cell migration as described in Ribatta et al., Intl. J. Dev. Biol., 40: 1189-97 (1999) and Li et al., Clin. Exp. Metastasis, 17:423-9 (1999) respectively. Suitable tumor cells lines are available, e.g. from American Type Tissue Culture Collection catalogs, and/or are described below.

H. Pharmaceutical Compositions

Purified nucleic acids, antisense molecules, purified protein, antibodies, antagonists, or inhibitors may all be used as pharmaceutical compositions. Delivery of specific molecules for therapeutic purposes in this invention is further described below.

The active compositions of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramuscular, intramammary, intraperitoneal, intrathecal, intraocular, retrobulbar, intrapulmonary (e.g., term release); by oral, sublingual, nasal, anal, vaginal, or transdermal delivery, or by surgical implantation at a particular site, e.g., embedded under the splenic capsule, brain, or in the cornea. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the active compositions may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

In the clinical setting an "effective amount" is an amount sufficient to effect beneficial or desired clinical results. An effective amount can be administered in one or more doses. In terms of treatment, an "effective amount" of polynucleotide, and/or polypeptide is an amount that results in amelioration of symptoms or a prolongation of survival in a patient. The effective amount is generally determined by the physician on a case-by-case basis and is within the skill of one in the art. Several factors are typically taken into account when determining, an appropriate dosage. These factors include age, sex and weight of the patient, the condition being treated, the severity of the condition and the form of the antibody being administered. For instance, in embodiments in which the antibody compositions of the present invention are being therapeutically administered, it is likely the concentration of a single chain antibody need not be as high as that of native antibodies in order to be therapeutically effective. Determination of the effective amounts is well within the capability of those skilled in the art, especially in light of the detailed disclosure provided herein. For any compound used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the C-proteinase activity). Such information can be used to more accurately determine useful doses in humans.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics," Ch. 1 p. 1. Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50-90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration. Refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials. As studies are conducted, further information will emerge regarding appropriate dosage levels and duration of treatment for specific diseases and conditions.

In a preferred embodiment, the present invention is directed at treatment of colon cancer, including colon cancer indicated by the presence of overexpression of Prox-1. A variety of different routes of administration are contemplated. For example, in the case of a tumor, the discrete tumor mass may be injected. The injections may be single or multiple; where multiple, injections are made at about 1 cm spacings across the accessible surface of the tumor. Alternatively, targeting the tumor vasculature by direct, local or regional intra-arterial injection are contemplated. The lymphatic systems, including regional lymph nodes, present another likely target for delivery. Further, systemic injection may be preferred.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

H. Transgenic Animals

A transgenic animal can be prepared in a number of ways. A transgenic organism is one that has an extra or exogenous fragment of DNA incorporated into its genome, sometimes replacing an endogenous piece of DNA. In order to achieve stable inheritance of the extra or exogenous DNA, the integration event must occur in a cell type that can give rise to functional germ cells. The two animal cell types that are used for generating transgenic animals are fertilized egg cells and embryonic stem cells. Embryonic stem (ES) cells can be returned from in vitro culture to a "host" embryo where they become incorporated into the developing animal and can give rise to transgenic cells in all tissues, including germ cells. The ES cells are transfected in culture and then the mutation is transmitted into the germline by injecting the cells into an embryo. The animals carrying mutated germ cells are then bred to produce transgenic offspring. The use of ES cells to make genetic changed in the mouse germline is well recognized. For a reviews of this technology, those of skill in the art are referred to Bronson & Smithies, *J. Biol. Chem.*, 269(44), 27155-27158, 1994; Torres, *Curr. Top. Dev. Biol.*, 36, 99-114; 1998 and the reference contained therein.

Generally, blastocysts are isolated from pregnant mice at a given stage in development, for example, the blastocyst from mice may be isolated at day 4 of development (where day 1 is defined as the day of plug), into an appropriate buffer that will sustain the ES cells in an undifferentiated, pluripotent state. ES cell lines may be isolated by a number of methods well known to those of skill in the art. For example, the blastocysts may be allowed to attach to the culture dish and approximately 7 days later, the outgrowing inner cell mass picked, trypsinized and transferred to another culture dish in the same culture media. ES cell colonies appear 2-3 weeks later with between 5-7 individual colonies arising from each explanted inner cell mass. The ES cell lines can then be expanded for further analysis. Alternatively, ES cell lines can be isolated using the immunosurgery technique (described in Martin, *Proc. Natl. Acad. Sci. USA* 78:7634-7638, 1981) where the trophectoderm cells are destroyed using anti-mouse antibodies prior to explanting the inner cell mass.

In generating transgenic animals, the ES cell lines that have been manipulated by homologous recombination are reintroduced into the embryonic environment by blastocyst injection (as described in Williams et al., *Cell* 52:121-131, 1988). Briefly, blastocysts are isolated from a pregnant mouse and expanded. The expanded blastocysts are maintained in oil-drop cultures at 4° C. for 10 minutes prior to culture. The ES cells are prepared by picking individual colonies, which are then incubated in phosphate-buffered saline, 0.5 mM EGTA for 5 minutes; a single cell suspension is prepared by incubation in a trypsin-EDTA solution containing 1% (v/v) chick serum for a further 5 minutes at 4° C. Five to twenty ES cells (in Dulbecco's modified Eagle's Medium with 10% (v/v) fetal calf serum and 3,000 units/ml DNAase 1 buffered in 20 mM HEPES [pH 8]) are injected into each blastocyst. The blastocysts are then transferred into pseudo-pregnant recipients and allowed to develop normally. The transgenic mice are identified by coat markers (Hogan et al., Manipulating the Mouse Embryo, Cold Spring Harbor, N.Y. (1986)). Additional methods of isolating and propagating ES cells may be found in, for example, U.S. Pat. No. 5,166,065; U.S. Pat. No. 5,449,620; U.S. Pat. No. 5,453,357; U.S. Pat. No. 5,670,372; U.S. Pat. No. 5,753,506; U.S. Pat. No. 5,985,659, each incorporated herein by reference.

An alternative method involving zygote injection method for making transgenic animals is described in, for example, U.S. Pat. No. 4,736,866, incorporated herein by reference. Additional methods for producing transgenic animals are generally described by Wagner and Hoppe (U.S. Pat. No. 4,873,191; which is incorporated herein by reference), Brinster et al. *Proc. Nat'l Acad. Sci. USA,* 82(13) 4438-4442, 1985; which is incorporated herein by reference in its entirety) and in *Manipulating the Mouse Embryo; A Laboratory Manual,* 2nd edition (eds., Hogan, Beddington, Costantimi and Long, Cold Spring Harbor Laboratory Press, 1994; which is incorporated herein by reference in its entirety).

Briefly, this method involves injecting DNA into a fertilized egg, or zygote, and then allowing the egg to develop in a pseudo-pregnant mother. The zygote can be obtained using male and female animals of the same strain or from male and female animals of different strains. The transgenic animal that is born, the founder, is bred to produce more animals with the same DNA insertion. In this method of making transgenic animals, the new DNA typically randomly integrates into the genome by a non-homologous recombination event. One to many thousands of copies of the DNA may integrate at a site in the genome Generally, the DNA is injected into one of the pronuclei, usually the larger male pronucleus. The zygotes are then either transferred the same day, or cultured overnight to form 2-cell embryos and then transferred into the oviducts of pseudo-pregnant females. The animals born are screened for the presence of the desired integrated DNA.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 mg/ml in 5 mM Tris, pH 7.4 and 0.1 mM EDTA.

Additional methods for purification of DNA for microinjection are described in Hogan et al. Manipulating the Mouse Embryo (Cold Spring Harbor Laboratory, Cold Spring Harbor, N.Y., 1986), in Palmiter et al. *Nature* 300:611 (1982); in The Qiagenologist, Application Protocols, 3rd edition, published by Qiagen, Inc., Chatsworth, Calif.; and in Sambrook et al. *Molecular Cloning: A Laboratory Manual* (Cold Spring Harbor Laboratory, Cold Spring Harbor, N.Y., 1989).

In an exemplary microinjection procedure, female mice six weeks of age are induced to superovulate. The superovulating females are placed with males and allowed to mate. After approximately 21 hours, the mated females are sacrificed and embryos are recovered from excised oviducts and placed in an appropriate buffer, e.g., Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipette (about 10 to 12 embryos). The pipette tip is inserted into the infundibulum and the embryos transferred. After the transfer, the incision is closed by two sutures. The pregnant animals then give birth to the founder animals which are used to establish the transgenic line.

I. Use of Prox-1-Based Compositions for Diagnostic Purposes

The demonstration that Prox-1 is overexpressed in precancerous and colon cancer cells also indicates that detection of Prox-1 polynucleotides and polypeptides (including variants thereof) are useful for diagnostic purposes. Therefore, preferred aspects of the present invention are directed to methods of screening and diagnosing colon cancer in an individual.

In one preferred embodiment, diagnostic methods of the invention are practiced through the detection of the Prox-1 protein. In general, methods for detecting a polypeptide of the invention can comprise contacting a biological sample with a compound that binds to and forms a complex with the polypeptide for a period sufficient to form the complex, and detecting the complex, so that if a complex is detected, a polypeptide of the invention is detected. Prox-1 protein detection can be accomplished using antibodies specific for the protein in any of a number of formats commonly used by those of skill in the art for such detection.

For example, elsewhere in the present application, the production and characterization of monoclonal antibodies specific for Prox-1 is described. Such antibodies may be employed in ELISA-based techniques and Western blotting techniques to detect the presence of Prox-1 in a biological sample from a subject being tested. Methods for setting up ELISA assays and preparing Western blots of a sample are well known to those of skill in the art. The biological sample can be any tissue or fluid in which colon cells or tissue might be present.

An anti-Prox-1 antibody or fragment thereof also is useful to monitor expression of this protein in individuals suffering from colon cancer. Typically, diagnostic assays entail detecting the formation of a complex resulting from the binding of an antibody or fragment thereof to Prox-1. For diagnostic purposes, the antibodies or antigen-binding fragments can be labeled or unlabeled. The antibodies or fragments can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654 and 4,098,876). When unlabeled, the antibodies or fragments can be detected using suitable means, as in agglutination assays, for example. Unlabeled antibodies or fragments can also be used in combination with another (i.e., one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

In one embodiment, the antibodies or fragments of the present invention can be utilized in enzyme immunoassays, wherein the subject antibody or fragment, or second antibodies, are conjugated to an enzyme. When a biological sample comprising a Prox-1 protein is combined with the subject antibodies, binding occurs between the antibodies and the Prox-1 protein. In one embodiment, a biological sample containing cells expressing a mammalian Prox-1 protein, or biological fluid containing secreted Prox-1 is combined with the subject antibodies, and binding occurs between the antibodies and the Prox-1 protein present in the biological sample comprising an epitope recognized by the antibody. These bound protein can be separated from unbound reagents and the presence of the antibody-enzyme conjugate specifically bound to the Prox-1 protein can be determined, for example, by contacting the sample with a substrate of the enzyme which produces a color or other detectable change when acted on by the enzyme. In another embodiment, the subject antibodies can be unlabeled, and a second, labeled antibody can be added which recognizes the subject antibody.

Similarly, the present invention also relates to a method of detecting and/or quantitating expression of a mammalian Prox-1 protein or a portion of the Prox-1 protein by a cell, in which a composition comprising a cell or fraction thereof (e.g., a soluble fraction) is contacted with an antibody or functional fragment thereof which binds to a mammalian Prox-1 protein or a portion of the Prox-1 protein under conditions appropriate for binding of the antibody or fragment thereto, and binding is monitored. Detection of the antibody, indicative of the formation of a complex between antibody and or a portion of the protein, indicates the presence of the protein.

The method can be used to detect expression of Prox-1 from the cells of an individual (e.g., in a sample, such as a body fluid, such as blood, saliva or other suitable sample). The level of expression of in a biological sample of that individual can also be determined, for instance, by flow cytometry, and the level of expression (e.g., staining intensity) can be correlated with disease susceptibility, progression or risk.

In certain other diagnostic embodiments, the polynucleotide sequences encoding Prox-1 protein may be used for the diagnosis of conditions or diseases with which the expression of Prox-1 protein is associated. In general, methods for detecting Prox-1 mRNA can comprise contacting a biological sample with a compound that binds to and forms a complex with Prox-1 mRNA for a period sufficient to form the complex, and detecting the complex in a quantitative or semi-quantitative way. Such methods can also comprise amplification techniques involving contacting a biological sample with nucleic acid primers that anneal to Prox-1 mRNA or its complement, and amplifying annealed polynucleotides, so that if a polynucleotide is amplified, a polynucleotide of the invention is detected. The biological sample can be any tissue or fluid in which Prox-1-expressing colon cells might be present.

In the amplification procedures, polynucleotide sequences encoding Prox-1 protein may be used in hybridization or PCR assays of fluids or tissues from biopsies to detect Prox-1 protein expression. Such methods may be qualitative or quantitative in nature and may include Southern or northern analysis, dot blot or other membrane-based technologies; PCR technologies; dip stick, pin, chip and ELISA technologies. All of these techniques are well known in the art and are the basis of many commercially available diagnostic kits.

One such procedure known in the art is quantitative real-time PCR. Real-time quantitative can be conveniently accomplished using the commercially available ABI PRISM™ 7700 Sequence Detection System, available from PE-Applied Biosystems, Foster City, Calif. and used according to manufacturer's instructions. PCR reagents can be obtained from PE-Applied Biosystems, Foster City, Calif. Gene target quantities obtained by real time RT-PCR may be normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry,* 1998, 265, 368-374. Controls are analyzed in parallel to verify the absence of DNA in the RNA preparation (-RT control) as well as the absence of primer dimers in control samples lacking template RNA. In addition, RT-PCR products may be analyzed by gel electrophoresis.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641, filed Dec. 21, 1990.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmnunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The tests of the present invention include cells, protein extracts of cells, or biological fluids such as, blood, serum, and plasma. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In addition, such assays may be useful in evaluating the efficacy of a particular therapeutic treatment regime in animal studies, in clinical trials, or in monitoring the treatment of an individual patient. In order to provide a basis for the diagnosis of disease, a normal or standard measurement of Prox-1 mRNA or protein expression is established. This generally involves Prox-1 measurements from healthy colon tissue taken from one or more subjects, measured using the same or similar reagents used for the test subjects. The healthy subject preferably is matched for sex and age, and optionally, ethnicity. Deviation between standard and subject values correlates with the presence of precancerous or cancerous tissue.

Once disease is established, a therapeutic agent is administered; and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Methods to quantify the expression of a particular molecule include radiolabeling (Melby et al., J Immunol Methods 159: 235-44, 1993) or biotinylating (Duplaa et al., Anal Biochem 229-36, 1993) nucleotides, coamplification of a control nucleic acid, and standard curves onto which the experimental results are interpolated.

In addition to being used as diagnostic methods, screening methods also may be used in a prognostic manner to monitor the efficacy of treatment. The methods may be performed immediately before, during and after treatment to monitor treatment success. The methods also should be performed at intervals, preferably every three to six months, on disease free patients to insure treatment success.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers, or strips of plastic or paper. Such containers allow one to efficiently transfer reagents from one compartment to another compartment such that the biological sample and reagents are not cross-contaminated, and the agents or solutions of each container can be added in a quantitative fashion from one compartment to another. Such containers will include a container which will accept the test sample, a container which contains, for example, the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

In further detail, kits for use in detecting the presence of a mammalian Prox-1 protein can include an antibody or functional fragment thereof which binds to a mammalian Prox-1 protein or portion of this protein, as well as one or more ancillary reagents suitable for detecting the presence of a complex between the antibody or fragment and Prox-1 or portion thereof. The antibody compositions of the present invention can be provided in lyophilized form, either alone or in combination with additional antibodies specific for other epitopes. The antibodies, which can be labeled or unlabeled, can be included in the kits with adjunct ingredients. For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit for instance in a separate vial or container. The second antibody, if present, is typically labeled, and can be formulated in an analogous manner with the antibody formulations described above.

J. Examples

The present invention is illustrated in the following examples, which are intended to be illustrative and not limiting. Upon consideration of the present disclosure, one of skill in the art will appreciate that many other embodiments and variations may be made in the scope of the present invention.

Example 1 provides methods and materials for the subsequent Examples.

Example 2 provides experimental results of studies designed to assess Prox-1 expression in colorectal cancer cells.

Example 3 details expression of Prox-1 in round but not in adherent subclones of the SW480 colon adenocarcinoma cell line.

Example 4 provides experimental results of Prox-1 silencing in SW480R cells.

Example 5 describes effects of Prox-1 ablation on Notch signaling in SW480R cells.

Example 6 describes the effects of suppression of Prox-1 on the growth of SW480R cells in soft agar.

Example 7 describes the effect Prox-1 suppression on prostaglandin biosynthesis.

Example 8 describes experiments aimed as assessing the effects of altered Notch signaling.

Example 9 describes experiments aimed at assessing the effects of Prox-1 suppression on the growth of SW480R tumors in nude mice.

Example 10 describes analysis of Prox-1 in natural colorectal tumors.

Example 11 describes one method for diagnosing or screening for colorectal cancer.

Example 12 describes experiments designed to compare Prox-1 expression in normal cololnic epithelium.

Example 13 describes experiments aimed at assessing Prox-1 expression in $Apc^{min/+}$ mice.

Example 14 describes studies conducted using SW480R cell line as an in vitro model to investigate the role of Prox-1 in colorectal carcinoma.

Example 15 describes experiments to characterize the effects of Prox-1 suppression and overexpression in colorectal cancer.

Example 16 describes experiments employing dominant negative mutants of Prox-1.

Example 1

Methods and Materials

Methods and material used or referred to in subsequent examples are set forth directly below.

Antibodies

Monoclonal mouse anti-vimentin, β-catenin (Transduction Laboratories), Ki-67 (Pharmingen) and chromogranin A (Ab-3, NeoMarkers), monoclonal rat anti-BrdU (Harlan Seralab) and polyclonal rabbit anti-Prox-1 were obtained from the indicated commercial sources. The fluorochrome-conjugated secondary antibodies were obtained from Jackson Immunoresearch.

For production of Prox-1 antibodies cDNA encoding Prox-1 homeobox domain and prospero domain (amino acids 578-750 of human Prox-1, SEQ ID NO: 3) was subcloned into pGEX2t vector to produce GST-Prox-1 fusion construct. This construct was expressed in *E. coli* and the GST-Prox-1 fusion protein from *E. coli* was purified using glutathione Sepharose according to the manufacturer's instructions (Amersham, Piscataway, N.J.). Fusion protein was used to immunize rabbits according to a standard protocol. Prox-1-specific antibodies were isolated from rabbit serum using sequential columns with GST- and GST-Prox-1-coupled to vinylsulfone agarose resin (Sigma). Purified antibody recognized an 85 kD protein in lysates from 293T cells transfected with Prox-1 but not from cells transfected with the empty vector.

Synthetic siRNAs siRNA duplexes were prepared from synthetic 21 nucleotide RNAs (Dharmacon Research). siRNA sequences were: 5'-CUGCAAGCUGGAUAGUGAAGU-3' (Prox-1 siRNA A16 sense) (SEQ ID NO: 4); 5'-UUCACUAUCCAGCUUG-CAGAU-3' (Prox-1 siRNA A16 antisense) (SEQ ID NO: 5);

5'-CUAUGAGCCAGUUUGAUAUUU-3' (Prox-1 siRNA A25 sense) (SEQ ID NO: 6); 5'-AUAUCAAACUGGCU-CAUAGUU-3' (Prox-1 siRNA A25 antisense) (SEQ ID NO: 7).

EGFP-targeting control siRNA A18 was essentially as described (Lewis et al., 2002) except that instead of thymidine 3' overhangs uracil overhangs were used; GACGUAAACGGCCACAAGUUU (EGFP siRNA A18 sense) (SEQ ID NO: 8); ACUUGUGGCCGUUUACGU-CUU (EGFP siRNA A18 antisense) (SEQ ID NO: 9).

siRNAs were 2'-ACE deprotected according to the manufacturer's instructions, dried in vacuum, resuspended in 400 µl water, dried again, resuspended in water, and annealed to form duplex siRNAs. For annealing equimolar amounts of siRNA strands (approximately 50-100 µM) were incubated in annealing buffer (100 mM potassium acetate 30 mM Hepes-KOH pH 7.4, 2 mM magnesium acetate) for 5 min at +95° C. followed by 30 min at +37° C. and 30 min at +25° C. After annealing the siRNA concentration was measured by spectrometry and siRNA aliquoted and stored at −20° C.

Cell Culture, Transfection, and Soft Agar Assay

SW480 cells were obtained from ATCC (CCL-228) and cultured in RPMI-1640 supplemented with 10% fetal bovine serum, 1 mM glutamine and antibiotics. HepG2 cells were cultured in DMEM, containing 10% fetal bovine serum 1 mM glutamine and antibiotics.

Transfection of siRNAs was carried out using lipofectamine 2000 (Invitrogen) according to manufacturer's instructions using 0.5% (v/v) lipofectamine 2000 reagent for SW480R and 0.4% (v/v) lipofectamine 2000 for adherent SW480 cells and either 2 nM or 100 nM (f.c.) of siRNA. Transfections were carried out in antibiotic-free media for 4-6 hours before changing cells back to normal culture media. For long-term experiments siRNA transfections were repeated after 48-72 h from previous transfection (at protein level the silencing effect was seen to remain efficient for at least 96 h). Normally approximately 90-95% transfection efficiency was achieved. Opti-MEM (Invitrogen) medium was used in preparation of transfection mixtures.

For luciferase assays, cells were transfected with Green Fluorescent Protein small interfering RNA (GFPsi RNA) or Prox-1 siRNAs 72 h prior to the transfection with the firefly lucefarese reporter constructs CBF1-luc, control pGL2-luc (Promega), TOPFlash and FOPFlash (Upstate). To normalize the transfection efficiency, cells were co-transfected with the Renilly firefly reporter pRL-TK (Promega). 36 h after the last transfection cells were lysed and lysates were analyzed for the luciferase activity using Dual-Luciferase™ kit according to the manufacturer's instructions (Promega).

For soft agar assay, $2 \times 10^3$ and $2 \times 10^4$ cells were seeded in triplicate in 1 ml of 0.33% (w/v) agar (Difco) containing D-MEM, 10% fetal bovine serum, 1 mM glutamine and antibiotics in 6-well plates containing 1 ml of 0.5% bottom agar layer. Cells were fed twice a week, and number of colonies per plate was scored after two weeks in culture.

RNA Isolation, Northern, and Western Blotting

Total RNA was isolated and DNAseI treated in RNeasy columns (Qiagen). For Cancer Array analysis, filters were hybridized in ExpressHyb with 32P-labeled probes for LYVE-1 and Prox-1 according to the manufacturer's instructions (Clontech). For Northern analysis, the blots were hybridized in Ultrahyb solution (Ambion) with 32P-labeled probes produced by RT-PCR using RNA from SW480R or SW480A cells. The primers were designed to amplify 300-700 bp of the coding sequence, and all PCR-fragments were sequenced to confirm their identity.

For the Affymetrix® gene expression analysis, sample preparations and hybridizations were carried out as described (Petrova et al. *Embo J* 21: 4593-9, 2002), using RNA extracted from two clones of SW480R or SW480A cells, or from two independent transfections of two different clones of SW480R cells with GFP siRNA or Prox-1 siRNA A16. To confirm the latter results, another transfection was carried out using Prox siRNA A25. To exclude the non-specific effects due to the transfection itself, non-transfected SW480R cells grown in parallel were also analyzed.

For Western blotting $2 \times 10^5$ cells were lysed in 500 µl of sample buffer, lysates were separated using 10% PAGE and transferred to the nitrocellulose membranes (Schleisher&Schull) using semi-dry transfer method for 1 h at 300 mA. Membranes were blocked in 5% non-fat dry milk, 0.1% Tween-20 in 50 mM Tris-HCl, pH 7.4, 150 mM NaCl, and incubated overnight with primary antibodies. Bound primary antibodies were detected using HRP-conjugated corresponding secondary antibodies and the ECL detection method (KPL).

Immunofluorescence and Immunohistochemistry

The cells were cultured on coverslips, fixed with MetOH and stained with the primary antibodies and fluorochrome-conjugated secondary antibody. F-actin was stained using TexasRed-conjugated phalloidin (Molecular Probes). Cells were counterstained with Hoechst 33258 fluorochrome (Sigma) and viewed in Zeiss Axioplan 2 fluorescent microscope.

For tissue staining staining, colon tumors and normal colon samples were embedded in Tissue-Tek® (Sakura), frozen and sectioned. The 4 µm sections were fixed in cold methanol for 10 min and stained with the primary antibodies followed by peroxidase staining using Vectastain Elite ABC kit (Vector Laboratories) and 3-amino-9-ethyl carbazole (Sigma), or by detection using fluorchrome conjugated secondary antibodies.

Example 2

Prox-1 mRNA is Elevated in Colorectal Tumors

Experiments were conducted to assess the expression of Prox-1 mRNA in human cancers using a cancer gene profiling array filter, which contains cDNAs from about 250 human cancers and corresponding normal control tissues. Prox-1 mRNA was significantly increased in 35 out of 53 samples of colorectal cancers. In contrast, only rarely or not at all was any increase seen in samples from breast, uterine, lung, kidney, ovarian, or thyroid tumors (FIGS. 1A, B, and C). Probes for Prox-1 (FIG. 1A) and the lymphatic endothelial marker LYVE-1 (FIG. 1B) were used. FIG. 1C demonstrates quantification of dot blot in FIG. 1A, the asterisk indicating tumor samples in which Prox-1 expression is significantly different from that of the normal tissue (P<0.005). Expression of Prox-1 was low or absent in all kidney cancer samples studied. Prox-1 is a marker for lymphatic vessels, which are abundant both in normal colonic submucosa and around colon carcinomas (White et al., *Cancer Res.* 62: 1669-75 (2002)). Therefore, the filter to the probe for the lymphatic endothelial hyaluronan receptor LYVE-1 was hybridized. Unlike Prox-1, LYVE-1 levels were higher in the normal samples, suggesting that the increased expression cannot be attributed to the lymphatic vessels (FIG. 1B).

Experiments were further conducted to assess the expression of Prox-1 in colon cancers and premalignant colonic lesions using affinity purified antibodies raised against Prox-1 homeobox and prospero domains, which are conserved between the mouse and human proteins. Staining of a panel of mouse tissues and E12.5 and E17.5 embryos revealed specific nuclear staining for Prox-1 in the previously reported sites of expression such as in lymphatic vessels, lens fiber cells and in a subset of neurons in the neural tube. Staining of eleven human colorectal adenomas and nine carcinomas and adjacent normal mucosa revealed increased expression of Prox-1 in nine adenomas and in six carcinomas (FIG. 2A-I). Increased Prox-1 staining was observed in all cells in seven adenomas and in two carcinomas, whereas in the other lesions a heterogeneous expression of Prox-1 occurred. In one tumor sample, no specific staining for Prox-1 was seen, while strong expression was observed in intratumoral lymphatic vessels.

Double immunofluorescent staining for Prox-1 and the neuroendocrine marker chromogranin A or proliferation marker Ki-67 was conducted in normal colonic epithelial cells. Nuclei were visualized with Hoechst 333421. In the normal colonic mucosa, Prox-1 was strongly expressed in some epithelial cells, a subset of which was positive for the pan-neuroendocrine marker chromogranin A. In addition, a weaker but significant Prox-1 expression was observed in the bottom of the crypts below the cell proliferation zone identified by staining for the Ki-67 antigen. The location of Prox-1 positive cells at the base of the crypts corresponds to the position of the intestinal stem cells (Bach et al., *Carcinogenesis* 21: 469-76 (2000)).

Example 3

Prox-1 is Expressed in Round but not in Adherent Subclones Of the SW480 Colon Adenocarcinoma Cell Line Additional studies were conducted to compare Prox-1 expression in various cells. No Prox-1 expression was seen in the majority of tumor cell lines studied. However, Prox-1 was mRNA was present in hepatocellular carcinoma cell line HepG2 and the colon carcinoma cell line SW480. BEC, blood endothelial cells, CAEC, coronary artery endothelial cells, and LEC, lymphatic endothelial cells, served as negative and positive controls. Immunofluorescent staining of HepG2 revealed strong expression in all HepG2 cells, whereas only a subset of SW480 cells were Prox-1 positiveDouble immunofluorescent staining for Prox-1 and for β-catenin or for the F-actin marker phalloidin demonstrated that Prox-1 expression is restricted to weakly adherent round SW480 cells which did not display focal adhesions or actin stress fibers, and that Prox-1 was very weakly expressed the adherent cells. The existence of two subtypes of cells in the SW480 cultures has been reported previously (Palmer, H. G. et al., *J Cell Biol.* 154: 369-87, 2001; Tomita, N. et al., Cancer Res. 52; 6840-7, 1992). The SW480R (round) cells displayed anchorage independent growth in vitro and highly malignant phenotype in vivo, whereas the SW480A (adherent) cells did not grow well in soft agar and formed small and well differentiated tumors when implanted into nude mice.

Several SW480R and SW480A clones were isolated, which could be continuously grown for at least 20 passages without conversion of phenotypes. SW480R and SW480A cells differed by the levels of Prox-1, as determined by Northern and Western blotting, with much higher expression in the round cells, and weak, if any, expression in the Adherent ones. The gene expression profiles of SW480R and SW480A cells were compared using oligonucleotide microarrays containing 22,000 annotated human genes, and identified about 1,000 genes whose expression differed by more than fourfold between these two cell types (Table I). SW480 cells were stained for intermediate filament protein vimentin and Prox-1. Northern blotting and hybridization were used for transcripts. Hybridization for GAPDH was used as a control. A striking difference was observed in the expression of cytoskeletal and cell adhesion proteins. In agreement with their decreased adhesion and round cell shape, the SW480R cells lacked many components of the actin, intermediate filament and microtubule networks, such as gelsolin, filamins A and B, ezrin, moesin, vimentin, various integrins, and tubulins (Table I). These cells expressed higher levels of the protoncogene c-met, as well as the receptor tyrosine kinase FGFR-4, which has been associated with malignant transformation in colorectal and other cancer (Bange, J. et al., *Cancer Res.* 62: 840-7, 2002; Cavallaro, U., Niedermeyer, J., Fuxa, M. & Christofori, G., *Nat. Cell Biol.* 3: 650-7, 2001; Yamada, S. M. et al., *Neurol Res.* 24: 244-8, 2002), and low levels of the tumor suppressor p21Cip1. FGFR-4 is a target for therapeutic intervention according to the invention, alone or in combination with Prox-1. Intervention using the same classes of inhibitors as described for Prox-1, as well as antibodies and antibody fragment substances, is specifically contemplated. In addition, all three tissue inhibitors of matrix metalloproteinases were absent from the SW480R cells, which may further account for their increased tumor growth in vivo. In contrast, the SW480A cells expressed higher levels of the chemokine receptor CXCR4, which is expressed in the normal colonic epithelium (Jordan et al., *J Clin Invest* 104,1061-9, 1999). In summary, the gene expression profile of the SW480R cells correlates well with a highly aggressive transformed phenotype, whereas the SW480A cells display more differentiated features typical of cells in the colonic crypts.

TABLE I

Examples of groups of genes differentially expressed in round versus adherent SW480 clones. Two round and two adherent clones were analyzed.

| Gene function and name | UniGene cluster | Gene symbol | Log$_2$ ratio, average | St. dev |
|---|---|---|---|---|
| 1. Cytoskeleton and adhesion | | | | |
| collagen, type XIII, alpha 1 | Hs.211933 | COL13A1 | −5.6 | 0.9 |
| fibronectin 1 | Hs.287820 | FN1 | −5.2 | 0.5 |
| integrin, alpha 7 | Hs.74369 | ITGA7 | −4.3 | 0.3 |
| vimentin | Hs.297753 | VIM | −4.1 | 0.6 |
| filamin B, beta (actin binding protein 278) | Hs.81008 | FLNB | −3.8 | 0.7 |
| integrin, beta 5 | Hs.149846 | ITGB5 | −3.6 | 0.5 |
| tubulin, beta polypeptide | Hs.274398 | TUBB | −3.3 | 0.7 |

TABLE I-continued

Examples of groups of genes differentially expressed in round versus adherent SW480 clones. Two round and two adherent clones were analyzed.

| Gene function and name | UniGene cluster | Gene symbol | Log$_2$ ratio, average | St. dev |
|---|---|---|---|---|
| PTPL1-associated RhoGAP 1 | Hs.70983 | PARG1 | −3.0 | 0.5 |
| collagen, type IX, alpha 3 | Hs.53563 | COL9A3 | −2.8 | 0.8 |
| paralemmin | Hs.78482 | PALM | −2.7 | 0.2 |
| PDZ and LIM domain 1 (elfin) | Hs.75807 | PDLIM1 | −2.7 | 0.2 |
| cadherin 11, type 2, OB-cadherin (osteoblast) | Hs.75929 | CDH11 | −2.6 | 0.7 |
| myosin IC | Hs.286226 | MYO1C | −2.6 | 0.6 |
| integrin, alpha 3 | Hs.265829 | ITGA3 | −2.6 | 0.4 |
| discs, large (*Drosophila*) homolog 1 | Hs.154294 | DLG1 | −2.5 | 0.1 |
| integrin, alphaV | Hs.295726 | ITGAV | −2.5 | 0.3 |
| CDC42 effector protein (Rho GTPase binding) 3 | Hs.260024 | CDC42EP3 | −2.4 | 0.4 |
| ephrin-B1 | Hs.144700 | EFNB1 | −2.3 | 0.4 |
| FERM, RhoGEF (ARHGEF) and pleckstrin domain protein 1 | Hs.183738 | FARP1 | −2.3 | 0.4 |
| myosin ID | Hs.39871 | MYO1D | −2.1 | 0.2 |
| PDZ and LIM domain 2 (mystique) | Hs.379109 | PDLIM2 | −2.1 | 0.4 |
| tubulin beta-5 | Hs.274398 | TUBB-5 | −1.9 | 0.3 |
| erythrocyte membrane protein band 4.1-like 1 | Hs.26395 | EPB41L1 | −1.9 | 0.1 |
| gelsolin (amyloidosis, Finnish type) | Hs.290070 | GSN | −1.9 | 0.3 |
| laminin, gamma 1 (formerly LAMB2) | Hs.432855 | LAMC1 | −1.8 | 0.1 |
| ras homolog gene family, member E | Hs.6838 | ARHE | −1.7 | 0.2 |
| IQ motif containing GTPase activating protein 1 | Hs.1742 | IQGAP1 | −1.7 | 0.3 |
| tight junction protein 1 (zona occludens 1) | Hs.74614 | TJP1 | −1.7 | 0.4 |
| catenin (cadherin-associated protein), alpha-like 1 | Hs.58488 | CTNNAL1 | −1.7 | 0.6 |
| collagen, type XVIII, alpha 1 | Hs.78409 | COL18A1 | −1.6 | 0.1 |
| filamin A, alpha (actin binding protein 280) | Hs.195464 | FLNA | −1.6 | 0.2 |
| actin related protein 2/3 complex, subunit 1A, 41 kDa | Hs.90370 | ARPC1A | −1.5 | 0.3 |
| alpha integrin binding protein 63 | — | AIBP63 | −1.4 | 0.3 |
| spectrin, alpha, non-erythrocytic 1 (alpha-fodrin) | Hs.77196 | SPTAN1 | −1.4 | 0.2 |
| villin 2 (ezrin) | Hs.155191 | VIL2 | −1.4 | 0.3 |
| actin related protein 2/3 complex, subunit 1B, 41 kDa | Hs.433506 | ARPC1B | −1.3 | 0.1 |
| plakophilin 4 | Hs.152151 | PKP4 | −1.3 | 0.3 |
| ras homolog gene family, member C | Hs.179735 | ARHC | −1.1 | 0.1 |
| moesin | Hs.170328 | MSN | −1.1 | 0.1 |
| myristoylated alanine-rich protein kinase C substrate | Hs.75607 | MARCKS | −1.1 | 0.2 |
| 2. Tumor growth and invasion | | | | |
| tissue inhibitor of metalloproteinase 2 | Hs.6441 | TIMP2 | −2.3 | 0.21 |
| tissue inhibitor of metalloproteinase 3 | Hs.245188 | TIMP3 | −1.5 | 0.14 |
| Cyclin-dependent kinase inhibitor 1A (p21, Cip1) | Hs.179665 | CDKN1A | −2.5 | 0 |
| tissue inhibitor of metalloproteinase 1 | Hs.5831 | TIMP1 | −1.5 | 0.4 |
| met proto-oncogene (hepatocyte growth factor receptor) | Hs.316752 | MET | 2.6 | 0.46 |
| Fibroblast growth receptor 4 | Hs.165950 | FGFR4 | 3.9 | 0.76 |
| 3. Expressed in normal intestinal epithelium | | | | |
| CXCR4 | Hs.89414 | CXCR4 | −1.3 | 0.1 |
| solute carrier family 7 (cationic amino acid transporter, y+ system), member 8 | Hs.22891 | SLC7A8 | −1.8 | |

TABLE I-continued

Examples of groups of genes differentially expressed in round versus adherent SW480 clones. Two round and two adherent clones were analyzed.

| Gene function and name | UniGene cluster | Gene symbol | Log$_2$ ratio, average | St. dev |
|---|---|---|---|---|
| 4. Notch pathway | | | | |
| Notch homolog 2 (*Drosophila*) | Hs.8121 | NOTCH2 | −1.4 | 0.15 |
| hairy homolog (*Drosophila*), HES1 | Hs.250666 | HRY | −2.1 | 0.2 |
| jagged 2 | Hs.166154 | JAG2 | 1.6 | 0.61 |
| 5. Wnt pathway | | | | |
| wingless-type MMTV integration site family, member 5A | Hs.152213 | WNT5A | −5.8 | 0.12 |
| dickkopf homolog 3 | Hs.4909 | DKK3 | −5.6 | 1.21 |
| wingless-type MMTV integration site family, member 6 | Hs.29764 | WNT6 | −4.2 | 0.23 |
| frizzled homolog 7 (*Drosophila*) | Hs.173859 | FZD7 | −4.1 | 0.65 |
| frizzled homolog 2 (*Drosophila*) | Hs.81217 | FZD2 | −3.7 | 0.56 |
| frizzled homolog 10 (*Drosophila*) | Hs.31664 | FZD10 | 2.97 | 0.86 |
| dickkopf homolog 4 | Hs.159311 | DKK4 | 7.37 | 0.71 |

Example 4

Prox-1 Silencing in SW480R Cells Leads to a Differentiated and Quiescent Phenotype Experiments were conducted to investigate whether Prox-1 plays role in the generation and maintenance of the highly transformed phenotype. Prox-1 mRNA and protein in the SW480R cells was suppressed using Prox-1 targeting siRNA. Absence of Prox-1 in Prox-1 siRNA but not the control GFP siRNA transfected cells was confirmed by immunofluorescent staining, and nuclei were visualized with Hoechst 33342. Prox-1 siRNA-transfected cells but not the untransfected or GFP siRNA transfected cells underwent a morphological change, which became visible by 72 hours and persisted at least for 10 days after the transient transfection. The Prox-1 siRNA transfected cells become first more elongated and displayed extensive membrane ruffling. Eventually the Prox-1 siRNA cells started to spread on the plate and a number of increased actin stress fibers could be visualized by phalloidine staining. BrdU incorporation experiments demonstrated that the Prox-1 siRNA transfected cells proliferated at the lower rate than GFPsi or nontransfected cells (22±0.5% of BrdU positive cells in Prox-1 siRNA A16, 18±1% Prox-1 siRNA A25 vs 34±4% GFP siRNA).

Changes in the gene expression profiles of the SW480R and SW480A cells 120 and 240 h posttransfection, when the morphological changes were apparent, were also analyzed. Only 29 down-regulated and 120 upregulated genes in Prox-1 siRNA versus GFP siRNA transfected cells (Table II) were identified. 41% of these genes were differentially expressed between the SW480R and SW480A cells, suggesting that Prox-1 at least partially determines the phenotype of SW480R cells. The ablation of Prox-1 led to upregulation of a number of known epithelial markers, such as annexin A1, CRPB2, S100A3, and EMP1, along with the increase in cell adhesion molecules OB-cadherin and integrins beta7, beta5 and alpha 1. In line with the observed growth arrest, also observed was the decrease in c-myc and a strong increase of CDK inhibitor p21Cip1. Highly similar changes in gene expression profile were observed when another unrelated Prox-1si RNA was used, suggesting that the cellular effects are due to the specific targeting of Prox-1, and they did not result from off-target silencing. In addition, titration experiments demonstrated that the induction of p21 and other target genes occurred even at the low (20 nM) concentration of Prox-1 siRNAs but not of the control GFP siRNA. Also, the mentioned gene changes were not observed in Prox-1 negative SW480A cells transfected with siRNAs at 100 nm concentration. The transfection efficiency was controlled using another siRNA, which successfully suppressed the expression of the target gene in SW480A cells.

TABLE II

Genes regulated by Prox-1 in SW480R cells. Asterisk indicates genes that were flagged as absent in either Prox-1 siRNA or GFP siRNA treated cells. Genes differentially expressed between SW480R and SW480ADH cells are shown in bold.

| | UniGene cluster | Gene symbol | Log$_2$ ratio, average | stdev |
|---|---|---|---|---|
| Genes down-regulated in the absence of Prox-1 | | | | |
| Nebulette | Hs.5025 | NEBL | −2.0 | 0.4 |
| transforming growth factor, beta-induced, 68 kDa | Hs.118787 | TGFBI | −1.9 | 0.1 |
| trinucleotide repeat containing 9 | Hs.110826 | TNRC9 | −1.9 | 0.2 |
| insulin-like growth factor binding protein 3 | Hs.77326 | IGFBP3 | −1.6 | 0.0 |
| calpain 1, (mu/I) large subunit | Hs.2575 | CAPN1 | −1.5 | 0.3 |
| inhibitor of DNA binding 1 | Hs.75424 | ID1 | −1.5 | 0.3 |

TABLE II-continued

Genes regulated by Prox-1 in SW480R cells. Asterisk indicates genes that were flagged as absent in either Prox-1 siRNA or GFP siRNA treated cells. Genes differentially expressed between SW480R and SW480ADH cells are shown in bold.

| | UniGene cluster | Gene symbol | Log$_2$ ratio, average | stdev |
|---|---|---|---|---|
| midkine (neurite growth-promoting factor 2) | Hs.82045 | MDK | −1.5 | 0.1 |
| FK506 binding protein 11, 19 kDa | Hs.24048 | FKBP11 | −1.4 | 0.1 |
| caspase recruitment domain family, member 10 | Hs.57973 | CARD10 | −1.3 | 0.1 |
| inhibin, beta B (activin AB beta polypeptide) | Hs.1735 | INHBB | −1.3 | 0.2 |
| L1 cell adhesion molecule | Hs.1757 | L1CAM | −1.2 | 0.1 |
| glutathione peroxidase 2 (gastrointestinal) | Hs.2704 | GPX2 | −1.2 | 0.0 |
| eukaryotic translation elongation factor 1 alpha 2 | Hs.2642 | EEF1A2 | −1.2 | 0.2 |
| hypothetical protein FLJ11149 | Hs.37558 | FLJ11149 | −1.2 | 0.2 |
| potassium voltage-gated channel, subfamily H (eag-related), member 2 | Hs.188021 | KCNH2 | −1.1 | 0.1 |
| KIAA0182 protein | Hs.75909 | KIAA0182 | −1.1 | 0.0 |
| lectin, galactoside-binding, soluble, 1 (galectin 1) | Hs.382367 | LGALS1 | −1.1 | 0.1 |
| *Homo sapiens* cDNA FLJ41000 fis, | — | — | −1.1 | 0.3 |
| ephrin-B2 | Hs.30942 | EFNB2 | −1.1 | 0.1 |
| v-myc myelocytomatosis viral oncogene homolog (avian) | Hs.79070 | MYC | −1.1 | 0.1 |
| S100 calcium binding protein A14 | Hs.288998 | S100A14 | −1.1 | 0.2 |
| **Alpha one globin [ *Homo sapiens*], mRNA sequence* | | | −1.1 | 0.1** |
| hypothetical protein FLJ10986* | Hs.273333 | FLJ10986 | −1.0 | 0.0 |
| hypothetical protein FLJ11149 | Hs.37558 | FLJ11149 | −1 | 0.0 |
| myelin transcription factor 1* | | MYT1 | −1.0 | 0.0 |
| nucleolar autoantigen (55 kD) similar to rat synaptonemal complex protein* | Hs.446459 | SC65 | −1.0 | 0.1 |
| tumor necrosis factor receptor superfamily, member 6b, decoy | Hs.455817 | TNFRSF6B | −1.0 | 0.1 |
| jagged 2 | Hs.166154 | JAG2 | −1.0 | 0.1 |
| mitochondrial ribosomal protein S2 | Hs.20776 | MRPS2 | −1.0 | 0.1 |
| Total: 29 genes | | | | |
| Genes up-regulated in the absence of Prox1 | | | | |
| insulin-like growth factor binding protein 7* | Hs.119206 | IGFBP7 | 5.8 | 0.4 |
| chitinase 3-like 1 (cartilage glycoprotein-39)* | Hs.75184 | CHI3L1 | 5.3 | 0.8 |
| chemokine (C-X-C motif) receptor 4* | Hs.89414 | CXCR4 | 4.5 | 1.1 |
| semaphorin 3C* | Hs.171921 | SEMA3C | 4.5 | 4.5 |
| cadherin 11, type 2, OB-cadherin (osteoblast)* | Hs.75929 | CDH11 | 3.8 | 0.3 |
| annexin A1 | Hs.78225 | ANXA1 | 3.7 | 1.1 |
| hypothetical protein MGC10796* | — | MGC10796 | 3.3 | 0.4 |
| CD44 antigen | Hs.169610 | CD44 | 2.6 | 1.1 |
| *Homo sapiens* clone 23785 mRNA sequence | — | — | 2.9 | 0.4 |
| epithelial membrane protein 1* | Hs.79368 | EMP1 | 2.9 | 0.1 |
| inhibitor of DNA binding 2, dominant negative helix-loop-helix protein* | Hs.180919 | ID2 | 2.8 | 0.1 |
| Human HepG2 3' region cDNA, clone hmd1f06, mRNA sequence | — | — | 2.8 | 0.3 |
| tumor necrosis factor receptor superfamily, member *11b (osteoprotegerin) | Hs.81791 | TNFRSF11B | 2.6 | 0.7 |
| likely homolog of mouse glucuronyl C5-epimerase* | Hs.183006 | GLCE | 2.6 | 1.1 |
| ribonuclease, RNase A family, 1 (pancreatic)* | Hs.78224 | RNASE1 | 2.6 | 0.1 |
| apolipoprotein B mRNA editing enzyme, catalytic polypeptide-like 3B* | Hs.226307 | APOBEC3B | 2.5 | 0.1 |
| hydroxyprostaglandin dehydrogenase 15-(NAD)* | Hs.77348 | HPGD | 2.5 | 1.1 |
| NPD009 protein | Hs.283675 | NPD009 | 2.5 | 0.6 |
| integrin, beta 7* | Hs.1741 | ITGB7 | 2.4 | 0.1 |
| fibroblast growth factor 20* | Hs.154302 | FGF20 | 2.3 | 1.0 |
| KIAA0455 gene product | Hs.13245 | KIAA0455 | 2.3 | 1.3 |
| cAMP-specific phosphodiesterase 8B1 [*Homo sapiens*], mRNA sequence* | Hs.78106 | PDE8B | 2.3 | 0.4 |
| ectodermal-neural cortex (with BTB-like domain)* | Hs.104925 | ENC1 | 2.3 | 0.2 |
| frizzled homolog 1 (*Drosophila*)* | Hs.94234 | FZD1 | 2.3 | 0.8 |
| S100 calcium binding protein A3* | Hs.433168 | S100A3 | 2.2 | 0.6 |

TABLE II-continued

Genes regulated by Prox-1 in SW480R cells. Asterisk indicates genes that were flagged as absent in either Prox-1 siRNA or GFP siRNA treated cells. Genes differentially expressed between SW480R and SW480ADH cells are shown in bold.

| | UniGene cluster | Gene symbol | Log$_2$ ratio, average | stdev |
|---|---|---|---|---|
| zeta-chain (TCR) associated protein kinase 70 kDa* | Hs.234569 | ZAP70 | 2.2 | 1.1 |
| platelet derived growth factor C* | Hs.43080 | PDGFC | 2.1 | 0.1 |
| cystatin D* | Hs.121489 | CST5 | 2.1 | 0.3 |
| CCAAT/enhancer binding protein (C/EBP), delta | Hs.76722 | CEBPD | 2.1 | 0.1 |
| sorbin and SH3 domain containing 1 | Hs.108924 | SORBS1 | 2.1 | 0.5 |
| metallothionein 2A | Hs.118786 | MT2A | 2.0 | 0.6 |
| RAS guanyl releasing protein 1 (calcium and DAG-regulated) | Hs.182591 | RASGRP1 | 2.0 | 0.4 |
| checkpoint suppressor 1 | Hs.211773 | CHES1 | 2.0 | 0.4 |
| chondroitin beta1,4 N-acetylgalactosaminyltransferase* | Hs.11260 | ChGn | 2.0 | 0.4 |
| filamin B, beta (actin binding protein 278)* | Hs.81008 | FLNB | 2.0 | 0.4 |
| aldehyde dehydrogenase 1 family, member A2* | Hs.95197 | ALDH1A2 | 2.0 | 0.6 |
| jagged 1 (Alagille syndrome) | Hs.91143 | JAG1 | 2.0 | 0.1 |
| A kinase (PRKA) anchor protein (gravin) 12* | Hs.788 | AKAP12 | 1.9 | 0.1 |
| metallothionein 1X* | Hs.380778 | MT1X | 1.9 | 0.8 |
| creatine kinase, mitochondrial 2 (sarcomeric) | Hs.80691 | CKMT2 | 1.8 | 0.6 |
| serum-inducible kinase | Hs.3838 | SNK | 1.8 | 0.1 |
| CGI-130 protein | Hs.32826 | CGI-130 | 1.8 | 0.1 |
| guanine nucleotide binding protein (G protein), alpha inhibiting activity polypeptide 1 | Hs.203862 | GNAI1 | 1.8 | 0.4 |
| related to the N terminus of tre* | Hs.278526 | RNTRE | 1.7 | 0.4 |
| solute carrier family 12 (sodium/potassium/chloride transporters), member 2 | Hs.110736 | SLC12A2 | 1.7 | 0.3 |
| Human clone 23612 mRNA sequence | — | — | 1.7 | 1.0 |
| ankyrin repeat and SOCS box-containing 4 | Hs.248062 | ASB4 | 1.7 | 0.8 |
| apolipoprotein B mRNA editing enzyme, catalytic polypeptide-like 3C | Hs.8583 | APOBEC3C | 1.7 | 0.1 |
| cellular retinoic acid binding protein 2* | Hs.183650 | CRABP2 | 1.7 | 0.1 |
| KIAA0657 protein* | Hs.6654 | KIAA0657 | 1.7 | 1.1 |
| phosphodiesterase 4D, cAMP-specific (phosphodiesterase E3 dunce homolog, Drosophila) | Hs.172081 | PDE4D | 1.7 | 0.1 |
| autism susceptibility candidate 2 | Hs.32168 | AUTS2 | 1.6 | 0.4 |
| hairy/enhancer-of-split related with YRPW motif 2* | Hs.144287 | HEY2 | 1.6 | 0.0 |
| immediate early response 5 | Hs.15725 | IER5 | 1.6 | 0.1 |
| E3 ubiquitin ligase SMURF2 | Hs.194477 | SMURF2 | 1.6 | 0.4 |
| ADP-ribosylation factor-like 7* | Hs.111554 | ARL7 | 1.6 | 1.0 |
| Ras and Rab interactor 2* | Hs.62349 | RIN2 | 1.6 | 0.4 |
| GS3955 protein, Tribbles homolog 2 | Hs.155418 | TRB2 | 1.6 | 0.5 |
| metallothionein 1L | Hs.448357 | MT1L | 1.5 | 0.6 |
| glutamate receptor, metabotropic 8 | Hs.86204 | GRM8 | 1.5 | 0.2 |
| klotho | Hs.94592 | KL | 1.5 | 0.1 |
| calmodulin-like 3 | Hs.239600 | CALML3 | 1.4 | 0.6 |
| integrin, alpha 1 | Hs.116774 | ITGA1 | 1.4 | 0.1 |
| lymphoid enhancer-binding factor 1 | Hs.44865 | LEF1 | 1.4 | 0.4 |
| epithelial V-like antigen 1 | Hs.116651 | EVA1 | 1.4 | 0.1 |
| likely ortholog of mouse limb-bud and heart gene* | Hs.57209 | LBH | 1.4 | 0.1 |
| insulin induced protein 2 | Hs.7089 | ISG2 | 1.4 | 0.2 |
| patched homolog (Drosophila) | Hs.159526 | PTCH | 1.4 | 0.1 |
| chemokine-like factor super family 6 | Hs.380627 | CKLFSF6 | 1.3 | 0.3 |
| lipoma HMGIC fusion partner | Hs.93765 | LHFP | 1.3 | 0.4 |
| transforming growth factor, alpha | Hs.170009 | TGFA | 1.3 | 0.4 |
| Homo sapiens mRNA; cDNA DKFZp762M127 (from clone DKFZp762M127), mRNA sequence cyclin I | — | — | 1.3 | 0.6 |
| | Hs.79933 | CCNI | 1.3 | 0.1 |
| hyaluronan synthase 2 | Hs.159226 | HAS2 | 1.3 | 0.5 |
| IQ motif containing GTPase activating protein 1 | Hs.1742 | IQGAP1 | 1.3 | 0.5 |
| zinc finger protein 216 | Hs.406096 | ZNF216 | 1.3 | 0.2 |
| cDNA DKFZp564O0122 | — | — | 1.3 | 0.2 |

TABLE II-continued

Genes regulated by Prox-1 in SW480R cells. Asterisk indicates genes that were flagged as absent in either Prox-1 siRNA or GFP siRNA treated cells. Genes differentially expressed between SW480R and SW480ADH cells are shown in bold.

|  | UniGene cluster | Gene symbol | $Log_2$ ratio, average | stdev |
|---|---|---|---|---|
| aryl hydrocarbon receptor | Hs.170087 | AHR | 1.2 | 0.6 |
| neuroepithelial cell transforming gene 1 | Hs.25155 | NET1 | 1.2 | 0.1 |
| sterol-C4-methyl oxidase-like | Hs.239926 | SC4MOL | 1.2 | 0.1 |
| tubulin, alpha 3 | Hs.433394 | TUBA3 | 1.2 | 0.1 |
| BCG-induced gene in monocytes, clone 103 | Hs.284205 | BIGM103 | 1.2 | 0.0 |
| cathepsin B | Hs.297939 | CTSB | 1.2 | 0.0 |
| keratin 6A | Hs.367762 | KRT6A | 1.2 | 0.4 |
| paraoxonase 2 | Hs.169857 | PON2 | 1.2 | 0.4 |
| suppressor of cytokine signaling 5 | Hs.169836 | SOCS5 | 1.2 | 0.4 |
| KIAA0877 protein | Hs.11217 | KIAA0877 | 1.2 | 0.2 |
| propionyl Coenzyme A carboxylase alpha | Hs.80741 | PCCA | 1.2 | 0.2 |
| solute carrier family 2 | Hs.7594 | SLC2A3 | 1.2 | 0.1 |
| solute carrier family 7 | Hs.22891 | SLC7A8 | 1.2 | 0.1 |
| Homo sapiens mRNA; cDNA DKFZp762M127 | — | — | 1.2 | 0.1 |
| aryl hydrocarbon receptor nuclear translocator-like | Hs.74515 | ARNTL | 1.1 | 0.3 |
| DnaJ (Hsp40) homolog, subfamily B, member 6 | Hs.181195 | DNAJB6 | 1.1 | 0.3 |
| hypothetical protein FLJ21276 | — | FLJ21276 | 1.1 | 0.1 |
| integrin, beta 5 | Hs.149846 | ITGB5 | 1.1 | 0.1 |
| PTK7 protein tyrosine kinase 7 | Hs.90572 | PTK7 | 1.1 | 0.3 |
| transforming growth factor, beta receptor II | Hs.82028 | TGFBR2 | 1.1 | 0.1 |
| Homo sapiens cDNA FLJ25134 fis | Hs.301306 |  | 1.1 | 0.0 |
| DKFZP564A2416 protein | Hs.5297 | DKFZP56 4A2416 | 1.1 | 0.1 |
| dual specificity phosphatase 6 | Hs.180383 | DUSP6 | 1.1 | 0.4 |
| midline 1 (Opitz/BBB syndrome) | Hs.27695 | MID1 | 1.1 | 0.1 |
| membrane protein, palmitoylated 1, 55 kDa | Hs.1861 | MPP1 | 1.1 | 0.1 |
| LIM domain protein | Hs.424312 | RIL | 1.1 | 0.1 |
| SH3-domain binding protein 5 (BTK-associated) | Hs.109150 | SH3BP5 | 1.1 | 0.1 |
| SIPL protein | Hs.64322 | SIPL | 1.1 | 0.1 |
| tumor protein D52-like 1 | Hs.16611 | TPD52L1 | 1.1 | 0.4 |
| 3-hydroxy-3-methylglutaryl-Coenzyme A reductase | Hs.11899 | HMGCR | 1.0 | 0.1 |
| homeo box B7 | Hs.819 | HOXB7 | 1.0 | 0.1 |
| HIV-1 Tat interactive protein 2, 30 kDa | Hs.90753 | HTATIP2 | 1.0 | 0.1 |
| insulin receptor substrate 2 | Hs.143648 | IRS2 | 1.0 | 0.1 |
| tubulin beta-5 | Hs.274398 | TUBB-5 | 1.0 | 0.0 |
| apoptosis antagonizing transcription factor | Hs.16178 | AATF | 1.0 | 0.1 |
| E2F transcription factor 3 | Hs.1189 | E2F3 | 1.0 | 0.1 |
| hypothetical protein FLJ12542 | Hs.236940 | FLJ12542 | 1.0 | 0.1 |
| phafin 2, Pleckstrin homology domain containing, family F member 2 | Hs.29724 | PLEKHF2 | 1.0 | 0.1 |
| proline 4-hydroxylase | Hs.3622 | P4HA2 | 1.0 | 0.1 |
| Homo sapiens G21VN02 mRNA, mRNA sequence, solute carrier family 5 (inositol transporters), member 3 | Hs.324787 | SLC5A3 | 1.0 | 0.1 |

Example 5

Ablation of Prox-1 Leads to Differentiation Through Up-Regulation Of Notch Signaling in the SW480R Cells Activation of β-catenin/TCF pathway plays a central role in colon tumorigenesis (Giles, R. H., van Es, J. H. & Clevers, H., Biochim Biophys Acta 1653: 1-24, 2003). Of interest for this study, suppression of β-catenin/TCF signaling in colon cancer cells decreases the levels of c-myc, increases p21Cip1 levels and induces cell cycle arrest (van de Wetering et al., Cell 111:, 241-50, 2002). However, suppression of Prox-1 did not affect the activity of β-catenin/TCF-responsive reporter or nuclear localization of β-catenin. Moreover, an increased expression of several β-catenin/TCF-4 target genes, such as CD44, ENC1 and Id2 was observed in the absence of Prox-1 (Table II and not shown). These data suggest that Prox-1 may act via an alternative pathway to promote growth of colon cancer cells, and that both β-catenin/TCF activation and overexpression of Prox-1 are necessary for cell transformation. Accordingly, contemplated herein are methods of alleviating colorectal cancer whereby a Prox-1 suppressor is administered in combination with a β-catenin/TCF signaling inhibitor. β-catenin/LCF signaling inhibitors may include dominant negative forms of TCF4, siRNAs and microRNAs targeting TCF4, β-catenin, and c-myc, as well as small molecules that would interfere with binding of β-catenin to TCF4 or TCF-4 to target DNA sequences. Protocols for making these types of inhibitors are detailed above with respect to Prox-1 inhibition.

The DNA and protein sequences for β-catenin (SEQ ID NOs: 10 and 11, respectively) are published and disclosed as Genbank Accession Number NM_001904. The DNA and protein sequences for TCF4 (SEQ ID NOs: 12 and 13, respectively) are published and disclosed as Genbank Accession Number NM_003199. Related to the β-catenin/TCF signaling pathway is the APC gene, the sequence of which is publicly available as Genbank Accession Number NM_000038. The DNA and amino acid sequences for APC are also provided herein as SEQ ID NOs: 42 and 43, respectively. The DNA and protein sequences for C-myc (SEQ ID NOs: 44 and 45, respectively) are published and disclosed as Genbank Accession Number NM_002467.

Notch signaling has been shown to be essential for the generation of cell lineages in the crypts of the mouse small intestine. High levels of Notch are thought to suppress the expression of the basic helix-loop-helix transcription factor Math1 via the induction of the transcriptional repressor Hes1, which will lead to the differentiation of progenitor cells into enterocytes. Conversely, high levels of Math1 result in the differentiation towards the neuroendocrine, Goblet and Paneth cell types in the small intestine (Jensen, J. et al., *Nat Genet* 24: 36-44, 2000; Yang, Q., Bermingham, N. A., Finegold, M. J. & Zoghbi, H. Y., *Science* 294: 2155-8, 2001). Among Notch signaling components, Notch2 and its target transcription factor Hes1 levels are higher in SW480A cells in comparison with the SW480R cells, suggesting that this pathway is functionally active in these cells. Interestingly, SW480R cells express higher levels of Notch ligand Jagged2. Suppression of Prox-1 resulted in up-regulation of the Notch ligand Jagged1 and the direct target of the Notch pathway, the transcription factor Hey2, whereas the expression of Jagged2 and prostaglandin D2 synthase, previously shown to be negatively regulated by Notch signaling was suppressed (Fujimori, K. et al., *J Biol Chem* 278: 6018-26, 2003). SW480R cells were transfected with GFP siRNA or Prox-1 siRNA and GFB1-luc, TOPFlash or control FOP flash reporters. Firefly luciferase activity was normalized to Renilla luciferase activity. Up-regulation of Notch-responsive reporter GBF1-luc was observed in SW480R cells transfected with Prox-1 siRNAs. Accordingly, contemplated herein is a method of alleviating the symptoms of colorectal cancer comprising the administration of a Prox-1 suppressor in combination with a Notch agonist or target transcription factor. Notch agonists include Jagged1, Jagged2, Delta1, Delta3, Delta4, and Serrate. Target Notch transcription factors include Hey1, Hey2, and Hes1.

The DNA and protein sequences for Notch-1 (SEQ ID NOs: 14 and 15, respectively) are published and disclosed as Genbank Accession Numbers NM_017617. Likewise, the DNA and protein sequences for various forms of Notch (including 2-4) are publicly available and included herein as SEQ ID NOs: 16-21. In addition, the DNA and protein sequences for various ligands of Notch (including Jagged1, Jagged2, Jagged2 (transcript variant 2), Delta1, Delta3, Delta4, and Jagged2 (transcript variant 1)) are publicly available and included herein as SEQ ID NOs: 22-35, respectively. DNA and protein sequences for target Notch transcription factors Hey1, Hey2, and Hes1 are also publicly available and are included herein as SEQ ID NOs: 36-41, respectively.

Example 6

Suppression of Prox-1 Inhibits Growth in Soft Agar

Figure 3:
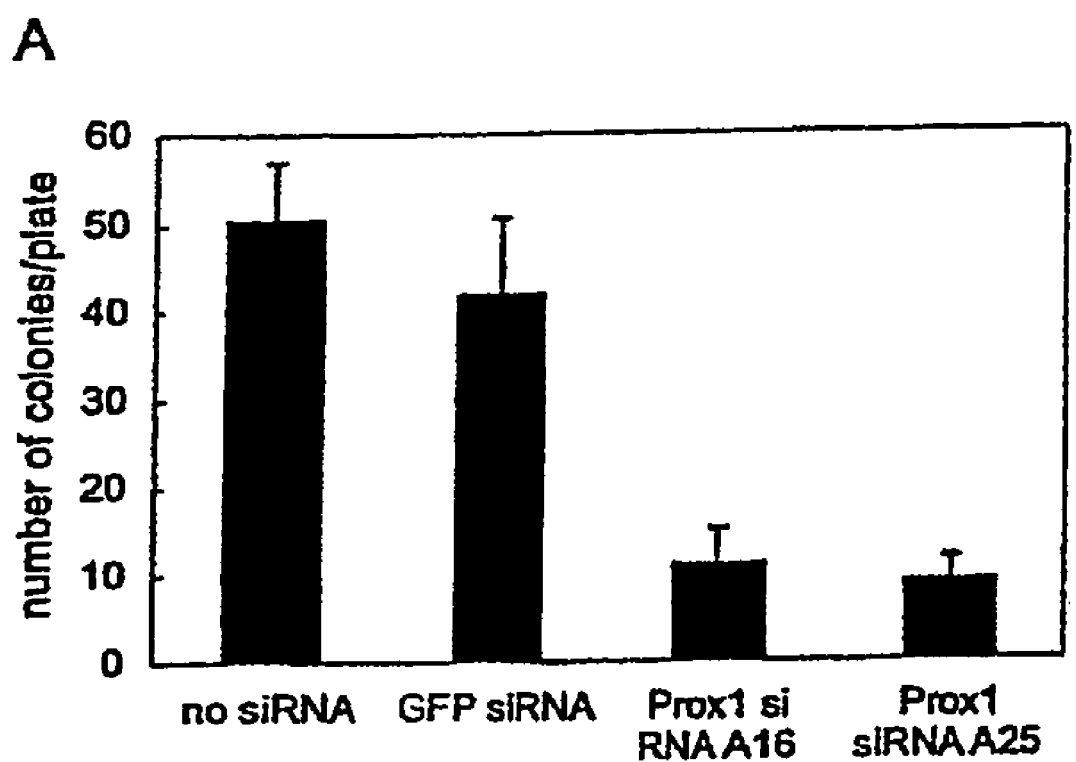
FIG. 3 depicts the efficacy of Prox-1 suppression for inhibiting SW480R cell growth in soft agar. SW480R cells were transfected with GFP siPRNA, Prox-1 siRNA A16 or Prox-1 siRNA A25 or left untreated, and seeded in soft agar in triplicate. The number of colonies was scored after two weeks of growth.

Since anchorage-independent growth is one of the hallmarks of malignant transformation, experiments were conducted to assess the effects of Prox-1 suppression on the growth of SW480R cells in soft agar. SW480R cells were transfected with GFP siPRNA, Prox-1 siRNA A16 or Prox-1 siRNA A25 repeatedly over an 8-day period, or left untreated, and seeded in soft agar in triplicate. The number of colonies was scored after two weeks of growth. Transfection with both Prox-1 siRNAs but not the control GFP siRNA significantly decreased the number of colonies formed after two weeks of growth in soft agar (FIG. 3A).

Example 7

Regulation of Prostaglandin Biosynthesis by Prox-1

COX-2 is a key enzyme involved in the conversion of arachidonic acid into the prostaglandin precursors PGG2 and PGH2, which are further transformed into biologically active prostaglandins by the action of corresponding synthases. Prostaglandins acts through binding to the G-protein coupled prostanoid receptors and they are rapidly inactivated by the action of 15-prostaglandin dehydrogenase (15-PGDH). COX-2 is overexpressed in the majority of colorectal cancers and in about half of colonic adenomas, suggesting that the increased PG production is important for tumor growth. In support of this view, treatment with non-steroid anti-inflammatory drugs, which acts as inhibitors of COX-2, significantly reduces the risk of developing colon cancer (Gupta, R. A. & Dubois, R. N., *Nat Rev Cancer* 1: 11-21, 2001). Accordingly, contemplated herein is a method of alleviating colorectal cancer via the administration of a Prox-1 suppressor in combination with a COX-2 inhibitor. Cox-2 inhibitors may include the following non-steroid anti-inflammatory drugs: aspirin, rofecoxib, celecoxib, amidophen, analgin, anapyrin, feloran, indomethacin, paracetoamol, piroxicam, sedalgin, diclofenac sodium, ketoprofan, Acular®, Ocufen®, and Voltarol®.

Experiments were conducted which found that suppression of Prox-1 in SW480R cells resulted in the up-regulation of the expression of 15-PGDH and downregulation of prostaglandin D2 synthase, whereas overexpression of Prox-1 in SW480F cells down-regulated 15-PGDH and up-regulated PGD2 synthase (Affymetrix results). These data suggest that Prox-1 may be important for the control of the balance of the total PG production in tumor cells, i.e., in the presence of Prox-1 decreased expression of 15-PGDH will result in higher net amounts of biologically active prostaglandins and enhanced tumor growth.

Because SW480 cells do not express COX-2, contemplated herein are experiments to assess the effects of Prox-1 on prostanoid biosynthesis in the SW480F cells stably transfected with COX-2 or in the cell line which is known to express this enzyme, such as HCA-7. To generate COX-2 expressing cells, SW480F cells are transfected with a mixture of a COX-2 expressing vector and the plasmid bearing hygromycin resistance gene, such as pCDNA3.1hygro (Invitrogen) using Lipofectamine 2000, as described in Materials and Methods, and the stable clones are selected using 200 μg/ml hygromycin B (Calbiochem) over a period of 2-3 weeks. Individual clones are isolated and the expression of COX-2 protein is tested using Western blotting. Functionality of COX-2 may be further verified in COX-2 expressing clones in comparison to the control cells, using ELISA to monitor PGE2 production according to the manufacturer's instructions (Cayman Chemical). To test the effects of Prox-1 on prostaglandin biosynthesis, COX-2 expressing cells can be infected with AdProx-1 or the control AdGFP virus, as described previously (Petrova et al., *Embo J.* 21: 4593-9), and the amount of biologically active PGE2, and total amount of metabolized PGE2 in cell conditioned medium, determined by ELISA (Cayman Chemicals). If overexpression of Prox-1 increases levels of the biologically active PGE2 in vitro, contemplated herein are studies to assess the link between Prox-1 overexpression and prostanoid biosynthesis in vivo. SW480R or HCA-7 stably overexpressing 15-PGDH will be produced using the protocol described above, and the tumorigenic potential of these cells in nude mice will be determined. In addition, contemplated are studies regarding the effects of the treatment with 15-PGDH inhibitor on growth of Prox-1 expressing or control xenografts in nude mice.

Example 8

Effects of Notch Signal Transduction

To investigate the effects of altered Notch signaling in SW480R cells described herein are experiments that overexpress constitutively active Notch1, Notch2, Notch3, and Notch4 intracellular domains, as well as Jagged1, soluble Jagged1, and Jagged2 using recombinant adenoviruses. Replication-deficient adenoviruses for the expression of constitutively active Notch 1-4 intracellular domains, and Notch ligands Jagged1, Jagged2, Delta1, Delta3, Delta4, and Serrate are produced. SW480R cells are infected with adenoviruses. 48-72 h postinfection cells are seeded in soft agar as described previously, and the number of colonies are scored after two weeks in culture. In parallel, total RNA is isolated and analysis of gene expression changes is conducted using Affymetrix® microarray according to the previously described procedures. If overexpression of Notch or its ligand results in the inhibition of cell growth in soft agar, further studies are conducted to investigate the effects of activation of Notch signaling on growth of tumors in nude mice.

Example 9

Effects of Prox-1 Suppression on SW480R in Nude Mice

Also contemplated herein are studies to assess the effects of Prox-1 suppression on the growth of SW480R tumors in nude mice. Nu/nu mice can be inoculated subcutaneously or intraperitoneally with $1-5\times10^6$ cells/mice using SW480R cells transfected with GFPsi RNA or Prox-1 siRNA, or transduced with the adenoviruses described in Example 8. Tumors are allowed to grow for 3-5 weeks, and tumor size measured twice a week. Animals are sacrificed by cervical dislocation, tumors excised, and processed for immunohistoshemical staining. The tumor histology, expression of differentiation markers, proliferation index and vascularization monitored using the antibodies against KI67 (proliferation), mucin, galectin-2, p21cip1 (differentiation), PECAM-1 and vWF (blood vessel markers), and the standard immunostaining protocols.

To assess of the effects of Prox-1-dependent genes, such as 15-PGDH, on prostaglandin metabolism and tumor growth in vivo, SW480R or HCA-7 cells recombinantly overexpressing 15-PGDH and control cells, are implanted subcutaneously into the nu/nu mice, and tumor growth and differentiation studied. In order to confirm the specificity of 15-PGDH effects, a subset of the control and 15-PGDH overexpressing tumor-bearing animals are treated with the 15-PGDH inhibitor CAY10397, administered intravenously, or in drinking water.

Example 10

Analysis of Prox-1 in Natural Colorectal Tumors

Experiments to asses the expression of Prox-1 in a mouse model of human familial adenomatous polyposis, Apc min/+ are also contemplated herein. The Apc min/+ mice bear a truncating mutation in one allele of Apc gene, and develop multiple intestinal polyps, which further progress to adenocarcinoma. Mice are commercially available from JAX. As another cancer model, SMAD3 deficient mice, which develop invasive colorectal cancer, is available. The DNA and protein sequences for APC (SEQ ID NOs: 42 and 43, respectively) are published and disclosed as Genbank Accession Number NM_000038.

Administration of a Prox-1 inhibitor and a placebo to mice of the above-described models is also contemplated. Prox-1 inhibitors and administration thereof are described herein. Prox-1 inhibitors available for administration include, but are not limited to, antisense oligonucleotides, siRNA constructs, or dominant negative proteins. Monitoring of the mice post-administration is contemplated to evaluate the effects of adenocarcinoma and colorectal cancer development and growth. Among the results are measurements of the speed of tumor growth in mice that received the Prox-1 inhibitor versus mice that received the placebo, thus, providing a beneficial efficacy model for the particular Prox-1 inhibitor. Also contemplated are methods for screening Prox-1 levels in family members with familial adenomatous polyposis. Methods for screening Prox-1 levels are described herein. Administration of a prophylactic to protect from progression, or the onset of cancer, is contemplated where elevated levels of Prox-1 are observed.

Example 11

Detection of Prox-1 Protein Expression in Colorectal Cancer

As described above, measuring Prox-1 protein expression in colon tissues may be a useful tool for diagnosing colon cancer and/or premalignancies. Prox-1 mRNA can be detected in colorectal cancer tissues as described in Example 2. The following prospective example may be conducted to determine whether Prox-1 protein correlates with Prox-1 transcript expression in colorectal cancer tissue. The immunohistochemical analysis can be carried out as follows using an anti-human Prox-1 antibody directed against the human Prox-1 peptide, as described in Example 1.

The tissues for screening are snap frozen in liquid nitrogen after dissection, embedded in OCT compound, and sectioned. Sections are fixed on −20° C. methanol for 10 min, and processed for staining.

To enhance epitope recovery, the tissues may undergo steam induced epitope recovery with a retrieval solution, including several different SHIER solutions with and without enzyme digestion at two different concentrations. The tissues can then be heated in the capillary gap in the upper chamber of a Black and Decker Steamer as described in Ladner et al. (*Cancer Research,* 60: 3493-3503, 2000).

Automated immunohistochemistry is carried out with the TECHMATE 1000 or TECHMATE 500 (BioTek Solutions, Ventura Medical System). Specifically, the tissues are blocked with 3% and 10% normal goat serum for 15 and 30 minutes respectively. Subsequently, the tissues are incubated with the primary antibody (anti-Prox-1 antibody) for 60 minutes at 3.0*g/ml. The tissues are stained with the biotinylated goat-anti-rabbit IgG secondary antibody for 25 minutes. Optimal results are obtained with overnight incubation. To ensure the staining procedure is working appropriately, anti-vimentin is used as a positive control and rabbit IgG is used as a negative control.

The antibody binding is detected by an avidin-biotin based tissue staining system where horse-radish peroixidase is used as a reporter enzyme and DAB (3,3'-Diaminobenzididine Tetrahydrochloride) is used as a chromogen. Specifically, the endogenous peroxides are blocked for 30 minutes, the avidin-biotin complex reagent is added and then the tissues are incubated in DAB for a total of 15 minutes. Finally, the tissues are counterstained with hemotoxylin to assess cell and tissue morphology.

The slides are mounted in Aquamount, and the tissues are examined visually under a light microscope. Tissue that is positive for increased Prox-1 protein expression as compared to healthy colon tissue, or other cancer tissues, indicate colorectal cancer and/or premalignant lesions.

While this prospective example provide one means of detecting colon cancer, other means will be obvious to those with skill in the art. Various options for detecting Prox-1 expression, and, therefore screen for colon cancer, include, among others, ELISA-based techniques and Western blotting techniques.

Example 12

Expression Pattern of Prox-1 in Normal Colonic Epithelium

Studies were conducted to compare Prox-1 expression in normal cololnic epithelium. In normal colonic mucosa, all Prox-1 expressing cells were positive for the intestinal epithelial transcription factor CDX2. There was no overlap with the expression of MUC2, expressed by the goblet cells; however, a subset of Prox-1 positive cells also expressed the pan-neuroendocrine marker chromogranin A. Also observed was weaker but significant Prox-1 expression in the bottom of the crypts below the cell proliferation zone identified by staining for the Ki67 antigen.

Colonic epithelium is composed of the slowly dividing stem cells located in the bottom of the crypt, the cell proliferation zone with transient amplifying cells, which give rise to the three main colonic epithelial cell types, and terminally differentiated cells, located in the upper part of the crypts. The location of Prox-1 positive cells at the base of the crypts, therefore, corresponded to the position of the intestinal stem cells. (Bach, S. P., Renehan, A. G. & Potten, C. S., *Carcinogenesis* 21, 469-76 (2000); Potten, C. S., Kellett, M., Roberts, S. A., Rew, D. A. & Wilson, G. D., *Gut* 33, 71-8 (1992)) A similar staining pattern was observed in the murine descending colon, whereas the duodenal epithelium was negative for Prox-1. Expression of $p21^{CIP1/WAF1}$ marks the differentiated compartment of colonic crypts independently of the cell type (Doglioni, C. et al., *J Pathol* 179, 248-53 (1996)). Accordingly, studies were conducted regarding the expression of Prox-1 in relation to $p21^{CIP1/WAF1}$. All Prox-1 positive cells located at the bottom of the crypts were negative for $p21^{CIP1/WAF1}$; however, most of the rare Prox-1 positive cells present in the upper parts of the crypts were also negative for $p21^{CIP1/WAF1}$, demonstrating a mutually exclusive relation between Prox-1 expression and terminal differentiation. p21 (CIP1)/(WAF1) (CDKN1) sequences are published and disclosed as Genbank Accession Numbers NM_078467 and NM_000389. These variants (1) and (2) encode the same protein.

Based on the data implicating Prospero/Prox-1 in cell fate determination in other cell types, and on its expression pattern in colonic epithelial cells it is contemplated that Prox-1 may be involved in the regulation of the neuroendocrine cell fate as well as the stem cell phenotype. This hypothesis is supported by the fact that Prox-1 is overexpressed in intestinal neoplasms from $Apc^{min/+}$ mice and that its expression is regulated by TCF/β-catenin pathway in vitro (see Examples 13 and 14). This hypothesis is also in agreement with previous results showing that targeted inactivation of Tcf712 gene encoding TCF-4 leads to the depletion of intestinal stem cell compartment and loss of neurodendocrine lineage (Korinek, V. et al., *Nat Genet* 19, 379-83 (1998)).

Example 13

Prox-1 is Overexpressed in Intestinal Neoplasms from $APC^{min/+}$ Mice, but not from $Ltbp4^{-/-}$ Deficient Mice Studies were also conducted to assess Prox-1 expression in $Apc^{min/+}$ mice. A truncating germline mutation in the Apc gene together with somatic inactivation of the remaining wild type allele, lead to abnormal β-catenin/TCF signaling in intestinal epithelial cells of $Apc^{min/+}$ mice and development of multiple intestinal polyps (Luongo, C., Moser, A. R., Gledhill, S. & Dove, W. F., *Cancer Res* 54, 5947-52 (1994); Su, L. K. et al., *Science* 256, 668-70 (1992)). High levels of Prox-1 in intestinal neoplasms of $Apc^{min/+}$ mice were observed. Prox-1 mRNA and protein were present in tumor cells with high cytoplasmic and nuclear β-catenin levels, but not in the differentiating cells of the neighboring normal glands with membrane localization of β-catenin.

Mutation in genes regulating TGFβ signaling pathway, such as TGFRII and SMAD4 occur in human colorectal cancer, and targeted inactivation of TGF-β1 binding protein LTBP-4 leads to colon cancer in mice (White, R. L., *Cell* 92, 591-2 (1998); Stemer-Kock, A. et al., *Genes Dev.* 16, 2264-73 (2002)). Studies were conducted to assess Prox-1 expression in Ltpb4−/− mice. In contrast to the results from Apc min/+, accumulation of Prox-1 in the colonic adenocarinomas from Ltpb4−/− mice, which generally preserve normal distribution of β-catenin, was not observed. These results strongly suggest that Prox-1 is a target of APC/β-catenin/TCF pathway in vivo. Tumors from Ltpb4−/− mice had strongly increased number of lymphatic vessels, positive both for Prox-1 and LYVE-1.

Example 14

Prox-1 Expression is Regulated by β-Catenin/TCF Pathway and DNA Methylation

Further studies were conducted using SW480R cell line as an in vitro model to investigate the role of Prox-1 in colorectal carcinoma. Suppression of Prox-1 expression using two different siRNAs (SEQ ID NOS: 4, 5, 6, and 7) did not affect the activity of a β-catenin/TCF-responsive reporter, the nuclear localization of β-catenin, or the cellular content of active, non-phosphorylated β-catenin, confirming that Prox-1 is not acting upstream of this pathway. In contrast, suppression of β-catenin using two independent siRNAs resulted in almost complete disappearance of Prox-1 mRNA and protein. In line with this finding, suppression of Prox-1 was also observed in SW480R cells transfected with dominant negative mutant of TCF4, which disrupts β-catenin/TCF mediated transcription (Morin P J, et al., *Science* 1997 March 21; 275(5307):1787-90). However, overexpression of $p21^{CIP1/WAF1}$, shown to induce cell differentiation in colorectal carcinoma cells (van de Wetering, M. et al., Cell 111, 241-50 (2002)), did not modify Prox-1 levels. Taken together, these data show that Prox-1 lies downstream of β-catenin/TCF4 and upstream of p21$^{CIP1/WAF1}$.

Also observed was increased expression of several known β-catenin/TCF-4 target genes, such as CD44, ENC1 and ID2 in the absence of Prox-1 (Table II, (Fujita et al., 2001; Rockman et al., 2001; Wielenga et al., 1999)), while others such as p21$^{CIP1/WAF1}$, annexin A1, and OB-cadherin were induced upon suppression of either β-catenin or Prox-1. These results underline the complexity of the regulatory cascade initiated by β-catenin/TCF in CRC cells and suggest that concerted regulation by Prox-1 and other β-catenin/TCF targets is necessary for neoplastic growth.

Studies were also conducted to compare the activation of β-catenin/TCF signaling pathway in SW480R and SW480A cells. The SW480R cells had slightly more active β-catenin and displayed a two-fold increase in the activation of the TCF-responsive promoter TopFLASH; however, both cell lines clearly displayed nuclear localization of β-catenin as previously reported (Palmer, H. G. et al., J Cell Biol 154, 369-87 (2001)). These observations, together with the fact that abnormal β-catenin/TCF pathway signaling is a feature of the majority of colorectal cancer cell lines, suggest that β-catenin/TCF activation is necessary but not sufficient for the induction of Prox-1 expression in colorectal cancer.

DNA methylation is frequently abnormal in colorectal cancer, and it was reported recently that Prox-1 expression is suppressed in human hematological cell lines due to hypermethylation of CpG islands in intron 1 of Prox-1 (Nagai, H. et al., Genes Chromosomes Cancer 38, 13-21 (2003)). Treatment of SW480A cells with the inhibitor of DNA methyltransferases 5-aza-2'-deoxycytidine did not result in the increase of Prox-1 mRNA, while there was increase in the expression of TIMP3. In contrast, 5-aza-2'-deoxycytidine almost completely suppressed Prox-1 expression in SW480R cells, suggesting that, at least in this cell type, the regulation of Prox-1 by DNA methylation is opposite to the one observed in leukemic cells.

Our finding that DNA demethylation decreases Prox-1 mRNA levels suggests the existence of a putative suppressor of Prox-1 transcription, whose expression becomes relieved upon treatment with 5-aza-2'-deoxycytidine. Since 5-aza-2'-deoxycytidine is used for the treatment of human cancers, our data also suggest that Prox-1 could be used as marker to identify the colorectal tumors which would respond favorably to this drug. Such screening of patients/tumors is intended as an aspect of the invention. The role of DNA methylation in the growth of intestinal neoplasms was previously demonstrated in mice heterozygous or hypomorphic for DNA methyltransferase 1, a major enzyme involved in the methylation of DNA. These mice do not develop intestinal adenomas when crossed with Apc$^{min/+}$ mice. In contrast, they develop lymphomas, demonstrating cell type specific effects of decreased DNA methylation for cancerous growth (Gaudet, F. et al., Science 300, 489-92 (2003), Eads, C. A. et al., Cancer Res 62, 1296-9 (2002)).

Example 15

Prox-1 Suppression and Overexpression in Colorectal Cancer

To characterize the effects of Prox-1 suppression and overexpression in colorectal cancer, stable colorectal cancer cell line clones inducibly expressing Prox-1 or Prox-1 targeting siRNAs are employed. Cells are implanted into laboratory animals, such as nu/nu mice, and tumor growth is studied in control mice and mice treated with doxycycline. As an alternative approach, Prox-1 or Prox-1 siRNA expressing lentiviruses are employed to provide long-term expression in colorectal cancer cell lines in vitro and in vivo.

To inducibly suppress and overexpress Prox-1 or Prox-1 siRNAs, Prox-1 cDNA was subcloned in pTetOS vector (Sarao and Dumont, Transgenics Res., 1998), where it is placed under the control of doxycycline regulated promoter. Prox-1 siRNAs were subcloned in pTer vector (van der Wetering et al., Embo Reports, 2003). Colorectal carcinoma cells stably expressing tTA activator may be transfected with Prox-1/TetOS or Prox-1 siRNS/pTer vectors. Clones may be selected in the presence of blasticidine and G480 and further tested for the expression of Prox-1 by immunostaining or Prox-1 siRNA by suppression of co-transfected Prox-1 in the presence of doxycycline. For production of Prox-1 lentiviruses, Prox-1 cDNA was subcloned into FUiresGFPW (Lois et al., Science, 2002). For production of Prox-1 siRNA lentiviruses, Prox-1 siRNAs 1 and 2 were subcloned into lentiviral vector pLL3.7 (Rubinson et al., Nat Genet., 2003).

Sequences of the DNA oligos used in the cloning of pLL3.7-Prox-1:

sense:
(SEQ ID NO 47)
TGGTCATCTGCAAGCTGGATTTCAAGAGAATCCAGCTTGCAGATGACCTT TTTC.

antisense:
(SEQ ID NO 48)
TCGAGAAAAAAGGTCATCTGCAAGCTGGATTCTCTTGAAATCCAGCTTGC AGTGACCA.

pLL3.7 PROX1-2: sense:
(SEQ ID NO 49)
TGAGCCAGTTTGATATGGATTTCAAGAGAATCCATATCAAACTGGCTCTT TTTTC.

antisense:
(SEQ ID NO 50)
TCGAGAAAAAAGAGCCAGTTTGATATGGATTCTCTTGAAATCCATATCAA ACTGCTCA.

Inducible Prox-1 targeting short hairpin RNA ("shRNA") expression may also be achieved via CRE recombinase activated induction system whereby an inactivating stuffer DNA sequence surrounded by modified loxP sites is removed from an shRNA expression cassette by the CRE recombinase activity, thus activating the shRNA expression. Alternatively a similar system may be used to inactivate shRNA expression upon introduction of CRE recombinase. Tiscornia et al PNAS 2004, and Coumoul et al NAR 2004) described these systems.

shRNA or "short hairpin RNA" is a short sequence of RNA which makes a tight hairpin turn and can be used to silence gene expression. This small hairpin RNA was first used in a lentiviral vector. (Abbas-Terki T. et al., Hum. Gene Ther. 13(18):2197-201 (2002)). shRNA generates siRNA in cells (An D S et al., Hum. Gene Ther. 14(12):1207-12 (2003)).

To study the effects of Prox-1 overexpression in vivo, transgenic mice overexpressing Prox-1 under the control of intestinal-specific promoter, such as villin, Cyp1A or FABPi are created using standard techniques. The proliferation and differentiation status of intestinal epithelial cells is studied by staining of intestinal tissues for PCNA, Ki67, CDKN1A, mucins, lysozyme, chromogranin A and carboxipeptidases II and IV. The crossing of Prox-1 transgenic animals with Apc$^{min/+}$ mice permits determination of whether Prox-1 overexpression influences the number and size of intestinal polyps in this mouse model of colorectal cancer.

Specifically, for in vivo studies of Prox-1 in intestinal differentiation, Prox-1 cDNA was subcloned in p12.4Vill plasmid, which places it under the control of 12.4 kb mous villin promoter (Madison et al., J. Biol. Chem. 2002, genomic contig NT_039170). The construct may be used for the production of villin-Prox-1 transgenic mice, which will overexpress Prox-1 at the sites of villin expression, i.e. intestinal epithelial cells. Also contemplated is subcloning Prox-1 cDNA into the vector z/AP (Lobe et al., Dev. Biol, 1999), to be able conditionally express Prox-1 in any given tissue. In this approach Prox-1 cDNA is placed between the loxP sites, and it is not expressed until Cre recombinase is present in the same cell. Excision of loxP sites places the transgene under the control of chicken β-actin promoter. To achieve intestinal specific overexpression of Prox-1 the transgenic animals containing z/AP-Prox-1 expression cassettes in their genomes may be crossed with villin-Cre mice (Madison et al., J. Biol. Chem. 2002). The latter approach may be preferable to the villin-PROX1 overexpression because of potentially higher expression levels of the transgene. Also contemplated in cloning Prox-1 cDNA under the control of rat Fabpi promoter (Rottman and Gordon, J. Biol. Chem., 1993, genomic contig NW_047627) or Cyp1A promoter (Sansom et al., Genes Dev., 2004, genomic contig NT_039474). The latter promoter has an advantage of being inducible upon administration of β-naphtoflavone. All of these transgenic mice are contemplated as aspects of the invention.

Example 16

Dominant Negative Mutants of Prox-1

Further contemplated herein are dominant negative mutants of Prox-1. Specifically, a Prox-1 mutant protein lacking the transactivation domains or DNA binding domains may act in a dominant negative manner. Experiments to investigate this hypothesis may be conducted by producing a truncated form of Prox-1 lacking the last 60 amino acids or the first 575 amino acids. Disruption of the DNA binding domain entails truncation of the protein to exclude amino acids 572-634 of SEQ ID NO. 3, based on homology to Prospero (*Drosophila*). Disruption of the transactivation domain entails the deletion of amino acids 635-737. These proteins may then be tested for their ability to repress the induction of Prox-1 target genes upon co-transfection with the wt Prox-1. If such an effect is observed, the construct can be used for the generation of transgenic animals with the purpose of suppression of Prox-1 effects in vivo, or for the anti-Prox-1 therapies in colorectal cancer.

The foregoing examples are intended to be illustrative of the invention and not intended to limit the claims which define the invention. All patent, journal, and other literature cited herein is incorporated herein by reference in the entirety.

While the invention is described specifically with respect to Prox-1, there are other genes described in tables herein that are differentially expressed. All materials and methods described herein are applicable to the genes described in the tables.

The invention claimed is:

1. A method of screening colon tissue for colon cancer, said method comprising:
 measuring (prospero homeobox protein 1) Prox-1 expression in a biological sample that comprises colon tissue from a human subject; and
 screening for colon cancer by:
  (a) detecting the presence of an elevated level of Prox-1 expression in said colon tissue in the biological sample that is statistically significantly greater than the level of Prox-1 expression in healthy colon tissue, wherein said presence of the elevated level of Prox-1 expression is indicative of the presence of colon cancer in the colon tissue of the biological sample; or
  (b) detecting the absence of an elevated level of Prox-1 expression in said colon tissue in the biological sample that is statistically significantly greater than the level of Prox-1 expression in healthy colon tissue, wherein said absence of the elevated level of Prox-1 expression is indicative of the absence of colon cancer in the colon tissue of the biological sample.

2. The method according to claim 1, further comprising a step, prior to said measuring, of obtaining the biological sample that comprises colon tissue from the human subject.

3. The method according to claim 1, wherein the measuring comprises measuring Prox-1 protein in the colon tissue of the biological sample.

4. The method of claim 3, wherein the measuring comprises contacting the colon tissue of the biological sample with a Prox-1 antibody or antigen-binding fragment thereof.

5. The method of claim 1, wherein the measuring comprises measuring Prox-1 mRNA in the colon tissue of the biological sample.

6. The method of claim 5, wherein the measuring comprises in situ hybridization to measure Prox-1 mRNA in the colon tissue of the biological sample.

7. The method of claim 5, wherein the measuring comprises steps of isolating mRNA from the colon tissue of the biological sample and measuring Prox-1 mRNA in the isolated mRNA.

8. The method of claim 1, wherein the measuring comprises quantitative polymerase chain reaction (PCR) to quantify Prox-1 mRNA in the colon tissue in the biological sample relative to Prox-1 mRNA in healthy colon tissue.

9. The method of claim 1, further comprising measuring expression of at least one gene selected from the group consisting of CD44, ectodermal-neural cortex protein 1 (Enc1), and inhibitor of DNA binding 2 (ID2) in the colon tissue of the biological sample.

10. The method of claim 1, further comprising measuring activation of β-catenin/TCF pathway in the colon tissue of the biological sample.

11. The method of claim 10, wherein activation of the β-catenin/TCF pathway is measured by at least one indicator in the colon tissue selected from the group consisting of: mutations in an APC gene; mutations in a β-catenin gene; and nuclear localization of β-catenin.

12. The method of claim 1, wherein the presence of the elevated level of Prox-1 expression is detected in said colon tissue of the biological sample, and wherein the method further comprises administering a composition comprising a Prox-1 inhibitor to the human subject.

13. The method of claim 1, wherein the screening step indicates that the human subject has elevated Prox-1 expression in colon tissue and wherein the screening step indicates that the human subject has colon cancer.

14. A method of selecting a human subject for therapy with a Prox-1 inhibitor comprising:
 (a) screening for colon cancer in the human subject by detecting in a biological sample that comprises colon tissue from the human subject the presence of an elevated level of Prox-1 expression that is statistically significantly greater than the level of Prox-1 expression in healthy colon tissue, wherein said presence of the elevated level of Prox-1 expression is indicative of the presence of colon cancer in the colon tissue of the biological; and
 (b) selecting the human subject identified according to (a) as having the elevated level of Prox-1 for treatment with a Prox-1 inhibitor.

15. The method of claim 14, further comprising a step, prior to said detecting, of obtaining the biological sample from the human subject.

16. The method of claim 14, further comprising administering a Prox-1 inhibitor to the human subject.

17. A method of screening colon tissue for colon cancer, said method comprising:
 measuring (prospero homeobox protein 1) Prox-1 expression in a biological sample that comprises colon tissue from a human subject; and
 screening for colon cancer by:
  (a) detecting the presence of a level of Prox-1 expression in said colon tissue in the biological sample that is statistically similar to the level of Prox-1 expression in colorectal cancer tissue, wherein said level of Prox-1 expression is indicative of the presence of colon cancer in the colon tissue of the biological sample; or
  (b) detecting the presence of a level of Prox-1 expression in said colon tissue in the biological sample that is statistically significantly lower than the level of Prox-1 expression in colorectal cancer tissue, wherein said presence of the lower level of Prox-1 expression is indicative of the absence of colon cancer in the colon tissue of the biological sample.

18. The method according to claim 17, wherein the measuring comprises measuring Prox-1 protein in the colon tissue of the biological sample.

19. The method of claim 18, wherein the measuring comprises contacting the colon tissue of the biological sample with a Prox-1 antibody or antigen-binding fragment thereof.

20. The method of claim 17, wherein the measuring comprises measuring Prox-1 mRNA in the colon tissue of the biological sample.

21. The method of claim 20, wherein the measuring comprises in situ hybridization to measure Prox-1 mRNA in the colon tissue of the biological sample.

22. The method according to claim 17, wherein the screening indicates that the human subject has colon cancer.

* * * * *